United States Patent
Kawano et al.

(10) Patent No.: US 10,851,079 B2
(45) Date of Patent: Dec. 1, 2020

(54) PIPERIDINE DERIVATIVE

(71) Applicant: OTSUKA PHARMACEUTICAL CO., LTD., Tokyo (JP)

(72) Inventors: Yoshikazu Kawano, Osaka (JP); Hiroshi Shimizu, Osaka (JP); Shunpei Ishikawa, Osaka (JP); Isao Takemura, Osaka (JP); Norimitsu Hariguchi, Osaka (JP); Miki Matsuba, Osaka (JP); Makoto Matsumoto, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/079,713

(22) PCT Filed: Feb. 27, 2017

(86) PCT No.: PCT/JP2017/007266
§ 371 (c)(1),
(2) Date: Aug. 24, 2018

(87) PCT Pub. No.: WO2017/146246
PCT Pub. Date: Aug. 31, 2017

(65) Prior Publication Data
US 2019/0040039 A1    Feb. 7, 2019

(30) Foreign Application Priority Data

Feb. 26, 2016    (JP) ................. 2016-036038

(51) Int. Cl.
| | | |
|---|---|---|
| C07D 401/12 | (2006.01) | |
| C07D 405/12 | (2006.01) | |
| C07D 411/12 | (2006.01) | |
| C07D 413/12 | (2006.01) | |
| C07D 417/12 | (2006.01) | |
| C07D 471/04 | (2006.01) | |
| C07D 211/44 | (2006.01) | |
| A61K 31/498 | (2006.01) | |
| A61K 31/55 | (2006.01) | |
| A61K 31/554 | (2006.01) | |
| A61K 31/4725 | (2006.01) | |
| A61K 31/517 | (2006.01) | |
| A61K 31/553 | (2006.01) | |
| A61K 31/454 | (2006.01) | |
| A61K 31/4545 | (2006.01) | |
| A61K 31/5415 | (2006.01) | |
| A61K 31/4525 | (2006.01) | |
| A61K 31/4709 | (2006.01) | |
| A61K 31/536 | (2006.01) | |

(52) U.S. Cl.
CPC .......... *C07D 401/12* (2013.01); *A61K 31/454* (2013.01); *A61K 31/4525* (2013.01); *A61K 31/4545* (2013.01); *A61K 31/4709* (2013.01); *A61K 31/4725* (2013.01); *A61K 31/498* (2013.01); *A61K 31/517* (2013.01); *A61K 31/536* (2013.01); *A61K 31/5415* (2013.01); *A61K 31/55* (2013.01); *A61K 31/553* (2013.01); *A61K 31/554* (2013.01); *C07D 211/44* (2013.01); *C07D 405/12* (2013.01); *C07D 411/12* (2013.01); *C07D 413/12* (2013.01); *C07D 417/12* (2013.01); *C07D 471/04* (2013.01)

(58) Field of Classification Search
CPC .................................................. C07D 401/12
See application file for complete search history.

(56) References Cited

U.S. PATENT DOCUMENTS

| | | | |
|---|---|---|---|
| 5,668,127 A | 9/1997 | Baker et al. | |
| 9,051,333 B2 | 6/2015 | Kawano et al. | |
| 10,464,926 B2 * | 11/2019 | Shimizu | C07D 215/227 |
| 2006/0094767 A1 | 5/2006 | Tsubouchi et al. | |
| 2008/0119478 A1 | 5/2008 | Tsubouchi et al. | |

(Continued)

FOREIGN PATENT DOCUMENTS

| | | |
|---|---|---|
| EP | 2 086 968 A1 | 8/2009 |
| JP | 11-508270 A | 7/1999 |

(Continued)

OTHER PUBLICATIONS

Michael D. Iseman, "A Clinician's Guide to Tuberculosis", 2000 by Lippincott Williams & Wilkins, pp. 271-320, ISBN 0-7817-1749-3 (28 pages total).

Kekkaku 2nd edition, Fumiyuki Kuze, Takahide Izumi, Igaku-shoin 1992 (8 pages total).

(Continued)

*Primary Examiner* — John S Kenyon
(74) *Attorney, Agent, or Firm* — Sughrue Mion, PLLC

(57) ABSTRACT

The purpose of the present invention is to provide a compound having excellent antibacterial activity against *mycobacterium tuberculosis*, multidrug-resistant tuberculosis bacteria, and/or non-tuberculous acid-fast bacteria. A compound represented by formula [I]:

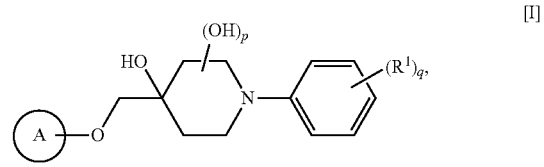

(in the formula, each symbol is as described in the attached specification), or a salt thereof can be used to diagnose, prevent, and/or treat tuberculosis.

14 Claims, No Drawings

(56) References Cited

U.S. PATENT DOCUMENTS

| | | |
|---|---|---|
| 2009/0018123 A1 | 1/2009 | Sindkhedkar et al. |
| 2011/0028466 A1 | 2/2011 | Thompson et al. |
| 2011/0059979 A1 | 3/2011 | Jamieson et al. |
| 2013/0065884 A1 | 3/2013 | No et al. |
| 2017/0253576 A1 | 9/2017 | Shimizu et al. |

FOREIGN PATENT DOCUMENTS

| | | | |
|---|---|---|---|
| JP | 2004-149527 | A | 5/2004 |
| JP | 2004-149527 | A5 | 7/2005 |
| JP | 2005-320316 | A | 11/2005 |
| JP | 2004-149527 | A5 | 5/2008 |
| JP | 2009-269859 | A | 11/2009 |
| WO | 97/01562 | A1 | 1/1997 |
| WO | 2005/016915 | A1 | 2/2005 |
| WO | 2007/023507 | A2 | 3/2007 |
| WO | 2011/014776 | A1 | 2/2011 |
| WO | 2011/113606 | A1 | 9/2011 |
| WO | 2012/141338 | A1 | 10/2012 |
| WO | 2016/031255 | A1 | 3/2016 |

OTHER PUBLICATIONS

Kuze, et al., "Prospects for Development of New Antimicrobials for Clinical Control of Tuberculosis", The 73rd Annual Meeting Symposium, Kekkaku, 1999, pp. 43-82, vol. 74, No. 1 (38 pages total).

"Global tuberculosis report 2013", World Health Organization, ISBN 978 92 4 156465 6 (303 pages total).

Verma, et al., "HIV-Tuberculosis Co-Infection", The Internet Journal of Pulmonary Medicine, 2007, pp. 1-5, vol. 10, No. 1 (5 pages total).

"The Global Plan to Stop TB 2011-2015", World Health Organization (101 pages total).

International Search Report in corresponding International Application No. PCT/JP2017/007266, dated May 23, 2017.

International Preliminary Report on Patentability with a Translation of Written Opinion in counterpart International Application No. PCT/JP2017/007266, dated Sep. 7, 2018.

Extended European Search Report dated Jul. 11, 2019 in European Application No. 17756680.9.

Communication dated Jul. 3, 2020, from the Intellectual Property Office of India in Application No. 201847035389.

* cited by examiner

PIPERIDINE DERIVATIVE

This application is a National Stage of International Application No. PCT/JP2017/007266 filed Feb. 27, 2017, claiming priority based on Japanese Patent Application No. 2016-036038 filed Feb. 26, 2016.

TECHNICAL FIELD

The present invention relates to piperidine derivatives useful for diagnosis, prevention, and/or treatment of tuberculosis, and medical use thereof.

BACKGROUND ART

Human tuberculosis bacteria (*Mycobacterium tuberculosis*) is widely known among mycobacteria, with which third part of human beings are said to be infected. *Mycobacterium africanum, Mycobacterium bovis, Mycobacterium caprae, Mycobacterium pinnipedii*, and *Mycobacterium microti* are known to belong to the tuberculosis bacteria group like human tuberculosis bacteria, and are known as mycobacteria having pathogenicity against human.

Multidrug chemotherapy for 6 months has been recommended as a treatment for these tuberculosis bacteria. A typical therapy comprises a treatment with 4 medicinal agents of rifampicin, isoniazid, pyrazinamide, and ethambutol (or streptomycin) for the first 2 months; and a treatment with 2 medicinal agents of rifampicin and isoniazid for the remaining 4 months.

It has been pointed out, however, that the medication compliance in the treatment for tuberculosis is poor due to such long-term treatment and adverse effects of the used drugs often cause the treatment to discontinue.

The adverse effects of these drugs have been reported (Nonpatent Literatures 1 and 2), for example, rifampicin has hepatic disorder, flu syndrome, drug allergy, and contraindication to combination use with other drugs caused by P450-related enzymes; isoniazid has peripheral neuropathy and serious hepatic disorder induced with a combination use with rifampicin; ethambutol has visual loss caused by optic nerve disorder; streptomycin has hearing loss caused by eighth cranial nerve involvement; pyrazinamide has hepatic disorder, gouty attack associated with the uric acid level, and vomiting. Amongst the adverse effects of the above 5 agents used as a first-line drug, in particular, hepatotoxicity commonly-caused by rifampicin, isoniazid, and pyrazinamide is known as the most frequent adverse effect.

It has been, in fact, reported that the cases where the standard chemotherapy cannot be carried out due to the adverse effects account for 70% of the cases where the drug administration is discontinued (about 23%, 52 cases) among the total of 228 inpatient cases surveyed (Nonpatent Literature 3).

Tuberculosis bacteria resistant to antitubercular agents or multidrug-resistant tuberculosis bacteria, for example, have been recently increasing, which has made the treatment of tuberculosis more difficult.

The World Health Organization (WHO) has reported that among those who have been infected with multidrug-resistant tuberculosis (MDR-TB) resistant to potent rifampicin and isoniazid, 450,000 people have newly developed and 170,000 people have died per year, and multidrug-resistant tuberculosis patients are currently estimated as 1,500,000 in the world. An extensively-drug-resistant tuberculosis (XDR-TB) which has been resistant to many drugs has been identified, which has become a threat to public health in the world (Nonpatent Literature 4).

One third of those who have been infected with HIV in the world have been suspected of co-infection with tuberculosis even though not progressing to active tuberculosis (Nonpatent Literature 5). Superinfection of HIV and tuberculosis is fatal, in which the one can accelerate the progression of the other, and vice versa, and tuberculosis can easily progress to active tuberculosis. In 2012, about 320,000 people died of tuberculosis associated with HIV, which means that about 25% of the deaths of HIV infected people were caused by tuberculosis. It has been also reported that patients superinfected with both HIV and tuberculosis can be associated with a 20 to 37 times higher risk of developing in tuberculosis than usual (Nonpatent Literature 6).

The American Thoracic Society and Centers for Disease Control and Prevention have recently reported the concept that carriage state itself of tuberculosis bacteria is a potential disease even though not developing to tuberculosis, and the usefulness of active treatment has been established for patients with a higher risk of developing to the disease.

In view of the current circumstances, a desired profile for antitubercular agents includes (1) those effective for multidrug-resistant tuberculosis bacteria, (2) those which enable a short-term chemotherapy, (3) those with less adverse effects, and (4) those effective for latent tuberculosis infection (LTBI).

*Mycobacterium avium* and *Mycobacterium intracellulare*, which are responsible bacteria for recently increasing MAC symptom (*Mycobacterium avium-intracellulare* complex symptom), as well as other non-tuberculous mycobacteria such as *Mycobacterium kansasii, Mycobacterium marinum, Mycobacterium simiae, Mycobacterium scrofulaceum, Mycobacterium szulgai, Mycobacterium xenopi, Mycobacterium malmoense, Mycobacterium haemophilum, Mycobacterium ulcerans, Mycobacterium shimoidei, Mycobacterium fortuitum, Mycobacterium chelonae, Mycobacterium smegmatis*, and *Mycobacterium aurum* have been known as bacteria having pathogenicity in human.

A typical chemotherapy of lung MAC symptom is polypharmacy based on three drugs of rifampicin, ethambutol, and clarithromycin, and streptomycin or kanamycin is, if needed, used in combination. Another treatment for non-tuberculous mycobacteria symptom currently includes combination use with an antitubercular agent such as rifampicin, isoniazid, ethambutol, streptomycin, kanamycin, a therapeutic agent for common bacterial infection such as a newquinolone agent, a macrolide antibacterial agent, an aminoglycoside antibacterial agent, and a tetracycline antibacterial agent.

It has been reported, however, that the treatment for non-tuberculous mycobacteria needs a longer-term medication than that in common bacterial infection, the treatment tends to become refractory, and some have resulted in death. To resolve the current situation, a development of more potent drugs has been desired.

For example, Patent Literature 1 discloses that 6-nitro-1, 2,3,4-tetrahydro[2,1-b]imidazopyrane compounds have a bactericidal activity against tuberculosis bacteria (H37Rv strain) and multidrug-resistant tuberculosis bacteria in vitro and a therapeutic effect in oral administration for a tuberculosis-infected animal model, and thus they are useful as an antitubercular agent.

Patent Literatures 2 and 3 disclose that 2,3-dihydroimidazo[2,1-b]oxazole compounds have a bactericidal activity against tuberculosis bacteria, multidrug-resistant tuberculosis bacteria, and atypical mycobacteria.

Patent Literature 4 discloses that nitroimidazooxazine and nitroimidazooxazole compounds can be used as a medicament against human tuberculosis bacteria (*Mycobacterium tuberculosis*).

Patent Literature 5 discloses that 6,7-dihydroimidazo[2,1-b][1,3]oxazine compounds have an excellent bactericidal activity against tuberculosis bacteria and multidrug-resistant tuberculosis bacteria.

The compounds disclosed in the above references, however, structurally differ from the compounds of the present invention.

CITATION LIST

Patent Literatures

[PTL 1] WO 97/01562 (JP-A-11-508270)
[PTL 2] JP-A-2004-149527
[PTL 3] JP-A-2005-320316
[PTL 4] WO 2011/014776
[PTL 5] WO 2012/141338

Non Patent Literatures

[NPL 1] A Clinician's Guide To Tuberculosis, Michael D. Iseman 2000 by Lippincott Williams & Wilkins, printed in the USA, ISBN 0-7817-1749-3
[NPL 2] Kekkaku 2nd edition, Fumiyuki Kuze, Takahide Izumi, Igaku-shoin 1992
[NPL 3] Kekkaku Vol. 74: 77-82, 1999
[NPL 4] Global tuberculosis report 2013
[NPL 5] The Internet Journal of Pulmonary Medicine 2008: Volume 10 Number 1
[NPL 6] The Global Plan To Stop TB 2011-2015

SUMMARY OF INVENTION

Problems to be Solved by the Invention

An object of the present invention is to provide compounds having a potent antibacterial activity against tuberculosis bacteria and multidrug-resistant tuberculosis bacteria. Another object of the present invention is to provide compounds having a potent antibacterial activity against non-tuberculous mycobacteria.

Means of Solving the Problems

The present inventors have achieved syntheses of novel piperidine compounds having a potent bactericidal activity against tuberculosis bacteria, multidrug-resistant tuberculosis bacteria, and non-tuberculous mycobacteria as a result of extensive studies to solve the problems. The present invention has been accomplished on the basis of the findings.

An embodiment of the present invention is a compound of Formula [I]:

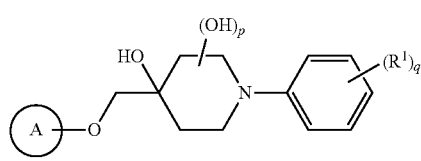

[I]

wherein Ring A is an optionally substituted hydrocarbon ring or optionally substituted heterocycle, provided that Ring A is not carbostyril or dihydrocarbostyril;

$R^1$ is halogen, —CN, —NO$_2$, —OH, —CHO, —COOH, —SH, —SO$_2$H, —SO$_3$H, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{2-6}$ alkenyl-O—, optionally substituted $C_{2-6}$ alkynyl-O—, optionally substituted $C_{1-6}$ alkyl-CO—, optionally substituted $C_{2-6}$ alkenyl-CO—, optionally substituted $C_{2-6}$ alkynyl-CO—, optionally substituted $C_{1-6}$ alkyl-COO—, optionally substituted $C_{1-6}$ alkoxy-CO—, optionally substituted $C_{1-6}$ alkyl-S—, optionally substituted $C_{1-6}$ alkyl-SO—, optionally substituted $C_{1-6}$ alkyl-SO$_2$—, optionally substituted $C_{3-6}$ cycloalkyl, optionally substituted $C_{3-6}$ cycloalkenyl, optionally substituted $C_{3-6}$ cycloalkoxy, optionally substituted $C_{3-6}$ cycloalkenyl-O—, optionally substituted $C_{3-6}$ cycloalkyl-CO—, optionally substituted $C_{3-6}$ cycloalkoxy-CO—, optionally substituted $C_{6-14}$ aryl, optionally substituted $C_{6-14}$ aryl-O—, optionally substituted $C_{6-14}$ aryl-CO—, optionally substituted $C_{6-14}$ aryl-O—CO—, optionally substituted $C_{7-17}$ aralkyl, optionally substituted $C_{7-17}$ aralkyl-O—, optionally substituted $C_{7-17}$ aralkyl-CO—, optionally substituted $C_{7-17}$ aralkyl-O—CO—, amino (wherein the amino group may be optionally substituted with the same or different at least one —CHO, optionally substituted $C_{1-6}$ alkyl, optionally substituted $C_{1-6}$ alkyl-CO—, optionally substituted $C_{1-6}$ alkoxy-CO—, or optionally substituted $C_{6-14}$ aryl-CO—), or —CONH$_2$ (wherein the amino group may be optionally substituted with the same or different at least one —CHO, optionally substituted $C_{1-6}$ alkyl, optionally substituted $C_{1-6}$ alkyl-CO—, optionally substituted $C_{1-6}$ alkoxy-CO—, or optionally substituted $C_{6-14}$ aryl-CO—);

p is an integer of 0 to 4; and q is an integer of 1 to 5;

provided that when q is 2 or more, then each of $R^1$ may be different from each other, or a salt thereof.

Effect of the Invention

Compound [I] in the present invention has specific activities in particular against mycobacteria (such as tuberculosis bacterial genus and non-tuberculous mycobacterial genus), and also has potent activities against multidrug-resistant tuberculosis bacteria. Compound [I] in the present invention is useful for diagnosis, prevention, and/or treatment of tuberculosis.

Compound [I] in the present invention shows not only the activities in vitro but also the activities in vivo in oral administration because the compound administered is favorably distributed in lung tissues which are the primary organ infected with the mycobacterial infectious disease.

Compound [I] in the present invention does not induce diarrhea as seen in known antibacterial agents with a wide spectrum for common bacteria such as gram-positive bacteria and gram-negative bacteria, and thereby may become a medicinal substance which allows for a long-term administration.

Compound [I] in the present invention is effective for intracellular parasitic bacteria such as human-origin tuberculosis bacteria which is parasitic in macrophage, and has a stronger bactericidal activity in a low concentration even in a bactericidal test than conventional antitubercular agents. It is thus expected that the relapse rate in tuberculosis is reduced, which eventually allows for a short-term chemotherapy.

DESCRIPTION OF EMBODIMENTS

The phrases and terms used herein are described in detail as below.

Examples of "alkyl" include straight or branched chain alkyl having 1 to 6 carbon atoms ($C_{1-6}$ alkyl), and specifically, include methyl, ethyl, propyl, isopropyl, butyl, isobutyl, sec-butyl, tert-butyl, pentyl, isopentyl, neopentyl, hexyl, isohexyl, and 3-methylpentyl.

Examples of "alkenyl" include straight or branched chain alkenyl having 2 to 6 carbon atoms and 1 to 3 double bonds ($C_{2-6}$ alkenyl), and specifically, include vinyl (ethenyl), 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of "alkynyl" include straight or branched chain alkynyl groups having 2 to 6 carbon atoms and 1 to 3 triple bonds, and specifically, include 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

Examples of "alkoxy" include straight or branched chain alkoxy having 1 to 6 carbon atoms ($C_{1-6}$ alkoxy), and specifically, include methoxy, ethoxy, propoxy, isopropoxy, butoxy, isobutoxy, sec-butoxy, tert-butoxy, pentyloxy, isopentyloxy, neopentyloxy, hexyloxy, isohexyloxy, and 3-methylpentyloxy.

Examples of "cycloalkyl" include cyclic alkyl having 3 to 6 carbon atoms ($C_{3-6}$ cycloalkyl), and specifically, include cyclopropyl, cyclobutyl, cyclopentyl, and cyclohexyl.

Examples of "cycloalkenyl" include cyclic alkenyl having 3 to 6 carbon atoms and 1 to 3 double bonds ($C_{3-6}$ cycloalkenyl), and specifically, include 2-cyclopentenyl, 3-cyclopentenyl, 2-cyclohexenyl, and 3-cyclohexenyl.

Examples of "cycloalkoxy" include cyclic alkoxy having 3 to 6 carbon atoms ($C_{3-6}$ cycloalkoxy), and specifically, include cyclopropyloxy, cyclobutyloxy, cyclopentyloxy, and cyclohexyloxy.

Examples of "aryl" include monocyclic, bicyclic, or tricyclic aromatic hydrocarbon having 6 to 14 carbon atoms ($C_{6-14}$ aryl), preferably $C_{6-10}$ aryl, and specifically, include phenyl, naphthyl, anthryl, and phenanthryl.

Examples of "aralkyl" include a straight or branched chain alkyl having 1 to 3 carbon atoms and being substituted with a monocyclic, bicyclic, or tricyclic aromatic hydrocarbon group having 6 to 14 carbon atoms ($C_{7-17}$ aralkyl), preferably $C_{7-12}$ aralkyl, and specifically, include benzyl, 1-phenylethyl, 2-phenylethyl, 1-naphthylmethyl, and 2-naphthylmethyl.

Examples of "amino" substituted with "alkyl" include amino mono- or di-substituted with the same or different $C_{1-6}$ alkyl, and specifically, include monoalkylamino such as methylamino, ethylamino, propylamino, isopropylamino, butylamino, isobutylamino, sec-butylamino, and tert-butylamino; and dialkylamino such as dimethylamino, diethylamino, dipropylamino, dibutylamino, diisobutylamino, di-sec-butylamino, di-tert-butylamino, and N-ethyl-N-methylamino.

Examples of "amino" substituted with "alkyl-CO—" include amino mono- or di-substituted with the same or different $C_{1-6}$ alkyl-CO—, and specifically, include monoalkylcarbonylamino such as acetylamino, propionylamino, butyrylamino, isobutyrylamino, pentanoylamino, tert-butylcarbonylamino, and hexanoylamino; and di-(alkylcarbonyl)amino such as diacetylamino, dipropionylamino, dibutyrylamino, diisobutyrylamino, dipentanoylamino, di-tert-butylcarbonylamino, and dihexanoylamino.

Examples of "amino" substituted with "alkoxy-CO—" include amino mono- or di-substituted with the same or different $C_{1-6}$ alkoxy-CO—, and specifically, include monoalkoxycarbonylamino such as methoxycarbonylamino, ethoxycarbonylamino, propoxycarbonylamino, butoxycarbonylamino, isobutyloxycarbonylamino, tert-butoxycarbonylamino, pentoxycarbonylamino, and hexoxycarbonylamino; and di-(alkoxycarbonyl)amino such as di-(methoxycarbonyl)amino, di-(ethoxycarbonyl)amino, di-(propoxycarbonyl)amino, di-(butoxycarbonyl)amino, di-(isobutyloxycarbonyl)amino, di-(tert-butoxycarbonyl)amino, di-(pentoxycarbonyl)amino, and di-(hexoxycarbonyl)amino.

Examples of "amino" substituted with "aryl-CO—" include amino mono- or di-substituted with the same or different $C_{6-14}$ aryl-CO—, and specifically, include monoarylcarbonylamino such as benzoylamino; and di-(arylcarbonyl)amino such as dibenzoylamino.

Examples of "amino" substituted with "aralkyl-CO—" include amino mono- or di-substituted with the same or different $C_{7-17}$ aralkyl-CO—, and specifically, include monoaralkylcarbonylamino such as benzylcarbonylamino and phenylethylcarbonylamino; and di-(aralkylcarbonyl)amino such as di-(benzylcarbonyl)amino and di-(phenylethylcarbonyl)amino.

Examples of "hydrocarbon ring" include a saturated or unsaturated monocyclic or polycyclic hydrocarbon ring, and for example, include a saturated or unsaturated 3- to 15-membered monocyclic, bicyclic, or tricyclic hydrocarbon ring. The "unsaturated" ring refers to an aromatic ring or a ring wherein bonds between ring member atoms of an aromatic ring are partially hydrogenated. A ring member atom of a hydrocarbon ring may be optionally substituted with oxo to form an oxide. The "hydrocarbon ring" specifically includes:

(a) saturated or unsaturated 3- to 8-membered, preferably 5- or 6-membered, monocyclic hydrocarbon ring; specifically, cyclopropane, cyclobutane, cyclopentane, cyclohexane, cycloheptane, cyclooctane, cyclobutene, cyclopentene, cyclohexene, cycloheptene, cyclooctene, and benzene; and (b) saturated or unsaturated 7- to 15-membered bicyclic or tricyclic hydrocarbon ring, preferably saturated or unsaturated 7- to 12-membered bicyclic hydrocarbon ring; specifically, indene, dihydroindene, naphthalene, dihydronaphthalene, tetrahydronaphthalene, anthracene, and phenanthrene.

Examples of "heterocycle" include a saturated or unsaturated monocyclic or polycyclic heterocycle comprising as a ring member atom 1 to 5 heteroatoms independently selected from the group consisting of nitrogen, oxygen, and sulfur, and for example, include a saturated or unsaturated 3- to 15-membered heteromonocycle, heterobicycle, or heterotricycle. The "unsaturated" ring refers to an aromatic ring or a ring wherein bonds between ring member atoms of an aromatic ring are partially hydrogenated. A "nitrogen-containing heterocycle" refers to heterocycle comprising at least one nitrogen as a ring member atom. A ring member atom of heterocycle may be optionally substituted with oxo to form an oxide or dioxide. The "heterocycle" specifically includes:

(a) saturated or unsaturated 3- to 8-membered, preferably 3- to 6-membered, more preferably 5- or 6-membered, heteromonocycle comprising 1 to 4 nitrogen atoms as a ring member atom; specifically, pyrrole, imidazole, pyrazole, pyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepane, and 1,4-diazepane;

(b) saturated or unsaturated 7- to 15-membered heterobicycle or heterotricycle comprising 1 to 5 nitrogen atoms as a ring member atom, preferably saturated or unsaturated 7- to 12-membered heterobicycle or heterotricycle comprising 1 to 3 nitrogen atoms as a ring member atom; specifically, indole, indoline (dihydroindole), isoindole, isoindoline (dihydroisoindole), benzimidazole, dihydrobenzimidazole, indazole, indazolin (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahydronaphthyridine, hexahydronaphthyridine, cinnoline, quinoxaline, dihydroquinoxaline, tetrahydroquinoxaline, quinazoline, dihydroquinazoline, tetrahydroquinazoline, pyrazolopyridine, tetrahydropyridoindole, benzazepine, tetrahydrobenzazepine, carbazole, phenanthridine, and dihydrophenanthridine;

(c) saturated or unsaturated 3- to 8-membered, preferably 5- or 6-membered, heteromonocycle comprising 1 or 2 oxygen atoms only as a ring member atom; specifically, furan, tetrahydropyrane, tetrahydrofuran, and dioxane;

(d) saturated or unsaturated 7- to 12-membered heterobicycle comprising 1 to 3 oxygen atoms only as a ring member atom; specifically, benzofuran, dihydrobenzofuran, chromane, benzodioxole, and benzodioxane;

(e) saturated or unsaturated 3- to 8-membered, preferably 5- or 6-membered, heteromonocycle comprising 1 sulfur atom only as a ring member atom; specifically, thiophene;

(f) saturated or unsaturated 7- to 12-membered bicyclic heterocycle comprising 1 to 3 sulfur atoms only as a ring member atom; specifically, benzothiophene;

(g) saturated or unsaturated 3- to 8-membered, preferably 5- or 6-membered, heteromonocycle comprising 1 or 2 oxygen atoms and 1 to 3 nitrogen atoms as a ring member atom; specifically, oxazole, isoxazole, oxadiazole, and morpholine;

(h) saturated or unsaturated 7- to 12-membered heterobicycle comprising 1 or 2 oxygen atoms and 1 to 3 nitrogen atoms as a ring member atom; specifically, benzoxazole, dihydrobenzoxazole, benzooxadiazole, benzisoxazole, benzoxazine, dihydrobenzoxazine, furopyridine, furopyrrole, benzoxazepine, and tetrahydrobenzoxazepine;

(i) saturated or unsaturated 3- to 8-membered, preferably 5- or 6-membered, heteromonocycle comprising 1 or 2 sulfur atoms and 1 to 3 nitrogen atoms as a ring member atom; specifically, thiazole, thiazoline (dihydrothiazole), thiadiazole, isothiazole, and thiazolidine;

(j) saturated or unsaturated 7- to 12-membered heterobicycle comprising 1 or 2 sulfur atoms and 1 to 3 nitrogen atoms as a ring member atom; specifically, benzothiazole, dihydrobenzothiazole, benzothiadiazole, thienopyridine, imidazothiazole, dihydroimidazothiazole, thienopyrazine, benzothiazine, dihydrobenzothiazine, benzothiazepine, and tetrahydrobenzothiazepine; and (k) saturated or unsaturated 7- to 12-membered heterobicycle comprising 1 or 2 oxygen atoms and 1 to 3 sulfur atoms as a ring member atom; specifically, benzoxathiin.

Examples of "halogen" include fluorine, chlorine, bromine, and iodine, and preferably, include fluorine, chlorine, and bromine. More preferable examples are fluorine or chlorine.

Each group defined herein may optionally bind to another group via a linker such as, for example, —O—, —CO—, —COO—, —S—, —SO—, —SO$_2$—, and —O—CO—.

Examples of a "substituent" in the term "optionally substituted α" wherein α refers to any groups described herein include at least one group independently selected from the group consisting of:
(A) halogen,
(B) —CN,
(C) —NO$_2$,
(D) =N—OH,
(E) —OH,
(F) —CHO,
(G) —COOH,
(H) —SO$_3$H,
(I) —SO$_2$H,
(J) —SH,
(K) =O,
(L) =S,
(M) alkyl optionally substituted with at least one group independently selected from the substituent groups (Ia) and (Ib),
(N) alkenyl optionally substituted with at least one group independently selected from the substituent groups (Ia) and (Ib),
(O) alkynyl optionally substituted with at least one group independently selected from the substituent groups (Ia) and (Ib),
(P) alkoxy optionally substituted with at least one group independently selected from the substituent groups (Ia) and (Ib),
(Q) alkenyl-O— optionally substituted with at least one group independently selected from the substituent groups (Ia) and (Ib),
(R) alkynyl-O— optionally substituted with at least one group independently selected from the substituent groups (Ia) and (Ib),
(S) alkyl-CO— optionally substituted with at least one group independently selected from the substituent groups (Ia) and (Ib),
(T) alkenyl-CO— optionally substituted with at least one group independently selected from the substituent groups (Ia) and (Ib),
(U) alkynyl-CO— optionally substituted with at least one group independently selected from the substituent groups (Ia) and (Ib),
(V) alkyl-COO— optionally substituted with at least one group independently selected from the substituent groups (Ia) and (Ib),
(W) alkoxy-CO— optionally substituted with at least one group independently selected from the substituent groups (Ia) and (Ib),
(X) alkyl-S— optionally substituted with at least one group independently selected from the substituent groups (Ia) and (Ib),
(Y) alkyl-SO— optionally substituted with at least one group independently selected from the substituent groups (Ia) and (Ib),
(Z) alkyl-SO$_2$— optionally substituted with at least one group independently selected from the substituent groups (Ia) and (Ib),
(AA) cycloalkyl optionally substituted with at least one group independently selected from the substituent groups (Ia), (Ib), (Ic), and =O,
(BB) cycloalkoxy optionally substituted with at least one group independently selected from the substituent groups (Ia), (Ib), (Ic), and =O, (CC) cycloalkenyl optionally substituted with at least one group independently selected from the substituent groups (Ia), (Ib), (Ic), and =O,
(DD) cycloalkenyl-O— optionally substituted with at least one group independently selected from the substituent groups (Ia), (Ib), (Ic), and =O,
(EE) cycloalkyl-CO— optionally substituted with at least one group independently selected from the substituent groups (Ia), (Ib), (Ic), and =O,
(FF) cycloalkoxy-CO— optionally substituted with at least one group independently selected from the substituent groups (Ia), (Ib), (Ic), and =O,
(GG) aryl optionally substituted with at least one group independently selected from the substituent groups (Ia), (Ib), and (Ic),
(HH) aryl-O— optionally substituted with at least one group independently selected from the substituent groups (Ia), (Ib), and (Ic),
(II) aryl-CO— optionally substituted with at least one group independently selected from the substituent groups (Ia), (Ib), and (Ic),
(JJ) aryl-O—CO— optionally substituted with at least one group independently selected from the substituent groups (Ia), (Ib), and (Ic),
(KK) aralkyl optionally substituted with at least one group independently selected from the substituent groups (Ia), (Ib), and (Ic),
(LL) aralkyl-O— optionally substituted with at least one group independently selected from the substituent groups (Ia), (Ib), and (Ic),
(MM) aralkyl-CO— optionally substituted with at least one group independently selected from the substituent groups (Ia), (Ib), and (Ic),
(NN) aralkyl-O—CO— optionally substituted with at least one group independently selected from the substituent groups (Ia), (Ib), and (Ic),
(OO) heterocyclyl group optionally substituted with at least one group independently selected from the substituent groups (Ia), (Ib), (Ic), and =O,
(PP) heterocyclyl-O— optionally substituted with at least one group independently selected from the substituent groups (Ia), (Ib), (Ic), and =O,
(QQ) heterocyclyl-CO— optionally substituted with at least one group independently selected from the substituent groups (Ia), (Ib), (Ic), and =O,
(RR) heterocyclyl-O—CO— optionally substituted with at least one group independently selected from the substituent groups (Ia), (Ib), (Ic), and =O,
(SS) amino optionally substituted with at least one group independently selected from the substituent groups (Ia) and (Ic), and
(TT) carbamoyl optionally substituted with at least one group independently selected from the substituent groups (Ia) and (Ic).

The number of substituents on the compounds of Formula [I] is not limited as long as it is chemically acceptable, and for example, includes 1 to 10, 1 to 8, 1 to 6, 1 to 4, and 1 to 3. When a is amino or carbamoyl, the number of substituents on a is 1 or 2. Substituents may bind to any atoms such as carbon atoms and heteroatoms as long as they are chemically acceptable.

The "substituent group (Ia)" is the group consisting of:
(a) alkyl-CO— that may optionally have at least one group independently selected from the substituent groups (IIa) and (IIb),
(b) alkenyl-CO— that may optionally have at least one group independently selected from the substituent groups (IIa) and (IIb),
(c) alkynyl-CO— that may optionally have at least one group independently selected from the substituent groups (IIa) and (IIb),
(d) alkoxy-CO— that may optionally have at least one group independently selected from the substituent groups (IIa) and (IIb),
(e) alkyl-S— that may optionally have at least one group independently selected from the substituent groups (IIa) and (IIb),
(f) alkyl-SO— that may optionally have at least one group independently selected from the substituent groups (IIa) and (IIb),
(g) alkyl-$SO_2$— that may optionally have at least one group independently selected from the substituent groups (IIa) and (IIb),
(h) cycloalkyl that may optionally have at least one group independently selected from the substituent groups (IIa), (IIb), (IIc), and =O,
(i) cycloalkoxy that may optionally have at least one group independently selected from the substituent groups (IIa), (IIb), (IIc), and =O,
(j) cycloalkenyl that may optionally have at least one group independently selected from the substituent groups (IIa), (IIb), (IIc), and =O,
(k) cycloalkyl-CO— that may optionally have at least one group independently selected from the substituent groups (IIa), (IIb), (IIc), and =O,
(l) cycloalkoxy-CO— that may optionally have at least one group independently selected from the substituent groups (IIa), (IIb), (IIc), and =O,
(m) aryl that may optionally have at least one group independently selected from the substituent groups (IIa), (IIb), and (IIc),
(n) aryl-CO— that may optionally have at least one group independently selected from the substituent groups (IIa), (IIb), and (IIc),
(o) aryl-O—CO— that may optionally have at least one group independently selected from the substituent groups (IIa), (IIb), and (IIc),
(p) aralkyl that may optionally have at least one group independently selected from the substituent groups (IIa), (IIb), and (IIc),
(q) aralkyl-CO— that may optionally have at least one group independently selected from the substituent groups (IIa), (IIb), and (IIc),
(r) aralkyl-O—CO— that may optionally have at least one group independently selected from the substituent groups (IIa), (IIb), and (IIc),
(s) heterocyclyl group that may optionally have at least one group independently selected from the substituent groups (IIa), (IIb), (IIc), and =O,
(t) heterocyclyl-CO— that may optionally have at least one group independently selected from the substituent groups (IIa), (IIb), (IIc), and =O,
(v) heterocyclyl-O—CO— that may optionally have at least one group independently selected from the substituent groups (IIa), (IIb), (IIc), and =O, and
(w) carbamoyl that may optionally have at least one group independently selected from the substituent groups (IIa) and (IIc).

The "substituent group (Ib)" is the group consisting of:
(a) halogen,
(b) —CN,
(c) —$NO_2$, (d) —OH,
(e) —CHO,
(f) —COOH,
(g) —SO$_3$H,
(h) —SH,
(i) alkoxy that may optionally have at least one group independently selected from the substituent groups (IIa) and (IIb),
(j) alkenyl-O— that may optionally have at least one group independently selected from the substituent groups (IIa) and (IIb),
(k) alkynyl-O— that may optionally have at least one group independently selected from the substituent groups (IIa) and (IIb),
(l) alkyl-COO— that may optionally have at least one group independently selected from the substituent groups (IIa) and (IIb),
(m) cycloalkenyl-O— that may optionally have at least one group independently selected from the substituent groups (IIa), (IIb), (IIc), and =O,
(n) aryl-O— that may optionally have at least one group independently selected from the substituent groups (IIa), (IIb), and (IIc),
(o) aralkyl-O— that may optionally have at least one group independently selected from the substituent groups (IIa), (IIb), and (IIc),
(p) heterocyclyl-O— that may optionally have at least one group independently selected from the substituent groups (IIa), (IIb), (IIc), and =O, and
(q) amino that may optionally have at least one group independently selected from the substituent groups (IIa) and (IIc).

The "substituent group (Ic)" is the group consisting of:
(a) alkyl that may optionally have at least one group independently selected from the substituent groups (IIa) and (IIb),
(b) alkenyl that may optionally have at least one group independently selected from the substituent groups (IIa) and (IIb), and
(c) alkynyl that may optionally have at least one group independently selected from the substituent groups (IIa) and (IIb).

The "substituent group (IIa)" is the group consisting of —CHO, alkyl-CO—, alkenyl-CO—, alkynyl-CO—, alkoxy-CO—, alkyl-SO$_2$—, cycloalkyl, cycloalkoxy, cycloalkenyl, cycloalkyl-CO—, cycloalkoxy-CO—, aryl, aryl-CO—, aryl-O—CO—, aralkyl, aralkyl-CO—, aralkyl-O—CO—, heterocycle, heterocyclyl-CO—, heterocyclyl-O—CO—, mono- or di-(alkyl-CO)-carbamoyl, and mono- or di-alkylcarbamoyl.

The "substituent group (IIb)" is the group consisting of halogen, —CN, —NO$_2$, —OH, —COOH, —SO$_3$H, —SH, —NH$_2$, alkoxy, alkenyl-O—, alkynyl-O—, alkyl-COO—, alkyl-S—, alkyl-SO—, cycloalkenyl-O—, aryl-O—, aralkyl-O—, heterocyclyl-O—, mono- or di-alkylamino, mono- or di-(alkyl-CO)-amino, mono- or di-alkoxycarbonylamino, mono- or di-arylcarbonylamino, and mono- or di-aralkylcarbonylamino.

The "substituent group (IIc)" is the group consisting of alkyl, alkenyl, and alkynyl.

Each of symbols and structures in the general formula [I] of the present invention includes the embodiments illustrated as follows.

In one embodiment, Ring A is an optionally substituted saturated or unsaturated monocyclic or polycyclic hydrocarbon ring or heterocycle.

In the present invention, Ring A is not carbostyril or dihydrocarbostyril. When Ring A is a monocyclic aromatic ring, its substituent is not optionally substituted C$_{6-10}$ aryl.

In another embodiment, Ring A is an optionally substituted 6-membered monocyclic hydrocarbon ring, optionally substituted 6-membered monocyclic heterocycle, optionally substituted 7- to 12-membered bicyclic hydrocarbon ring, or optionally substituted 7- to 12-membered bicyclic or tricyclic heterocycle, the heterocycle comprising as a ring member atom at least one, for example, 1 to 5, heteroatoms independently selected from the group consisting of nitrogen, oxygen, and sulfur.

In another embodiment, substituents on Ring A include at least one, for example, 1 to 9, preferably 1 to 6, more preferably 1 to 4, groups independently selected from the group consisting of:
(1) halogen,
(2) —CN,
(3) —NO$_2$,
(4) =N—OH,
(5) —OH,
(6) =O,
(7) =S,
(8) C$_{1-6}$ alkyl optionally substituted with at least one group independently selected from the group consisting of:
  (i) halogen,
  (ii) —OH,
  (iii) —COOR$^a$ wherein R$^a$ is hydrogen or C$_{1-6}$ alkyl,
  (iv) —C$_{6-10}$ aryl, and
  (v) —CONR$^b$R$^c$ wherein R$^b$ and R$^c$ are each independently hydrogen or C$_{1-6}$ alkyl,
(9) C$_{1-6}$ alkoxy optionally substituted with the same or different at least one halogen,
(10) —COR$^d$ wherein R$^d$ is —OH, C$_{1-6}$ alkyl, or C$_{1-6}$ alkoxy,
(11) C$_{1-6}$ alkyl-S—,
(12) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(13) —CONR$^b$R$^c$ wherein R$^b$ and R$^c$ are the same as defined above,
(14) —NR$^b$R$^c$ wherein R$^b$ and R$^c$ are the same as defined above,
(15) C$_{6-10}$ aryl optionally substituted with the same or different at least one halogen,
(16) C$_{6-10}$ aryl-O—,
(17) C$_{7-12}$ aralkyl-O—, and
(18) saturated 3- to 6-membered nitrogen-containing heteromonocycle optionally substituted with at least one =O.

In still another embodiment, the 6-membered monocyclic hydrocarbon ring, 6-membered heteromonocycle, 7- to 12-membered bicyclic hydrocarbon ring, or 7- to 12-membered bicyclic or tricyclic heterocycle in Ring A is benzene, pyridine, dihydroindene, naphthalene, tetrahydronaphthalene, indole, dihydroindole, dihydroisoindole, benzofuran, indazole, benzimidazole, dihydrobenzimidazole, benzoxazole, benzisoxazole, benzothiazole, dihydrobenzothiazole, quinoline, dihydroquinoline, tetrahydroquinoline, isoquinoline, dihydroisoquinoline, tetrahydroisoquinoline, tetrahydronaphthyridine, quinoxaline, dihydroquinoxaline, tetrahydroquinoxaline, benzoxathiin, dihydroquinazoline, tetrahydroquinazoline, dihydrobenzoxazine, benzothiazine, dihydrobenzothiazine, tetrahydrobenzazepine, tetrahydrobenzoxazepine, tetrahydrobenzothiazepine, carbazole, or dihydrophenanthridine.

In still another embodiment, Ring A has any one of the structures of Formulae (A-I) to (A-III):

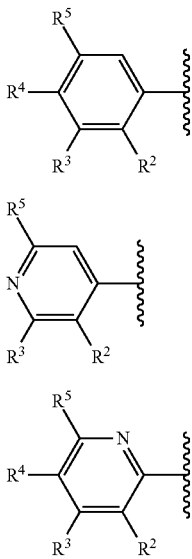

(A-I)

(A-II)

(A-III)

wherein $R^2$, $R^3$, $R^4$, and $R^5$ are each independently:
(a1) hydrogen,
(a2) halogen,
(a3) —CN,
(a4) —NO$_2$,
(a5) —OH,
(a6) C$_{1-6}$ alkyl optionally substituted with at least one group independently selected from the group consisting of:
  (i) halogen,
  (ii) —OH,
  (iii) —COOR$^a$ wherein R$^a$ is hydrogen or C$_{1-6}$ alkyl,
  (iv) —C$_{6-10}$ aryl, and
  (v) —CONR$^b$R$^c$ wherein R$^b$ and R$^c$ are each independently hydrogen or C$_{1-6}$ alkyl,
(a7) C$_{1-6}$ alkoxy optionally substituted with the same or different at least one halogen,
(a8) —COR$^d$ wherein R$^d$ is —OH, C$_{1-6}$ alkyl, or C$_{1-6}$ alkoxy,
(a9) C$_{1-6}$ alkyl-S—,
(a10) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(a11) —CONR$^b$R$^c$ wherein R$^b$ and R$^c$ are the same as defined above,
(a12) —NR$^b$R$^c$ wherein R$^b$ and R$^c$ are the same as defined above,
(a13) C$_{6-10}$ aryl-O—,
(a14) C$_{7-12}$ aralkyl-O—, or
(a15) saturated 3- to 6-membered nitrogen-containing heteromonocycle optionally substituted with at least one =O;

$R^2$ and $R^3$ may alternatively combine together with the carbon atoms to which they attach to form a monocyclic or fused ring, Ring B, and in that case, Ring B may be optionally substituted with R$^6$ and Ring A comprising Ring B forms a 7- to 12-membered bicyclic hydrocarbon ring or 7- to 12-membered bicyclic or tricyclic heterocycle, and/or $R^4$ and $R^5$ may alternatively combine together with the carbon atoms to which they attach to form a monocyclic or fused ring, Ring C, and in that case, Ring C may be optionally substituted with R$^6$ and Ring A comprising Ring C forms a 7- to 12-membered bicyclic hydrocarbon ring or 7- to 12-membered bicyclic or tricyclic heterocycle;

R$^6$ is, for example, 1 to 6, preferably 1 to 4, groups independently selected from the group consisting of:

(b1) halogen,
(b2) —CN,
(b3) —NO$_2$,
(b4) =N—OH,
(b5) —OH,
(b6) =O,
(b7) =S,
(b8) C$_{1-6}$ alkyl optionally substituted with at least one group independently selected from the group consisting of:
  (i) halogen,
  (ii) —OH,
  (iii) —COOR$^a$ wherein R$^a$ is hydrogen or C$_{1-6}$ alkyl,
  (iv) —C$_{6-10}$ aryl, and
  (v) —CONR$^b$R$^c$ wherein R$^b$ and R$^c$ are each independently hydrogen or C$_{1-6}$ alkyl,
(b9) C$_{1-6}$ alkoxy optionally substituted with the same or different at least one halogen,
(b10) —COR$^d$ wherein R$^d$ is —OH, C$_{1-6}$ alkyl, or C$_{1-6}$ alkoxy,
(b11) C$_{1-6}$ alkyl-S—,
(b12) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(b13) —CONR$^b$R$^c$ wherein R$^b$ and R$^c$ are the same as defined above,
(b14) —NR$^b$R$^c$ wherein R$^b$ and R$^c$ are the same as defined above, and
(b15) C$_{6-10}$ aryl optionally substituted with the same or different at least one halogen; and
a wavy line is a binding point.

The monocyclic or fused ring, Ring B, which R$^2$ and R$^3$ combine together with the carbon atoms to which they attach to form includes any rings so that Ring A comprising Ring B forms an optionally substituted 7- to 12-membered bicyclic hydrocarbon ring or optionally substituted 7- to 12-membered bicyclic or tricyclic heterocycle. Ring B specifically includes 5- or 6-membered monocyclic hydrocarbon ring, 5- to 7-membered monocyclic heterocycle, or 7- to 12-membered bicyclic heterocycle, the heterocycle comprising as a ring member atom 1 to 5, preferably 1 or 2, heteroatoms independently selected from the group consisting of nitrogen, oxygen, and sulfur.

The monocyclic or fused ring, Ring C, which R$^4$ and R$^5$ combine together with the carbon atoms to which they attach to form includes any rings so that Ring A comprising Ring C forms an optionally substituted 7- to 12-membered bicyclic hydrocarbon ring or optionally substituted 7- to 12-membered bicyclic or tricyclic heterocycle. Ring C specifically includes 5- or 6-membered monocyclic hydrocarbon ring, 5- to 7-membered monocyclic heterocycle, or 7- to 12-membered bicyclic heterocycle, the heterocycle comprising as a ring member atom 1 to 5, preferably 1 or 2, heteroatoms independently selected from the group consisting of nitrogen, oxygen, and sulfur.

In still another embodiment, $R^2$, $R^3$, $R^4$, and $R^5$ are each independently
(a1) hydrogen,
(a2) halogen,
(a3) C$_{1-6}$ alkyl optionally substituted with at least one group independently selected from the group consisting of:
  (i) halogen,
  (ii) —OH,
  (iii) —COOR$^a$ wherein R$^a$ is hydrogen or C$_{1-6}$ alkyl, and
  (iv) —CONR$^b$R$^c$ wherein R$^b$ and R$^c$ are each independently hydrogen or C$_{1-6}$ alkyl,
(a4) —COOR$^f$ wherein R$^f$ is hydrogen or C$_{1-6}$ alkyl,
(a5) —NHCOR$^e$ wherein R$^e$ is hydrogen, C$_{1-6}$ alkyl, C$_{1-6}$ alkoxy, C$_{6-10}$ aryl, or C$_{7-12}$ aralkyl, (a6) —CONR$^b$R$^c$ wherein R$^b$ and R$^c$ are the same as defined above,
(a7) —NR$^b$R$^c$ wherein R$^b$ and R$^c$ are the same as defined above, or
(a8) saturated 3- to 6-membered nitrogen-containing hetero-monocycle optionally substituted with at least one =O;

R$^2$ and R$^3$ may alternatively combine together with the carbon atoms to which they attach to form a monocyclic or fused ring, Ring B, and in that case, Ring B may be optionally substituted with R$^6$ and Ring A comprising Ring B forms a 7- to 12-membered bicyclic hydrocarbon ring or 7- to 12-membered bicyclic or tricyclic heterocycle, and/or R$^4$ and R$^5$ may alternatively combine together with the carbon atoms to which they attach to form a monocyclic or fused ring, Ring C, and in that case, Ring C may be optionally substituted with R$^6$ and Ring A comprising Ring C forms a 7- to 12-membered bicyclic hydrocarbon ring or 7- to 12-membered bicyclic or tricyclic heterocycle.

In still another embodiment, R$^6$ is, for example, 1 to 6, preferably 1 to 4, groups independently selected from the group consisting of:
(b1) halogen,
(b2) =N—OH,
(b3) —OH,
(b4) =O,
(b5) =S,
(b6) C$_{1-6}$ alkyl optionally substituted with the same or different at least one halogen or C$_{6-10}$ aryl,
(b7) C$_{1-6}$ alkoxy,
(b8) —COR$^d$ wherein R$^d$ is —OH, C$_{1-6}$ alkyl, or C$_{1-6}$ alkoxy,
(b9) —NHCOR$^e$ wherein R$^e$ is the same as defined above,
(b10) —NR$^b$R$^c$ wherein R$^b$ and R$^c$ are the same as defined above, and
(b11) C$_{6-10}$ aryl optionally substituted with the same or different at least one halogen.

In still another embodiment, Ring A is:
(1) a benzene ring optionally substituted with 1 to 3 groups independently selected from the group consisting of:
 (i) halogen,
 (ii) C$_{1-6}$ alkyl optionally substituted with at least one group independently selected from the group consisting of halogen, —OH, —COOH, —CONH$_2$, and C$_{1-6}$ alkoxy-CO—,
 (iii) —COOR$^f$ wherein R$^f$ is hydrogen or C$_{1-6}$ alkyl,
 (iv) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
 (v) —CONR$^b$R$^c$ wherein R$^b$ and R$^c$ are each independently hydrogen or C$_{1-6}$ alkyl,
 (vi) —NR$^b$R$^c$ wherein R$^b$ and R$^c$ are the same as defined above, and
 (vii) saturated 3- to 6-membered nitrogen-containing heteromonocycle optionally substituted with at least one =O, or
(2) a dihydroindene, naphthalene, tetrahydronaphthalene, indole, dihydroindole, dihydroisoindole, benzofuran, indazole, benzimidazole, dihydrobenzimidazole, benzoxazole, benzisoxazole, benzothiazole, dihydrobenzothiazole, quinoline, dihydroquinoline, tetrahydroquinoline, isoquinoline, dihydroisoquinoline, tetrahydroisoquinoline, tetrahydronaphthyridine, quinoxaline, dihydroquinoxaline, tetrahydroquinoxaline, benzoxathiin, dihydroquinazoline, tetrahydroquinazoline, dihydrobenzoxazine, benzothiazine, dihydrobenzothiazine, tetrahydrobenzazepine, tetrahydrobenzoxazepine, tetrahydrobenzothiazepine, carbazole, or dihydrophenanthridine ring, the ring being optionally substituted with 1 to 4 groups independently selected from the group consisting of:
 (i) halogen,
 (ii) =N—OH,
 (iii) —OH,
 (iv) =O,
 (v) =S,
 (vi) C$_{1-6}$ alkyl optionally substituted with the same or different at least one C$_{6-10}$ aryl,
 (vii) C$_{1-6}$ alkoxy,
 (viii) —COR$^d$ wherein R$^d$ is —OH, C$_{1-6}$ alkyl, or C$_{1-6}$ alkoxy,
 (ix) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
 (x) —NR$^b$R$^c$ wherein R$^b$ and R$^c$ are each independently hydrogen or C$_{1-6}$ alkyl, and
 (xi) C$_{6-10}$ aryl optionally substituted with the same or different at least one halogen.

In still another embodiment, Ring A has any one of the following structures:

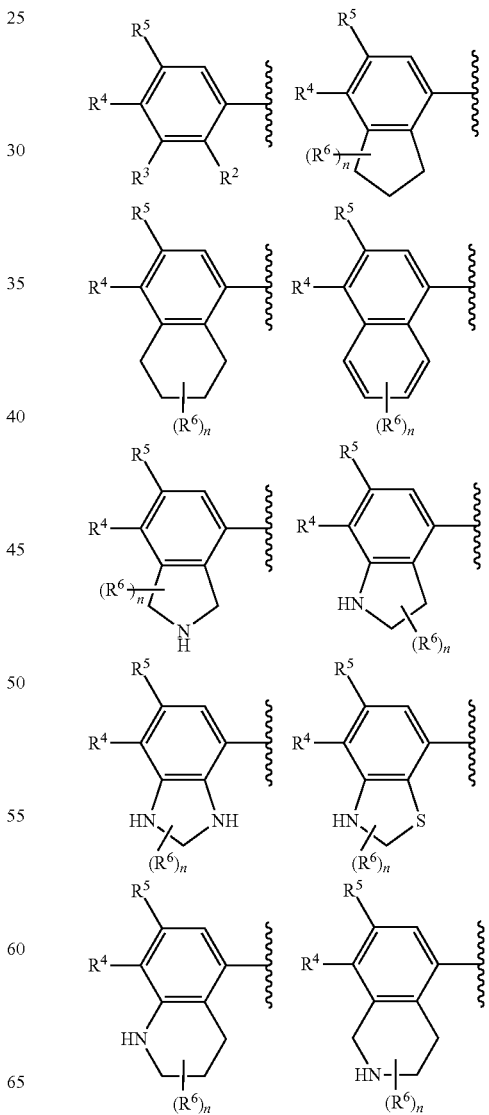

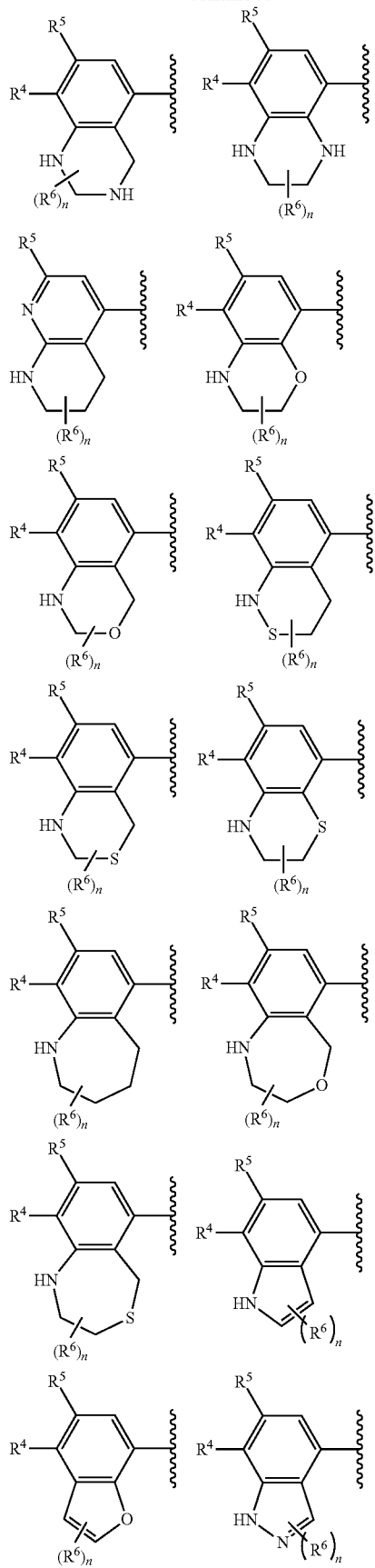
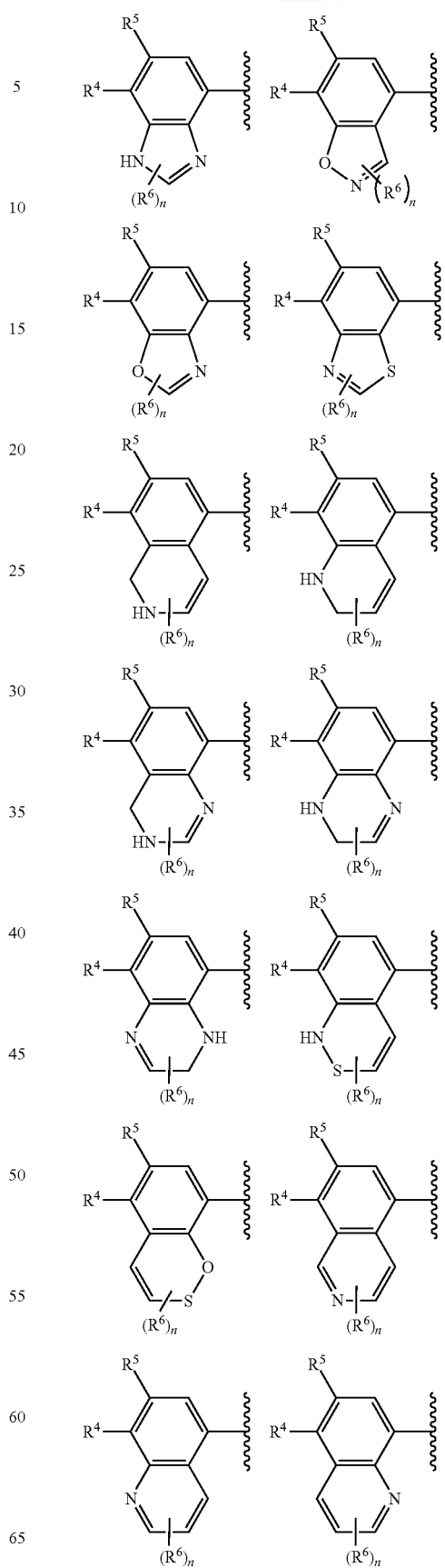

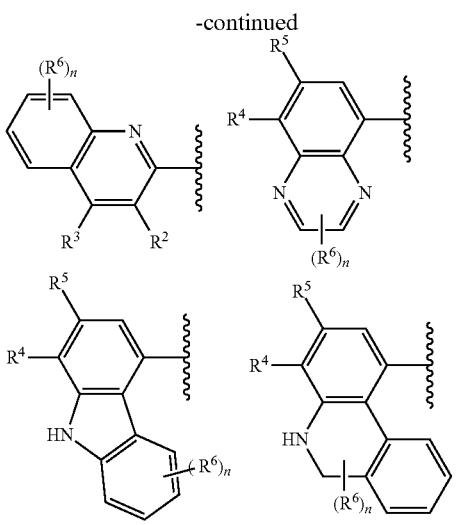

wherein $R^2$, $R^3$, $R^4$, $R^5$, and $R^6$ are the same as defined herein; and n is an integer of 0 to 6, preferably 0 to 4;

provided that when n is 2 or more, each of $R^6$ may be different with each other; and when $R^6$ is =N—OH, =O, or =S, $R^6$ binds to a corresponding ring via its double bond.

In still another embodiment, Ring A is:
(1) a benzene ring optionally substituted with 1 to 3 groups independently selected from the group consisting of:
  (i) halogen,
  (ii) $C_{1-6}$ alkyl optionally substituted with at least one group independently selected from the group consisting of halogen, —OH, —COOH, —CONH$_2$, and $C_{1-6}$ alkoxy-CO—,
  (iii) —COOR$^f$ wherein R$^f$ is hydrogen or $C_{1-6}$ alkyl,
  (iv) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
  (v) —CONR$^b$R$^c$ wherein R$^b$ and R$^c$ are each independently hydrogen or $C_{1-6}$ alkyl,
  (vi) —NR$^b$R$^c$ wherein R$^b$ and R$^c$ are the same as defined above, and
  (vii) saturated 3- to 6-membered nitrogen-containing heteromonocycle optionally substituted with at least one =O,
(2) indole optionally substituted with 1 to 3 groups independently selected from the group consisting of halogen and $C_{1-6}$ alkoxy-CO—,
(3) dihydroindole optionally substituted with 1 to 3 groups independently selected from the group consisting of halogen and =O,
(4) dihydroisoindole optionally substituted with 1 to 3 groups independently selected from the group consisting of halogen, $C_{1-6}$ alkyl, and =O,
(5) dihydroindene optionally substituted with 1 to 3 groups independently selected from the group consisting of halogen, —OH, =N—OH, and =O,
(6) benzofuran optionally substituted with the same or different at least one halogen,
(7) indazole optionally substituted with the same or different at least one halogen,
(8) benzimidazole optionally substituted with phenyl optionally substituted with the same or different at least one halogen,
(9) dihydrobenzimidazole optionally substituted with 1 to 3 groups independently selected from the group consisting of $C_{1-6}$ alkyl and =O,
(10) benzoxazole optionally substituted with the same or different at least one $C_{1-6}$ alkyl,
(11) benzisoxazole optionally substituted with the same or different at least one $C_{1-6}$ alkyl,
(12) benzothiazole optionally substituted with 1 to 3 groups independently selected from the group consisting of halogen, —NH$_2$, and mono-($C_{1-6}$ alkyl)-amino,
(13) dihydrobenzothiazole optionally substituted with 1 to 3 groups independently selected from the group consisting of halogen and =O,
(14) naphthalene optionally substituted with the same or different at least one —NHCO—$C_{1-6}$ alkyl,
(15) tetrahydronaphthalene optionally substituted with 1 to 3 groups independently selected from the group consisting of —OH and =O,
(16) quinoline optionally substituted with 1 to 3 groups independently selected from the group consisting of halogen and $C_{1-6}$ alkoxy,
(17) dihydroquinoline optionally substituted with 1 to 3 groups independently selected from the group consisting of halogen and =S,
(18) tetrahydroquinoline optionally substituted with 1 to 3 groups independently selected from the group consisting of halogen and $C_{1-6}$ alkyl-CO—,
(19) isoquinoline,
(20) dihydroisoquinoline optionally substituted with at least one =O,
(21) tetrahydroisoquinoline optionally substituted with at least one =O,
(22) tetrahydronaphthyridine optionally substituted with at least one =O,
(23) quinoxaline optionally substituted with the same or different at least one $C_{1-6}$ alkoxy,
(24) dihydroquinoxaline optionally substituted with 1 to 4 groups independently selected from the group consisting of $C_{1-6}$ alkyl and =O,
(25) tetrahydroquinoxaline optionally substituted with 1 to 4 groups independently selected from the group consisting of halogen, $C_{1-6}$ alkyl, and =O,
(26) benzoxathiin optionally substituted with at least one =O,
(27) dihydroquinazoline optionally substituted with at least one =O,
(28) tetrahydroquinazoline optionally substituted with 1 to 3 groups independently selected from the group consisting of halogen, $C_{1-6}$ alkyl, and =O,
(29) dihydrobenzoxazine optionally substituted with 1 to 3 groups independently selected from the group consisting of halogen and =O,
(30) benzothiazine optionally substituted with 1 to 3 groups independently selected from the group consisting of =O and benzyl,
(31) dihydrobenzothiazine optionally substituted with at least one =O,
(32) tetrahydrobenzazepine optionally substituted with 1 to 3 groups independently selected from the group consisting of halogen and =O,
(33) tetrahydrobenzoxazepine optionally substituted with at least one =O,
(34) tetrahydrobenzothiazepine optionally substituted with at least one =O,
(35) carbazole, or
(36) dihydrophenanthridine optionally substituted with at least one =O.

In still another embodiment, Ring A is:
(1) a benzene ring optionally substituted with 1 to 3 groups independently selected from the group consisting of fluoro, chloro, methyl, —CH$_2$OH, —CH$_2$CH$_2$OH, —CH$_2$CH$_2$CH$_2$OH, —CH$_2$COOH, —CH$_2$CH$_2$COOH, —CH$_2$COOCH$_2$CH$_3$, —CH$_2$CH$_2$COOCH$_2$CH$_3$, —CH$_2$CONH$_2$, —CH$_2$CH$_2$CONH$_2$, —COOH, —NH$_2$, —COOCH$_3$, —CONHCH$_3$, —NHCHO, —NHCOCH$_3$, —NHCOCH$_2$CH$_3$, —NHCO(CH$_2$)$_2$CH$_3$, —NHCOOCH$_3$, —NHCOPh, —NHCOCH$_2$Ph, —NHCO(CH$_2$)$_2$Ph, and oxoimidazolidinyl, (2) indole optionally substituted with 1 or 2 groups independently selected from the group consisting of fluoro, chloro, and —COOCH$_3$, (3) dihydroindole optionally substituted with 1 or 2 groups independently selected from the group consisting of fluoro, chloro, and =O, (4) dihydroisoindole optionally substituted with 1 or 2 groups independently selected from the group consisting of chloro, tert-butyl, and =O, (5) dihydroindene optionally substituted with 1 or 2 groups independently selected from the group consisting of chloro, —OH, =N—OH, and =O, (6) benzofuran optionally substituted with one bromo, (7) indazole optionally substituted with one chloro, (8) benzimidazole optionally substituted with one fluorophenyl, (9) dihydrobenzimidazole optionally substituted with 1 or 2 groups independently selected from the group consisting of methyl and =O,

(10) benzoxazole optionally substituted with one methyl,

(11) benzisoxazole optionally substituted with one methyl,

(12) benzothiazole optionally substituted with 1 or 2 groups independently selected from the group consisting of fluoro, chloro, —NH$_2$, and methylamino,

(13) dihydrobenzothiazole optionally substituted with 1 or 2 groups independently selected from the group consisting of fluoro, chloro, and =O,

(14) naphthalene optionally substituted with one —NHCOCH$_3$,

(15) tetrahydronaphthalene optionally substituted with one —OH or one =O,

(16) quinoline optionally substituted with 1 or 2 groups independently selected from the group consisting of fluoro, chloro, and methoxy,

(17) dihydroquinoline optionally substituted with 1 or 2 groups independently selected from the group consisting of chloro and =S,

(18) tetrahydroquinoline optionally substituted with one fluoro or one —COCH$_3$,

(19) isoquinoline,

(20) dihydroisoquinoline optionally substituted with one =O,

(21) tetrahydroisoquinoline optionally substituted with one =O,

(22) tetrahydronaphthyridine optionally substituted with one =O,

(23) quinoxaline optionally substituted with one methoxy,

(24) dihydroquinoxaline optionally substituted with 1 or 2 groups independently selected from the group consisting of methyl and =O,

(25) tetrahydroquinoxaline optionally substituted with 1 to 4 groups independently selected from the group consisting of fluoro, methyl, and =O,

(26) benzoxathiin optionally substituted with 1 or 2 =O,

(27) dihydroquinazoline optionally substituted with one =O,

(28) tetrahydroquinazoline optionally substituted with 1 or 2 groups independently selected from the group consisting of methyl, fluoro, and =O,

(29) dihydrobenzoxazine optionally substituted with 1 or 2 groups independently selected from the group consisting of chloro and =O,

(30) benzothiazine optionally substituted with 1 to 3 groups independently selected from the group consisting of benzyl and =O,

(31) dihydrobenzothiazine optionally substituted with 1 or 2 =O,

(32) tetrahydrobenzazepine optionally substituted with 1 or 2 groups independently selected from the group consisting of chloro and =O,

(33) tetrahydrobenzoxazepine optionally substituted with one =O,

(34) tetrahydrobenzothiazepine optionally substituted with 1 to 3 =O,

(35) carbazole, or

(36) dihydrophenanthridine optionally substituted with one =O.

In still another embodiment, Ring A is:

(1) a benzene ring optionally substituted with 1 to 3 groups independently selected from the group consisting of fluoro, chloro, methyl, —CH$_2$OH, —CH$_2$CONH$_2$, —COOCH$_3$, —CONHCH$_3$, —NHCHO, and —NHCOCH$_3$, (2) indole optionally substituted with 1 or 2 chloro, (3) dihydroindole optionally substituted with 1 or 2 groups independently selected from the group consisting of fluoro, chloro, and =O, (4) dihydroisoindole optionally substituted with 1 or 2 groups independently selected from the group consisting of tert-butyl, and =O, (5) dihydroindene optionally substituted with 1 or 2 groups independently selected from the group consisting of chloro, —OH, and =O, (6) benzofuran optionally substituted with one bromo, (7) indazole optionally substituted with one chloro, (8) benzimidazole, (9) dihydrobenzimidazole optionally substituted with 1 or 2 groups independently selected from the group consisting of methyl and =O,

(10) benzoxazole optionally substituted with one methyl,

(11) benzisoxazole optionally substituted with one methyl,

(12) benzothiazole optionally substituted with 1 or 2 groups independently selected from the group consisting of fluoro, chloro, and —NH$_2$,

(13) dihydrobenzothiazole optionally substituted with 1 or 2 groups independently selected from the group consisting of fluoro, chloro, and =O,

(14) quinoline optionally substituted with 1 or 2 chloro,

(15) dihydroquinoline optionally substituted with 1 or 2 groups independently selected from the group consisting of chloro and =S,

(16) tetrahydroquinoline optionally substituted with one fluoro,

(17) isoquinoline,

(18) tetrahydronaphthyridine optionally substituted with one =O,

(19) dihydroquinoxaline optionally substituted with 1 or 2 groups independently selected from the group consisting of methyl and =O,

(20) tetrahydroquinoxaline optionally substituted with 1 to 4 groups independently selected from the group consisting of fluoro, methyl, and =O,

(21) tetrahydroquinazoline optionally substituted with 1 or 2 groups independently selected from the group consisting of methyl, fluoro, and =O,

(22) dihydrobenzoxazine optionally substituted with 1 or 2 groups independently selected from the group consisting of chloro and =O,
(23) tetrahydrobenzazepine optionally substituted with 1 or 2 groups independently selected from the group consisting of chloro and =O,
(24) tetrahydrobenzoxazepine optionally substituted with one =O, or
(25) tetrahydrobenzothiazepine optionally substituted with one =O.

In still another embodiment, Ring A has a structure of Formula (A-I).

In one embodiment, n is an integer of 0 to 6. In another embodiment, n is an integer of 0 to 4.

In one embodiment, $R^1$ is halogen, —CN, —NO$_2$, —OH, —CHO, —COOH, —SH, —SO$_2$H, —SO$_3$H, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{2-6}$ alkenyl-O—, optionally substituted $C_{2-6}$ alkynyl-O—, optionally substituted $C_{1-6}$ alkyl-CO—, optionally substituted $C_{2-6}$ alkenyl-CO—, optionally substituted $C_{2-6}$ alkynyl-CO—, optionally substituted $C_{1-6}$ alkyl-COO—, optionally substituted $C_{1-6}$ alkoxy-CO—, optionally substituted $C_{1-6}$ alkyl-S—, optionally substituted $C_{1-6}$ alkyl-SO—, optionally substituted $C_{1-6}$ alkyl-SO$_2$—, optionally substituted $C_{3-6}$ cycloalkyl, optionally substituted $C_{3-6}$ cycloalkenyl, optionally substituted $C_{3-6}$ cycloalkoxy, optionally substituted $C_{3-6}$ cycloalkenyl-O—, optionally substituted $C_{3-6}$ cycloalkyl-CO—, optionally substituted $C_{3-6}$ cycloalkoxy-CO—, optionally substituted $C_{6-14}$ aryl, optionally substituted $C_{6-14}$ aryl-O—, optionally substituted $C_{6-14}$ aryl-CO—, optionally substituted $C_{6-14}$ aryl-O—CO—, optionally substituted $C_{7-17}$ aralkyl, optionally substituted $C_{7-17}$ aralkyl-O—, optionally substituted $C_{7-17}$ aralkyl-CO—, optionally substituted $C_{7-17}$ aralkyl-O—CO—, amino (wherein the amino group may be optionally substituted with the same or different at least one —CHO, optionally substituted $C_{1-6}$ alkyl, optionally substituted $C_{1-6}$ alkyl-CO—, optionally substituted $C_{1-6}$ alkoxy-CO—, or optionally substituted $C_{6-14}$ aryl-CO—), or —CONH$_2$ (wherein the amino group may be optionally substituted with the same or different at least one —CHO, optionally substituted $C_{1-6}$ alkyl, optionally substituted $C_{1-6}$ alkyl-CO—, optionally substituted $C_{1-6}$ alkoxy-CO—, or optionally substituted $C_{6-14}$ aryl-CO—).

In another embodiment, $R^1$ is the same or different
(1) halogen,
(2) —CN,
(3) —NO$_2$,
(4) —OH,
(5) $C_{1-6}$ alkyl optionally substituted with at least one group independently selected from the group consisting of:
  (i) halogen,
  (ii) —OH,
  (iii) $C_{1-6}$ alkoxy, and
  (iv) $C_{6-10}$ aryl-O— optionally substituted with the same or different at least one halogen,
(6) $C_{1-6}$ alkoxy optionally substituted with at least one group independently selected from the group consisting of:
  (i) halogen,
  (ii) $C_{1-6}$ alkoxy optionally substituted with the same or different at least one $C_{1-6}$ alkoxy,
  (iii) $C_{6-10}$ aryl-O— optionally substituted with the same or different at least one halogen,
  (iv) heterocycle optionally substituted with the same or different at least one $C_{1-6}$ alkyl optionally substituted with the same or different at least one halogen, and
  (v) amino optionally substituted with the same or different 1 or 2 $C_{1-6}$ alkyl,
(7) $C_{1-6}$ alkoxy-CO—,
(8) $C_{1-6}$ alkyl-S—,
(9) $C_{6-10}$ aryl optionally substituted with the same or different at least one halogen,
(10) $C_{6-10}$ aryl-O—, or
(11) $C_{7-15}$ aralkyl-O— optionally substituted with at least one group independently selected from the group consisting of:
  (i) halogen,
  (ii) $C_{1-6}$ alkyl optionally substituted with the same or different at least one halogen, and
  (iii) $C_{1-6}$ alkoxy optionally substituted with the same or different at least one halogen.

In still another embodiment, $R^1$ is the same or different
(1) halogen,
(2) $C_{1-6}$ alkyl optionally substituted with the same or different at least one halogen, or
(3) $C_{1-6}$ alkoxy optionally substituted with the same or different at least one halogen.

In still another embodiment, $R^1$ is the same or different halogen.

In still another embodiment, $R^1$ is the same or different fluoro, chloro, or bromo.

In one embodiment, p is an integer of 0 to 4. In another embodiment, p is an integer of 0 or 1.

In one embodiment, q is an integer of 1 to 5. In another embodiment, q is an integer of 1 to 3. In still another embodiment, q is an integer of 2 or 3.

In one embodiment, q is an integer of 1 to 5. In another embodiment, q is an integer of 1 to 3. In still another embodiment, q is an integer of 2 or 3.

In one embodiment of the present invention, a pharmaceutical composition comprising a compound of Formula [I] or a salt thereof and a pharmaceutically acceptable carrier is provided.

In another embodiment, a medicinal agent for diagnosing, preventing, and/or treating tuberculosis, comprising a compound of Formula [I] or a salt thereof and a pharmaceutically acceptable carrier is provided.

In still another embodiment, a compound of Formula [I] or a salt thereof for use in diagnosing, preventing, and/or treating tuberculosis is provided.

In still another embodiment, use of a compound of Formula [I] or a salt thereof in the manufacture of a pharmaceutical for diagnosing, preventing, and/or treating tuberculosis is provided.

In still another embodiment, a method of diagnosing, preventing, and/or treating tuberculosis, comprising administering an effective amount of a compound of Formula [I] or a salt thereof to a subject is provided.

The present invention includes the embodiments illustrated as follows.

[1] A compound of Formula [I]:

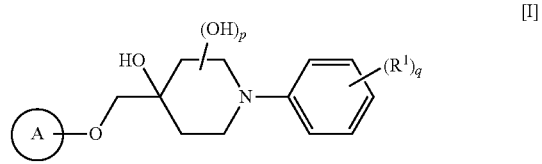

wherein Ring A is an optionally substituted hydrocarbon ring or optionally substituted heterocycle, provided that Ring A is not carbostyril or dihydrocarbostyril;
R$^1$ is halogen, —CN, —NO$_2$, —OH, —CHO, —COOH, —SH, —SO$_2$H, —SO$_3$H, optionally substituted C$_{1-6}$ alkyl, optionally substituted C$_{2-6}$ alkenyl, optionally substituted C$_{2-6}$ alkynyl, optionally substituted C$_{1-6}$ alkoxy, optionally substituted C$_{2-6}$ alkenyl-O—, optionally substituted C$_{2-6}$ alkynyl-O—, optionally substituted C$_{1-6}$ alkyl-CO—, optionally substituted C$_{2-6}$ alkenyl-CO—, optionally substituted C$_{2-6}$ alkynyl-CO—, optionally substituted C$_{1-6}$ alkyl-COO—, optionally substituted C$_{1-6}$ alkoxy-CO—, optionally substituted C$_{1-6}$ alkyl-S—, optionally substituted C$_{1-6}$ alkyl-SO—, optionally substituted C$_{1-6}$ alkyl-SO$_2$—, optionally substituted C$_{3-6}$ cycloalkyl, optionally substituted C$_{3-6}$ cycloalkenyl, optionally substituted C$_{3-6}$ cycloalkoxy, optionally substituted C$_{3-6}$ cycloalkenyl-O—, optionally substituted C$_{3-6}$ cycloalkyl-CO—, optionally substituted C$_{3-6}$ cycloalkoxy-CO—, optionally substituted C$_{6-14}$ aryl, optionally substituted C$_{6-14}$ aryl-O—, optionally substituted C$_{6-14}$ aryl-CO—, optionally substituted C$_{6-14}$ aryl-O—CO—, optionally substituted C$_{7-17}$ aralkyl, optionally substituted C$_{7-17}$ aralkyl-O—, optionally substituted C$_{7-17}$ aralkyl-CO—, optionally substituted C$_{7-17}$ aralkyl-O—CO—, amino (wherein the amino group may be optionally substituted with the same or different at least one group of —CHO, optionally substituted C$_{1-6}$ alkyl, optionally substituted C$_{1-6}$ alkyl-CO—, optionally substituted C$_{1-6}$ alkoxy-CO—, or optionally substituted C$_{6-14}$ aryl-CO—), or —CONH$_2$ (wherein the amino group may be optionally substituted with the same or different at least one group of —CHO, optionally substituted C$_{1-6}$ alkyl, optionally substituted C$_{1-6}$ alkyl-CO—, optionally substituted C$_{1-6}$ alkoxy-CO—, or optionally substituted C$_{6-14}$ aryl-CO—);
  p is an integer of 0 to 4; and
  q is an integer of 1 to 5;
  provided that when q is 2 or more, then each of R$^1$ may be different from each other, or a salt thereof.
[2] The compound according to [1], wherein Ring A is an optionally substituted 6-membered monocyclic hydrocarbon ring, optionally substituted 6-membered monocyclic heterocycle, optionally substituted 7- to 12-membered bicyclic hydrocarbon ring, or optionally substituted 7- to 12-membered bicyclic or tricyclic heterocycle, the heterocycle group comprising as a ring member atom at least one, for example, 1 to 5, heteroatoms independently selected from the group consisting of nitrogen, oxygen, and sulfur;
  a substituent of Ring A is at least one, for example, 1 to 9, preferably 1 to 6, more preferably 1 to 4, groups independently selected from the group consisting of:
(1) halogen,
(2) —CN,
(3) —NO$_2$,
(4) =N—OH,
(5) —OH,
(6) =O,
(7) =S,
(8) C$_{1-6}$ alkyl optionally substituted with at least one group independently selected from the group consisting of:
  (i) halogen,
  (ii) —OH,
  (iii) —COOR$^a$ wherein R$^a$ is hydrogen or C$_{1-6}$ alkyl,
  (iv) —C$_{6-10}$ aryl, and
  (v) —CONR$^b$R$^c$ wherein R$^b$ and R$^c$ are each independently hydrogen or C$_{1-6}$ alkyl,
(9) C$_{1-6}$ alkoxy optionally substituted with the same or different at least one halogen,
(10) —COR$^d$ wherein R$^d$ is —OH, C$_{1-6}$ alkyl, or C$_{1-6}$ alkoxy,
(11) C$_{1-6}$ alkyl-S—,
(12) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(13) —CONR$^b$R$^c$ wherein R$^b$ and R$^c$ are the same as defined above,
(14) —NR$^b$R$^c$ wherein R$^b$ and R$^c$ are the same as defined above,
(15) C$_{6-10}$ aryl optionally substituted with the same or different at least one halogen,
(16) C$_{6-10}$ aryl-O—,
(17) C$_{7-12}$ aralkyl-O—, and
(18) saturated 3- to 6-membered nitrogen-containing heteromonocycle optionally substituted with at least one =O;
  provided that when Ring A is a monocyclic aromatic ring, a substituent thereof is not optionally substituted C$_{6-10}$ aryl, or a salt thereof.
[3] The compound according to [2], wherein the 6-membered monocyclic hydrocarbon ring, 6-membered monocyclic heterocycle, 7- to 12-membered bicyclic hydrocarbon ring, or 7- to 12-membered bicyclic or tricyclic heterocycle in Ring A is benzene, pyridine, dihydroindene, naphthalene, tetrahydronaphthalene, indole, dihydroindole, dihydroisoindole, benzofuran, indazole, benzimidazole, dihydrobenzimidazole, benzoxazole, benzisoxazole, benzothiazole, dihydrobenzothiazole, quinoline, dihydroquinoline, tetrahydroquinoline, isoquinoline, dihydroisoquinoline, tetrahydroisoquinoline, tetrahydronaphthyridine, quinoxaline, dihydroquinoxaline, tetrahydroquinoxaline, benzoxathiin, dihydroquinazoline, tetrahydroquinazoline, dihydrobenzoxazine, benzothiazine, dihydrobenzothiazine, tetrahydrobenzazepine, tetrahydrobenzoxazepine, tetrahydrobenzothiazepine, carbazole, or dihydrophenanthridine, or a salt thereof.
[4] The compound according to any one of [1] to [3], wherein Ring A has any one of the structures of Formulae (A-I) to (A-III):

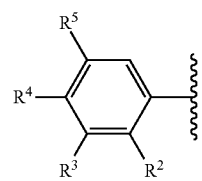

(A-I)

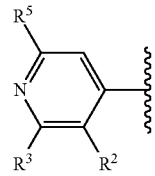

(A-II)

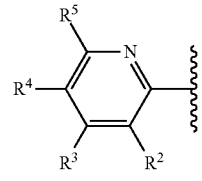

(A-III)

wherein R$^2$, R$^3$, R$^4$, and R$^5$ are each independently
(a1) hydrogen,
(a2) halogen,
(a3) —CN,
(a4) —NO$_2$, (a5) —OH,
(a6) $C_{1-6}$ alkyl optionally substituted with at least one group independently selected from the group consisting of:
   (i) halogen,
   (ii) —OH,
   (iii) —COOR$^a$ wherein R$^a$ is hydrogen or $C_{1-6}$ alkyl,
   (iv) —$C_{6-10}$ aryl, and
   (v) —CONR$^b$R$^c$ wherein R$^b$ and R$^c$ are each independently hydrogen or $C_{1-6}$ alkyl,
(a7) $C_{1-6}$ alkoxy optionally substituted with the same or different at least one halogen,
(a8) —COR$^d$ wherein R$^d$ is —OH, $C_{1-6}$ alkyl, or $C_{1-6}$ alkoxy,
(a9) $C_{1-6}$ alkyl-S—,
(a10) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
(a11) —CONR$^b$R$^c$ wherein R$^b$ and R$^c$ are the same as defined above,
(a12) —NR$^b$R$^c$ wherein R$^b$ and R$^c$ are the same as defined above,
(a13) $C_{6-10}$ aryl-O—,
(a14) $C_{7-12}$ aralkyl-O—, or
(a15) saturated 3- to 6-membered nitrogen-containing heteromonocycle optionally substituted with at least one =O;

$R^2$ and $R^3$ may alternatively combine together with the carbon atoms to which they attach to form a monocyclic or fused ring, Ring B, wherein Ring B may be optionally substituted with $R^6$ and Ring A comprising Ring B forms a 7- to 12-membered bicyclic hydrocarbon ring or 7- to 12-membered bicyclic or tricyclic heterocycle, and/or $R^4$ and $R^5$ may alternatively combine together with the carbon atoms to which they attach to form a monocyclic or fused ring, Ring C, wherein Ring C may be optionally substituted with $R^6$ and Ring A comprising Ring C forms a 7- to 12-membered bicyclic hydrocarbon ring or 7- to 12-membered bicyclic or tricyclic heterocycle;

$R^6$ is, for example, 1 to 6, preferably 1 to 4, groups independently selected from the group consisting of:
(b1) halogen,
(b2) —CN,
(b3) —NO$_2$,
(b4) =N—OH,
(b5) —OH,
(b6) =O,
(b7) =S,
(b8) $C_{1-6}$ alkyl optionally substituted with at least one group independently selected from the group consisting of:
   (i) halogen,
   (ii) —OH,
   (iii) —COOR$^a$ wherein R$^a$ is hydrogen or $C_{1-6}$ alkyl,
   (iv) —$C_{6-10}$ aryl, and
   (v) —CONR$^b$R$^c$ wherein R$^b$ and R$^c$ are each independently hydrogen or $C_{1-6}$ alkyl,
(b9) $C_{1-6}$ alkoxy optionally substituted with the same or different at least one halogen,
(b10) —COR$^d$ wherein R$^d$ is —OH, $C_{1-6}$ alkyl, or $C_{1-6}$ alkoxy,
(b11) $C_{1-6}$ alkyl-S—,
(b12) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
(b13) —CONR$^b$R$^c$ wherein R$^b$ and R$^c$ are the same as defined above,
(b14) —NR$^b$R$^c$ wherein R$^b$ and R$^c$ are the same as defined above, and
(b15) $C_{6-10}$ aryl optionally substituted with the same or different at least one halogen; and a wavy line is a binding point, or a salt thereof.

[5] The compound according to [4], wherein $R^2$, $R^3$, $R^4$, and $R^5$ are each independently
(a1) hydrogen,
(a2) halogen,
(a3) $C_{1-6}$ alkyl optionally substituted with at least one group independently selected from the group consisting of:
   (i) halogen,
   (ii) —OH,
   (iii) —COOR$^a$ wherein R$^a$ is hydrogen or $C_{1-6}$ alkyl, and
   (iv) —CONR$^b$R$^c$ wherein R$^b$ and R$^c$ are each independently hydrogen or $C_{1-6}$ alkyl,
(a4) —COOR$^f$ wherein R$^f$ is hydrogen or $C_{1-6}$ alkyl,
(a5) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
(a6) —CONR$^b$R$^c$ wherein R$^b$ and R$^c$ are the same as defined above,
(a7) —NR$^b$R$^c$ wherein R$^b$ and R$^c$ are the same as defined above, or
(a8) saturated 3- to 6-membered nitrogen-containing heteromonocycle optionally substituted with at least one =O;

$R^2$ and $R^3$ may alternatively combine together with the carbon atoms to which they attach to form a monocyclic or fused ring, Ring B, wherein Ring B may be optionally substituted with $R^6$ and Ring A comprising Ring B forms a 7- to 12-membered bicyclic hydrocarbon ring or 7- to 12-membered bicyclic or tricyclic heterocycle, and/or $R^4$ and $R^5$ may alternatively combine together with the carbon atoms to which they attach to form a monocyclic or fused ring, Ring C, wherein Ring C may be optionally substituted with $R^6$ and Ring A comprising Ring C forms a 7- to 12-membered bicyclic hydrocarbon ring or 7- to 12-membered bicyclic or tricyclic heterocycle; and $R^6$ is, for example, 1 to 6, preferably 1 to 4, groups independently selected from the group consisting of:
(b1) halogen,
(b2) =N—OH,
(b3) —OH,
(b4) =O,
(b5) =S,
(b6) $C_{1-6}$ alkyl optionally substituted with the same or different at least one halogen or $C_{6-10}$ aryl,
(b7) $C_{1-6}$ alkoxy,
(b8) —COR$^d$ wherein R$^d$ is —OH, $C_{1-6}$ alkyl, or $C_{1-6}$ alkoxy,
(b9) —NHCOR$^e$ wherein R$^e$ is the same as defined above,
(b10) —NR$^b$R$^c$ wherein R$^b$ and R$^c$ are the same as defined above, and
(b11) $C_{6-10}$ aryl optionally substituted with the same or different at least one halogen, or a salt thereof.

[6] The compound according to any one of [1] to [5], wherein Ring A is
(1) a benzene ring optionally substituted with 1 to 3 groups independently selected from the group consisting of:
   (i) halogen,
   (ii) $C_{1-6}$ alkyl optionally substituted with at least one group independently selected from the group consisting of halogen, —OH, —COOH, —CONH$_2$, and $C_{1-6}$ alkoxy-CO—,
   (iii) —COOR$^f$ wherein R$^f$ is hydrogen or $C_{1-6}$ alkyl,
   (iv) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
   (v) —CONR$^b$R$^c$ wherein R$^b$ and R$^c$ are each independently hydrogen or $C_{1-6}$ alkyl,
   (vi) —NR$^b$R$^c$ wherein R$^b$ and R$^c$ are the same as defined above, and
   (vii) saturated 3- to 6-membered nitrogen-containing heteromonocycle optionally substituted with at least one =O, or (2) a dihydroindene, naphthalene, tetrahydronaphthalene, indole, dihydroindole, dihydroisoindole, benzofuran, indazole, benzimidazole, dihydrobenzimidazole, benzoxazole, benzisoxazole, benzothiazole, dihydrobenzothiazole, quinoline, dihydroquinoline, tetrahydroquinoline, isoquinoline, dihydroisoquinoline, tetrahydroisoquinoline, tetrahydronaphthyridine, quinoxaline, dihydroquinoxaline, tetrahydroquinoxaline, benzoxathiin, dihydroquinazoline, tetrahydroquinazoline, dihydrobenzoxazine, benzothiazine, dihydrobenzothiazine, tetrahydrobenzazepine, tetrahydrobenzoxazepine, tetrahydrobenzothiazepine, carbazole, or dihydrophenanthridine ring, the ring being optionally substituted with 1 to 4 groups independently selected from the group consisting of:
  (i) halogen,
  (ii) =N—OH,
  (iii) —OH,
  (iv) =O,
  (v) =S,
  (vi) $C_{1-6}$ alkyl optionally substituted with the same or different at least one $C_{6-10}$ aryl,
  (vii) $C_{1-6}$ alkoxy,
  (viii) —$COR^d$ wherein $R^d$ is —OH, $C_{1-6}$ alkyl, or $C_{1-6}$ alkoxy,
  (ix) —$NHCOR^e$ wherein $R^e$ is hydrogen, $C_{1-6}$ alkyl, $C_{1-6}$ alkoxy, $C_{6-10}$ aryl, or $C_{7-12}$ aralkyl,
  (x) —$NR^bR^c$ wherein $R^b$ and $R^c$ are each independently hydrogen or $C_{1-6}$ alkyl, and
  (xi) $C_{6-10}$ aryl optionally substituted with the same or different at least one halogen, or a salt thereof.
[7] The compound according to any one of [1] to [6], wherein Ring A has any one of the following structures:

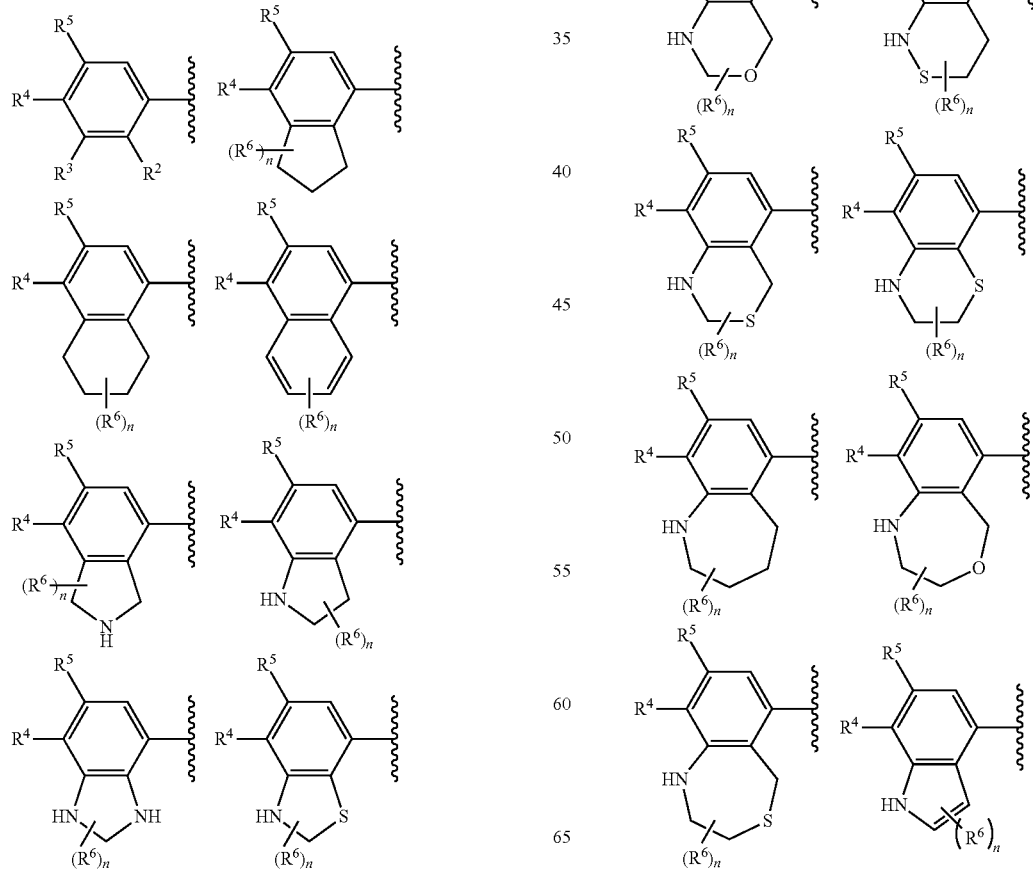
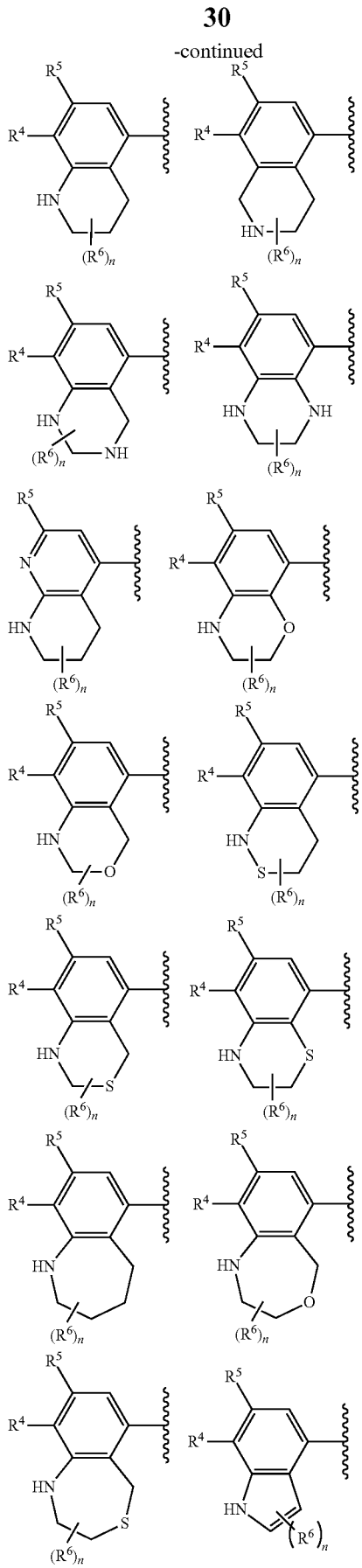

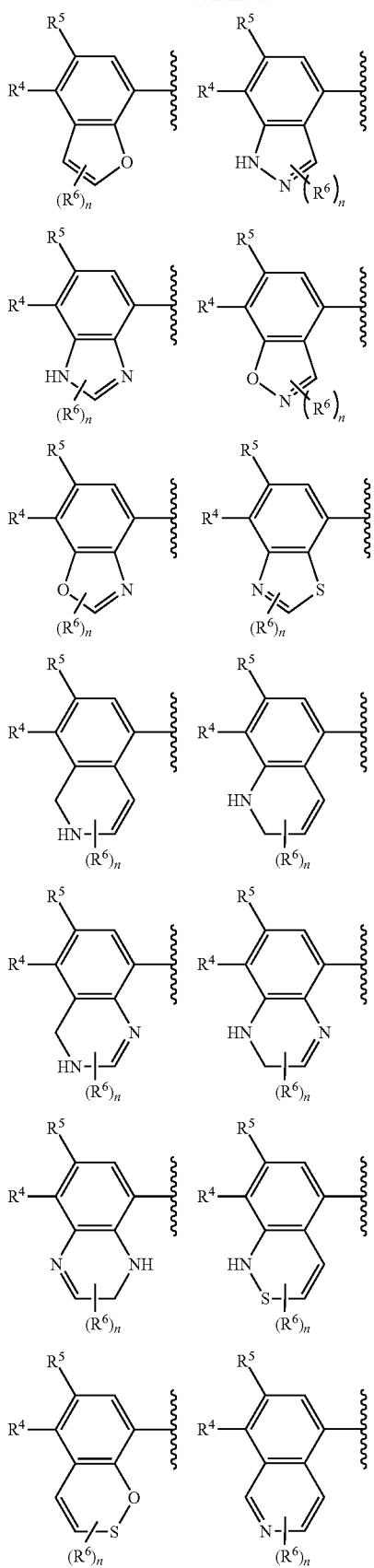
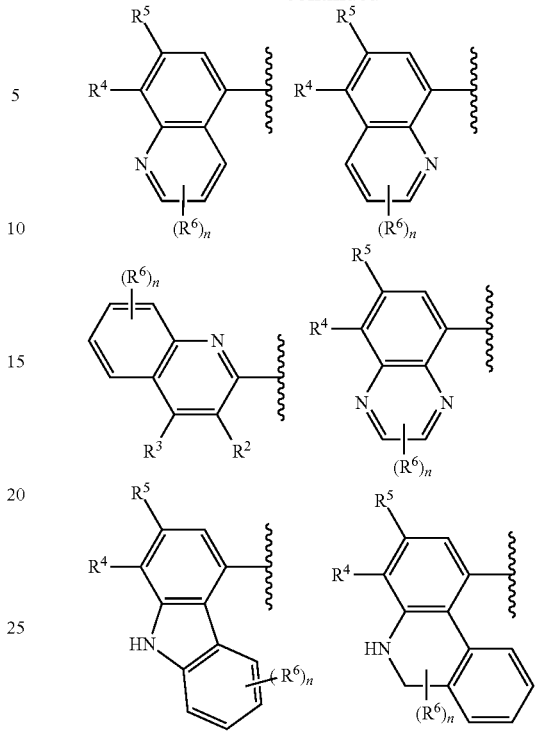

wherein $R^2$, $R^3$, $R^4$, $R^5$, and $R^6$ are as defined herein;
n is an integer of 0 to 4;
provided that when n is 2 or more, then each of $R^6$ may be different with each other;
when $R^6$ is =N—OH, =O, or =S, then $R^6$ binds to a corresponding ring via its double bond, or a salt thereof.

[8] The compound according to any one of [1] to [7], wherein Ring A is
(1) a benzene ring optionally substituted with 1 to 3 groups independently selected from the group consisting of:
 (i) halogen,
 (ii) $C_{1-6}$ alkyl optionally substituted with at least one group independently selected from the group consisting of halogen, —OH, —COOH, —CONH$_2$, and $C_{1-6}$ alkoxy-CO—,
 (iii) —COOR$^f$ wherein R$^f$ is hydrogen or $C_{1-6}$ alkyl,
 (iv) —NHCOR$^e$ wherein R$^e$ is hydrogen, $C_{1-6}$ alkyl, $C_{1-6}$ alkoxy, $C_{6-10}$ aryl, or $C_{7-12}$ aralkyl,
 (v) —CONR$^b$R$^c$ wherein R$^b$ and R$^c$ are each independently hydrogen or $C_{1-6}$ alkyl,
 (vi) —NR$^b$R$^c$ wherein R$^b$ and R$^c$ are the same as defined above, and
 (vii) saturated 3- to 6-membered nitrogen-containing heteromonocycle optionally substituted with at least one =O,
(2) indole optionally substituted with 1 to 3 groups independently selected from the group consisting of halogen and $C_{1-6}$ alkoxy-CO—,
(3) dihydroindole optionally substituted with 1 to 3 groups independently selected from the group consisting of halogen and =O,
(4) dihydroisoindole optionally substituted with 1 to 3 groups independently selected from the group consisting of halogen, $C_{1-6}$ alkyl, and =O,
(5) dihydroindene optionally substituted with 1 to 3 groups independently selected from the group consisting of halogen, —OH, =N—OH, and =O, (6) benzofuran optionally substituted with the same or different at least one halogen,
(7) indazole optionally substituted with the same or different at least one halogen,
(8) benzimidazole optionally substituted with phenyl optionally substituted with the same or different at least one halogen,
(9) dihydrobenzimidazole optionally substituted with 1 to 3 groups independently selected from the group consisting of $C_{1-6}$ alkyl and $=O$,
(10) benzoxazole optionally substituted with the same or different at least one $C_{1-6}$ alkyl,
(11) benzisoxazole optionally substituted with the same or different at least one $C_{1-6}$ alkyl,
(12) benzothiazole optionally substituted with 1 to 3 groups independently selected from the group consisting of halogen, $-NH_2$, and mono-$(C_{1-6}$ alkyl)-amino,
(13) dihydrobenzothiazole optionally substituted with 1 to 3 groups independently selected from the group consisting of halogen and $=O$,
(14) naphthalene optionally substituted with the same or different at least one $-NHCO-C_{1-6}$ alkyl,
(15) tetrahydronaphthalene optionally substituted with 1 to 3 groups independently selected from the group consisting of $-OH$ and $=O$,
(16) quinoline optionally substituted with 1 to 3 groups independently selected from the group consisting of halogen and $C_{1-6}$ alkoxy,
(17) dihydroquinoline optionally substituted with 1 to 3 groups independently selected from the group consisting of halogen and $=S$,
(18) tetrahydroquinoline optionally substituted with 1 to 3 groups independently selected from the group consisting of halogen and $C_{1-6}$ alkyl-CO—,
(19) isoquinoline,
(20) dihydroisoquinoline optionally substituted with at least one $=O$,
(21) tetrahydroisoquinoline optionally substituted with at least one $=O$,
(22) tetrahydronaphthyridine optionally substituted with at least one $=O$,
(23) quinoxaline optionally substituted with the same or different at least one $C_{1-6}$ alkoxy,
(24) dihydroquinoxaline optionally substituted with 1 to 4 groups independently selected from the group consisting of $C_{1-6}$ alkyl and $=O$,
(25) tetrahydroquinoxaline optionally substituted with 1 to 4 groups independently selected from the group consisting of halogen, $C_{1-6}$ alkyl, and $=O$,
(26) benzoxathiin optionally substituted with at least one $=O$,
(27) dihydroquinazoline optionally substituted with at least one $=O$,
(28) tetrahydroquinazoline optionally substituted with 1 to 3 groups independently selected from the group consisting of halogen, $C_{1-6}$ alkyl, and $=O$,
(29) dihydrobenzoxazine optionally substituted with 1 to 3 groups independently selected from the group consisting of halogen and $=O$,
(30) benzothiazine optionally substituted with 1 to 3 groups independently selected from the group consisting of $=O$ and benzyl,
(31) dihydrobenzothiazine optionally substituted with at least one $=O$,
(32) tetrahydrobenzazepine optionally substituted with 1 to 3 groups independently selected from the group consisting of halogen and $=O$,
(33) tetrahydrobenzoxazepine optionally substituted with at least one $=O$,
(34) tetrahydrobenzothiazepine optionally substituted with at least one $=O$,
(35) carbazole, or
(36) dihydrophenanthridine optionally substituted with at least one $=O$, or a salt thereof.
[9] The compound according to any one of [1] to [8], wherein $R^1$ is the same or different
(1) halogen,
(2) $-CN$,
(3) $-NO_2$,
(4) $-OH$,
(5) $C_{1-6}$ alkyl optionally substituted with at least one group independently selected from the group consisting of:
  (i) halogen,
  (ii) $-OH$,
  (iii) $C_{1-6}$ alkoxy, and
  (iv) $C_{6-10}$ aryl-O— optionally substituted with the same or different at least one halogen,
(6) $C_{1-6}$ alkoxy optionally substituted with at least one group independently selected from the group consisting of:
  (i) halogen,
  (ii) $C_{1-6}$ alkoxy optionally substituted with the same or different at least one $C_{1-6}$ alkoxy,
  (iii) $C_{6-10}$ aryl-O— optionally substituted with the same or different at least one halogen,
  (iv) heterocycle optionally substituted with the same or different at least one $C_{1-6}$ alkyl optionally substituted with the same or different at least one halogen, and
  (v) amino optionally substituted with the same or different 1 or 2 $C_{1-6}$ alkyl,
(7) $C_{1-6}$ alkoxy-CO—,
(8) $C_{1-6}$ alkyl-S—,
(9) $C_{6-10}$ aryl optionally substituted with the same or different at least one halogen,
(10) $C_{6-10}$ aryl-O—, or
(11) $C_{7-15}$ aralkyl-O— optionally substituted with at least one group independently selected from the group consisting of:
  (i) halogen,
  (ii) $C_{1-6}$ alkyl optionally substituted with the same or different at least one halogen, and
  (iii) $C_{1-6}$ alkoxy optionally substituted with the same or different at least one halogen, or a salt thereof.
[10] The compound according to any one of [1] to [9], wherein $R^1$ is the same or different
(1) halogen,
(2) $C_{1-6}$ alkyl optionally substituted with the same or different at least one halogen, or
(3) $C_{1-6}$ alkoxy optionally substituted with the same or different at least one halogen, or a salt thereof.
[11] The compound according to any one of [1] to [10], wherein $R^1$ is the same or different halogen, preferably fluoro, chloro, or bromo, or a salt thereof.
[12] The compound according to any one of [1] to [11], wherein Ring A is
(1) a benzene ring optionally substituted with 1 to 3 groups independently selected from the group consisting of fluoro, chloro, methyl, $-CH_2OH$, $-CH_2CH_2OH$, $-CH_2CH_2CH_2OH$, $-CH_2COOH$, $-CH_2CH_2COOH$, $-CH_2COOCH_2CH_3$, $-CH_2CH_2COOCH_2CH_3$, $-CH_2CONH_2$, $-CH_2CH_2CONH_2$, $-COOH$, $-NH_2$, $-COOCH_3$, $-CONHCH_3$, $-NHCHO$, $-NHCOCH_3$, $-NHCOCH_2CH_3$, $-NHCO(CH_2)_2CH_3$, $-NHCOOCH_3$, $-NHCOPh$, $-NHCOCH_2Ph$, $-NHCO(CH_2)_2Ph$, and oxoimidazolidinyl, (2) indole optionally substituted with 1 or 2 groups independently selected from the group consisting of fluoro, chloro, and —COOCH$_3$,
(3) dihydroindole optionally substituted with 1 or 2 groups independently selected from the group consisting of fluoro, chloro, and =O,
(4) dihydroisoindole optionally substituted with 1 or 2 groups independently selected from the group consisting of chloro, tert-butyl, and =O,
(5) dihydroindene optionally substituted with 1 or 2 groups independently selected from the group consisting of chloro, —OH, =N—OH, and =O,
(6) benzofuran optionally substituted with one bromo,
(7) indazole optionally substituted with one chloro,
(8) benzimidazole optionally substituted with one fluorophenyl,
(9) dihydrobenzimidazole optionally substituted with 1 or 2 groups independently selected from the group consisting of methyl and =O,
(10) benzoxazole optionally substituted with one methyl,
(11) benzisoxazole optionally substituted with one methyl,
(12) benzothiazole optionally substituted with 1 or 2 groups independently selected from the group consisting of fluoro, chloro, —NH$_2$, and methylamino,
(13) dihydrobenzothiazole optionally substituted with 1 or 2 groups independently selected from the group consisting of fluoro, chloro, and =O,
(14) naphthalene optionally substituted with one —NHCOCH$_3$,
(15) tetrahydronaphthalene optionally substituted with one —OH or one =O,
(16) quinoline optionally substituted with 1 or 2 groups independently selected from the group consisting of fluoro, chloro, and methoxy,
(17) dihydroquinoline optionally substituted with 1 or 2 groups independently selected from the group consisting of chloro and =S,
(18) tetrahydroquinoline optionally substituted with one fluoro or one —COCH$_3$,
(19) isoquinoline,
(20) dihydroisoquinoline optionally substituted with one =O,
(21) tetrahydroisoquinoline optionally substituted with one =O,
(22) tetrahydronaphthyridine optionally substituted with one =O,
(23) quinoxaline optionally substituted with one methoxy,
(24) dihydroquinoxaline optionally substituted with 1 or 2 groups independently selected from the group consisting of methyl and =O,
(25) tetrahydroquinoxaline optionally substituted with 1 to 4 groups independently selected from the group consisting of fluoro, methyl, and =O,
(26) benzoxathiin optionally substituted with 1 or 2 =O,
(27) dihydroquinazoline optionally substituted with one =O,
(28) tetrahydroquinazoline optionally substituted with 1 or 2 groups independently selected from the group consisting of methyl, fluoro, and =O,
(29) dihydrobenzoxazine optionally substituted with 1 or 2 groups independently selected from the group consisting of chloro and =O,
(30) benzothiazine optionally substituted with 1 to 3 groups independently selected from the group consisting of benzyl and =O,
(31) dihydrobenzothiazine optionally substituted with 1 or 2 =O,
(32) tetrahydrobenzazepine optionally substituted with 1 or 2 groups independently selected from the group consisting of chloro and =O,
(33) tetrahydrobenzoxazepine optionally substituted with one =O,
(34) tetrahydrobenzothiazepine optionally substituted with 1 to 3 =O,
(35) carbazole, or
(36) dihydrophenanthridine optionally substituted with one =O;
R$^1$ is the same or different fluoro, chloro, or bromo;
p is an integer of 0 or 1; and
q is an integer of 2 or 3, or a salt thereof.

[13] The compound according to any one of [1] to [12], wherein Ring A is
(1) a benzene ring optionally substituted with 1 to 3 groups independently selected from the group consisting of fluoro, chloro, methyl, —CH$_2$OH, —CH$_2$CONH$_2$, —COOCH$_3$, —CONHCH$_3$, —NHCHO, and —NHCOCH$_3$,
(2) indole optionally substituted with 1 or 2 chloro,
(3) dihydroindole optionally substituted with 1 or 2 groups independently selected from the group consisting of fluoro, chloro, and =O,
(4) dihydroisoindole optionally substituted with 1 or 2 groups independently selected from the group consisting of tert-butyl and =O,
(5) dihydroindene optionally substituted with 1 or 2 groups independently selected from the group consisting of chloro, —OH, and =O,
(6) benzofuran optionally substituted with one bromo,
(7) indazole optionally substituted with one chloro,
(8) benzimidazole,
(9) dihydrobenzimidazole optionally substituted with 1 or 2 groups independently selected from the group consisting of methyl and =O,
(10) benzoxazole optionally substituted with one methyl,
(11) benzisoxazole optionally substituted with one methyl,
(12) benzothiazole optionally substituted with 1 or 2 groups independently selected from the group consisting of fluoro, chloro, and —NH$_2$,
(13) dihydrobenzothiazole optionally substituted with 1 or 2 groups independently selected from the group consisting of fluoro, chloro, and =O,
(14) quinoline optionally substituted with 1 or 2 chloro,
(15) dihydroquinoline optionally substituted with 1 or 2 groups independently selected from the group consisting of chloro and =S,
(16) tetrahydroquinoline optionally substituted with one fluoro,
(17) isoquinoline,
(18) tetrahydronaphthyridine optionally substituted with one =O,
(19) dihydroquinoxaline optionally substituted with 1 or 2 groups independently selected from the group consisting of methyl and =O,
(20) tetrahydroquinoxaline optionally substituted with 1 to 4 groups independently selected from the group consisting of fluoro, methyl, and =O,
(21) tetrahydroquinazoline optionally substituted with 1 or 2 groups independently selected from the group consisting of methyl, fluoro, and =O,
(22) dihydrobenzoxazine optionally substituted with 1 or 2 groups independently selected from the group consisting of chloro and =O,
(23) dihydrobenzothiazine optionally substituted with 1 or 2 =O,

(24) tetrahydrobenzazepine optionally substituted with 1 or 2 groups independently selected from the group consisting of chloro and =O,

(25) tetrahydrobenzoxazepine optionally substituted with one =O, or

(26) tetrahydrobenzothiazepine optionally substituted with one =O;

$R^1$ is the same or different fluoro, chloro, or bromo;

p is an integer of 0 or 1;

q is an integer of 2 or 3, or a salt thereof.

[14] The compound according to [4], wherein Ring A has the structure of Formula (A-I), or a salt thereof.

[15] The compound according to [1], which is selected from the group consisting of the following compounds:

1-(4-chloro-2-fluorophenyl)-4-(isoquinolin-5-yloxymethyl)piperidin-4-ol;

(3R,4R)-1-(4-chloro-2,6-difluorophenyl)-4-[(5-chloroquinolin-8-yl)oxymethyl]piperidine-3,4-diol;

2-tert-butyl-4-[[(3R,4R)-1-(4-chloro-2,6-difluorophenyl)-3,4-dihydroxypiperidin-4-yl]methoxy]-3H-isoindol-1-one;

3-methyl-4-[[(3R,4R)-1-(4-chloro-2,6-difluorophenyl)-3,4-dihydroxypiperidin-4-yl]methoxy]-1H-benzimidazol-2-one;

4-[[(3R,4R)-1-(4-chloro-2,6-difluorophenyl)-3,4-dihydroxypiperidin-4-yl]methoxy]-2,3-dihydroinden-1-one;

(3R,4R)-4-[(4-bromo-1-benzofuran-7-yl)oxymethyl]-1-(4-chloro-2,6-difluorophenyl)piperidine-3,4-diol;

(3R,4R)-1-(4-chloro-2,6-difluorophenyl)-4-[(1-hydroxy-2,3-dihydro-1H-inden-4-yl)oxymethyl]piperidine-3,4-diol;

(3R,4R)-1-(4-chloro-2,6-difluorophenyl)-4-(1H-indazol-4-yloxymethyl)piperidine-3,4-diol;

(3R,4R)-1-(4-chloro-2,6-difluorophenyl)-4-[(3-methyl-1,2-benzoxazol-4-yl)oxymethyl]piperidine-3,4-diol;

(3R,4R)-4-(1H-benzimidazol-4-yloxymethyl)-1-(4-chloro-2,6-difluorophenyl)piperidine-3,4-diol;

3-methyl-5-[[(3R,4R)-1-(4-chloro-2,6-difluorophenyl)-3,4-dihydroxypiperidin-4-yl]methoxy]-1,4-dihydroquinazolin-2-one;

(3R,4R)-1-(4-chloro-2,6-difluorophenyl)-4-[(8-fluoro-1,2,3,4-tetrahydroquinolin-5-yl)oxymethyl]piperidine-3,4-diol;

(3R,4R)-1-(4-chloro-2-fluorophenyl)-4-[(7-chloro-1H-indazol-4-yl)oxymethyl]piperidine-3,4-diol;

5-[[(3R,4R)-1-(4-bromo-2-fluorophenyl)-3,4-dihydroxypiperidin-4-yl]methoxy]-1H-quinoxalin-2-one;

8-[[(3R,4R)-1-(4-chloro-2-fluorophenyl)-3,4-dihydroxypiperidin-4-yl]methoxy]-1H-quinoxalin-2-one;

1-methyl-5-[[(3R,4R)-1-(4-chloro-2,6-difluorophenyl)-3,4-dihydroxypiperidin-4-yl]methoxy]quinoxalin-2-one;

N-[5-fluoro-2-[[(3R,4R)-1-(4-chloro-2,6-difluorophenyl)-3,4-dihydroxypiperidin-4-yl]methoxy]phenyl]acetamide;

6-[[(3R,4R)-1-(4-chloro-2,6-difluorophenyl)-3,4-dihydroxypiperidin-4-yl]methoxy]-1,5-dihydro-4,1-benzoxazepin-2-one;

5-[[(3R,4R)-1-(4-chloro-2,6-difluorophenyl)-3,4-dihydroxypiperidin-4-yl]methoxy]-1,4-dihydro-3,1-benzothiazin-2-one;

5-[[(3R,4R)-1-(4-bromo-2-fluorophenyl)-3,4-dihydroxypiperidin-4-yl]methoxy]-3,4-dihydro-1H-1,8-naphthyridin-2-one;

6-[[(3R,4R)-1-(4-chloro-2,6-difluorophenyl)-3,4-dihydroxypiperidin-4-yl]methoxy]-1,5-dihydro-4,1-benzothiazepin-2-one;

8-[[(3R,4R)-1-(4-chloro-2-fluorophenyl)-3,4-dihydroxypiperidin-4-yl]methoxy]-4H-1,4-benzothiazin-3-one;

9-chloro-6-[[1-(4-chloro-2,6-difluorophenyl)-4-hydroxypiperidin-4-yl]methoxy]-1,3,4,5-tetrahydro-1-benzazepin-2-one;

5-chloro-8-[[1-(4-chloro-2,6-difluorophenyl)-4-hydroxypiperidin-4-yl]methoxy]-4H-1,4-benzoxazin-3-one;

9-chloro-6-[[(3R,4R)-1-(4-chloro-2,6-difluorophenyl)-3,4-dihydroxypiperidin-4-yl]methoxy]-1,3,4,5-tetrahydro-1-benzazepin-2-one;

7-chloro-4-[[(3R,4R)-1-(4-chloro-2,6-difluorophenyl)-3,4-dihydroxypiperidin-4-yl]methoxy]-2,3-dihydroinden-1-one;

methyl 5-chloro-2-[[(3R,4R)-1-(4-chloro-2,6-difluorophenyl)-3,4-dihydroxypiperidin-4-yl]methoxy]benzoate;

7-chloro-4-[[(3R,4R)-1-(4-chloro-2,6-difluorophenyl)-3,4-dihydroxypiperidin-4-yl]methoxy]-1,3-dihydroindol-2-one;

(3R,4R)-1-(4-chloro-2,6-difluorophenyl)-4-[[4-chloro-2-(hydroxymethyl)phenoxy]methyl]piperidine-3,4-diol;

5-chloro-2-[[(3R,4R)-1-(4-chloro-2,6-difluorophenyl)-3,4-dihydroxypiperidin-4-yl]methoxy]-N-methylbenzamide;

N-[6-chloro-3-[[(3R,4R)-1-(4-chloro-2,6-difluorophenyl)-3,4-dihydroxypiperidin-4-yl]methoxy]-2-methylphenyl]formamide;

8-chloro-5-[[(3R,4R)-1-(4-chloro-2,6-difluorophenyl)-3,4-dihydroxypiperidin-4-yl]methoxy]-1H-quinoline-2-thione;

5-chloro-8-[[(3R,4R)-1-(4-chloro-2,6-difluorophenyl)-3,4-dihydroxypiperidin-4-yl]methoxy]-4H-1,4-benzoxazin-3-one;

(3R,4R)-1-(4-chloro-2,6-difluorophenyl)-4-[(7-chloro-1H-indole-4-yl)oxymethyl]piperidine-3,4-diol;

2-[5-fluoro-2-[[(3R,4R)-1-(4-chloro-2,6-difluorophenyl)-3,4-dihydroxypiperidin-4-yl]methoxy]phenyl]acetamide;

7-chloro-4-[[(3R,4R)-1-(4-bromo-2-fluorophenyl)-3,4-dihydroxypiperidin-4-yl]methoxy]-1,3-dihydroindol-2-one;

4-chloro-7-[[(3R,4R)-1-(4-chloro-2,6-difluorophenyl)-3,4-dihydroxypiperidin-4-yl]methoxy]-3H-1,3-benzothiazol-2-one;

(3R,4R)-4-[(2-amino-4-chloro-1,3-benzothiazol-7-yl)oxymethyl]-1-(4-chloro-2,6-difluorophenyl)piperidine-3,4-diol;

8-fluoro-5-[[(3R,4R)-1-(4-bromo-2-fluorophenyl)-3,4-dihydroxypiperidin-4-yl]methoxy]-3,4-dihydro-1H-quinazolin-2-one;

8-chloro-5-[[(3R,4R)-1-(4-chloro-2-fluorophenyl)-3,4-dihydroxypiperidin-4-yl]methoxy]-1,4-dihydro-3,1-benzoxazin-2-one;

(3R,4R)-1-(4-chloro-2,6-difluorophenyl)-4-[(2-chloro-4-fluoro-1,3-benzothiazol-7-yl)oxymethyl]piperidine-3,4-diol;

4-fluoro-7-[[(3R,4R)-1-(4-bromo-2-fluorophenyl)-3,4-dihydroxypiperidin-4-yl]methoxy]-3H-1,3-benzothiazol-2-one;

5-[[1-(4-chloro-2,6-difluorophenyl)-4-hydroxypiperidin-4-yl]methoxy]-1,4-dihydro-3,1-benzoxazin-2-one;

4-[[1-(4-chloro-2,6-difluorophenyl)-4-hydroxypiperidin-4-yl]methoxy]-7-fluoro-1,3-dihydroindol-2-one;

8-[[(3R,4R)-1-(4-chloro-2,6-difluorophenyl)-3,4-dihydroxypiperidin-4-yl]methoxy]-4-methyl-1H-quinoxaline-2,3-dione; and 7-[[1-(4-chloro-2,6-difluorophenyl)-4-hydroxypiperidin-4-yl]methoxy]-4-fluoro-3H-1,3-benzothiazol-2-one, or a salt thereof.

[16] A pharmaceutical composition comprising a compound according to any one of [1] to [15] or a salt thereof and a pharmaceutically acceptable carrier.

[17] A medicinal agent for diagnosing, preventing, and/or treating tuberculosis (e.g., primary tuberculosis, secondary tuberculosis, pulmonary tuberculosis, and extrapulmonary tuberculosis such as meningitis, peritonitis, renal tuberculosis, adrenal tuberculosis, bone tuberculosis, joint tuberculosis, intestinal tuberculosis, cutaneous tuberculosis, laryngeal tuberculosis, and lymph node tuberculosis), comprising a compound according to any one of [1] to [15] or a salt thereof and a pharmaceutically acceptable carrier.

[18] A compound according to any one of [1] to [15] or a salt thereof for use in diagnosing, preventing, and/or treating tuberculosis.

[19] Use of a compound according to any one of [1] to [15] or a salt thereof in the manufacture of a pharmaceutical for diagnosing, preventing, and/or treating tuberculosis.

[20] A method of diagnosing, preventing, and/or treating tuberculosis, comprising administering an effective amount of a compound according to any one of [1] to [15] or a salt thereof to a subject.

The proposal of preferable embodiments and options in respect of different features of the compounds, methods, uses, and compositions in the present invention herein includes the proposal of combinations of those preferable embodiments and options for the different features, insofar as they are combinable and compatible.

[Preparations]

A method of preparing Compound [I] in the present invention is explained as below. Compound [I] in the present invention may be, for example, prepared according to the preparations as below. The preparations as below are illustrative and a method of preparing Compound [I] is not limited thereto.

Examples of "hydrocarbons" as a solvent include, for example, aliphatic hydrocarbons such as hexane and pentane; alicyclic hydrocarbons such as cyclopentane and cyclohexane; and aromatic hydrocarbons such as benzene and toluene.

Examples of "halogenated hydrocarbons" as a solvent include, for example, chloroform and dichloromethane.

Examples of "alcohols" as a solvent include, for example, methanol, ethanol, 2-propanol, propanol, and tert-butanol.

Examples of "ethers" as a solvent include, for example, chained ethers such as diethyl ether, diisopropyl ether, dibutyl ether, and diphenyl ether; and circular ethers such as 1,4-dioxane and tetrahydrofurane.

Examples of "esters" as a solvent include, for example, ethyl acetate and ethyl propionate.

Examples of "ketones" as a solvent include, for example, acetone, methyl ethyl ketone, and methyl isobutyl ketone.

Examples of "amides" as a solvent include, for example, N,N-dimethylformamide, N,N-dimethylacetamide, and N-methyl-2-pyrrolidone.

Examples of "nitriles" as a solvent include, for example, acetonitrile and propionitrile.

Examples of "sulfoxides" as a solvent include, for example, dimethyl sulfoxide.

Examples of "alkali metal hydroxides" as a base include, for example, sodium hydroxide, potassium hydroxide, and cesium hydroxide.

Examples of "alkali metal hydrides" as a base include, for example, sodium hydride, potassium hydride, and cesium hydride.

Examples of "alkali metal carboxylates" as a base include, for example, sodium acetate, potassium acetate, and sodium butyrate.

Examples of "alkali metal carbonates" as a base include, for example, sodium carbonate, potassium carbonate, cesium carbonate, and lithium carbonate.

Examples of "alkali metal hydrogencarbonates" as a base include, for example, sodium hydrogencarbonate, potassium hydrogencarbonate, and cesium hydrogencarbonate.

Examples of "alkali metal phosphates" as a base include, for example, sodium phosphate and potassium phosphate.

Examples of "aromatic amines" as a base include, for example, pyridine and lutidine.

Examples of "tertiary amines" as a base include, for example, triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, tetramethylethylenediamine, tetramethylpropylenediamine, and 1,8-diazabicyclo[5,4,0]undec-7-ene (diazabicycloundecene).

Examples of "metal amides" as a base include, for example, lithium diisopropylamide and lithium hexamethyldisilazide.

Examples of "metal alkoxides" as a base include, for example, sodium methoxide, sodium ethoxide, sodium tert-butoxide, potassium tert-butoxide, and sodium phenoxide.

Examples of "inorganic acids" as an acid include, for example, hydrochloric acid, sulfuric acid, nitric acid, hydrobromic acid, and phosphoric acid.

Examples of "organic acids" as an acid include, for example, acetic acid, trifluoroacetic acid, oxalic acid, phthalic acid, fumaric acid, tartaric acid, maleic acid, citric acid, succinic acid, methanesulfonic acid, p-toluenesulfonic acid, and 10-camphorsulfonic acid.

Examples of the "protecting group of hydroxy" include, but not limited to, any protecting groups of hydroxy used in the field of synthetic organic chemistry, and include, for example, alkyl groups (e.g., methyl, ethyl, isopropyl, tert-butyl, trifluoromethyl, hydroxymethyl, 2-hydroxyethyl, acetylmethyl); alkenyl groups (e.g., ethenyl, 1-propenyl, 2-propenyl, 1-methyl-2-propenyl); alkynyl groups (e.g., ethynyl, 1-propynyl, 2-propynyl, 1-methyl-2-propynyl); formyl; alkyl (alkenyl) carbonyl groups (e.g., acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, (E)-2-methyl-2-butenoyl); arylcarbonyl groups (e.g., benzoyl, α-naphthoyl, β-naphthoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, 4-phenylbenzoyl); alkoxycarbonyl groups (e.g., methoxycarbonyl, tert-butoxycarbonyl, 2,2,2-trichloroethoxycarbonyl, 2-trimethylsilylethoxycarbonyl, 9-fluorenylmethyloxycarbonyl); tetrahydro(thio)pyranyl (furanyl) groups (e.g., tetrahydropyran-2-yl, 3-bromotetrahydropyran-2-yl, 4-methoxytetrahydropyran-4-yl, tetrahydrothiopyran-2-yl, 4-methoxytetrahydrothiopyran-4-yl, tetrahydrofuran-2-yl, tetrahydrothiofuran-2-yl); silyl groups (e.g., trimethylsilyl, triethylsilyl, isopropyl dimethylsilyl, tert-butyldimethyl silyl, methyldiisopropyl silyl, methyl di-tert-butylsilyl, triisopropylsilyl, diphenylmethyl silyl, diphenylbutyl silyl, diphenylisopropyl silyl, phenyldiisopropyl silyl); alkoxymethyl groups (e.g., methoxymethyl, 1,1-dimethyl-1-methoxymethyl, ethoxymethyl, propoxymethyl, isopropoxymethyl, butoxymethyl, tert-butoxymethyl, 2-methoxyethoxymethyl, 2,2,2-trichloroethoxymethyl, bis(2-chloroethoxy)methyl); alkoxyethyl groups (e.g., 1-ethoxyethyl, 1-(isopropoxy)ethyl); halogenated ethyl groups (e.g., 2,2,2-trichloroethyl); aralkyl groups (e.g., benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl); alkenyloxycarbonyl groups (e.g., vinyloxycarbonyl, allyloxycarbonyl); and aralkyloxycarbonyl groups (e.g., benzyloxycarbonyl, 4-methoxybenzyloxycarbonyl, 3,4-dimethoxybenzyloxycarbonyl, 2-nitrobenzyloxycarbonyl, 4-nitrobenzyloxycarbonyl).

Examples of the "protecting group of carboxy" include, but not limited to, any protecting groups of carboxy used in the field of synthetic organic chemistry, and include, for example, the "alkyl groups", "alkenyl groups", "alkynyl groups", "aralkyl groups", and "silyl groups" as above listed in the examples of the "protecting group of hydroxy" and similar groups thereof.

Examples of the "protecting group of amino" include, but not limited to, any protecting groups of amino used in the field of synthetic organic chemistry, and include, for example, the "alkyl (alkenyl) carbonyl groups", "arylcarbonyl groups", "alkoxycarbonyl groups", "silyl groups", "aralkyl groups", "alkenyloxycarbonyl groups", and "aralkyloxycarbonyl groups" as above listed in the "protecting group of hydroxy" and similar groups thereof.

Examples of the "protecting group of terminal acetylene" include, but not limited to, any protecting groups of terminal acetylene used in the field of synthetic organic chemistry, and include, for example, the "silyl groups" as above listed in the "protecting group of hydroxy" and similar groups thereof.

Examples of the "leaving group" include, for example, halogen (e.g., fluorine, chlorine, bromine, iodine), alkylsulfonyloxy groups (e.g., methylsulfonyloxy, ethylsulfonyloxy, trifluoromethylsulfonyloxy), and arylsulfonyloxy groups (e.g., benzenesulfonyloxy, p-toluenesulfonyloxy, 2,4,6-trimethylbenzenesulfonyloxy, 2-nitrobenzenesulfonyloxy, 4-nitrobenzenesulfonyloxy).

[Preparation A: General Synthetic Route 1]

Scheme A-1

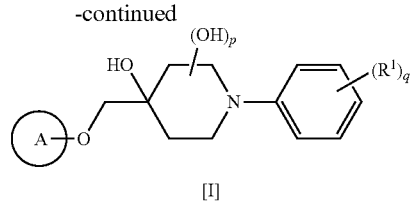

-continued

In the scheme, each symbol has the same meaning as defined above.

(Step A-1-1: (1)+(2)→[I])

Compound [I] may be obtained by, for example, reacting Compound (1) with Compound (2) in an inert solvent in the presence of a base or acid.

The amount of Compound (2) is typically from 0.1 to 10 molar equivalents, preferably from 0.2 to 5 molar equivalents, to Compound (1).

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 0.01 to 10 molar equivalents, preferably from 0.1 to 5 molar equivalents, to Compound (1).

The acid includes, for example, inorganic acids and organic acids, which may be used in combination with two or more of these agents with optional ratios. The amount of the acid is typically from 1 molar equivalent to excess amounts to Compound (1).

The inert solvent includes, for example, hydrocarbons, hydrocarbon halides, ethers, esters, ketones, alcohols, water, amides, nitriles, and sulfoxides, which may be used in combination with two or more of these agents with optional ratios.

The reaction temperature is typically from −80 to 150° C., preferably from 40 to 150° C. The reaction time is typically from 0.1 to 200 hours.

Scheme A-2

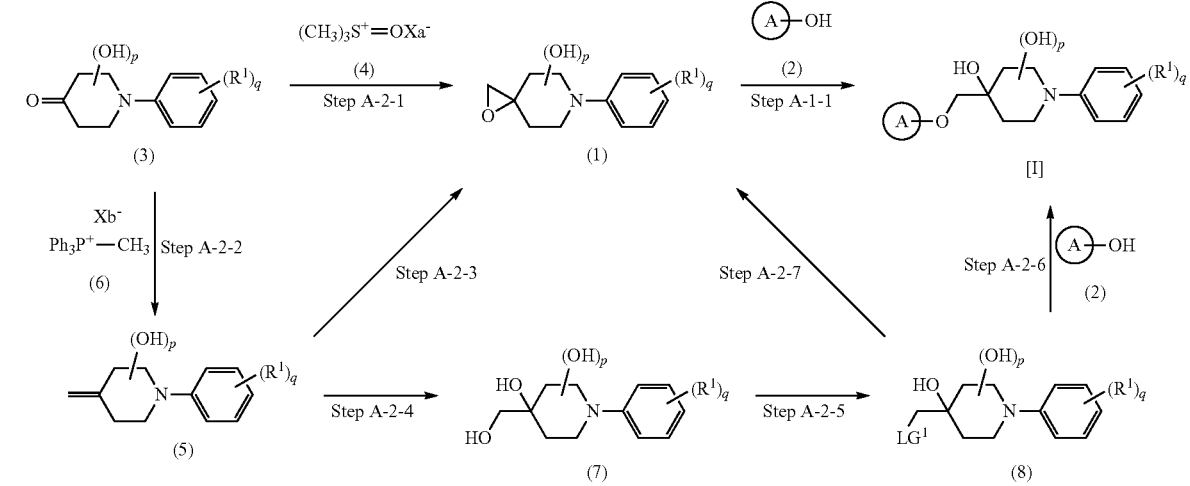

In the scheme, Xa⁻ and Xb⁻ are each a halide ion; $LG^1$ is a leaving group; and the other symbols have the same meanings as defined above.

(Step A-2-1: (3)+(4)→(1))

Compound (1) may be obtained by, for example, reacting Compound (3) with Compound (4) in an inert solvent in the presence of a base (Corey-Chaykovsky reaction).

The amount of Compound (4) is typically from 0.1 to 10 molar equivalents, preferably from 0.2 to 5 molar equivalents, to Compound (3).

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (3).

A salt may be added, if necessary.

The salt includes, for example, alkali metal halides such as cesium fluoride, cesium chloride, cesium bromide, cesium iodide, potassium fluoride, potassium chloride, potassium bromide, potassium iodide, sodium fluoride, sodium chloride, sodium bromide, sodium iodide, lithium fluoride, lithium chloride, lithium bromide, and lithium iodide. The amount of the salt is typically from 1 to 10 molar equivalents, preferably from 1 to 5 molar equivalents, to Compound (3).

The inert solvent includes, for example, hydrocarbons, hydrocarbon halides, water, alcohols, ethers, esters, amides, and sulfoxides, which may be used in combination with two or more of these agents with optional ratios.

The reaction temperature is typically from −80 to 150° C. The reaction time is typically from 0.1 to 200 hours.

(Step A-2-2: (3)+(6)→(5))

Compound (5) may be obtained by, for example, reacting Compound (3) with Compound (6) in an inert solvent in the presence of a base (Wittig reaction).

The amount of Compound (6) is typically from 0.1 to 10 molar equivalents, preferably from 0.2 to 5 molar equivalents, to Compound (3).

The base includes, for example, alkali metal hydrides, metal amides, metal alkoxides, and organic lithium agents, which may be used in combination with two or more of these agents with optional ratios. The amount of the base is typically from 1 to 10 molar equivalents, preferably from 1 to 5 molar equivalents, to Compound (3).

The inert solvent includes, for example, hydrocarbons, hydrocarbon halides, and ethers, which may be used in combination with two or more of these agents with optional ratios.

The reaction temperature is typically from −80 to 150° C. The reaction time is typically from 0.1 to 200 hours.

(Step A-2-3: (5)→(1))

Compound (1) may be obtained by, for example, reacting Compound (5) in an inert solvent in the presence of an oxidizing agent.

The oxidizing agent includes, inorganic peroxides (e.g., hydrogen peroxide, sodium hypochlorite, sodium periodate), organic peroxides (e.g., m-chloroperoxybenzoic acid, perbenzoic acid, peracetic acid, trifluoroperacetic acid), and dioxiranes (e.g., dimethyldioxirane). The amount of the oxidizing agent is typically from 1 to 10 molar equivalents, preferably from 1 to 5 molar equivalents, to Compound (5).

A base may be used, if necessary.

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (5).

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step A-2-4: (5)→(7))

Compound (7) may be obtained by, for example, reacting Compound (5) in an inert solvent in the presence of osmium tetraoxide and a reoxidizing agent.

The amount of osmium tetraoxide is typically from 0.01 to 0.5 molar equivalents to Compound (5). Potassium osmate ($K_2OsO_2(OH)_4$) may be used instead of osmium tetraoxide. Osmium tetraoxide may be also used in the form of an immobilized catalyst where osmium tetraoxide is supported on a solvent-resistant polymer. The immobilized catalyst includes "Osmium Oxide, Immobilized Catalyst I (Os IC-I)" (trade name) (Wako pure chemical industries).

The reoxidizing agent includes, for example, N-methylmorpholine oxide, trimethylamine oxide, tert-butyl hydroperoxide, and potassium hexacyanoferrate ($K_3Fe(CN)_6$), which may be used in combination with two or more of these agents with optional ratios. The amount of the reoxidizing agent is typically from 1 to 10 molar equivalents, preferably from 1 to 5 molar equivalents, to Compound (5).

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step A-2-5: (7)→(8))

Compound (8) may be obtained by converting a specific hydroxy group of Compound (7) into a leaving group.

When the leaving group in Compound (8) is alkylsulfonyloxy groups or arylsulfonyloxy groups, for example, Compound (7) may be reacted with a corresponding sulfonic acid anhydride (e.g., trifluoromethanesulfonic anhydride) or sulfonyl halide (e.g., benzenesulfonyl chloride, p-toluenesulfonyl chloride, and methanesulfonyl chloride) in an inert solvent in the presence of a base to give Compound (8). The amount of sulfonic acid anhydride or sulfonyl halide is typically from 1 to 10 molar equivalents, preferably from 1 to 5 molar equivalents, to Compound (7).

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (7).

The inert solvent includes, for example, hydrocarbons, hydrocarbon halides, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step A-2-6: (8)+(2)→[I])

Compound [I] may be obtained by, for example, reacting Compound (8) with Compound (2) in an inert solvent in the presence of a base or acid. The reaction may be carried out under similar conditions to the above Step A-1-1.

(Step A-2-7: (8)→(1))

Compound (1) may be obtained by, for example, reacting Compound (8) in an inert solvent in the presence of a base. The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (8).

The inert solvent includes, for example, hydrocarbons, hydrocarbon halides, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

In the scheme, $R^7$ is trialkylsilyl; $LG^2$ is a leaving group; pa is an integer of 0 to 4; and the other symbols have the same meanings as defined above.

(Step A-3-1: (3a)→(3b))

Compound (3b) among Compound (3) may be obtained by, for example, α-aminooxylation of Compound (3a) with a nitroso compound in an inert solvent in the presence of a catalyst of proline or a derivative thereof, followed by hydrolysis in the presence of a copper (II) sulfate catalyst.

The amount of copper (II) sulfate is typically from 0.001 to 3 molar equivalents to Compound (3a).

The nitroso compound includes nitrosobenzene which may optionally have a substituent. The amount of the nitroso compound is typically from 1 to 10 molar equivalents, preferably 1 to 2 molar equivalents, to Compound (3a).

The proline or a derivative thereof includes L- or D-proline and 5-(pyrrolidin-2-yl)-1H-tetrazole. The amount of proline or a derivative thereof is typically from 0.001 to 3 molar equivalents to Compound (3a).

Scheme A-3

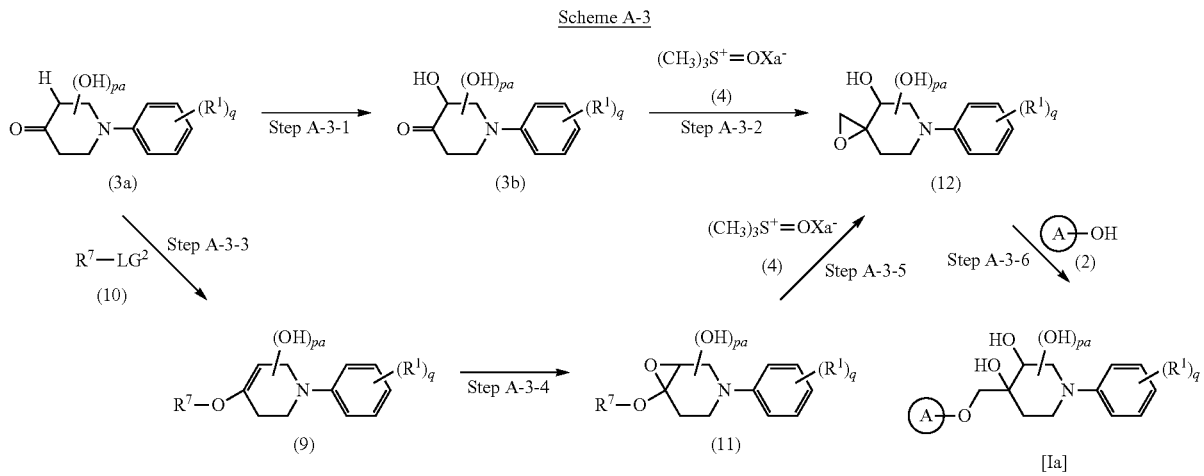

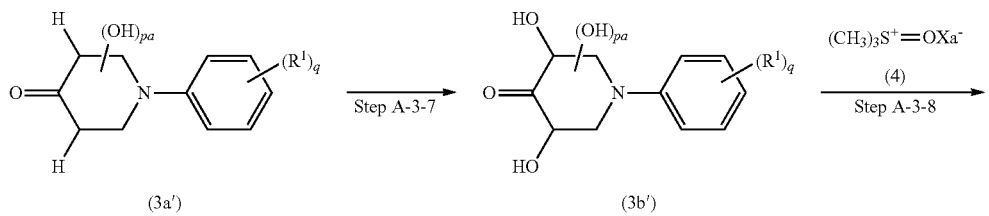

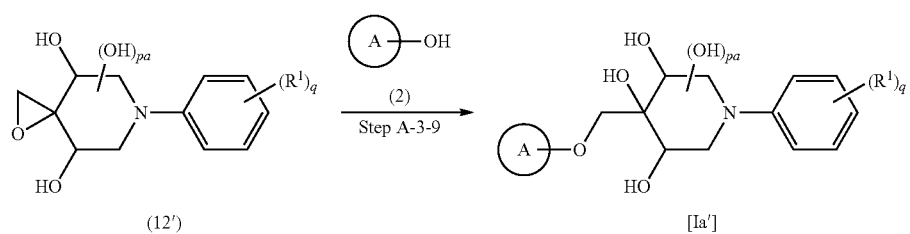

Typically, a compound of Formula (3ba):

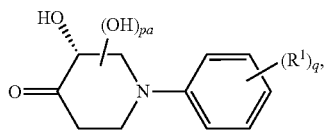

wherein each symbol has the same meaning as defined above, among Compound (3b) may be primarily obtained with L-proline or (S)-5-(pyrrolidin-2-yl)-1H-tetrazole for proline or a derivative thereof.

Typically, a compound of Formula (3bb):

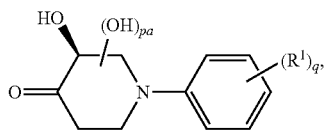

wherein each symbol has the same meaning as defined above, among Compound (3b) may be primarily obtained with D-proline or (R)-5-(pyrrolidin-2-yl)-1H-tetrazole for proline or a derivative thereof.

The inert solvent includes, for example, hydrocarbons, hydrocarbon halides, water, alcohols, ethers, amides, and sulfoxides, which may be used in combination with two or more of these agents with optional ratios.

The reaction temperature is typically from −80 to 150° C. The reaction time is typically from 0.1 to 200 hours.

(Step A-3-2: (3b)+(4)→(12))

Compound (12) may be obtained by, for example, reacting Compound (3b) with Compound (4) in an inert solvent in the presence of a base (Corey-Chaykovsky reaction). The reaction may be carried out under similar conditions to the above Step A-2-1.

(Step A-3-3: (3a)+(10)→(9))

Compound (9) may be obtained by, for example, reacting Compound (3a) with Compound (10) in an inert solvent in the presence of a base.

The amount of Compound (10) is typically from 1 to 10 molar equivalents, preferably from 1 to 5 molar equivalents, to Compound (3a).

Sodium iodide may be added, if necessary. The amount of sodium iodide is typically from 0.01 to 10 molar equivalents, preferably from 0.1 to 5 molar equivalents, to Compound (3a).

The base includes, for example, alkali metal hydroxides, alkali metal hydrides, alkali metal carbonates, alkali metal hydrogen carbonates, alkali metal phosphates, aromatic amines, tertiary amines, and metal amides, which may be used in combination with two or more of these agents with optional ratios. The amount of the base is typically from 1 to 10 molar equivalents, preferably from 1 to 5 molar equivalents, to Compound (3a).

The inert solvent includes, for example, hydrocarbons, hydrocarbon halides, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step A-3-4: (9)→(11))

Compound (11) may be obtained by, for example, reacting Compound (9) in an inert solvent in the presence of an oxidizing agent.

The oxidizing agent includes inorganic peroxides (e.g., hydrogen peroxide, sodium hypochlorite, and sodium periodate), organic peroxides (e.g., m-chloroperoxybenzoic acid, perbenzoic acid, peracetic acid, and trifluoroperacetic acid), and dioxiranes (e.g., dimethyldioxirane). The amount of the oxidizing agent is typically from 1 to 10 molar equivalents, preferably from 1 to 5 molar equivalents, to Compound (9).

A compound of Formula (11a):

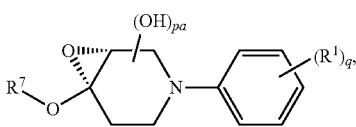

wherein each symbol has the same meaning as defined above, may be primarily obtained for Compound (11) by Shi asymmetric epoxidation with Shi epoxation catalyst (1-O, 2-O:4-O, 5-O-diisopropylidene-β-D-erythro-2,3-hexodiulo-2,6-pyranose). The amount of Shi epoxidation catalyst is typically from 0.001 to 3 molar equivalents to Compound (9).

When ketone compounds such as Shi epoxidation catalyst are used, a co-oxidant may be used instead of an oxidizing agent. The co-oxidant includes oxone (registered trade mark). The amount of the co-oxidant is typically from 1 to 10 molar equivalents, preferably from 1 to 5 molar equivalents, to Compound (9).

A base may be used, if necessary.

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (9).

An additive may be added, if necessary. The additive includes disodium ethylenediaminetetraacetate. The amount of the additive is typically from 0.0001 to 0.1 molar equivalents to Compound (9).

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step A-3-5: (11)+(4)→(12))

Compound (12) may be obtained by, for example, reacting Compound (11) with Compound (4) in an inert solvent in the presence of a base (Corey-Chaykovsky reaction). The reaction may be carried out under similar conditions to the above Step A-2-1.

(Step A-3-6: (12)+(2)→[Ia])

Compound [Ia] among Compound [I] may be obtained by, for example, reacting Compound (12) with Compound (2) in an inert solvent in the presence of a base. The reaction may be carried out under similar conditions to the above Step A-1-1.

(Step A-3-7: (3a')→(3b'))

Compound (3b') among Compound (3) may be obtained by, for example, α-aminohydroxylation of Compound (3a') with a nitroso compound in an inert solvent in the presence of a catalyst of proline or a derivative thereof, followed by hydrolysis in the presence of a copper (II) sulfate catalyst. The reaction may be carried out under similar conditions to the above Step A-3-1. The amount of the nitroso compound is typically from 2 to 10 molar equivalents, preferably from 2 to 5 molar equivalents, to Compound (3a').

(Step A-3-8: (3b')+(4)→(12'))

Compound (12') may be obtained by, for example, reacting Compound (3b') with Compound (4) in an inert solvent in the presence of a base (Corey-Chaykovsky reaction). The reaction may be carried out under similar conditions to the above Step A-2-1.

(Step A-3-9: (12')+(2)→[Ia'])

Compound [Ia'] among Compound [I] may be obtained by, for example, reacting Compound (12') with Compound (2) in an inert solvent in the presence of a base. The reaction may be carried out under similar conditions to the above Step A-1-1.

(II) chloride, tetrakis(triphenylphosphine)palladium (0), tris(dibenzylideneacetone)dipalladium (0), 1,1-bis(diphenylphosphino)ferrocenedichloropalladium (II), dichlorobis(triphenylphosphine)palladium (II), bis(tri(tert-butylphosphine))palladium (0), phenylallylchloro-[1,3-bis(diisopropylphenyl)-2-imidazole-2-ylidene]palladium (II), and phenylallylchloro-[1,3-bis(diisopropylphenyl)-2-imidazolidinylidene]palladium (II); copper catalysts such as copper (I) iodide and copper (I) oxide; rhodium catalysts such as tris(triphenylphosphine)rhodium (III) chloride; and nickel catalysts such as tetrakis(triphenylphosphine)nickel (0), which may be used in combination with two or more of these agents with optional ratios. The amount of the transition metal catalyst is typically from 0.001 to 3 molar equivalents to Compound (13).

A ligand may be added, if necessary. The ligand includes, for example, triphenylphosphine, tri(tert-butyl)phosphine, 2,2'-bis(diphenylphosphino)-1,1'-binaphthyl, 2-(dicyclohexylphosphino)-2',4',6'-triisopropyl-1,1'-biphenyl, and 4,5'-bis(diphenylphosphino)-9,9'-dimethylxanthene. The amount of the ligand is typically from 0.001 to 3 molar equivalents to Compound (13).

Scheme A-4

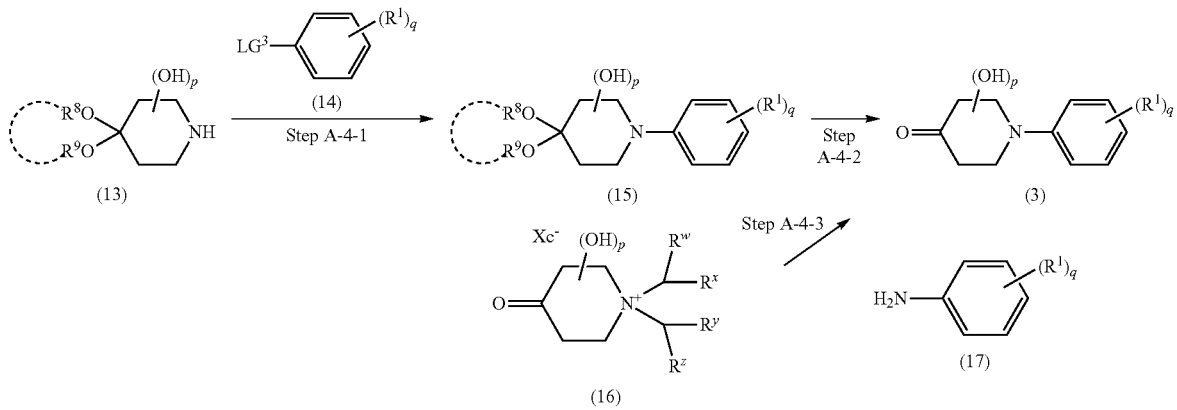

In the scheme, $R^8$ and $R^9$ are each independently alkyl, or $OR^8$ and $OR^9$ may combine together with the carbon atom to which they attach to form an acetal ring; $LG^3$ is a leaving group; $R^w$, $R^x$, $R^y$, and $R^z$ are each independently hydrogen atom, optionally substituted alkyl, optionally substituted alkenyl, optionally substituted alkoxycarbonyl, optionally substituted aryl, or carboxy; $Xc^-$ is an inert anion such as halide ion; and the other symbols have the same meanings as defined above.

(Step A-4-1: (13)+(14)→(15))

Compound (15) may be obtained by, for example, reacting Compound (13) with Compound (14) in an inert solvent in the presence of a base. The amount of Compound (14) is typically from 0.1 to 10 molar equivalents, preferably from 0.2 to 5 molar equivalents, to Compound (13).

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (13).

A transition metal catalyst may be used, if necessary.

The transition metal catalyst includes, for example, palladium catalysts such as palladium (II) acetate, palladium The inert solvent includes, for example, hydrocarbons, hydrocarbon halides, ethers, esters, ketones, alcohols, water, amides, nitriles, and sulfoxides, which may be used in combination with two or more of these agents with optional ratios.

The reaction temperature is typically from −80 to 150° C. The reaction time is typically from 0.1 to 200 hours.

(Step A-4-2: (15)→(3))

Compound (3) may be obtained by, for example, treating Compound (15) with an acid.

The acid includes, for example, inorganic acids and organic acids, which may be used in combination with two or more of these agents with optional ratios. The amount of the acid is typically from 1 molar equivalent to excess amounts to Compound (15).

Such an acid may be used for a solvent or an inert solvent may be used in addition to an acid.

The inert solvent includes, for example, hydrocarbons, hydrocarbon halides, water, alcohols, ethers, ketones, amides, and sulfoxides, which may be used in combination with two or more of these agents with optional ratios.

The reaction temperature is typically from −80 to 150° C. The reaction time is typically from 0.1 to 200 hours.

(Step A-4-3: (16)+(17)→(3))

Compound (3) may be also obtained by, for example, reacting Compound (16) with Compound (17) in an inert solvent.

The amount of Compound (17) is typically from 0.1 to 5 molar equivalents, preferably from 0.2 to 5 molar equivalents, to Compound (16).

An additive may be added, if necessary. The additive includes, for example, sodium acetate, sodium hydrogen carbonate, potassium carbonate, proline, thioureas, tertiary amines, and acetic acid. The amount of the additive is typically from 0.01 to 10 molar equivalents, preferably from 0.02 to 5 molar equivalents, to Compound (16).

The inert solvent includes, for example, water, alcohols, hydrocarbons, hydrocarbon halides, ethers, esters, ketones, amides, nitriles, and sulfoxides, which may be used in combination with two or more of these agents with optional ratios.

The reaction temperature is typically from 40 to 150° C. The reaction time is typically from 0.1 to 200 hours.

[Preparation B: General Synthetic Route 2]

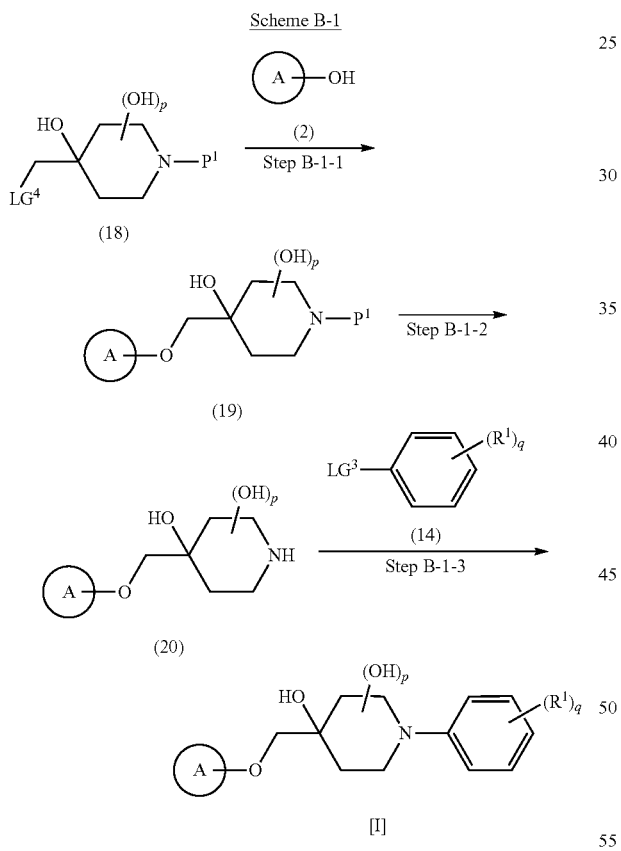

In the scheme, $LG^4$ is a leaving group; $P^1$ is a protective group of amino group; and the other symbols have the same meanings as defined above.

(Step B-1-1: (18)+(2)→(19))

Compound (19) may be obtained by, for example, reacting Compound (18) with Compound (2) in an inert solvent in the presence of a base or acid. The reaction may be carried out under similar conditions to the above Step A-1-1.

(Step B-1-2: (19)→(20))

Compound (20) may be obtained by deprotection of Compound (19).

Any known reaction may be used for the deprotection, and for example, when $P^1$ is tert-butoxycarbonyl (Boc) group, Compound (19) may be deprotected in an inert solvent or without any solvent in the presence of an acid (e.g., hydrochloric acid and trifluoroacetic acid) to give Compound (20).

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step B-1-3: (20)+(14)→[I])

Compound [I] may be obtained by, for example, reacting Compound (20) with Compound (14) in an inert solvent in the presence of a base. The reaction may be carried out under similar conditions to the above Step A-4-1.

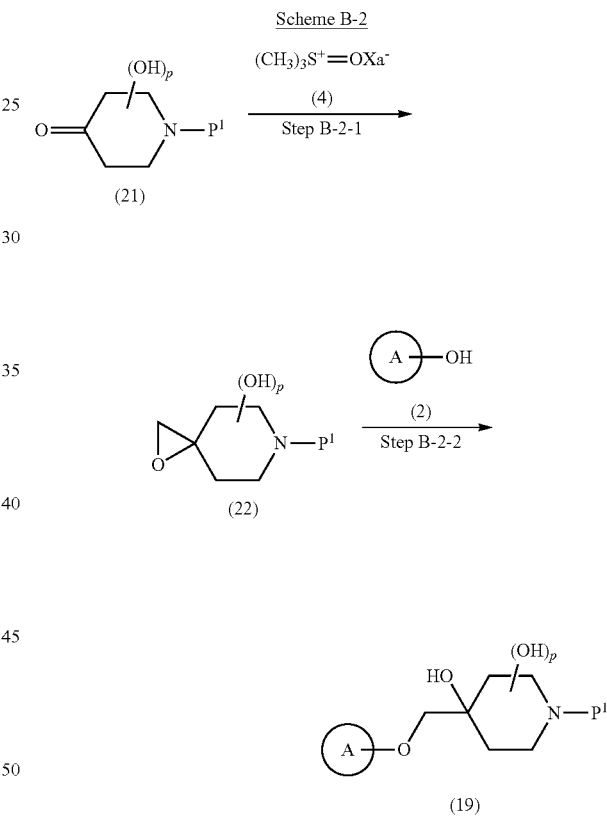

In the scheme, each symbol has the same meaning as defined above.

(Step B-2-1: (21)+(4)→(22))

Compound (22) may be obtained by, for example, reacting Compound (21) with Compound (4) in an inert solvent in the presence of a base (Corey-Chaykovsky reaction). The reaction may be carried out under similar conditions to the above Step A-2-1.

(Step B-2-2: (22)+(2)→(19))

Compound (19) may be obtained by, for example, reacting Compound (22) with Compound (2) in an inert solvent in the presence of a base or acid. The reaction may be carried out under similar conditions to the above Step A-1-1.

Scheme B-3

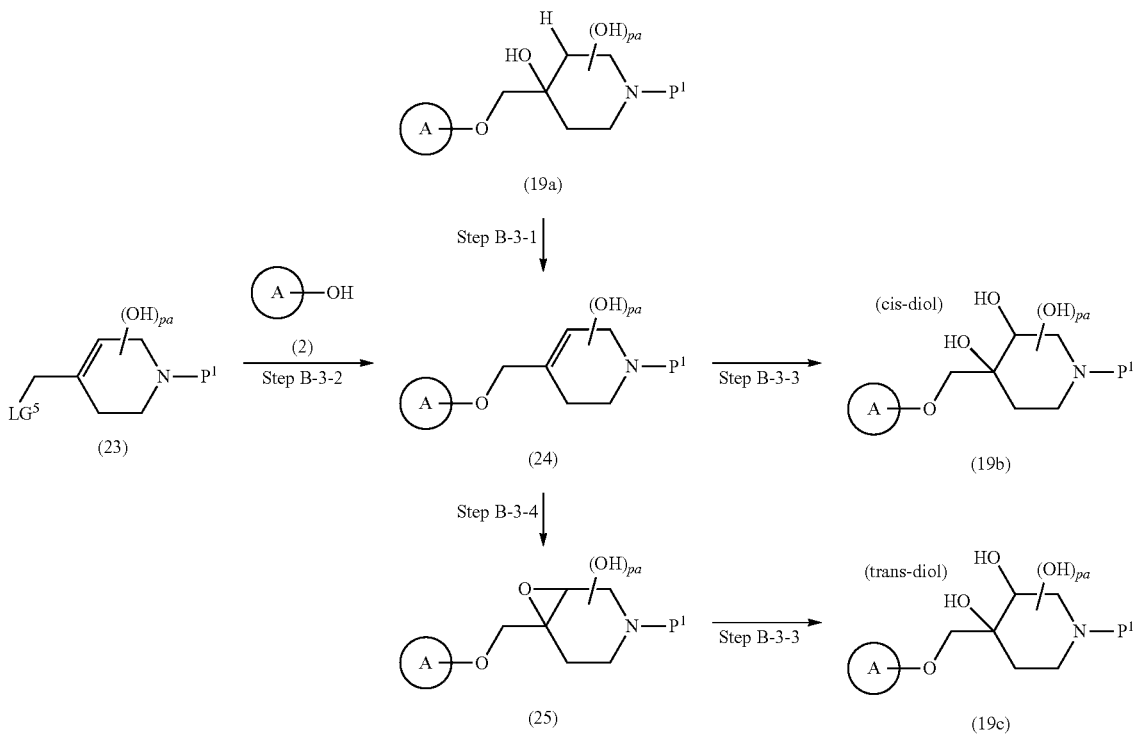

In the scheme, LG⁵ is a leaving group; and the other symbols have the same meanings as defined above.
(Step B-3-1: (19a)→(24))

Compound (24) may be obtained by, for example, converting hydroxy group of Compound (19a) into a leaving group under known methods, followed by olefination.

For example, Compound (19a) may be reacted with sulfonic acid anhydride (e.g., trifluoromethanesulfonic anhydride) or sulfonyl halide (e.g., benzenesulfonyl chloride, p-toluenesulfonyl chloride, and methanesulfonyl chloride) in an inert solvent in the presence of a base to convert hydroxy group into a leaving group, followed by elimination to give Compound (24). The amount of sulfonic acid anhydride or sulfonyl halide is typically from 1 to 10 molar equivalents, preferably from 1 to 5 molar equivalents, to Compound (19a).

The base includes, for example, alkali metal hydroxides, alkali metal hydrides, alkali metal carbonates, alkali metal hydrogen carbonates, alkali metal phosphates, aromatic amines, tertiary amines, metal amides, and metal alkoxides, which may be used in combination with two or more of these agents with optional ratios. The amount of the base is typically from 1 to 10 molar equivalents, preferably from 1 to 5 molar equivalents, to Compound (19a).

The inert solvent includes, for example, hydrocarbons, hydrocarbon halides, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.
(Step B-3-2: (23)+(2)→(24))

Compound (24) may be obtained by, for example, reacting Compound (23) with Compound (2) in an inert solvent in the presence of a base or acid. The reaction may be carried out under similar conditions to the above Step A-1-1.
(Step B-3-3: (24)→(19b))

Compound (19b) among Compound (19) may be obtained by, for example, reacting Compound (24) in an inert solvent in the presence of osmium tetraoxide and a reoxidizing agent.

The amount of osmium tetraoxide is typically from 0.01 to 0.5 molar equivalents to Compound (24). Potassium osmate (K₂OsO₂(OH)₄) may be used instead of osmium tetraoxide. Osmium tetraoxide may be also used in the form of an immobilized catalyst where osmium tetraoxide is supported on a solvent-resistant polymer. The immobilized catalyst includes "Osmium Oxide, Immobilized Catalyst I (Os IC-I)" (trade name) (Wako pure chemical industries).

The reoxidizing agent includes, for example, N-methylmorpholine oxide, trimethylamine oxide, tert-butyl hydroperoxide, and potassium hexacyanoferrate (K₃Fe(CN)₆), which may be used in combination with two or more of these agents with optional ratios. The amount of the reoxidizing agent is typically from 1 to 10 molar equivalents, preferably from 1 to 5 molar equivalents, to Compound (24).

Sharpless asymmetric dihydroxylation may be also carried out with an asymmetric amine ligand.

The asymmetric amine ligand includes, for example, hydroquinine ethers such as hydroquinine anthraquinone-1,4-diyl diether [(DHQ)₂AQN], hydroquinine 2,5-diphenyl-4,6-pyrimidinediyl diether [(DHQ)₂PYR], and hydroquinine 1,4-phthalazinediyl diether [(DHQ)₂PHAL]; and hydroquinidine ethers such as hydroquinidine anthraquinone-1,4-diyl diether [(DHQD)₂AQN], hydroquinidine 2,5-diphenyl-4,6-pyrimidinediyl diether [(DHQD)₂PYR], and hydroquinidine 1,4-phthalazinediyl diether [(DHQD)₂PHAL]. The amount of the asymmetric amine ligand is typically from 0.001 to 1 molar equivalent to Compound (24).

For example, when hydroquinine ethers are used, typically, a compound of Formula (19ba):

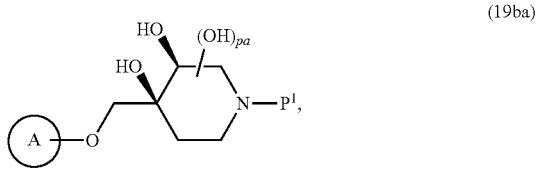

wherein each symbol has the same meaning as defined above, may be primarily obtained for Compound (19b).

For example, when hydroquinidine ethers are used, typically, a compound of Formula (19bb):

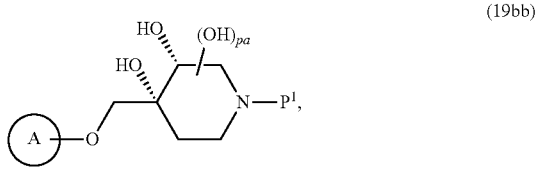

wherein each symbol has the same meaning as defined above, may be primarily obtained for Compound (19b).

A base may be added, if necessary. The base includes alkali metal carbonates, alkali metal hydrogen carbonates, alkali metal hydroxides, aromatic amines, and tertiary amines. The amount of the base is typically from 0.001 to 3 molar equivalents to Compound (24).

An additive may be added, if necessary. The additive includes methanesulfonamide. The amount of the additive is typically from 0.001 to 3 molar equivalents to Compound (24).

A commercially available reagent kit such as AD-mix-α (containing $K_2OsO_2(OH)_4$, $(DHQ)_2PHAL$, $K_3Fe(CN)_6$, and $K_2CO_3$) and AD-mix-β ($K_2OsO_2(OH)_4$, $(DHQD)_2PHAL$, $K_3Fe(CN)_6$, and $K_2CO_3$) may be used.

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

(Step B-3-4: (24)→(25))

Compound (25) may be obtained by, for example, reacting Compound (24) in an inert solvent in the presence of an oxidizing agent. The reaction may be carried out under similar conditions to the above Step A-3-4.

(Step B-3-5: (25)→(19c))

Compound (19c) among Compound (19) may be obtained by, for example, treating Compound (25) with an acid.

The acid includes, for example, inorganic acids such as hydrochloric acid, sulfuric acid, nitric acid, hydrobromic acid, and phosphoric acid; and organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid, and 10-camphorsulfonic acid, which may be used in combination with two or more of these agents with optional ratios. The amount of the acid is typically from 1 molar equivalent to excess amounts to Compound (25).

Such an acid may be used for a solvent, or an inert solvent may be used in addition to an acid.

The inert solvent includes, for example, hydrocarbons, hydrocarbon halides, water, alcohols, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

[Preparation C: Various Derivatization]

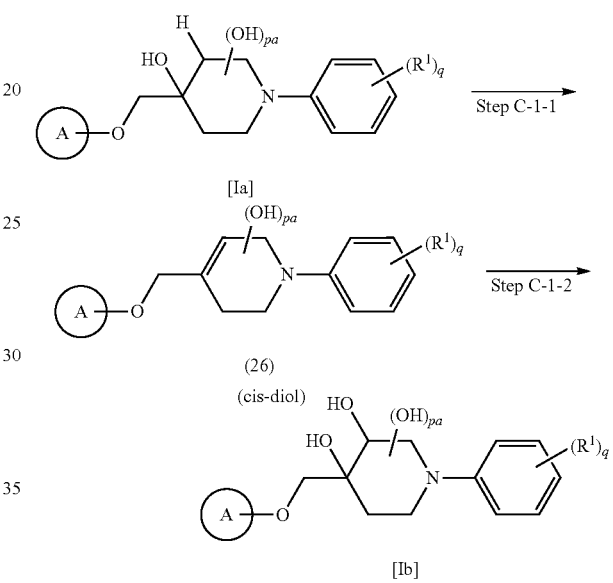

In the scheme, each symbol has the same meaning as defined above.

(Step C-1-1: [Ia]→(26))

Compound (26) may be obtained by, for example, converting hydroxy group of Compound [Ia] into a leaving group under known methods, followed by olefination. The reaction may be carried out under similar conditions to the above Step B-3-1.

(Step C-1-2: (26)→[Ib])

Compound [Ib] among Compound [I] may be obtained by, for example, reacting Compound (26) in an inert solvent in the presence of osmium tetraoxide and a reoxidizing agent. The reaction may be carried out under similar conditions to the above Step B-3-3.

As is the case with the above Step B-3-3, for example, when hydroquinine ethers are used for a catalyst, typically, a compound of Formula [Iba]:

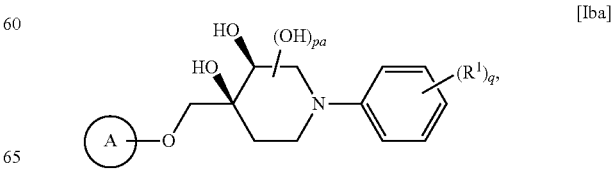

wherein each symbol has the same meaning as defined above, may be primarily obtained for Compound [Ib].

For example, when hydroquinidine ethers are used, typically, a compound of Formula [Ibb]:

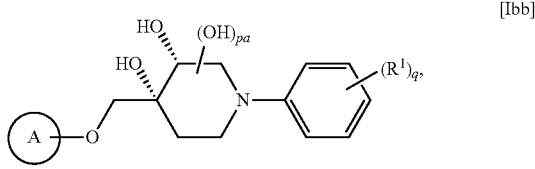

[Ibb]

wherein each symbol has the same meaning as defined above, may be primarily obtained for Compound [Ib].

Scheme C-2

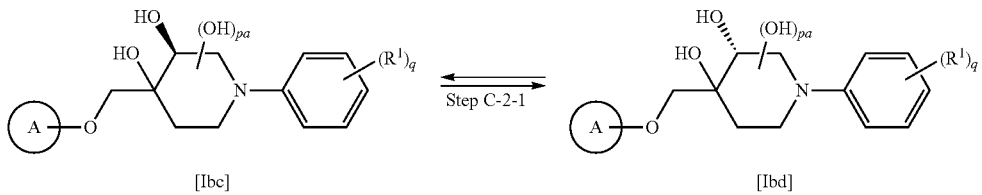

In the scheme, each symbol has the same meaning as defined above.

(Step C-2-1: [Ibc]←→[Ibd])

Compound [Ibd] among Compound [I] may be obtained from Compound [Ibc] by Mitsunobu reaction, followed by hydrolysis.

The Mitsunobu reaction may be carried out by, for example, reacting Compound [Ibc] with carboxylic acid in an inert solvent in the presence of azodicarboxylic acid ester and phosphine.

The azodicarboxylic acid ester includes, for example, methyl azodicarboxylate, ethyl azodicarboxylate, diisopropyl azodicarboxylate, dibenzyl azodicarboxylate, di-tert-butyl azodicarboxylate, and 1,1'-(azodicarbonyl)dipiperidine. The amount of the azodicarboxylic acid ester is typically from 0.1 to 10 molar equivalents, preferably from 0.2 to 5 molar equivalents, to Compound [Ibc].

The phosphine includes, for example, triphenylphosphine, tricyclohexylphosphine, and tributylphosphine. The amount of phosphine is typically from 0.1 to 10 molar equivalents, preferably from 0.2 to 5 molar equivalents, to Compound [Ibc].

The carboxylic acid includes benzoic acid, p-nitrobenzoic acid, and p-methoxybenzoic acid. The use of carboxylic acid is typically from 0.1 to 10 molar equivalents, preferably from 0.2 to 5 molar equivalents, to Compound [Ibc].

The hydrolysis after Mitsunobu reaction may be carried out, for example, under reaction in an inert solvent in the presence of a base.

The base includes, for example, alkali metal hydroxides, alkali metal hydrides, alkali metal carbonates, alkali metal phosphates, and metal amides, which may be used in combination with two or more of these agents with optional ratios. The use of the base is typically from 1 molar equivalent to excess amounts to Compound [Ibc].

The inert solvent includes, for example, hydrocarbons, hydrocarbon halides, ethers, esters, ketones, amides, nitriles, and sulfoxides, which may be used in combination with two or more of these agents with optional ratios.

The reaction temperature is typically from −80 to 150° C. The reaction time is typically from 0.1 to 200 hours.

Compound [Ibc] may be obtained from Compound [Ibd] in a similar manner.

Compound [I] in the present invention can be prepared by any synthetic processes described in the above respective steps or processes in accordance therewith. Starting materials, intermediates, and their starting materials in the respective steps can be prepared in view of any synthetic processes described in the above respective steps or processes in accordance therewith, any synthetic processes described in Reference Examples and Examples herein or processes in accordance therewith, or any processes known or publicly known at the filing date of the present application. When these are commercially available, commercialized products may be directly used. Compound [I] in the present invention may also be prepared, if necessary, with modifications of the preparations, types, numbers, and/or positions of substituents in the starting materials and/or intermediates, or the reaction conditions herein, in view of publicly known methods.

In the preparation of Compound [I] in the present invention, the obtained compounds may be further derivatized, if necessary, by subjecting the compounds to any known reactions such as various alkylation, acylation, amidation, esterification, etherification, halogenation, hydroxylation, amination, aryl coupling, condensation including carbon extension reaction, addition, substitution, oxidation, reduction, dehydration, and hydrolysis in addition to the above respective steps.

Any functional groups of starting materials and intermediates in the above respective steps may be protected with appropriate protective groups before a particular reaction and the protective groups may be deprotected after the particular reaction, if necessary, using any known methods (e.g., methods described in P. G. M. Wuts and T. W. Greene, "Greene's Protective Groups in Organic Synthesis" (4th ed., 2006)).

Any intermediates and final products in the above respective steps may be directly used in subsequent steps, or may be isolated and purified after completion of reactions. For example, these compounds may be isolated and purified by cooling reaction mixtures, followed by isolation procedures such as filtration, concentration, and extraction, to isolate crude reaction products, which are then subject to general purification procedures such as column chromatography and recrystallization.

Any starting materials, intermediates, and final products in the above respective steps as well as Compound [I] in the present invention include corresponding compounds in the form of a solvate wherein a solvent is added thereto (e.g., hydrates and ethanolate).

Any starting materials, intermediates, and final products as well as Compound [I] in the present invention include corresponding geometric isomers, stereoisomers, optical isomers, and tautomers. These various isomers can be separated by any known separation methods. For example, a racemic compound can be separated to a sterically pure isomer by common optical resolution (e.g., optical resolution by crystallization and direct optical resolution by chromatography). An optically active compound can also be prepared with an appropriate optically active starting material. Any prepared compounds may be isolated as chemically stable tautomers thereof.

Any starting materials and final products in the above respective steps may be used in an appropriate salt form. Examples of such a salt include those exemplified below for a salt of Compound [I] in the present invention.

When a compound obtained in each step or a commercially available product is in a free form, it can be converted to a corresponding desired salt by a known method per se. When a compound obtained in each step or a commercially available product is in a salt form, it can be converted to a corresponding free form or another desired salt form by a known method per se.

Compound [I] in the present invention includes a pharmaceutically acceptable salt form thereof.

Among Compound [I] in the present invention, any compounds with one or more basic groups may form a salt with any common pharmaceutically acceptable acids. Examples of the acids include inorganic acids such as hydrochloric acid, hydrobromic acid, nitric acid, sulfuric acid, and phosphoric acid; and organic acids such as methanesulfonic acid, p-toluenesulfonic acid, acetic acid, citric acid, tartaric acid, maleic acid, fumaric acid, malic acid, and lactic acid.

Among Compound [I] in the present invention, any compounds with one or more acidic groups may form a salt with any common pharmaceutically acceptable base. Examples of such a base include inorganic bases such as sodium hydroxide, potassium hydroxide, calcium hydroxide, sodium carbonate, potassium carbonate, sodium hydrogencarbonate, and potassium hydrogencarbonate; organic bases such as methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, and choline; and ammonium salts.

Compound [I] in the present invention may also form a salt with amino acids such as lysine, arginine, asparagine acid, and glutamic acid.

Compound [I] in the present invention includes any compounds wherein one or more atoms are replaced with one or more isotopic atoms. Examples of the isotopic atoms include deuterium ($^2$H), tritium ($^3$H), $^{13}$C, $^{14}$N, and $^{18}$O.

Compound [I] in the present invention also includes a prodrug form thereof. The "prodrug" refers to any compounds that are chemically or metabolically converted into Compound [I] as the active metabolite under physiological conditions after administration in vivo, and includes those which a part of substituents of Compound [I] is chemically modified. Prodrugs may be utilized for several purposes including enhancement of water solubility, improvement of bioavailability, reduction of side effects, and drug selectivity against target sites. Substituents for modification to form a prodrug include any reactive functional groups such as —OH, —COOH, and amino. Such modifications of functional groups may be optionally selected from the "substituents" used herein.

A medical formulation (referred to as a "pharmaceutical composition" hereinafter) comprising as the active ingredient Compound [I] in the present invention is illustrated as below.

The medical formulation is a formulation where Compound [I] in the present invention is formulated into the form of a common medical formulation, which is prepared with Compound [I] in the present invention and a pharmaceutically acceptable carrier. Such a carrier includes diluents and excipients such as fillers, bulking agents, binders, humidity adding agents, disintegrants, surface active agents, and lubricants commonly used.

Such a medical formulation may be selected from various forms depending on therapeutic purposes, and examples of the formulation include, for example, tablets, pills, powders, liquids, suspensions, emulsions, granules, capsules, suppositories, and injections (such as liquids and suspensions).

Any publicly known carriers may be widely used for a carrier used in formulating tablets, and include, for example, excipients such as lactose, sucrose, sodium chloride, glucose, urea, starch, calcium carbonate, kaolin, and crystalline cellulose; binders such as water, ethanol, propanol, simple syrup, glucose solution, starch solution, gelatin solution, carboxymethyl cellulose, shellac, methyl cellulose, potassium phosphate, and polyvinylpyrrolidone; disintegrants such as dry starch, sodium alginate, agar powders, laminaran powders, sodium hydrogencarbonate, calcium carbonate, polyoxyethylene sorbitan fatty acid esters, sodium lauryl sulfate, monoglyceride stearate, starch, and lactose; disintegration suppressants such as sucrose, stearin, cacao butter, and hydrogenated oil; absorption promoters such as quaternary ammonium salt and sodium lauryl sulfate; humectants such as glycerin and starch; adsorbents such as starch, lactose, kaolin, bentonite, and colloidal silica; and lubricants such as purified talc, stearate, boric acid powders, and polyethylene glycol.

Tablets may be also formulated, if needed, as tablets with common coatings including, for example, sugar-coated tablets, gelatin-encapsulated tablets, enteric coated tablets, film-coated tablets, double-coated tablets, and multi-layered tablets.

Any publicly known carriers may be widely used for a carrier used in formulating pills, and include, for example, excipients such as glucose, lactose, starch, cacao butter, hydrogenated vegetable oil, kaolin, and talc; binders such as gum arabic powders, tragacanth powders, gelatin, and ethanol; and disintegrants such as laminaran and agar.

Any publicly known carriers may be widely used for a carrier used in formulating suppositories, and include, for example, polyethylene glycol, cacao butter, higher alcohol, esters of higher alcohol, gelatin, and semisynthetic glyceride.

When injections are formulated, liquids, emulsions, and suspensions are preferably sterilized and isotonic with blood. Any publicly known diluents may be widely used for a diluent used in formulating these liquids, emulsions, and suspensions, and include, for example, water, ethanol, propylene glycol, ethoxylated isostearyl alcohol, polyoxylated isostearyl alcohol, and polyoxyethylene sorbitan fatty acid esters. In those cases, medical formulations may comprise a sufficient amount of salt, glucose, or glycerin to prepare an isotonic solution, and may also comprise common solubilizing agents, buffering agents, soothing agents, and the like, and if necessary, colorants, preserving agents, perfumes, flavoring agents, sweetening agents, and other medicinal products.

The amount of Compound [I] in the present invention contained in a medical formulation is not limited and may be optionally adjusted within a broad range of amounts; it is preferable that a medical formulation typically comprises 1 to 70% by weight of Compound [I] in the present invention.

A method of administering a medical formulation in the present invention is not limited and the medical formulation may be administered with a method depending on various dosage forms, ages, genders, and disease states of patients, and other conditions. For example, tablets, pills, liquids, suspensions, emulsions, granules, and capsules may be orally administered. Injections may be intravenously administered solely or in combination with a common replacement fluid such as glucose and amino acid, and if needed, may be solely administered intramuscularly, intradermally, subcutaneously, or intraperitoneally. Suppositories may be rectally administered.

A dosage amount of the medical formulation may be optionally adjusted depending on dosage regimens, ages, genders, and the extent of diseases of patients, and other conditions; the medical formulation may be typically administered in 0.01 to 100 mg/kg, preferably 0.1 to 50 mg/kg, of body weight per day in a single dose or multiple doses.

The dosage amount may vary on the basis of various conditions, and dosage amounts below the above range may be sufficient in some cases and dosage amounts beyond the range may be necessary in other cases.

Compound [I] in the present invention may be specifically effective against, particularly, Mycobacteria such as *Mycobacterium* (*M.*) *tuberculosis*, including *M. tuberculosis* complex and non-tuberculosis mycobacteria, and may also have potent activity against multidrug-resistant tuberculosis bacteria. Compound [I] may show antibacterial activity not only in vitro but also in vivo in oral administration because it successfully distributes in lung tissues which are primarily infected organs. Compound [I] in the present invention may, therefore, be useful for a medicinal agent for diagnosing, preventing, and/or treating tuberculosis. The term "tuberculosis" herein includes primary tuberculosis, secondary tuberculosis, pulmonary tuberculosis, and extrapulmonary tuberculosis (such as meningitis, peritonitis, renal tuberculosis, adrenal tuberculosis, bone tuberculosis, joint tuberculosis, intestinal tuberculosis, cutaneous tuberculosis, laryngeal tuberculosis, and lymph node tuberculosis).

Compound [I] in the present invention does not substantially induce diarrhea as seen in known antibacterial agents with a broad spectrum against common bacteria such as gram-positive bacteria and gram-negative bacteria, and may become a medicinal substance that allows for a long-term administration.

Compound [I] in the present invention is effective for intracellular parasitic bacteria such as human-origin tuberculosis bacteria which is parasitic in macrophage and has stronger bactericidal activity in a lower concentration than existing antitubercular agents in a bactericidal test. It is, therefore, expected that the relapse rate in tuberculosis is reduced, which eventually allows for a short-term chemotherapy.

Compound [I] in the present invention shows lower toxicity than existing drugs, and application to long-term use in the treatment for latent tuberculosis is also expected.

EXAMPLES

The present invention is also described in more detail with reference to Test Examples, Reference Examples, and Examples as below, but is not limited thereto. These examples may be modified without departing from the scope of the invention.

The following abbreviations may be used herein.
REX: Reference Example number
EX: Example number
STR: structural formula (In formulae, the structure with "Chiral" refers to an absolute configuration.)
RProp: Preparation (The number means that the compound was prepared from corresponding starting materials in a similar manner to a Reference Example compound with the number as a Reference Example number.)
Prop: Preparation (The number means that the compound was prepared from corresponding starting materials in a similar manner to an Example compound with the number as an Example number.)
Data: physical data (NMR1: δ (ppm) in $^1$H-NMR in dimethyl sulfoxide-$d_6$; NMR2: δ (ppm) in $^1$H-NMR in $CDCl_3$)
Ph: phenyl
9-BBN: 9-borabicyclo[3.3.1]nonane
n-BuLi: n-butyllithium
CDI: 1,1'-carbonyldiimidazole
DBU: 1,8-diazabicyclo[5.4.0]-7-undecene
DCC: dicyclohexylcarbodiimide
DEAD: diethyl azodicarboxylate
DIBAL: diisobutylaluminum hydride
DIBOC: di-t-butyl dicarbonate
DIPEA: diisopropylethylamine
DMAP: 4-(dimethylamino)pyridine
DPPA: diphenylphosphoryl azide
HOBt: 1-hydroxybenzotriazole
KOtBu: potassium t-butoxide
KOH: potassium hydroxide
LAH: lithium aluminum hydride
LDA: lithium diisopropylamide
LHMDS: lithium hexamethyldisilazide
LiOH: lithium hydroxide
MCPBA: m-chloroperoxybenzoic acid
NaH: sodium hydride
NaOH: sodium hydroxide
Pd/C: palladium on carbon
PEG: polyethylene glycol
TEA: triethylamine
TFA: trifluoroacetic acid
WSC: 3-ethyl-1-(3-dimethylaminopropyl)carbodiimide
ZCl: benzyl chloroformate
DCE: 1,2-dichloroethane
DME: dimethoxyethane
DMF: N,N-dimethylformamide
DMSO: dimethyl sulfoxide
AcOEt: ethyl acetate
EtOH: ethanol
IPA: 2-propanol
MeCN: acetonitrile
MeOH: methanol
MEK: 2-butanone
NMP: N-methylpyrrolidone
THF: tetrahydrofuran
DCM: dichloromethane
AcOH: acetic acid
HCl: hydrochloric acid
PPTS: pyridinium p-toluenesulfonate
$BBr_3$: boron tribromide
$Et_2O$: diethyl ether
Hexane: n-hexane
IPE: diisopropyl ether
NaOtBu: sodium t-butoxide DHP: 3,4-dihydro-2H-pyrane
NCS: N-chlorosuccinimide
DMA: N,N-dimethylacetamide
$K_3PO_4$: tripotassium phosphate
$Cs_2CO_3$: cesium carbonate
$K_2CO_3$: potassium carbonate
$NaBH_4$: sodium borohydride
$KHCO_3$: potassium hydrogen carbonate
$NaHCO_3$: sodium hydrogen carbonate
AcONa: sodium acetate The "room temperature" in the Examples below basically refers to from about 10° C. to about 35° C. The ratios in mixed solvents refer to the volume ratio unless otherwise specified. % refers to % by weight unless otherwise specified.

$^1$H NMR (proton nuclear magnetic resonance spectrum) was determined at room temperature by Fourier transform NMR (any one of Bruker AVANCE 300 (300 MHz), Bruker AVANCE 500 (500 MHz), Bruker AVANCE III 400 (400 MHz), and Bruker AVANCE III 500 (500 MHz)).

In silica gel column chromatography, aminopropylsilane-bonded silica gels were used when the term "basic" is described.

Absolute configurations of compounds were determined by known X-ray crystallography (e.g., Shigeru Ooba and Shigenobu Yano, "Kagakusha no tame no Kiso-Koza 12 X-ray crystallography" (1st ed., 1999)) or estimated from the empirical rules of Shi asymmetric epoxidation (Waldemar Adam, Rainer T. Fell, Chantu R. Saha-Moller and Cong-Gui Zhao: Tetrahedron: Asymmetry 1998, 9, 397-401. Yuanming Zhu, Yong Tu, Hongwu Yu, Yian Shi: Tetrahedron Lett. 1988, 29, 2437-2440).

Compound [I] in the present invention was evaluated on pharmacological activity according to the following Test Examples.

Test Example

Antibacterial Test (Agar Plate Dilution Method)

The minimum inhibitory concentrations against Mycobacteria tuberculosis (*M. tuberculosis* H37Rv and *M. tuberculosis* Kurono) were determined with 7H11 media (BBL) for the test compounds as shown in the table below. The bacterial strains were previously cultured on 7H9 media (BBL), cryopreserved at −80° C., and viable bacterial counts were calculated. The preserved bacterial solution was used to prepare a bacterial solution with about $10^6$ CFU/mL of the final viable bacterial count. About 5 μL of this bacterial solution was inoculated into the 7H11 agar medium containing a test compound. After incubation at 37° C. for days, the minimum inhibitory concentration was determined. The minimum inhibitory concentrations against Mycobacteria tuberculosis were determined as 3.13 μg/mL or below for the following Example compounds:
Ex 1, 6, 9, 11, 17, 23, 24, 28, 32, 34, 41, 44, 47, 50, 51, 53, 62, 65, 66, 68, 71, 76, 79, 80, 84, 90, 92, 95, 98, 101, 105, 108, 111, 113, 117, 120, 122, 127, 131, 133, 135, 140, 141, 145, 146, 147.

REFERENCE EXAMPLE

Reference Example 1

A mixture of salicylaldehyde (8.73 mL), acetone (150 mL), $K_2CO_3$ (12.45 g), 4-methoxybenzyl chloride (13.3 mL), and sodium iodide (13.5 g) was stirred overnight under heating to reflux. The reaction solution was filtered through Celite, and the filtrate was concentrated under reduced pressure. The residue was dissolved in AcOEt, dried over anhydrous sodium sulfate, and then filtered. The filtrate was concentrated under reduced pressure. The residue was washed with $Et_2O$/Hexane to give 2-[(4-methoxyphenyl)methoxy]benzaldehyde (14.0 g).

Reference Example 2

A mixture of 2-[(4-methoxyphenyl)methoxy]benzaldehyde (10.0 g), 2-amino-2-methylpropane (8.67 mL), and MeOH (80 mL) was stirred at room temperature overnight. To the reaction was added $NaBH_4$ (2.34 g) at 0° C., and the mixture was stirred at the same temperature for 1 hour. Water was added to the reaction solution, and the mixture was concentrated under reduced pressure. Water was added to the residue, and the mixture was extracted with AcOEt and washed with brine. The organic layer was dried over anhydrous sodium sulfate, and then filtered. The filtrate was concentrated under reduced pressure. The residue was purified by basic silica gel column chromatography (DCM/AcOEt) to give N-[[2-[(4-methoxyphenyl)methoxy]phenyl]methyl]-2-methylpropane-2-amine (11.4 g).

Reference Example 3

To a solution of triphosgene (3.0 g) in DCM (70 mL) were added dropwise N-[[2-[(4-methoxyphenyl)methoxy]phenyl]methyl]-2-methylpropane-2-amine (7.57 g) and TEA (11.8 mL) at 0° C., and the mixture was stirred at room temperature for 10 minutes. The reaction solution was concentrated under reduced pressure, and the residue was dissolved in MeCN (35 mL). Then, thereto was added potassium ethylxanthate (3.44 g) at room temperature, and the mixture was stirred at the same temperature for 15 minutes. The reaction solution was concentrated under reduced pressure, and water was added to the residue. The mixture was extracted with AcOEt and washed with water. The organic layer was dried over anhydrous sodium sulfate, and then filtered. The filtrate was concentrated under reduced pressure. The residue was purified by silica gel column chromatography (DCM/AcOEt) to give O-ethyl [tert-butyl-[[2-[(4-methoxyphenyl)methoxy]phenyl]methyl]carbamoyl]sulfanylmethanethioate (8.1 g).

Reference Example 4

A solution of O-ethyl [tert-butyl-[[2-[(4-methoxyphenyl)methoxy]phenyl]methyl]carbamoyl]sulfanylmethanethioate (3.5 g) in DCE (40 mL) was added to lauroyl peroxide (3.74 g) in 4 divided portions at room temperature with stirring. After 4 hours, the reaction solution was concentrated under reduced pressure, and then to the residue was added MeCN (70 mL). The mixture was stirred at room temperature for 10 minutes. The precipitate was filtered, and the filtrate was concentrated under reduced pressure. The residue was purified by silica gel column chromatography (Hexane/AcOEt) to give 2-tert-butyl-4-[(4-methoxyphenyl)methoxy]-3H-isoindol-1-one (1.0 g).

Reference Example 5

A solution of 2-tert-butyl-4-[(4-methoxyphenyl)methoxy]-3H-isoindol-1-one (0.96 g) in TFA (10 mL) was stirred for 30 hours under heating to reflux. The reaction solution was concentrated under reduced pressure and then azeotroped with toluene to remove solvent. The residue was purified by silica gel column chromatography (DCM/MeOH) to give 4-hydroxy-2,3-dihydroisoindol-1-one (0.33 g) for a high polarity product.

Reference Example 6

2-tert-Butyl-4-hydroxy-3H-isoindol-1-one (0.05 g) was obtained for a low polarity product of Reference Example 5.

Reference Example 12

To a solution of 1-methoxy-5H-phenanthridin-6-one (140 mg) in DCM (2 mL) was added $BBr_3$ (1 mol/mL DCM solution) (1.24 mL) at 0° C., and the mixture was stirred at room temperature for 4 hours. The reaction solution was concentrated under reduced pressure, and then water was added to the residue. The precipitate was filtered to give 1-hydroxy-5H-phenanthridin-6-one (0.13 g).

Reference Example 13

To a suspension of 3-phenylmethoxybenzene-1,2-diamine (7.70 g) in EtOH (40 mL)/water (80 mL) was added ethyl glyoxylate (47% toluene solution) (7.84 mL), and the mixture was stirred at room temperature overnight. Water was added to the reaction solution, and the precipitate was filtered and then washed with DCM (50 mL) to give 5-phenylmethoxy-1H-quinoxalin-2-one (3.97 g).

Reference Example 14

A solution of 5-phenylmethoxy-1H-quinoxalin-2-one (3.85 g) in phosphoryl chloride (20 mL) was stirred at 60° C. for 1.5 hours. The reaction solution was concentrated under reduced pressure, and to the residue were added DCM and ice. The mixture was neutralized with aqueous saturated $NaHCO_3$ solution, and then extracted with DCM and washed with brine. The organic layer was dried over anhydrous sodium sulfate, and then filtered. The filtrate was concentrated under reduced pressure to give 2-chloro-5-phenylmethoxyquinoxaline (3.00 g).

Reference Example 15

To a solution of 2-chloro-5-phenylmethoxyquinoxaline (3.00 g) in DMF (30 mL) was added dropwise sodium methoxide (5 mol/mL methanol solution) (6.65 mL), and the mixture was stirred at room temperature for 3 hours. Water (150 mL) was added to the reaction solution, and the mixture was stirred. Then, the precipitate was filtered to give 2-methoxy-5-phenylmethoxyquinoxaline (2.81 g).

Reference Example 16

To a suspension of 2-methoxy-5-phenylmethoxyquinoxaline (2.81 g) in EtOH (28 mL)/AcOEt (28 mL) was added 10% Pd/C (50% wet) (0.28 g) under nitrogen atmosphere, and then the reaction system was replaced with hydrogen and stirred at room temperature for 30 minutes. Insoluble substances were filtered, and the filtrate was concentrated under reduced pressure. The residue was purified by basic silica gel column chromatography (AcOEt) to give 2-methoxyquinoxalin-5-ol (1.71 g).

Reference Example 17

To a solution of 2-amino-3-nitrophenol (25.0 g) in DMF (65 ml) was added $K_2CO_3$ (26.9 g) under argon atmosphere, and the mixture was stirred at room temperature for 1 hour. Then, to the reaction solution was added dropwise methyl iodide (12.2 mL), and the mixture was stirred at room temperature for 48 hours. Water was added to the reaction solution, and the solution was extracted with AcOEt. The extract was washed with water and brine, dried over anhydrous sodium sulfate, and then filtered. The filtrate was concentrated under reduced pressure. The residue was dissolved in DCM, and basic silica gel (150 g) was added thereto. The mixture was stirred. Insoluble substances were filtered, and then the filtrate was concentrated under reduced pressure. The residue was washed with Hexane to give 2-methoxy-6-nitroaniline (23.6 g).

Reference Example 18

To a solution of 2-methoxy-6-nitroaniline (3.0 g) in EtOH (30 mL) was added 10% Pd/C (50% wet) (0.3 g) under nitrogen atmosphere, and then the reaction system was replaced with hydrogen and stirred at room temperature for 3 hours. Insoluble substances were filtered, and then the filtrate was concentrated under reduced pressure to give 3-methoxybenzene-1,2-diamine (2.5 g).

Reference Example 19

To a 40% aqueous sodium hydrogen sulfite solution (10 mL) was added 4-fluorobenzaldehyde (1.45 mL), and the mixture was stirred at room temperature for 1 hour. To the reaction solution was added a solution of 3-methoxybenzene-1,2-diamine (1.7 g) in EtOH (45 mL), and the mixture was stirred for 2 hours under heating to reflux. Water was added to the reaction solution, and the mixture was stirred at room temperature for 10 minutes. Then, the precipitate was filtered and the resulted solid was washed with $Et_2O$ to give 2-(4-fluorophenyl)-4-methoxy-1H-benzimidazole (2.38 g).

Reference Example 20

To 2-(4-fluorophenyl)-4-methoxy-1H-benzimidazole (2.0 g) were added 48% aqueous hydrobromic acid solution (30 mL) and AcOH (5 mL), and the mixture was stirred for 5 hours under heating to reflux. The reaction solution was concentrated under reduced pressure, and water was added to the residue. The precipitate was filtered. Aqueous $NaHCO_3$ solution was added to the resulted precipitate, and the mixture was extracted with AcOEt, and then washed with water. The organic layer was dried over anhydrous sodium sulfate, and then filtered, and the filtrate was concentrated under reduced pressure. The residue was washed with AcOEt to give 2-(4-fluorophenyl)-1H-benzimidazol-4-ol (1.46 g).

Reference Example 21

A mixture of 8-fluoro-5-hydroxy-3,4-dihydro-1H-quinolin-2-one (25 g), DCM (500 mL), DHP (37.8 mL), and PPTS (6.94 g) was stirred at room temperature for 42 hours. Aqueous $NaHCO_3$ solution was added to the reaction solution, and the mixture was extracted with DCM. The organic layer was dried over anhydrous sodium sulfate, and then filtered. The filtrate was concentrated under reduced pressure. The residue was washed with $Et_2O$/Hexane to give 8-fluoro-5-(oxan-2-yloxy)-3,4-dihydro-1H-quinolin-2-one (36.1 g).

Reference Example 22

To a solution of LAH (0.43 g) in THF (80 mL) was added 8-fluoro-5-(oxan-2-yloxy)-3,4-dihydro-1H-quinolin-2-one (3.0 g) at 0° C., and the mixture was stirred at room temperature for 10 minutes. Then, the mixture was stirred for 1 hour under heating to reflux. The reaction solution was cooled under ice, and thereto was added dropwise aqueous saturated sodium sulfate solution. The mixture was stirred until no hydrogen was produced. 5N aqueous sodium hydroxide solution was added to the reaction solution, and the mixture was stirred at room temperature for 1 hour. To the mixture was added anhydrous sodium sulfate, and then insoluble substances were filtered. The filtrate was concentrated under reduced pressure to give 8-fluoro-5-(oxan-2-yloxy)-1,2,3,4-tetrahydroquinoline (2.84 g).

Reference Example 23

To a mixture of 8-fluoro-5-(oxan-2-yloxy)-1,2,3,4-tetrahydroquinoline (2.84 g), DCM (60 mL), and TEA (3.15 mL) was added dropwise acetyl chloride (0.95 mL) at 0° C., and the mixture was stirred at the same temperature for 5 hours. Water was added to the reaction solution, and the mixture was extracted with DCM, and then washed with water and brine. The organic layer was dried over anhydrous sodium sulfate, and then filtered. The filtrate was concentrated under reduced pressure. The residue was purified by basic silica gel column chromatography (Hexane/AcOEt) to give 1-[8-fluoro-5-(oxan-2-yloxy)-3,4-dihydro-2H-quinolin-1-yl]ethanone (2.20 g).

Reference Example 24

To 1-[8-fluoro-5-(oxan-2-yloxy)-3,4-dihydro-2H-quinolin-1-yl]ethanone (2.5 g) were added EtOH (30 mL) and 2N HCl (6 mL), and the mixture was stirred at room temperature for 5 hours. Water was added to the reaction solution, and EtOH was removed under reduced pressure. The precipitate was filtered to give 1-(8-fluoro-5-hydroxy-3,4-dihydro-2H-quinolin-1-yl)ethanone (1.23 g).

Reference Example 25

To methylamine (40% MeOH solution) (100 mL) was added 2-(bromomethyl)-1-methoxy-3-nitrobenzene (10.0 g) under ice cooling, and the mixture was stirred at the same temperature for 1 hour. The reaction solution was concentrated under reduced pressure, and water was added to the residue. The mixture was extracted with AcOEt, and the organic layer was dried over anhydrous sodium sulfate, and then filtered. The filtrate was concentrated under reduced pressure to give 1-(2-methoxy-6-nitrophenyl)-N-methylmethaneamine (7.97 g).

Reference Example 26

To a solution of 1-(2-methoxy-6-nitrophenyl)-N-methylmethaneamine (7.97 g) and TEA (6.79 mL) in DCM (80 mL) was added dropwise phenyl chloroformate (5.61 mL) under ice cooling, and the mixture was stirred at the same temperature for 3 hours. The reaction solution was concentrated under reduced pressure. AcOEt was added to the residue, and then insoluble substances were filtered. The filtrate was concentrated under reduced pressure, and the residue was purified by silica gel column chromatography (Hexane/AcOEt) to give phenyl N-[(2-methoxy-6-nitrophenyl)methyl]-N-methylcarbamate (11.6 g).

Reference Example 27

To a solution of phenyl N-[(2-methoxy-6-nitrophenyl)methyl]-N-methylcarbamate (11.6 g) in AcOH (100 mL) were added iron powders (8.16 g), and the mixture was stirred at 100° C. for 3 hours. The reaction solution was filtered, and the filtrate was concentrated under reduced pressure. IPE was added to the residue. The precipitate was filtered, and then purified by silica gel column chromatography (AcOEt/MeOH) to give 5-methoxy-3-methyl-1,4-dihydroquinazolin-2-one (5.03 g).

Reference Example 29

To a solution of 2-hydroxy-3-methoxybenzaldehyde (7.0 g) in DCM (100 mL) was added methanesulfonyl chloride (6.58 g) at −15° C., and then thereto was added dropwise a solution of TEA (9.32 g) in DCM (10 mL) at −10° C. or below. The mixture was stirred at the same temperature for 1 hour, and then stirred at room temperature for 1 hour. The reaction solution was washed with diluted hydrochloric acid, water, and brine. The organic layer was dried over anhydrous sodium sulfate, and then filtered. The filtrate was concentrated under reduced pressure to give (2-formyl-6-methoxyphenyl) methanesulfonate (10.3 g).

Reference Example 30

To a solution of (2-formyl-6-methoxyphenyl)methanesulfonate (5.0 g) in pyridine (30 mL) were added potassium hydroxide powders (3.05 g) under ice cooling, and the mixture was stirred at the same temperature for 30 minutes. The reaction solution was poured into diluted hydrochloric acid, extracted with AcOEt, and washed with brine. The organic layer was dried over anhydrous sodium sulfate, and then filtered. The filtrate was concentrated under reduced pressure. The residue was washed with Hexane to give 8-methoxy-2,2-dioxo-3,4-dihydro-1,2-benzoxathiin-4-ol (1.92 g).

Reference Example 31

To a solution of 8-methoxy-2,2-dioxo-3,4-dihydro-1,2-benzoxathiin-4-ol (2.0 g) in pyridine (7 mL) was added thionyl chloride (0.95 mL) under ice cooling, and the mixture was stirred at room temperature for 1 hour, and then stirred for 3 hours under heating to reflux. The reaction solution was concentrated under reduced pressure, and then the residue was dissolved in DCM and washed with 10% HCl, water, and brine. The organic layer was dried over anhydrous magnesium sulfate, and then filtered. The filtrate was concentrated under reduced pressure. The residue was purified by silica gel column chromatography (Hexane/DCM) to give 8-methoxy-1,2-benzoxathiin-2,2-dioxide (1.68 g).

Reference Example 32

To 8-methoxy-1,2-benzoxathiin-2,2-dioxide (500 mg) was added 47% aqueous hydrobromic acid solution (10 mL), and the mixture was stirred for 3 hours under heating to reflux. The reaction solution was cooled to room temperature and extracted with DCM, and then the organic layer was concentrated under reduced pressure. The residue was washed with Hexane to give 2,2-dioxo-1,2-benzoxathiin-8-ol (430 mg).

Reference Example 33

To a solution of (2-amino-6-methoxyphenyl)methanol (5.00 g) in DMF (100 mL) was added potassium ethylxanthate (26.2 g) under argon atmosphere, and the mixture was stirred at 100° C. for 24 hours. The reaction solution was concentrated under reduced pressure. The residue was dissolved in 1N aqueous NaOH solution (300 mL), and then thereto was added 3% hydrogen peroxide water (300 mL). The mixture was stirred at room temperature overnight. The precipitate was filtered, and IPA (15 mL) was added to the resulted solid. The mixture was heated to reflux for 2 hours, and then stirred at room temperature for 2 hours. The precipitate was filtered to give 5-methoxy-1,4-dihydro-3,1-benzothiazin-2-one (2.96 g).

Reference Example 34

To a suspension of 5-methoxy-1,4-dihydro-3,1-benzothiazin-2-one (1.45 g) in DCM (14 mL) was added dropwise $BBr_3$ (1 mol/mL DCM solution) (14.9 mL) under ice cooling, and the mixture was stirred at the same temperature for 1.5 hours. The reaction solution was neutralized with aqueous saturated $NaHCO_3$ solution, and then the precipitate was filtered to give 5-hydroxy-1,4-dihydro-3,1-benzothiazin-2-one (1.09 g).

Reference Example 35

To a solution of (2-amino-6-methoxyphenyl)methanol (5.00 g) in acetone (40 mL)/$H_2O$ (20 mL) was added $K_2CO_3$ (6.77 g) under ice cooling, and then to the mixture was added dropwise chloroacetyl chloride (3.12 mL). The mixture was stirred at the same temperature for 1.5 hours. Water was added to the reaction solution, and the mixture was extracted with AcOEt and washed with water and brine. The organic layer was dried over anhydrous sodium sulfate, and then filtered. The filtrate was concentrated under reduced pressure. The residue was purified by silica gel column chromatography (Hexane/AcOEt) to give 2-chloro-N-[2-(hydroxymethyl)-3-methoxyphenyl]acetamide (4.15 g).

Reference Example 36

To a solution of 2-chloro-N-[2-(hydroxymethyl)-3-methoxyphenyl]acetamide (4.15 g) in THF (180 mL) was added 55% NaH (1.03 g) under ice cooling under argon atmosphere, and then the mixture was stirred at room temperature for 17 hours. AcOH (0.41 mL) was added dropwise to the reaction solution, and then the mixture was concentrated under reduced pressure. Water and AcOEt were added to the residue, and then the precipitate was filtered to give 6-methoxy-1,5-dihydro-4,1-benzoxazepin-2-one (1.28 g).

Reference Example 37

A mixture of 6-methoxy-1,5-dihydro-4,1-benzoxazepin-2-one (1.47 g), sodium 4-methylbenzenethiolate (1.67 g), and NMP (15 mL) was stirred at 130 to 140° C. for 2.5 hours under argon atmosphere. The reaction solution was cooled to room temperature, and then thereto were added water and AcOH (0.98 mL), and the mixture was extracted with AcOEt and washed with water and brine. The organic layer was dried over anhydrous sodium sulfate, and then filtered. The filtrate was concentrated under reduced pressure. The residue was purified by silica gel column chromatography (Hexane/AcOEt) to give 6-hydroxy-1,5-dihydro-4,1-benzoxazepin-2-one (0.84 g).

Reference Example 38

To a solution of 2-(bromomethyl)-1-methoxy-3-nitrobenzene (15.0 g) and methyl thioglycolate (6.00 mL) in DMF (75 mL) was added $NaHCO_3$ (10.2 g) under argon atmosphere, and the mixture was stirred at room temperature for 24 hours. Water was added to the reaction solution, and the mixture was extracted with AcOEt and washed with water and brine. The organic layer was dried over anhydrous sodium sulfate, and then filtered. The filtrate was concentrated under reduced pressure to give methyl 2-[(2-methoxy-6-nitrophenyl)methylsulfanyl]acetate (16.6 g).

Reference Example 39

To a solution of methyl 2-[(2-methoxy-6-nitrophenyl)methylsulfanyl]acetate (16.5 g) in EtOH (160 mL)/water (80 mL) were added ammonium chloride (9.77 g) and zinc powders (39.8 g), and the mixture was stirred at room temperature for 15 minutes, and then stirred at 90° C. for 2 hours. The reaction solution was cooled to room temperature, and then insoluble substances were filtered. The filtrate was concentrated under reduced pressure. To the residue were added DCM and anhydrous sodium sulfate, and the mixture was stirred, and then insoluble substances were filtered. The filtrate was concentrated under reduced pressure. The residue was dissolved in EtOH (160 mL), and then thereto was added 5N aqueous NaOH solution (18.3 mL). The mixture was stirred at room temperature for 8 hours. The reaction solution was concentrated under reduced pressure, and to the residue were added water (100 mL) and 5N HCl (18.5 mL). The mixture was extracted with AcOEt, and then washed with water and brine. The organic layer was dried over anhydrous sodium sulfate, and then filtered. The filtrate was concentrated under reduced pressure to give 2-[(2-amino-6-methoxyphenyl)methylsulfanyl]acetic acid (10.9 g).

Reference Example 40

To a solution of 2-[(2-amino-6-methoxyphenyl)methylsulfanyl]acetic acid (10.1 g) in DMF (100 mL) were added HOBt (0.340 g), DIPEA (11.6 mL), and WSC (11.1 g), and the mixture was stirred at room temperature for 2 hours. To the reaction solution was added water (500 mL), and then the precipitate was filtered to give 6-methoxy-1,5-dihydro-4,1-benzothiazepin-2-one (5.41 g).

Reference Example 41

A mixture of 6-methoxy-1,5-dihydro-4,1-benzothiazepin-2-one (5.23 g), sodium 4-methylbenzenethiolate (5.48 g), and NMP (50 mL) was stirred at 130 to 140° C. for 3 hours under argon atmosphere. The reaction solution was cooled to room temperature, and then thereto were added water, AcOH (3.22 mL), and AcOEt. The precipitate was filtered to give 6-hydroxy-1,5-dihydro-4,1-benzothiazepin-2-one (3.96 g).

Reference Example 42

To a suspension of 6-hydroxy-1,5-dihydro-4,1-benzothiazepin-2-one (2.50 g) in NMP (75 mL) was added dropwise a solution of Oxone (Registered trade mark) (15.7 g) in water (50 mL) under ice cooling, and the mixture was stirred at room temperature for 20 hours. To the reaction solution was added a solution of Oxone (Registered trade mark) (3.94 g) in water (12 mL), and the mixture was stirred for 11 hours. To the reaction solution were added water (200 mL) and AcOEt (50 mL), and then insoluble substances were filtered to give 6-hydroxy-4,4-dioxo-1,5-dihydro-4,1-benzothiazepin-2-one (1.92 g).

Reference Example 43

A mixture of 5-methoxy-3,4-dihydro-1H-1,8-naphthyridin-2-one (3.85 g), sodium 4-methylbenzenethiolate (4.74 g), and DMF (38 mL) was stirred at 130 to 140° C. for 1.5 hours under argon atmosphere. The reaction solution was concentrated under reduced pressure, and to the residue were added MeOH (75 mL) and AcOH (1.98 mL). Then, the precipitate was filtered to give 5-hydroxy-3,4-dihydro-1H-1,8-naphthyridin-2-one (2.99 g).

Reference Example 44

To a solution of 9-chloro-6-methoxy-1,3,4,5-tetrahydro-1-benzazepin-2-one (804 mg) in DCM (8 mL) was added $BBr_3$ (1 mol/mL DCM solution) (7.13 mL) under ice cooling, and then the mixture was stirred at room temperature for 3 hours. The precipitate was filtered, and then washed with water, Hexane, and $Et_2O$ to give 9-chloro-6-hydroxy-1,3,4,5-tetrahydro-1-benzazepin-2-one (748 mg).

Reference Example 45

To a solution of 8-[tert-butyl(diphenyl)silyl]oxy-5-chloro-4H-1,4-benzoxazin-3-one (1.95 g) in THF (10 mL) was added tetrabutylammonium fluoride (1 mol/mL THF solution) (5.34 mL), and the mixture was stirred at room temperature for 15 hours. To the reaction solution was added water, and the mixture was extracted with AcOEt, and then washed with brine. The organic layer was dried over anhydrous sodium sulfate, and then filtered. The filtrate was concentrated under reduced pressure. The residue was washed with IPE to give 5-chloro-8-hydroxy-4H-1,4-benzoxazin-3-one (0.79 g).

Reference Example 46

To a solution of N-(2-chloro-5-methoxyphenyl)propanamide (564 mg) in DCM (6 mL) was added $BBr_3$ (1 mol/mL DCM solution) (6.6 mL) under ice cooling, and then the mixture was stirred at room temperature for 1 hour. To the reaction solution was added water, and the mixture was extracted with AcOEt. The organic layer was concentrated under reduced pressure, and then the residue was washed with Hexane to give N-(2-chloro-5-hydroxyphenyl)propanamide (377 mg).

Reference Example 49

To a solution of 2-chloro-5-methoxyaniline (500 mg) and TEA (0.49 mL) in MeCN (4 mL) was added phenylacetyl chloride (0.42 mL) at 0° C., and the mixture was stirred at room temperature for 30 minutes. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give N-(2-chloro-5-methoxyphenyl)-2-phenylacetamide (657 mg).

Reference Example 54

To a solution of N-(3-methoxy-2-methylphenyl)formamide (1.04 g) in MeCN (12.6 mL) was added NCS (0.925 g), and the mixture was stirred at room temperature for 1 hour, and then stirred for 2 hours under heating to reflux. The reaction solution was concentrated under reduced pressure, and then the residue was washed with AcOEt and Hexane to give N-(6-chloro-3-methoxy-2-methylphenyl)formamide (560 mg).

Reference Example 55

To a solution of N-(6-chloro-3-methoxy-2-methylphenyl)formamide (345 mg) in DCM (35 mL) was added $BBr_3$ (1 mol/mL DCM solution) (3.46 mL) under ice cooling, and the mixture was stirred at room temperature for 3 hours. To the reaction solution was added THF (20 mL), and the mixture was stirred at 50° C. for 30 minutes. To the reaction solution was added water, and the mixture was extracted with AcOEt and washed with brine. The organic layer was dried over anhydrous sodium sulfate, and then filtered. The filtrate was concentrated under reduced pressure. The residue was washed with AcOEt and Hexane to give N-(6-chloro-3-hydroxy-2-methylphenyl)formamide (142 mg).

Reference Example 56

To a solution of 3-methoxy-2-methylaniline (1.0 g) in MeCN (10 mL) was added methyl chloroformate (0.704 mL) at 0° C., and the mixture was stirred at the same temperature for 30 minutes. To the reaction solution was added water, and the mixture was extracted with AcOEt and washed with brine. The organic layer was dried over anhydrous sodium sulfate, and then filtered. The filtrate was concentrated under reduced pressure to give methyl N-(3-methoxy-2-methylphenyl)carbamate (815 mg).

Reference Example 59

To a solution of 8-chloro-5-methoxy-3,4-dihydro-1H-quinolin-2-one (3.0 g) in THF (30 mL) was added Lawesson's reagent (3.82 g), and the mixture was stirred under heating to reflux for 3.5 hours. The reaction solution was concentrated under reduced pressure, and the residue was washed with AcOEt and Hexane to give 8-chloro-5-methoxy-3,4-dihydro-1H-quinoline-2-thione (2.44 g).

Reference Example 62

To a suspension of 4-chloro-7-hydroxy-3H-1,3-benzothiazol-2-one (1.2 g) in DCM (12 mL) were added TEA (1.83 mL) and acetyl chloride (0.93 mL) under ice cooling, and then the mixture was stirred at room temperature for 30 minutes. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give (2-acetyloxy-4-chloro-1,3-benzothiazol-7-yl) acetate (1.02 g).

Reference Example 63

To a solution of (2-acetyloxy-4-chloro-1,3-benzothiazol-7-yl) acetate (1.02 g) in MeOH (50 mL) was added 28% ammonia water (0.5 mL), and the mixture was stirred at room temperature for 10 minutes. The reaction solution was concentrated under reduced pressure, and then to the residue was added water. The precipitate was filtered to give (4-chloro-2-oxo-3H-1,3-benzothiazol-7-yl) acetate (573 mg).

Reference Example 64

To (4-chloro-2-oxo-3H-1,3-benzothiazol-7-yl) acetate (872 mg) was added phosphoryl chloride (9 mL), and the mixture was stirred under heating to reflux for 16 hours. The reaction solution was poured into ice water, and then extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give (2,4-dichloro-1,3-benzothiazol-7-yl) acetate (207 mg).

Reference Example 65

To a solution of (2,4-dichloro-1,3-benzothiazol-7-yl) acetate (207 mg) in MeOH (5 mL)/THF (1 mL) was added concentrated HCl (0.3 mL), and the mixture was stirred at room temperature for 7 hours. To the reaction solution was added water, and the precipitate was filtered to give 2,4-dichloro-1,3-benzothiazole-7-ol (160 mg).

Reference Example 66

To a solution of methyl 7-fluoro-4-phenylmethoxy-1H-indole-2-carboxylate (3.9 g) in DMF (30 mL) was added 10% Pd/C (300 mg) under nitrogen atmosphere, and then the reaction system was replaced with hydrogen and stirred at 70° C. for 6 hours. To the reaction solution were added 10% Pd/C (300 mg) and MeOH (30 mL), and the mixture was stirred at 50° C. for 10 hours under hydrogen. Insoluble substances were filtered, and water was added to the filtrate. The mixture was extracted with a mixed solvent of AcOEt/MeOH and washed with brine. The organic layer was dried over anhydrous sodium sulfate, and then filtered. The filtrate was concentrated under reduced pressure. The residue was purified by silica gel column chromatography (Hexane/AcOEt) to give methyl 7-fluoro-4-hydroxy-1H-indole-2-carboxylate (653 mg).

Reference Example 67

To a solution of 2-amino-3-fluoro-6-methoxybenzonitrile (820 mg) in THF (8 mL) was added borane-THF complex (0.9 mol/mL THF solution) (22.2 mL) under ice cooling, and the mixture was stirred at room temperature for 24 hours. To the reaction solution was added MeOH (2 mL), and the mixture was stirred. Then, thereto was added 4N HCl (3 mL), and the precipitate was filtered and washed with AcOEt. The resulted solid was dissolved in water and the solution was weakly basified with 30% ammonia water, and then extracted with AcOEt and washed with brine. The organic layer was dried over anhydrous sodium sulfate, and then filtered. The filtrate was concentrated under reduced pressure to give 2-(aminomethyl)-6-fluoro-3-methoxyaniline (730 mg).

Reference Example 68

To a suspension of 2-(aminomethyl)-6-fluoro-3-methoxyaniline (730 mg) in THF (15 mL) were added triphosgene (471 mg) and DIPEA (2.62 mL) under ice cooling, and the mixture was stirred at room temperature for 3 days. To the reaction solution were added water, AcOEt, and hexane, and the precipitate was filtered to give 8-fluoro-5-methoxy-3,4-dihydro-1H-quinazolin-2-one (577 mg).

Reference Example 70

To a solution of 5-hydroxy-1,4-dihydro-3,1-benzoxazin-2-one (6.42 g) and t-butyldiphenylchlorosilane (15.0 mL) in DMF (96 mL) was added imidazole (5.29 g) under ice cooling, and the mixture was stirred at room temperature for 17 hours. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give 5-[tert-butyl(diphenyl)silyl]oxy-1,4-dihydro-3,1-benzoxazin-2-one (11.5 g).

Reference Example 71

To a solution of 5-[tert-butyl(diphenyl)silyl]oxy-1,4-dihydro-3,1-benzoxazin-2-one (8.39 g) in DCE (125 mL) was added NCS (2.78 g), and the mixture was stirred at 80° C. for hours. The reaction solution was concentrated under reduced pressure, and the residue was purified by silica gel column chromatography (Hexane/AcOEt) to give 5-[tert-butyl(diphenyl)silyl]oxy-8-chloro-1,4-dihydro-3,1-benzoxazin-2-one (6.0 g).

Reference Example 73

To a solution of 4-fluoro-7-methoxy-1,3-benzothiazole-2-amine (4.46 g) in concentrated HCl (83 mL) and AcOH/DCE/$H_2O$ (1/4/3) (224 mL) was added a solution of sodium nitrite (4.66 g) in water (10 mL) under ice cooling, and the mixture was stirred at room temperature for 2 hours. To the reaction solution was added water, and the mixture was extracted with DCM and washed with water. The organic layer was dried over anhydrous magnesium sulfate, and then purified by silica gel column chromatography (DCM) to give 2-chloro-4-fluoro-7-methoxy-1,3-benzothiazole (3.89 g).

Reference Example 75

A mixture of 5-fluoro-2-(methoxymethoxy)aniline (1.5 g), 2-chloroethylisocyanate (0.897 mL), and THF (10 mL) was stirred at room temperature overnight. To the reaction solution was added water, and the precipitate was filtered. The resulted solid was washed with $Et_2O$ to give 1-(2-chloroethyl)-3-[5-fluoro-2-(methoxymethoxy)phenyl]urea (2.28 g).

Reference Example 76

To a mixture of 1-(2-chloroethyl)-3-[5-fluoro-2-(methoxymethoxy)phenyl]urea (2.25 g) and DMF (20 ml) was added 55% NaH (0.43 g) under ice cooling, and the mixture was stirred at room temperature overnight. To the reaction solution was added water, and the mixture was extracted with AcOEt and washed with water and brine. The organic layer was dried over anhydrous sodium sulfate, and then filtered. The filtrate was concentrated under reduced pressure. The residue was washed with $Et_2O$ to give 1-[5-fluoro-2-(methoxymethoxy)phenyl]imidazolidin-2-one (0.36 g).

Reference Example 77

A mixture of 1-[5-fluoro-2-(methoxymethoxy)phenyl]imidazolidin-2-one (0.36 g), MeOH (3 mL), and 4N HCl—

AcOEt solution (3 mL) was stirred at room temperature overnight. To the reaction solution was added water, and the mixture was extracted with AcOEt. The organic layer was dried over anhydrous sodium sulfate, and then filtered. The filtrate was concentrated under reduced pressure. The residue was washed with $Et_2O$ to give 1-(5-fluoro-2-hydroxyphenyl)imidazolidin-2-one (0.28 g).

Reference Example 78

To a solution of 3-amino-4-fluorophenol (7.8 g) and pyridine (5.46 mL) in DMA (70 mL) was added dropwise a solution of (2E)-3-ethoxyprop-2-enoyl chloride (8.67 g) in DMA (30 mL) under ice cooling. The mixture was stirred at the same temperature for 2 hours, and then stirred at room temperature for 30 minutes. The reaction solution was poured into water (500 mL), and then the precipitate was filtered to give (E)-3-ethoxy-N-(2-fluoro-5-hydroxyphenyl)prop-2-enamide (8.16 g).

Reference Example 79

To concentrated HCl (270 mL) was added dropwise a solution of (E)-3-ethoxy-N-(2-fluoro-5-hydroxyphenyl)prop-2-enamide (27.0 g) in MeOH (135 mL) at 65° C., and the mixture was stirred at 85° C. for 30 minutes. The reaction solution was poured into water and stirred at room temperature for 1 hour, and then the precipitate was filtered and washed with methanol to give 8-fluoro-5-hydroxy-1H-quinolin-2-one (19.2 g).

Reference Example 80

To a solution of 8-fluoro-5-hydroxyquinolin-2(1H)-one (8.0 g) in DMF (40 mL) was added dropwise thionyl chloride (8.15 mL), and the mixture was stirred at 40° C. for 4 hours. The reaction solution was cooled to room temperature and poured into ice water, and the precipitate was filtered. The resulted solid was dissolved in AcOEt and dried over anhydrous sodium sulfate, and then filtered. The filtrate was concentrated under reduced pressure. The residue was washed with $Et_2O$/Hexane to give 2-chloro-8-fluoroquinolin-5-ol (8.48 g).

Reference Example 81

To a suspension of 2-chloro-8-fluoroquinolin-5-ol (2.0 g) in DCM (30 mL) were added DHP (2.78 mL) and PPTS (0.25 g), and the mixture was stirred at room temperature for 5 hours. To the reaction solution was added aqueous $NaHCO_3$ solution, and then the mixture was extracted with DCM and washed with brine. The organic layer was dried over anhydrous sodium sulfate, and then filtered. The filtrate was concentrated under reduced pressure. The residue was purified by silica gel column chromatography (Hexane/AcOEt) to give 2-chloro-8-fluoro-5-(oxan-2-yloxy)quinoline (2.65 g).

Reference Example 82

To a solution of 2-chloro-8-fluoro-5-(tetrahydro-2H-pyran-2-yloxy)quinoline (2.65 g) in DMF (25 mL) was added dropwise sodium methoxide (5 mol/mL methanol solution) (5.6 mL), and the mixture was stirred at room temperature for 10 hours. The reaction solution was poured into water and neutralized with AcOH (1.1 mL), and then extracted with AcOEt and washed with water and brine. The organic layer was dried over anhydrous sodium sulfate, and then filtered. The filtrate was concentrated under reduced pressure. The residue was dissolved in MeOH (25 mL), and thereto was added 5N HCl (2 mL). The mixture was stirred at room temperature for 5 hours. To the reaction solution were added aqueous saturated $NaHCO_3$ solution (150 mL) and water (150 mL), and the mixture was stirred at room temperature for 1 hour. Then, the precipitate was filtered to give 8-fluoro-2-methoxyquinolin-5-ol (1.61 g).

Reference Example 83

2-Bromo-5-chloro-1,3-difluorobenzene (1.02 g), NaOtBu (519 mg), tris(dibenzylideneacetone)dipalladium (41.2 mg), 2,2'-bis(diphenylphosphino-1,1'-binaphthyl (84 mg), 1,4-dioxa-8-azaspiro[4,5]decane (0.65 mL), and toluene (3 mL) were sealed in a microwave reactor tube, and the mixture was stirred at 130° C. for 1 hour under microwave irradiation. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give 8-(4-chloro-2,6-difluorophenyl)-1,4-dioxa-8-azaspiro[4.5]decane (0.48 g).

Reference Example 84

To a solution of 8-(4-chloro-2,6-difluorophenyl)-1,4-dioxa-8-azaspiro[4.5]decane (482 mg) in acetone (10 mL) was added 5N HCl (5 mL), and the mixture was stirred under heating to reflux for 3 hours. The reaction solution was concentrated under reduced pressure, and then the residue was neutralized with 5N aqueous NaOH solution, extracted with AcOEt, and washed with brine. The organic layer was dried over anhydrous sodium sulfate, and then filtered. The filtrate was concentrated under reduced pressure. The residue was purified by silica gel column chromatography (Hexane/AcOE) to give 1-(4-chloro-2,6-difluorophenyl)piperidin-4-one (330 mg).

Reference Example 87

To a solution of 1-(4-bromo-2-fluorophenyl)piperidin-4-one (20.0 g) in MeCN (60 mL) were added TEA (12.8 mL), tert-butyldimethylchlorosilane (12.7 g), and sodium iodide (12.7 g) under ice cooling, and the mixture was stirred under heating to reflux for 1 hour under nitrogen atmosphere. The reaction solution was cooled to room temperature, and then thereto was added Hexane. Insoluble substances were filtered. The filtrate was washed with water and brine, dried over anhydrous sodium sulfate, and then filtered. The filtrate was concentrated under reduced pressure to give [1-(4-bromo-2-fluorophenyl)-3,6-dihydro-2H-pyridine-4-yl]oxy-tert-butyl-dimethylsilane (28.8 g).

Reference Example 90

To a solution of $K_2CO_3$ (9.44 g) and disodium ethylenediaminetetraacetate (4.7 mg) in water (32 mL) was added a solution of [1-(4-bromo-2-fluorophenyl)-3,6-dihydro-2H-pyridin-4-yl]oxy-tert-butyl-dimethylsilane (8.80 g) in MeCN/1-propanol/toluene (1/1/2) (95 mL), and then thereto was added Shi catalyst (1.77 g) under ice cooling. Then, thereto was added dropwise 30% aqueous hydrogen peroxide solution (9.31 mL) over 30 minutes with keeping the internal temperature at 2° C., and then the mixture was stirred for 12 hours with keeping the internal temperature of 10° C. or below. To the reaction solution was added Hexane, and the mixture was extracted and washed with water, brine, and aqueous sodium sulfite solution. The organic layer was dried over anhydrous sodium sulfate, and then filtered. The filtrate was concentrated under reduced pressure to give [(1R,6R)-3-(4-bromo-2-fluorophenyl)-7-oxa-3-azabicyclo[4.1.0]heptan-6-yl]oxy-tert-butyl-dimethylsilane (8.79 g).

Reference Example 91

Recrystallization from EtOH after reaction in accordance with a similar manner to Reference Example 92 gave (3R,4R)-6-(4-chloro-2,6-difluorophenyl)-1-oxa-6-azaspiro[2.5]octan-4-ol (99% ee).

Reference Example 92

To a solution of tert-butyl-dimethyl-[[(1R,6R)-3-(4-chloro-2-fluorophenyl)-7-oxa-3-azabicyclo[4.1.0]heptan-6-yl]oxy]silane (41.8 g) in DMSO (300 mL) was added trimethylsulfoxonium iodide (28.3 g), and then thereto was added 85% potassium hydroxide (powder) (8.50 g) under water bath, and the mixture was stirred at room temperature for 1 hour. The reaction solution was poured into ice water (500 mL)-aqueous saturated ammonium chloride solution (250 mL), extracted with a mixed solvent of toluene/AcOEt, and washed with water. The organic layer was dried over anhydrous sodium sulfate, and then filtered. The filtrate was concentrated under reduced pressure. The residue was washed with IPE to give (3R,4R)-6-(4-chloro-2-fluorophenyl)-1-oxa-6-azaspiro[2.5]octan-4-ol (11.1 g, 99% ee).

Reference Example 93

Recrystallization from Hexane/AcOEt after reaction in accordance with a similar manner to Reference Example 92 gave (3R,4R)-6-(4-bromo-2-fluorophenyl)-1-oxa-6-azaspiro[2.5]octan-4-ol (99% ee).

Reference Example 94

To a solution of trimethylsulfoxonium iodide (2.19 g) in DMSO (11 mL) was added NaOtBu (0.96 g), and the mixture was stirred at room temperature for 30 minutes. Then, to the reaction solution was added a solution of 1-(4-chloro-2-fluorophenyl)piperidin-4-one (2.16 g) in DMSO (11 mL), and the mixture was stirred at room temperature for 2 hours. To the reaction solution was added water, and the mixture was extracted with AcOEt and washed with water and brine. The organic layer was dried over anhydrous sodium sulfate, and then filtered. The filtrate was concentrated under reduced pressure. The residue was purified by silica gel column chromatography (Hexane/AcOE) to give 6-(4-chloro-2-fluorophenyl)-1-oxa-6-azaspiro[2.5]octane (1.92 g).

Reference Example 97

To a solution of 8-[tert-butyl(diphenyl)silyl]oxy-4H-1,4-benzoxazin-3-one (3.57 g) in MeCN (36 mL) was added NCS (1.30 g), and the mixture was stirred under heating to reflux for 2 hours. To the reaction solution was added water, and the mixture was extracted with AcOEt and washed with brine. The organic layer was dried over anhydrous sodium sulfate, and then filtered. The filtrate was concentrated under reduced pressure to give a chlorinated regioisomer mixture (1:1). The resulted mixture was purified by silica gel column chromatography (Hexane/AcOEt) to give 8-[tert-butyl(diphenyl)silyl]oxy-5-chloro-4H-1,4-benzoxazin-3-one (1.95 g) for a lower polarity product.

EXAMPLE

Example 1

To 6-(4-chloro-2-fluorophenyl)-1-oxa-6-azaspiro[2.5]octane (232 mg) were added 5-hydroxyisoquinoline (153 mg), DMF (2 mL), IPA (2 mL), and K$_3$PO$_4$ (41 mg), and the mixture was stirred at 70° C. for 19 hours. To the reaction solution was added water, and the mixture was extracted with AcOEt and washed with water and brine. The organic layer was dried over anhydrous sodium sulfate, and then filtered. The filtrate was concentrated under reduced pressure. The residue was purified by silica gel column chromatography (Hexane/AcOEt), and then the resulted solid was washed with Hexane/AcOEt to give 1-(4-chloro-2-fluorophenyl)-4-(isoquinolin-5-yloxymethyl)piperidin-4-ol (90 mg).

Example 5

To a solution of 2-quinolinol (151.2 mg) in DMF (5 mL) were added 6-(4-chloro-2-fluorophenyl)-1-oxa-6-azaspiro[2.5]octane (302.2 mg) and Cs$_2$CO$_3$ (1.02 g), and the mixture was stirred at 70° C. overnight. To the reaction solution was added AcOEt, and then insoluble substances were filtered. The filtrate was concentrated under reduced pressure. The residue was purified by silica gel column chromatography (Hexane/AcOEt) to give 1-(4-chloro-2-fluorophenyl)-4-(quinolin-2-yloxymethyl)piperidin-4-ol (88 mg).

Example 6

To 5-chloro-8-quinolinol (200 mg) were added (3R,4R)-6-(4-chloro-2,6-difluorophenyl)-1-oxa-6-azaspiro[2.5]octan-4-ol (307 mg), IPA/H$_2$O (5/1) (3 mL), and K$_2$CO$_3$ (30.8 mg) under nitrogen atmosphere, and the mixture was stirred under heating to reflux for 7 hours. To the reaction solution was added water, and the mixture was extracted with AcOEt and washed with water and brine. The organic layer was dried over anhydrous sodium sulfate, and then filtered. The filtrate was concentrated under reduced pressure. The residue purified by silica gel column chromatography (Hexane/AcOEt) to give (3R,4R)-1-(4-chloro-2,6-difluorophenyl)-4-[(5-chloroquinolin-8-yl)oxymethyl]piperidine-3,4-diol (262 mg).

Example 19

To 4-[[(3R,4R)-1-(4-chloro-2,6-difluorophenyl)-3,4-dihydroxypiperidin-4-yl]methoxy]-2,3-dihydroinden-1-one (150 mg) were added hydroxylamine hydrochloride (36.9 mg), AcONa (43.5 mg), and EtOH (4 mL), and the mixture was stirred under heating to reflux for 2 hours. To the reaction solution was added water, and the precipitate was filtered to give (3R,4R)-1-(4-chloro-2,6-difluorophenyl)-4-[[(1E)-1-hydroxyimino-2,3-dihydroinden-4-yl]oxymethyl]piperidine-3,4-diol (152 mg).

Example 24

To a solution of 4-[[(3R,4R)-1-(4-chloro-2,6-difluorophenyl)-3,4-dihydroxypiperidin-4-yl]methoxy]-2,3-dihydroinden-1-one (150 mg) in MeOH (3 mL) was added NaBH$_4$ (13.4 mg) at room temperature, and the mixture was stirred at the same temperature for 1 hour. To the reaction solution was added water, and the mixture was extracted with AcOEt and washed with water and brine. The organic layer was dried over anhydrous sodium sulfate, and then filtered. The filtrate was concentrated under reduced pressure. The residue was purified by silica gel column chromatography (Hexane/AcOEt) to give (3R,4R)-1-(4-chloro-2,6-difluorophenyl)-4-[(1-hydroxy-2,3-dihydro-1H-inden-4-yl)oxymethyl]piperidine-3,4-diol (145 mg).

Example 44

1-[8-Fluoro-5-[[(3R,4R)-1-(4-chloro-2,6-difluorophenyl)-3,4-dihydroxypiperidin-4-yl]methoxy]-3,4-dihydro-2H-quinolin-1-yl]ethanone (400 mg) and 5N HCl (8 mL) were mixed and stirred at 100° C. for 38 hours. The reaction solution was cooled to room temperature, basified with 5N aqueous NaOH solution, and then extracted with DCM. The organic layer was dried over anhydrous sodium sulfate, and then filtered. The filtrate was concentrated under reduced pressure. The residue was dissolved in EtOH (1 mL), and thereto was added 4N HCl-ethyl acetate solution. The mixture was stirred at room temperature for 30 minutes. The precipitate was filtered to give (3R,4R)-1-(4-chloro-2,6-difluorophenyl)-4-[(8-fluoro-1,2,3,4-tetrahydroquinolin-5-yl)oxymethyl]piperidine-3,4-diol hydrochloride (245 mg).

Example 49

To a suspension of (3R,4R)-1-(4-chloro-2-fluorophenyl)-4-[(2-methoxyquinoxalin-5-yl)oxymethyl]piperidine-3,4-diol (0.33 g) in EtOH (5 mL) was added 5N aqueous NaOH solution (2.28 mL), and the mixture was stirred at 85° C. for 39 hours. The reaction solution was concentrated under reduced pressure, and to the residue was added water. The mixture was adjusted with AcOH to be about pH 4, and then the precipitate was filtered. The resulted solid was purified by basic silica gel column chromatography (THF/MeOH), and then washed with EtOH to give 5-[[(3R,4R)-1-(4-chloro-2-fluorophenyl)-3,4-dihydroxypiperidin-4-yl]methoxy]-1H-quinoxalin-2-one (0.19 g).

Example 53

A solution of (3R,4R)-1-(4-chloro-2,6-difluorophenyl)-4-[(2-methoxyquinoxalin-5-yl)oxymethyl]piperidine-3,4-diol (0.37 g) and lithium bromide (0.356 g) in DMF (4 mL) was stirred at 140° C. for 24 hours under argon atmosphere. The reaction solution was concentrated under reduced pressure, and to the residue was added aqueous saturated ammonium chloride solution. The mixture was extracted with a mixed solvent of AcOEt/THF and washed with water. The organic layer was dried over anhydrous sodium sulfate, and then filtered. The filtrate was concentrated under reduced pressure. The residue was separated with basic silica gel column chromatography (THF/MeOH) into low and high polarity products. The low polarity product was washed with ether to give 1-methyl-5-[[(3R,4R)-1-(4-chloro-2,6-difluorophenyl)-3,4-dihydroxypiperidin-4-yl]methoxy]quinoxalin-2-one (0.105 g).

Example 54

The high polarity product in Example 53 was washed with ether to give 5-[[(3R,4R)-1-(4-chloro-2,6-difluorophenyl)-3,4-dihydroxypiperidin-4-yl]methoxy]-1H-quinoxalin-2-one (0.024 g).

Example 55

A low polarity product obtained in reaction and separation procedures similar to Example 53 was washed with ether to give 1-methyl-8-[[(3R,4R)-1-(4-chloro-2,6-difluorophenyl)-3,4-dihydroxypiperidin-4-yl]methoxy]quinoxalin-2-one.

Example 56

A high polarity product in Example 55 was washed with ether to give 8-[[(3R,4R)-1-(4-chloro-2,6-difluorophenyl)-3,4-dihydroxypiperidin-4-yl]methoxy]-1H-quinoxalin-2-one.

Example 74

A suspension of 6-hydroxy-1,5-dihydro-4,1-benzothiazepin-2-one (0.15 g), (3R,4R)-6-(4-bromo-2-fluorophenyl)-1-oxa-6-azaspiro[2.5]octan-4-ol (0.21 g), and KHCO$_3$ (0.014 g) in IPA (1.6 mL)/DMF (0.4 mL) was stirred at 70-80° C. for 20 hours. To the reaction solution was added 5N aqueous NaOH solution (6 mL), and the mixture was extracted with a mixed solvent of AcOEt/THF and washed with 5N aqueous NaOH solution and brine. The organic layer was dried over anhydrous sodium sulfate, and then filtered. The filtrate was concentrated under reduced pressure. The residue was purified by basic silica gel column chromatography (DCM/MeOH), and the resulted solid was washed with DCM to give 6-[[(3R,4R)-1-(4-bromo-2-fluorophenyl)-3,4-dihydroxypiperidin-4-yl]methoxy]-1,5-dihydro-4,1-benzothiazepin-2-one (0.064 g).

Example 89

Methyl 2-chloro-5-hydroxybenzoate (227 mg), (3R,4R)-6-(4-chloro-2,6-difluorophenyl)-1-oxa-6-azaspiro[2.5]octan-4-ol (335 mg), K$_2$CO$_3$ (33.6 mg), and IPA/H$_2$O (5/1) (4.5 mL) were mixed and stirred under heating to reflux for 7 hours, and then thereto was added 5N aqueous NaOH solution (2.43 mL). The mixture was stirred under heating to reflux for 1 hour. The reaction solution was cooled to room temperature, and then acidified with 5N HCl and stirred overnight. The precipitate was filtered and washed with water and Et$_2$O to give 2-chloro-5-[[(3R,4R)-1-(4-chloro-2,6-difluorophenyl)-3,4-dihydroxypiperidin-4-yl]methoxy]benzoic acid (385 mg).

Example 90

A suspension of 7-chloro-4-hydroxy-1-indanone (71 mg), (3R,4R)-6-(4-chloro-2,6-difluorophenyl)-1-oxa-6-azaspiro[2.5]octan-4-ol (107 mg), and K$_2$CO$_3$ (10.8 mg) in DMF (1.4 mL) was stirred at 80° C. for 10 hours. To the reaction solution was added water, and the mixture was extracted with AcOEt-MeOH and washed with brine. The organic layer was dried over anhydrous sodium sulfate, and then filtered. The filtrate was concentrated under reduced pressure. The residue was purified by silica gel column chromatography (Hexane/AcOEt) to give 7-chloro-4-[[(3R,4R)-1-(4-chloro-2,6-difluorophenyl)-3,4-dihydroxypiperidin-4-yl]methoxy]-2,3-dihydroinden-1-one (58 mg).

Example 94

To a solution of methyl 5-chloro-2-[[(3R,4R)-1-(4-chloro-2,6-difluorophenyl)-3,4-dihydroxypiperidin-4-yl]methoxy]

benzoate (178 mg) in THF (1.8 mL) was added 5N aqueous NaOH solution (0.6 mL), and the mixture was stirred at room temperature for 2.5 hours, and then stirred at 80° C. for 3.5 hours. The reaction solution was cooled to room temperature, and then thereto was added 5N HCl. The mixture was extracted with AcOEt and washed with brine. The organic layer was dried over anhydrous sodium sulfate, and then filtered. The filtrate was concentrated under reduced pressure. The residue was washed with chloroform to give 5-chloro-2-[[(3R,4R)-1-(4-chloro-2,6-difluorophenyl)-3,4-dihydroxypiperidin-4-yl]methoxy]benzoic acid (170 mg).

Example 98

A suspension of methyl 5-chloro-2-hydroxybenzoate (513 mg), (3R,4R)-6-(4-chloro-2,6-difluorophenyl)-1-oxa-6-azaspiro[2.5]octan-4-ol (505 mg), and $K_2CO_3$ (50.7 mg) in DMF (5 mL) was stirred at 100° C. for 6 hours. The reaction solution was cooled to room temperature, and then thereto was added saturated ammonia chloride water. The mixture was extracted with AcOEt and washed with brine. The organic layer was dried over anhydrous sodium sulfate, and then filtered. The filtrate was concentrated under reduced pressure. To the residue were added DME (7 mL) and $NaBH_4$ (347 mg) at room temperature, and then thereto was added dropwise MeOH (1.7 mL). The mixture was stirred at the same temperature for 1 hour. To the reaction solution was added water, and the mixture was extracted with AcOEt and washed with brine. The organic layer was dried over anhydrous sodium sulfate, and then filtered. The filtrate was concentrated under reduced pressure. The residue was washed with Hexane/$Et_2O$ to give (3R,4R)-1-(4-chloro-2,6-difluorophenyl)-4-[[4-chloro-2-(hydroxymethyl)phenoxy]methyl]piperidine-3,4-diol (311 mg).

Example 99

To a solution of 2-chloro-5-[[(3R,4R)-1-(4-chloro-2,6-difluorophenyl)-3,4-dihydroxypiperidin-4-yl]methoxy]benzoic acid (260 mg), 1-ethyl-3-(3-dimethylaminopropyl)carbodiimide hydrochloride (167 mg), and 1-hydroxybenzotriazole (133 mg) in NMP (10 mL) was added 25% aqueous methylamine solution (0.22 mL), and the mixture was stirred at room temperature for 2 hours. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give 2-chloro-5-[[(3R,4R)-1-(4-chloro-2,6-difluorophenyl)-3,4-dihydroxypiperidin-4-yl]methoxy]-N-methylbenzamide (133 mg).

Example 100

To a solution of methyl 2-chloro-5-[[(3R,4R)-1-(4-chloro-2,6-difluorophenyl)-3,4-dihydroxypiperidin-4-yl]methoxy]benzate (475 mg) in DME (3.3 mL) was added $NaBH_4$ (194 mg) at room temperature, and then thereto was added dropwise MeOH (1.6 mL). The mixture was stirred at the same temperature for 2 hours, and then at 60° C. for 1 hour. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt), and then washed with Hexane/$Et_2O$ to give (3R,4R)-1-(4-chloro-2,6-difluorophenyl)-4-[[4-chloro-3-(hydroxymethyl)phenoxy]methyl]piperidine-3,4-diol (244 mg).

Example 114

To a solution of 3-[2-[[(3R,4R)-1-(4-chloro-2,6-difluorophenyl)-3,4-dihydroxypiperidin-4-yl]methoxy]-5-fluorophenyl]propionic acid (81 mg) in THF (15 mL) were added O-(7-azabenzotriazol-1-yl)-N,N,N',N'-tetramethyluronium hexafluorophosphate (134 mg), N,N-diisopropylethylamine (0.11 mL), and ammonium chloride (25.4 mg), and the mixture was stirred at room temperature for 20 hours. The reaction solution was concentrated under reduced pressure, and the residue was purified by silica gel column chromatography (Hexane/AcOEt) to give 3-[2-[[(3R,4R)-1-(4-chloro-2,6-difluorophenyl)-3,4-dihydroxypiperidin-4-yl]methoxy]-5-fluorophenyl]propanamide (59 mg).

Example 115

To a solution of ethyl 2-[2-[[(3R,4R)-1-(4-chloro-2,6-difluorophenyl)-3,4-dihydroxypiperidin-4-yl]methoxy]-5-fluorophenyl]acetate (129 mg) in THF (2.6 mL) was added 5N aqueous NaOH solution (0.44 mL), and the mixture was stirred at room temperature for 3 hours, and then stirred at 60° C. for 3 hours. The reaction solution was cooled to room temperature and weakly acidified with 2N HCl, and then extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give 2-[2-[[(3R,4R)-1-(4-chloro-2,6-difluorophenyl)-3,4-dihydroxypiperidin-4-yl]methoxy]-5-fluorophenyl]acetic acid (108 mg).

Example 116

To a suspension of LAH (95 mg) in THF (2 mL) was added a solution of ethyl 3-[2-[[(3R,4R)-1-(4-chloro-2,6-difluorophenyl)-3,4-dihydroxypiperidin-4-yl]methoxy]-5-fluorophenyl]propanoate (240 mg) in THF (6 mL) under nitrogen atmosphere, and the mixture was stirred at room temperature for 20 hours, and then stirred at 60° C. for 10 hours and at room temperature for 3 days. To the reaction solution were sequentially added water (0.1 mL), 5N aqueous NaOH solution (0.1 mL), and water (2 mL), and the mixture was stirred for a while. Then, thereto was added anhydrous sodium sulfate, and insoluble substances were filtered. The filtrate was concentrated under reduced pressure, and the residue was purified by silica gel column chromatography (Hexane/AcOEt) to give (3R,4R)-1-(4-chloro-2,6-difluorophenyl)-4-[[4-fluoro-2-(3-hydroxypropyl)phenoxy]methyl]piperidine-3,4-diol (56 mg).

Example 117

To a solution of 2-[2-[[(3R,4R)-1-(4-chloro-2,6-difluorophenyl)-3,4-dihydroxypiperidin-4-yl]methoxy]-5-fluorophenyl]acetic acid (91 mg) in THF (15 mL) were added O-(7-azabenzotriazol-1-yl)-N,N,N',N'-tetramethyluronium hexaflurophosphate (155 mg), N,N-diisopropylethylamine (0.12 mL), and ammonium chloride (29.5 mg), and the mixture was stirred at room temperature for 3 days. The reaction solution was concentrated under reduced pressure, and the residue was purified by silica gel column chromatography (Hexane/AcOEt) to give 2-[5-fluoro-2-[[(3R,4R)-

1-(4-chloro-2,6-difluorophenyl)-3,4-dihydroxypiperidin-4-yl]methoxy]phenyl]acetamide (58 mg).

Example 118

To a solution of ethyl 2-[2-[[(3R,4R)-1-(4-chloro-2,6-difluorophenyl)-3,4-dihydroxypiperidin-4-yl]methoxy]-5-fluorophenyl]acetate (67 mg) in THF (1.3 mL) was added NaBH$_4$ (26.7 mg), and then thereto was added EtOH (0.65 mL). The mixture was stirred at room temperature for 2 hours. To the reaction solution was added water, and the mixture was extracted with AcOEt and washed with brine. The organic layer was dried over anhydrous sodium sulfate, and then filtered. The filtrate was concentrated under reduced pressure. The residue was purified by silica gel column chromatography (Hexane/AcOEt) to give (3R,4R)-1-(4-chloro-2,6-difluorophenyl)-4-[[4-fluoro-2-(2-hydroxyethyl)phenoxy]methyl]piperidine-3,4-diol (58 mg).

Example 123

To a mixture of 7-fluoro-4-hydroxyindolin-2-one (203 mg), (3R,4R)-6-(4-chloro-2,6-difluorophenyl)-1-oxa-6-azaspiro[2.5]octan-4-ol (335 mg), and K$_2$CO$_3$ (185 mg) was added 2-butanone (4 mL), and the mixture was stirred at 60° C. for 2 hours and at 70° C. for 9 hours. Then, thereto was added 7-fluoro-4-hydroxyindolin-2-one (102 mg), and the mixture was stirred at the same temperature for 6 hours. To the reaction solution was added aqueous ammonium chloride solution, and the mixture was extracted with AcOEt-MeOH and washed with brine. The organic layer was dried over anhydrous sodium sulfate, and then filtered.

The filtrate was concentrated under reduced pressure. The residue was purified by silica gel column chromatography (DCM/MeOH), followed by silica gel column chromatography (Hexane/AcOEt) to give 7-fluoro-4-[[(3R,4R)-1-(4-chloro-2,6-difluorophenyl)-3,4-dihydroxypiperidin-4-yl]methoxy]-1,3-dihydroindol-2-one (38 mg).

Example 126

To a solution of (3R,4R)-1-(4-chloro-2,6-difluorophenyl)-4-[(2,4-dichloro-1,3-benzothiazol-7-yl)oxymethyl]piperidine-3,4-diol (44 mg) in THF (1 mL) was added 2N aqueous methylamine solution (0.89 mL), and then the vessel was sealed and the reaction mixture was stirred at 60° C. for 8 hours. The reaction solution was concentrated under reduced pressure, and to the residue was added AcOEt. The mixture was washed with aqueous NaHCO$_3$ solution and brine. The organic layer was dried over anhydrous sodium sulfate, and then filtered. The filtrate was concentrated under reduced pressure. The residue was washed with DIPE to give (3R,4R)-1-(4-chloro-2,6-difluorophenyl)-4-[[4-chloro-2-(methylamino)-1,3-benzothiazol-7-yl]oxymethyl]piperidine-3,4-diol (39 mg).

Example 127

To (3R,4R)-1-(4-chloro-2,6-difluorophenyl)-4-[(2,4-dichloro-1,3-benzothiazol-7-yl)oxymethyl]piperidine-3,4-diol (44 mg) was added 0.5N ammonia/dioxane solution (7.1 mL), and then the vessel was sealed and the reaction mixture was stirred at 100° C. for 19 hours. Then, thereto was added 0.5N ammonia/dioxane solution (3.55 mL), and the mixture was stirred at 120° C. for 1 hour. The reaction solution was concentrated under reduced pressure, and the residue was purified by basic silica gel column chromatography (Hexane/AcOEt) to give (3R,4R)-4-[(2-amino-4-chloro-1,3-benzothiazol-7-yl)oxymethyl]-1-(4-chloro-2,6-difluorophenyl)piperidine-3,4-diol (15 mg).

Example 138

To a suspension of (3R,4R)-1-(4-chloro-2,6-difluorophenyl)-4-[(2-chloro-4-fluoro-1,3-benzothiazol-7-yl)oxymethyl]piperidine-3,4-diol (223 mg) in acetic acid (2.2 mL) was added AcONa (382 mg), and the mixture was stirred at 140° C. for 26 hours. The reaction solution was concentrated under reduced pressure, and then thereto were added EtOH (3.3 mL) and 5N HCl (2.2 mL). The mixture was stirred under heating to reflux for 2 hours. To the reaction solution was added water, and the mixture was extracted with AcOEt-MeOH and washed with brine. The organic layer was dried over anhydrous sodium sulfate, and then filtered. The filtrate was concentrated under reduced pressure. The residue was purified by silica gel column chromatography (Hexane/AcOEt) to give 4-fluoro-7-[[(3R,4R)-1-(4-chloro-2,6-difluorophenyl)-3,4-dihydroxypiperidin-4-yl]methoxy]-3H-1,3-benzothiazol-2-one (120 mg).

Example 145

To a mixture of 7-fluoro-4-hydroxyindolin-2-one (45 mg), 6-(4-chloro-2,6-difluorophenyl)-1-oxa-6-azaspiro[2.5]octane (69.9 mg), and K$_2$CO$_3$ (40.9 mg) was added 2-butanone (1 mL), and the mixture was stirred at 70° C. for 9 hours. To the reaction solution was added water, and the mixture was extracted with AcOEt and washed with brine. The organic layer was dried over anhydrous sodium sulfate, and then filtered. The filtrate was concentrated under reduced pressure. The residue was purified by basic silica gel column chromatography (Hexane/AcOEt) to give 4-[[1-(4-chloro-2,6-difluorophenyl)-4-hydroxypiperidin-4-yl]methoxy]-7-fluoro-1,3-dihydroindol-2-one (6.8 mg).

Example 147

To a suspension of 1-(4-chloro-2,6-difluorophenyl)-4-[(2-chloro-4-fluoro-1,3-benzothiazol-7-yl)oxymethyl]piperidin-4-ol (400 mg) in AcOH (4 mL) was added AcONa (708 mg), and the mixture was stirred at 140° C. for 26 hours. The reaction solution was concentrated under reduced pressure, and thereto were added EtOH (6 mL) and 5N HCl (4 mL). The mixture was stirred under heating to reflux for 2 hours. To the reaction solution was added water, and the mixture was extracted with AcOEt-MeOH and washed with brine. The organic layer was dried over anhydrous sodium sulfate, and then filtered. The filtrate was concentrated under reduced pressure. The residue was washed with AcOEt-Hexane to give 7-[[1-(4-chloro-2,6-difluorophenyl)-4-hydroxypiperidin-4-yl]methoxy]-4-fluoro-3H-1,3-benzothiazol-2-one (195 mg).

Structures, physical data, and preparations for Reference Example compounds and Example compounds prepared in accordance with the above methods are shown in the following tables.

TABLE 1-1

| REX | STR |
|---|---|
| 1 | |

TABLE 1-1-continued

| REX | STR |
|---|---|
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 1-2

| REX | STR |
|---|---|
| 15 | (structure) |

TABLE 1-2-continued
| REX | STR |
|---|---|
| 16 | 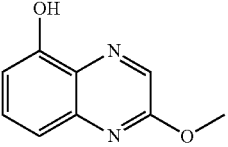 |
| 17 | 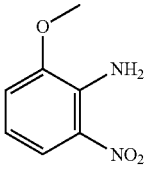 |
| 18 | 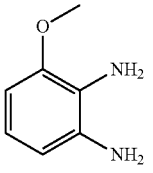 |
| 19 | 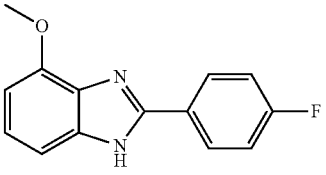 |
| 20 | 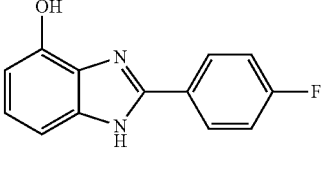 |
| 21 | 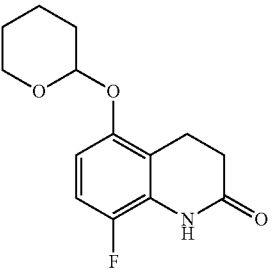 |
| 22 | 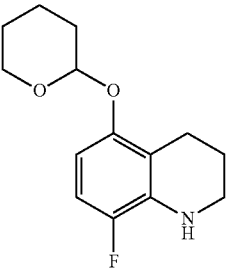 |
| 23 | 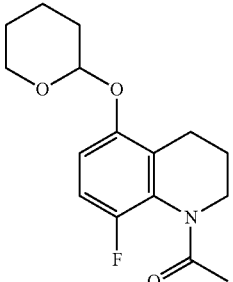 |
| 24 | 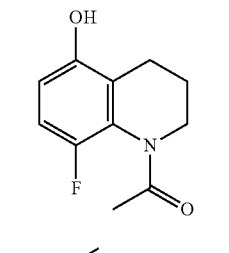 |
| 25 | 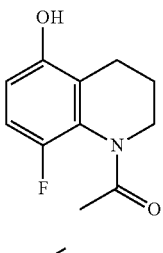 |
| 26 | 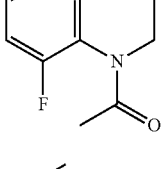 |
| 27 | 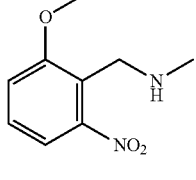 |
| 28 | 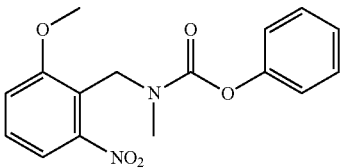 |
TABLE 1-3
| REX | STR |
|---|---|
| 29 | 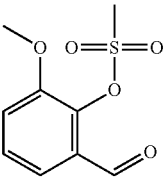 |

TABLE 1-3-continued

| REX | STR |
|---|---|
| 30 | (structure) |
| 31 | (structure) |
| 32 | (structure) |
| 33 | (structure) |
| 34 | (structure) |
| 35 | (structure) |
| 36 | (structure) |
| 37 | (structure) |

TABLE 1-3-continued

| REX | STR |
|---|---|
| 38 | (structure) |
| 39 | (structure) |
| 40 | (structure) |
| 41 | (structure) |
| 42 | (structure) |

TABLE 1-4

| REX | STR |
|---|---|
| 43 | (structure) |
| 44 | (structure) |

TABLE 1-4-continued

| REX | STR |
|---|---|
| 45 | (8-hydroxy-5-chloro-2H-benzo[b][1,4]oxazin-3(4H)-one) |
| 46 | N-(2-chloro-5-hydroxyphenyl)propanamide |
| 47 | N-(2-chloro-5-hydroxyphenyl)butanamide |
| 48 | N-(2-chloro-5-hydroxyphenyl)benzamide |
| 49 | N-(2-chloro-5-methoxyphenyl)-2-phenylacetamide |
| 50 | N-(2-chloro-5-hydroxyphenyl)-2-phenylacetamide |
| 51 | N-(2-chloro-5-hydroxyphenyl)-3-phenylpropanamide |

TABLE 1-4-continued

| REX | STR |
|---|---|
| 52 | N-(6-chloro-3-methoxy-2-methylphenyl)acetamide |
| 53 | N-(6-chloro-3-hydroxy-2-methylphenyl)acetamide |
| 54 | N-(6-chloro-3-methoxy-2-methylphenyl)formamide |
| 55 | N-(6-chloro-3-hydroxy-2-methylphenyl)formamide |
| 56 | methyl (3-methoxy-2-methylphenyl)carbamate |

TABLE 1-5

| REX | STR |
|---|---|
| 57 | methyl (6-chloro-3-methoxy-2-methylphenyl)carbamate |
| 58 | methyl (6-chloro-3-hydroxy-2-methylphenyl)carbamate |

TABLE 1-5-continued

| REX | STR |
|---|---|
| 59 | 5-methoxy-8-chloro-3,4-dihydroquinoline-2(1H)-thione |
| 60 | 5-hydroxy-8-chloro-3,4-dihydroquinoline-2(1H)-thione |
| 61 | 7-hydroxy-4-chloro-benzothiazol-2(3H)-one |
| 62 | 2,7-diacetoxy-4-chloro-benzothiazole |
| 63 | 7-acetoxy-4-chloro-benzothiazol-2(3H)-one |
| 64 | 7-acetoxy-2,4-dichloro-benzothiazole |
| 65 | 7-hydroxy-2,4-dichloro-benzothiazole |

TABLE 1-5-continued

| REX | STR |
|---|---|
| 66 | methyl 4-hydroxy-7-fluoro-1H-indole-2-carboxylate |
| 67 | 2-methoxy-3-(aminomethyl)-4-amino-5-fluorobenzene (approx.) |
| 68 | 5-methoxy-8-fluoro-3,4-dihydroquinazolin-2(1H)-one |
| 69 | 5-hydroxy-8-fluoro-3,4-dihydroquinazolin-2(1H)-one |
| 70 | 5-(tert-butyldiphenylsilyloxy)-4H-benzo[d][1,3]oxazin-2(1H)-one |

TABLE 1-6

| REX | STR |
|---|---|
| 71 | 5-(tert-butyldiphenylsilyloxy)-8-chloro-4H-benzo[d][1,3]oxazin-2(1H)-one |

TABLE 1-6-continued

| REX | STR |
|---|---|
| 72 | (chemical structure) |
| 73 | (chemical structure) |
| 74 | (chemical structure) |
| 75 | (chemical structure) |
| 76 | (chemical structure) |
| 77 | (chemical structure) |
| 78 | (chemical structure) |
| 79 | (chemical structure) |
| 80 | (chemical structure) |
| 81 | (chemical structure) |
| 82 | (chemical structure) |
| 83 | (chemical structure) |
| 84 | (chemical structure) |

TABLE 1-7

| REX | STR |
|---|---|
| 85 | (chemical structure) |

TABLE 1-7-continued
| REX | STR |
|---|---|
| 86 | 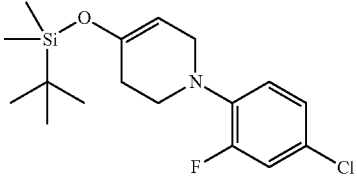 |
| 87 | 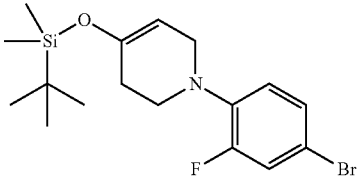 |
| 88 | 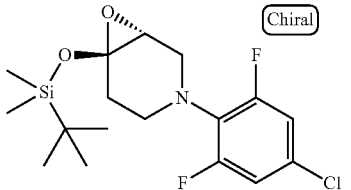 Chiral |
| 89 | 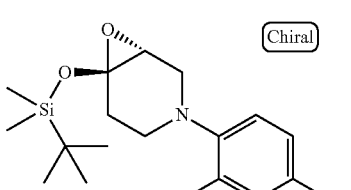 Chiral |
| 90 | 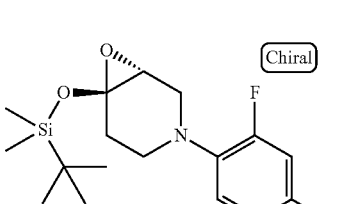 Chiral |
| 91 | 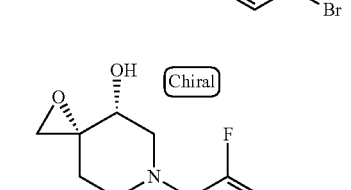 Chiral |
| 92 | 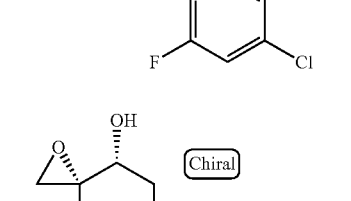 Chiral |
| 93 | 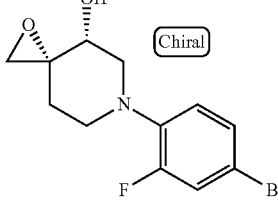 Chiral |
| 94 | 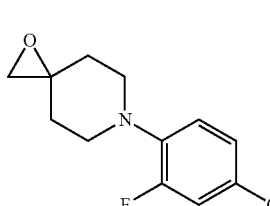 |
| 95 | 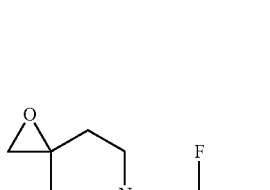 |
| 96 | 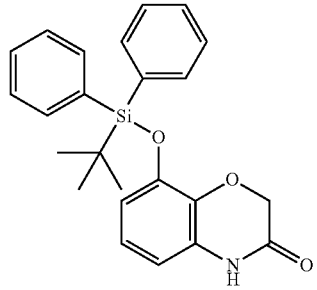 |
| 97 | 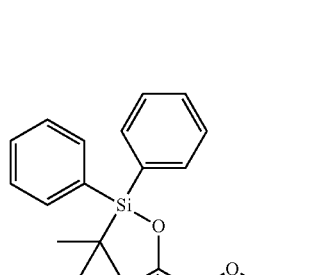 |

TABLE 2-1

| REX | RProp | Data |
|---|---|---|
| 1 | — | NMR2; 3.75 (3H, s), 5.04 (2H, s), 6.83-6.88 (2H, m), 6.93-6.98 (1H, m), 6.98 (1H, d, J = 8.4 Hz), 7.26-7.32 (2H, m), 7.43-7.49 (1H, m), 7.77 (1H, dd, J = 7.7 Hz, 1.9 Hz), 10.45 (1H, d, J = 0.7 Hz). |
| 2 | — | NMR2; 1.10 (9H, s), 1.29-1.45 (1H, m), 3.72 (2H, s), 3.81 (3H, s), 5.00 (2H, s), 6.88-6.95 (4H, m), 7.19 (1H, dt, J = 1.7 Hz, 7.8 Hz), 7.29 (1H, dd, J = 7.8 Hz, 1.5 Hz), 7.33-7.39 (2H, m). |
| 3 | — | NMR2; 1.44 (9H, s), 1.45 (3H, t, J = 7.1 Hz), 3.83 (3H, s), 4.65 (2H, q, J = 7.1 Hz), 4.74 (2H, s), 5.02 (2H, s), 6.91-6.96 (2H, m), 6.96-7.01 (2H, m), 7.17-7.26 (2H, m), 7.31-7.37 (2H, m). |
| 4 | — | NMR2; 1.55 (9H, s), 3.83 (3H, s), 4.38 (2H, s), 5.07 (2H, s), 6.91-6.97 (2H, m), 7.03 (1H, dd, J = 7.4 Hz, 1.3 Hz), 7.33-7.42 (4H, m). |
| 5 | — | NMR1: 4.24 (2H, s), 6.98 (1H, d, J = 7.4 Hz), 7.12 (1H, d, J = 7.4 Hz), 7.29 (1H, t, J = 7.4 Hz), 8.49 (1H, brs), 10.03 (1H, brs). |
| 6 | — | NMR2; 1.58 (9H, s), 4.51 (2H, s), 7.04 (1H, dd, J = 7.9 Hz, 0.7 Hz), 7.24-7.30 (1H, m), 7.35 (1H, d, J = 7.5 Hz, 0.5 Hz), 8.31 (1H, brs). |
| 7 | 1 | NMR2; 3.82 (3H, s), 5.11 (2H, s), 6.90-6.95 (2H, m), 7.01 (1H, d, J = 8.9 Hz), 7.31-7.36 (2H, m), 7.46 (1H, dd, J = 8.9 Hz, 2.8 Hz), 7.79 (1H, d, J = 2.8 Hz), 10.43 (1H, s). |
| 8 | 2 | NMR2; 1.10 (9H, s), 1.18-1.34 (1H, m), 3.68 (2H, s), 3.82 (3H, s), 4.98 (2H, s), 6.83 (1H, d, J = 8.7 Hz), 6.88-6.94 (2H, m), 7.14 (1H, dd, J = 8.7 Hz, 2.7 Hz), 7.31 (1H, d, J = 2.7 Hz), 7.31-7.36 (2H, m). |
| 9 | 3 | NMR2; 1.44 (9H, s), 1.47 (3H, t, J = 7.1 Hz), 3.83 (3H, s), 4.66 (2H, q, J = 7.1 Hz), 4.69 (2H, s), 4.99 (2H, s), 6.83-6.88 (1H, m), 6.90-6.96 (2H, m), 7.15-7.21 (2H, m), 7.28-7.35 (2H, m). |
| 10 | 4 | NMR2; 1.54 (9H, s), 3.83 (3H, s), 4.32 (2H, s), 5.05 (2H, s), 6.91-6.97 (3H, m), 7.27 (1H, d, J = 8.6 Hz), 7.31-7.36 (2H, m). |
| 11 | 5 | NMR1: 4.19 (2H, s), 6.95 (1H, d, J = 8.5 Hz), 7.24 (1H, d, J = 8.5 Hz), 8.60 (1H, brs), 10.24 (1H, brs). |

TABLE 2-2

| REX | RProp | Data |
|---|---|---|
| 12 | — | NMR1: 6.77 (1H, dd, J = 8.0 Hz, 1.0 Hz), 6.86 (1H, dd, J = 8.0 Hz, 1.0 Hz), 7.26 (1H, t, J = 8.0 Hz), 7.55-7.62 (1H, m), 7.77-7.84 (1H, m), 8.34 (1H, d, J = 8.0 Hz, 1.3 Hz), 9.32 (1H, d, J = 8.0 Hz), 10.74 (1H, brs), 11.56 (1H, brs). |
| 13 | — | NMR1: 5.25 (2H, s), 6.87 (1H, dd, J = 8.3 Hz, 0.8 Hz), 6.97 (1H, dd, J = 8.3 Hz, 0.8 Hz), 7.33-7.38 (1H, m), 7.40-7.44 (2H, m), 7.46 (1H, t, J = 8.3 Hz), 7.49-7.54 (2H, m), 8.08 (1H, d, J = 1.9 Hz), 12.39 (1H, brs). |
| 14 | — | NMR2: 5.42 (2H, s), 7.12 (1H, dd, J = 7.8 Hz, 1.1 Hz), 7.31-7.35 (1H, m), 7.37-7.41 (2H, m), 7.48-7.52 (2H, m), 7.60 (1H, dd, J = 8.6 Hz, 1.1 Hz), 7.63-7.68 (1H, m), 8.80 (1H, s). |
| 15 | — | NMR2: 4.10 (3H, s), 5.40 (2H, s), 6.94 (1H, dd, J = 7.9 Hz, 1.0 Hz), 7.29-7.33 (1H, m), 7.35-7.40 (2H, m), 7.42 ((1H, dd, J = 8.4 Hz, 1.0 Hz), 7.48-7.53 (3H, m), 8.49 (1H, s). |
| 16 | — | NMR2: 4.10 (3H, s), 7.05 (1H, dd, J = 7.8 Hz, 1.1 Hz), 7.36 (1H, dd, J = 8.4 Hz, 1.1 Hz), 7.55-7.60 (1H, m), 7.62 (1H, s), 8.31 (1H, s). |
| 17 | — | NMR2; 3.76 (3H, s), 6.27 (2H, brs), 6.45 (1H, dd, J = 8.9 Hz, 7.6 Hz), 6.73 (1H, d, J = 7.6 Hz), 7.57 (1H, dd, J = 8.9 Hz, 1.2 Hz). |
| 18 | — | NMR2; 3.43 (4H, brs), 3.83 (3H, s), 6.36-6.43 (2H, m), 6.66 (1H, t, J = 8.1 Hz). |
| 19 | — | NMR1: 3.97 (3H, s), 6.60-6.90 (1H, m), 7.05-7.29 (2H, m), 7.33-7.48 (2H, m), 8.10-8.40 (2H, m), 12.95 (1H, brs). |
| 20 | — | NMR1: 6.46-6.72 (1H. m), 6.88-7.20 (2H, m), 7.30-7.48 (2H, m), 8.10-8.42 (2H, m), 9.52-10.20 (1H, m), 12.60-12.90 (1H, m). |
| 21 | — | NMR1: 1.48-1.67 (3H, m), 1.71-1.94 (3H, m), 2.43-2.50 (2H, m), 2.83-2.97 (2H, m), 3.50-3.58 (1H, m), 3.68-3.78 (1H, m), 5.39-5.45 (1H, m), 6.67-6.74 (1H, m), 6.96-7.04 (1H, m), 10.03 (1H, brs). |

TABLE 2-2-continued

| REX | RProp | Data |
|---|---|---|
| 22 | — | NMR2; 1.54-1.73 (3H, m), 1.79-1.90 (2H, m), 1.90-2.04 (3H, m), 2.64-2.80 (2H, m), 3.25-3.33 (2H, m), 3.56-3.63 (1H, m), 3.86-3.94 (1H, m), 4.00 (1H, brs), 5.29-5.34 (1H, m), 6.27-6.34 (1H, m), 6.67-6.75 (1H, m). |
| 23 | — | NMR2; 1.57-1.75 (3H, m), 1.76-1.93 (3H, m), 1.94-2.05 (2H, m), 2.11 (3H, brs), 2.40-3.20 (3H, br), 3.57-3.68 (1H, m), 3.80-3.95 (1H, m), 4.32-4.96 (1H, br), 5.32-5.40 (1H, m), 6.86-6.97 (2H, m). |

TABLE 2-3

| REX | RProp | Data |
|---|---|---|
| 24 | — | NMR1: 1.60-2.20 (5H, m), 2.30-3.20 (2H, m), 3.50-4.90 (2H, m), 6.55-6.73 (1H, m), 6.80-7.04 (1H, m), 9.51 (1H, brs). |
| 25 | — | NMR2: 1.65-1.82 (1H, m), 2.45 (3H, s), 3.86 (2H, s), 3.92 (3H, s), 7.11 (1H, dd, J = 8.0 Hz, 1.0 Hz), 7.35 (1H, t, J = 8.0 Hz), 7.39 (1H, dd, J = 8.0 Hz, 1.0 Hz). |
| 26 | — | NMR2: 2.94 (1.8H, s), 2.99 (1.2H, s), 3.93 (3H, s), 4.80 (0.8H, s), 4.92 (1.2H, s), 7.02-7.20 (4H, m), 7.31-7.37 (3H, m), 7.37-7.45 (1H, m). |
| 27 | — | NMR1: 2.86 (3H, s), 3.76 (3H, s), 4.30 (2H, s), 6.36 (1H, d, J = 8.0 Hz), 6.51 (1H, d, J = 8.0 Hz), 7.07 (1H, t, J = 8.0 Hz), 9.11 (1H, s). |
| 28 | 12 | NMR1: 2.86 (3H, s), 4.27 (2H, s), 6.20 (1H, d, J = 8.0 Hz), 6.33 (1H, d, J = 8.0 Hz), 6.89 (1H, t, J = 8.0 Hz), 9.01 (1H, s), 9.62 (1H, s). |
| 29 | — | NMR2: 3.37 (3H, s), 3.96 (3H, s), 7.28 (1H, d, J = 8.1 Hz), 7.39 (1H, t, J = 7.9 Hz), 7.54 (1H, dd, J = 7.7 Hz, 1.5 Hz), 10.34 (1H, s). |
| 30 | — | NMR2: 3.90 (3H, s), 3.92-4.20 (2H, m), 5.25-5.45 (1H, m), 6.95-7.45 (3H, m). |
| 31 | — | NMR2: 3.94 (3H, s), 6.79 (1H, d, J = 10.3 Hz), 6.95-7.15 (2H, m), 7.20-7.35 (2H, m). |
| 32 | — | NMR2: 6.01 (1H, brs), 6.78 (1H, d, J = 10.3 Hz), 6.85-7.50 (4H, m). |
| 33 | — | NMR2: 3.86 (3H, s), 4.16 (2H, s), 6.47 (1H, d, J = 8.2 Hz), 6.65 (1H, d, J = 8.2 Hz), 7.19 (1H, t, J = 8.2 Hz), 8.30 (1H, brs). |
| 34 | — | NMR1: 4.08 (2H, s), 6.46 (1H, dd, J = 8.1 Hz, 0.8 Hz), 6.56 (1H, dd, J = 8.1 Hz, 0.8 Hz), 7.01 (1H, t, J = 8.1 Hz), 9.90 (1H, s), 10.59 (1H, s). |
| 35 | — | NMR2: 2.05 (1H, brs), 3.84 (3H, s), 4.21 (2H, s), 4.85 (2H, s), 6.75 (1H, d, J = 8.3 Hz), 7.30 (1H, t, J = 8.3 Hz), 7.59 (1H, d, J = 8.3 Hz), 9.48 (1H, brs). |
| 36 | — | NMR2: 3.82 (3H, s), 4.49 (2H, s), 4.89 (2H, s), 6.46 (1H, d, J = 8.2 Hz), 6.62 (1H, d, J = 8.2 Hz), 7.18 (1H, t, J = 8.2 Hz), 7.56 (1H, brs). |
| 37 | — | NMR1: 4.32 (2H, s), 4.73 (2H, s), 6.51 (1H, dd, J = 8.1 Hz, 0.8 Hz), 6.58 (1H, dd, J = 8.1 Hz, 0.8 Hz), 6.99 (1H, t, J = 8.1 Hz), 9.71 (1H, s), 9.99 (1H, s). |

TABLE 2-4

| REX | RProp | Data |
|---|---|---|
| 38 | — | NMR2: 3.29 (2H, s), 3.71 (3H, s), 3.92 (3H, s), 4.18 (2H, s), 7.12 (1H, d, J = 8.3 Hz), 7.36 (1H, t, J = 8.3 Hz), 7.50 (1H, d, J = 8.3 Hz). |
| 39 | — | NMR2: 3.26 (2H, s), 3.79 (3H, s), 3.94 (2H, s), 4.32-5.15 (3H, m), 6.35 (1H, d, J = 8.1 Hz), 6.37 (1H, d, J = 8.1 Hz), 7.05 (1H, t, J = 8.1 Hz). |
| 40 | — | NMR2: 3.06 (2H, s), 3.89 (3H, s), 3.98 (2H, s), 6.67 (1H, d, J = 8.2 Hz), 6.85 (1H, d, J = 8.2 Hz), 7.18 (1H, brs), 7.24 (1H, t, J = 8.2 Hz). |
| 41 | — | NMR1: 2.88 (2H, s), 3.77 (2H, s), 6.49 (1H, dd, J = 8.1 Hz, 0.7 Hz), 6.75 (1H, dd, J = 8.1 Hz, 0.7 Hz), 7.08 (1H, t, J = 8.1 Hz), 9.53 (1H, s), 9.90 (1H, s). |

TABLE 2-4-continued

| REX | RProp | Data |
|---|---|---|
| 42 | — | NMR1: 3.94 (2H, s), 4.42 (2H, s), 6.64 (1H, dd, J = 8.1 Hz, 0.7 Hz), 6.82 (1H, dd, J = 8.1 Hz, 0.7 Hz), 7.24 (1H, t, J = 8.1 Hz), 10.31 (1H, s), 10.46 (1H, s). |
| 43 | — | NMR1: 2.43 (2H, t, J = 7.7 Hz), 2.73 (2H, t, J = 7.7 Hz), 6.48 (1H, d, J = 5.5 Hz), 7.80 (1H, d, J = 5.5 Hz), 10.17 (1H, s), 10.62 (1H, brs). |
| 44 | — | NMR1: 1.98-2.04 (2H, m), 2.08-2.11 (2H, m), 2.68-2.71 (2H, m), 6.70 (1H, d, J = 8.8 Hz), 7.14 (1H, d, J = 8.8 Hz), 9.16 (1H, brs), 9.78 (1H, brs). |
| 45 | — | NMR1: 4.55 (2H, s), 6.52 (1H, d, J = 8.8 Hz), 6.88 (1H, d, J = 8.8 Hz), 9.65 (1H, brs), 10.31 (1H, brs). |
| 46 | — | NMR2; 1.32 (3H, t, J = 7.6 Hz), 2.53 (2H, q, J = 7.6 Hz), 6.62 (1H, dd, J = 2.9 Hz, 8.8 Hz), 7.22 (1H, d, J = 8.8 Hz), 7.83 (1H, brs), 8.35 (1H, d, J = 2.9 Hz), 8.53 (1H, brs). |
| 47 | 46 | NMR2; 1.05 (3H, t, J = 7.61 Hz), 1.77-1.85 (2H, m), 2.44-2.48 (2H, m), 6.59-6.63 (1H, m), 7.21 (1H, d, J = 8.8 Hz), 7.78 (1H, brs), 7.99 (1H, brs), 8.29-8.34 (1H, m). |
| 48 | 46 | NMR2; 6.69 (1H, dd, J = 2.9 Hz, 8.8 Hz), 7.09 (1H, d, J = 2.9 Hz), 7.31 (1H, d, J = 8.8 Hz), 7.52-7.55 (2H, m), 7.59-7.63 (1H, m), 7.96-7.98 (2H, m), 9.80 (1H, brs), 9.85 (1H, brs). |
| 49 | 47 | NMR2; 3.79 (3H, s), 3.79 (2H, s), 6.56 (1H, dd, J = 3.0 Hz, 8.9 Hz), 7.15 (1H, d, J = 8.9 Hz), 7.34-7.37 (3H, m), 7.40-7.44 (2H, m), 7.66 (1H, brs), 8.09 (1H, d, J = 3.0 Hz). |
| 50 | 46 | NMR2; 3.84 (2H, s), 6.59 (1H, dd, J = 2.9 Hz, 8.8 Hz), 7.13 (1H, d, J = 8.8 Hz), 7.35-7.41 (3H, m), 7.42-7.46 (2H, m), 7.81 (1H, brs), 8.36 (1H, d, J = 2.9 Hz), 8.48 (1H, brs). |

TABLE 2-5

| REX | RProp | Data |
|---|---|---|
| 51 | 46 | NMR2; 2.77-2.80 (2H, m), 3.07-3.11 (2H, m), 6.61 (1H, dd, J = 2.9 Hz, 8.8 Hz), 7.18 (1H, d, J = 8.8 Hz), 7.21-7.26 (3H, m), 7.29-7.32 (2H, m), 7.64 (1H, brs), 7.98 (1H, brs), 8.27 (1H, d, J = 2.9 Hz). |
| 52 | 54 | NMR2; 2.10 (3H, s), 2.21 (3H, s), 3.81 (3H, s), 6.71 (1H, d, J = 8.9 Hz), 7.10 (1H, brs), 7.20 (1H, d, J = 8.9 Hz). |
| 53 | 46 | NMR2; 2.10 (3H, s), 2.27 (3H, s), 6.14 (1H, brs), 6.52 (1H, d, J = 8.7 Hz), 6.94 (1H, brs), 7.01 (1H, d, J = 8.7 Hz). |
| 54 | — | NMR2; 2.15 (1.5H, s), 2.22 (1.5H, s), 3.83 (1.6H, s), 3.85 (1.5H, s), 6.76 (1H, d, J = 11.1 Hz), 6.97 (1H, brs), 7.24 (0.5H, d, J = 11.1 Hz), 7.27 (0.5H, d, J = 11.1 Hz), 8.19 (0.5H, d, J = 14.4 Hz), 8.42 (0.5H, d, J = 1.6 Hz). |
| 55 | — | NMR2; 1.97 (2.34H, s), 2.06 (0.66H, s), 6.77 (0.78H, d, J = 8.7 Hz), 6.79 (0.22H, d, J = 8.7 Hz), 7.13 (0.78H, d, J = 8.7 Hz), 7.19 (0.22H, d, J = 8.7 Hz), 8.01 (0.22H, d, J = 11.2 Hz), 8.24 (0.78H, d, J = 1.5 Hz), 9.50 (0.22H, d, J = 11.2 Hz), 9.68 (0.78H, brs), 9.74 (0.78H, brs), 9.87 (0.22H, brs). |
| 56 | — | NMR2; 2.11 (3H, s), 3.77 (3H, s), 3.82 (3H, s), 6.37-6.43 (1H, m), 6.66 (1H, d, J = 8.3 Hz), 7.16 (1H, t, J = 8.3 Hz), 7.39 (1H, brs). |
| 57 | 54 | NMR2; 2.16 (3H, s), 3.77 (3H, brs), 3.82 (3H, s), 6.28 (1H, brs), 6.72 (1H, d, J = 8.9 Hz), 7.21 (1H, d, J = 8.9 Hz). |
| 58 | 46 | NMR2; 2.13 (3H, s), 3.81 (3H, brs), 6.27-6.53 (3H, m), 6.91-7.04 (1H, m). |
| 59 | — | NMR1: 2.72-2.76 (2H, m), 2.91-2.95 (2H, m), 3.81 (3H, s), 6.84 (1H, d, J = 11.2 Hz), 7.33 (1H, d, J = 11.0 Hz), 11.02 (1H, brs). |
| 60 | 46 | NMR1: 2.69-2.73 (2H, m), 2.90-2.94 (2H, m), 6.64 (1H, d, J = 11.0 Hz), 7.14 (1H, d, J = 11.0 Hz), 9.97 (1H, brs), 10.84 (1H, brs). |
| 61 | 46 | NMR1: 6.62 (1H, d, J = 11.0 Hz), 7.16 (1H, d, J = 11.0 Hz), 10.63 (1H, brs), 12.06 (1H, brs). |
| 62 | — | NMR2; 2.35 (3H, s), 2.77 (3H, s), 7.08 (1H, d, J = 11.1 Hz), 7.34 (1H, d, J = 11.1 Hz). |
| 63 | — | NMR2; 2.35 (3H, s), 6.97 (1H, d, J = 11.0 Hz), 7.27 (1H, d, J = 11.0 Hz), 8.32 (1H, brs). |
| 64 | — | NMR2: 2.38 (3H, s), 7.23 (1H, d, J = 8.6 Hz), 7.52 (1H, d, J = 8.6 Hz). |

TABLE 2-6

| REX | RProp | Data |
|---|---|---|
| 65 | — | NMR1: 6.91 (1H, d, J = 8.6 Hz), 7.48 (1H, d, J = 8.6 Hz), 11.11 (1H, brs). |
| 66 | — | NMR1: 3.86 (3H, s), 6.28 (1H, dd, J = 3.1 Hz, 8.3 Hz), 6.87 (1H, dd, J = 8.3 Hz, 11.1 Hz), 7.23-7.24 (1H, m), 9.92 (1H, brs), 12.25 (1H, brs). |
| 67 | — | NMR2; 1.46 (2H, brs), 3.75 (3H, s), 3.93 (2H, s), 4.50 (2H, brs), 6.18 (1H, dd, J = 3.9 Hz, 9.0 Hz), 6.83 (1H, dd, J = 9.0 Hz, 10.5 Hz). |
| 68 | — | NMR1: 3.74 (3H, s), 4.25 (2H, d, J = 1.3 Hz), 6.48 (1H, dd, J = 3.6 Hz, 9.1 Hz), 6.88 (1H, brs), 7.01 (1H, dd, J = 9.1 Hz, 10.3 Hz), 8.92 (1H, brs). |
| 69 | 46 | NMR1: 4.22 (2H, d, J = 1.3 Hz), 6.29 (1H, dd, J = 3.8 Hz, 8.9 Hz), 6.82-6.86 (2H, m), 8.79 (1H, brs), 9.56 (1H, brs). |
| 70 | — | NMR2; 1.03 (9H, s), 5.45 (2H, s), 5.96 (1H, d, J = 8.1 Hz), 6.41 (1H, d, J = 8.1 Hz), 6.84 (1H, t, J = 8.1 Hz), 7.43-7.47 (4H, m), 7.48-7.52 (2H, m), 7.65-7.67 (4H, m), 10.14 (1H, brs). |
| 71 | — | NMR2; 1.09 (9H, s), 5.51 (2H, s), 6.08 (1H, d, J = 8.9 Hz), 6.84 (1H, d, J = 8.9 Hz), 7.24 (1H, brs), 7.38-7.41 (4H, m), 7.45-7.48 (2H, m), 7.64-7.67 (4H, m). |
| 72 | 45 | NMR1: 5.22 (2H, s), 6.53 (1H, d, J = 8.8 Hz), 7.16 (1H, d, J = 8.8 Hz), 9.71 (1H, brs), 10.22 (1H, brs). |
| 73 | — | NMR1: 3.95 (3H, s), 7.11 (1H, dd, J = 3.2 Hz, 8.9 Hz), 7.42 (1H, dd, J = 8.9 Hz, 10.5 Hz). |
| 74 | 46 | NMR1: 6.87 (1H, dd, J = 3.5 Hz, 8.8 Hz), 7.26 (1H, dd, J = 8.8 Hz, 10.5 Hz), 10.79 (1H, brs). |
| 75 | — | NMR1: 3.33 (3H, s), 3.41-3.47 (2H, m), 3.64-3.71 (2H, m), 5.20 (2H, s), 6.66 (1H, dt, J = 3.2 Hz, 8.3 Hz), 7.05 (1H, dd, J = 5.5 Hz, 9.0 Hz), 7.31-7.39 (1H, m), 8.00 (1H, dd, J = 3.2 Hz 11.8 Hz), 8.32 (1H, brs). |
| 76 | — | NMR1: 3.36-3.44 (2H, m), 3.39 (3H, s), 3.76-3.85 (2H, m), 5.17 (2H, s), 6.79 (1H, brs), 7.01 (1H, dt, J = 3.2 Hz, 9.0 Hz), 7.14 (1H, dd, J = 5.5 Hz, 9.1 Hz), 7.18 (1H, dd, J = 3.2 Hz, 10.0 Hz). |
| 77 | — | NMR1: 3.45-3.54 (2H, m), 3.75-3.83 (2H, m), 4.69 (1H, s), 6.88 (1H, dd, J = 5.7 Hz, 9.0 Hz), 6.92 (1H, dt, J = 3.1 Hz, 9.0 Hz), 7.07 (1H, dd, J = 3.1 Hz, 10.0 Hz), 9.61 (1H, brs) |

TABLE 2-7

| REX | RProp | Data |
|---|---|---|
| 78 | — | NMR2: 1.38 (3H, t, J = 7.0 Hz), 3.99 (2H, q, J = 7.0 Hz), 5.36 (1H, d, J = 12.1 Hz), 6.49-6.35 (1H, m), 6.94 (1H, dd, J = 9.0 Hz, 8.9 Hz), 7.22 (1H, brs), 7.67 (1H, d, J = 12.1 Hz), 8.08 (1H, brs), 8.23-8.29 (1H, m). |
| 79 | — | NMR1: 6.46 (1H, d, J = 9.8 Hz), 6.52 (1H, dd, J = 8.8 Hz, 3.7 Hz), 7.21 (1H, dd, J = 10.9 Hz, 8.8 Hz), 8.02 (1H, dd, J = 9.8 Hz, 1.6 Hz), 10.33 (1H, brs), 11.60 (1H, brs). |
| 80 | — | NMR1: 6.88-6.94 (1H, m), 7.45-7.52 (1H, m), 7.56 (1H, d, J = 8.5 Hz), 8.47-8.55 (1H, m), 10.74 (1H, brs). |
| 81 | — | NMR2: 1.60-1.83 (3H, m), 1.93-2.15 (3H, m), 3.64-3.69 (1H, m), 3.84-3.91 (1H, m), 5.57 (1H, t, J = 3.1 Hz), 7.13 (1H, dd, J = 8.7 Hz, 3.7 Hz), 7.33 (1H, d, J = 10.2 Hz, 8.7 Hz), 7.43 (1H, d, J = 8.8 Hz), 8.53 (1H, dd, J = 8.8 Hz, 1.6 Hz). |
| 82 | — | NMR2: 4.11 (3H, s), 5.38 (1H, brs), 6.60 (1H, dd, J = 8.4 Hz, 3.5 Hz), 6.93 (1H, d, J = 9.1 Hz), 7.16 (1H, dd, J = 10.6 Hz, 8.4 Hz), 8.34 (1H, dd, J = 9.1 Hz, 1.7 Hz). |
| 83 | — | NMR2: 1.83 (4H, t, J = 5.5 Hz), 3.23 (4H, t, J = 5.5 Hz), 3.99 (4H, s), 6.83-6.89 (2H, m). |
| 84 | — | NMR2: 2.58 (4H, t, J = 6.0 Hz), 3.46 (4H, t, J = 6.0 Hz), 6.89-6.95 (2H, m). |
| 85 | 87 | NMR2: 0.17 (6H, s), 0.93 (9H, s), 2.20-2.24 (2H, m), 3.29-3.32 (2H, m), 3.64-3.66 (2H, m), 4.87-4.89 (1H, m), 6.84-6.89 (2H, m). |
| 86 | 87 | NMR2: 0.16 (6H, s), 0.93 (9H, s), 2.19-2.26 (2H, m), 3.28 (2H, t, J = 5.7 Hz), 3.60 (2H, dd, J = 5.7 Hz, 2.5 Hz), 4.89-4.92 (1H, m), 6.88 (1H, t, J = 8.9 Hz), 6.99-7.06 (2H, m). |
| 87 | — | NMR2: 0.16 (6H, s), 0.93 (9H, s), 2.19-2.26 (2H, m), 3.28 (2H, t, J = 5.7 Hz), 3.60 (2H, dd, J = 5.7 Hz, 2.5 Hz), 4.89-4.92 (1H, m), 6.82 (1H, t, J = 8.9 Hz), 7.13-7.20 (2H, m). |

TABLE 2-7-continued

| REX | RProp | Data |
|---|---|---|
| 88 | 90 | NMR2: 0.14 (3H, s), 0.18 (3H, s), 0.90 (9H, s), 2.13-2.19 (1H, m) 2.23-2.31 (1H, m), 2.91-2.97 (1H, m), 3.07-3.14 (1H, m), 3.33-3.40 (2H, m), 3.51 (1H, dd, 13.7 Hz, 4.0 Hz), 6.83-6.90 (2H, m). |
| 89 | 90 | NMR2: 0.14 (3H, s), 0.18 (3H, s), 0.90 (9H, s), 2.20-2.24 (1H, m), 2.29-2.34 (1H, m), 2.82-2.88 (1H, m), 3.07-3.11 (1H, m), 3.17 (1H, d, J = 14.0 Hz), 3.37 (1H, d, J = 4.3), 3.57-3.62 (1H, m), 6.79 (1H, t, J = 9.2 Hz), 6.99-7.04 (2H, m). |

TABLE 2-8

| REX | RProp | Data |
|---|---|---|
| 90 | — | NMR2: 0.14 (3H, s), 0.18 (3H, s), 0.90 (9H, s), 2.19-2.25 (1H, m), 2.29-2.36 (1H, m), 2.81-2.89 (1H, m), 3.08-3.14 (1H, m), 3.17 (1H, d, J = 13.7 Hz), 3.37 (1H, d, J = 4.5 Hz), 3.56-3.63 (1H, m), 6.72 (1H, t, J = 9.0 Hz), 7.13-7.19 (2H, m). |
| 91 | 92 | NMR2: 1.76 (1H, dt, J = 14.0 Hz, 4.0 Hz), 2.05 (1H, d, J = 11.0 Hz), 2.09 (1H, ddd, J = 14.0 Hz, 9.5 Hz, 4.5 Hz), 2.69 (1H, d, J = 4.5 Hz), 3.06 (1H, d, J = 4.5 Hz), 3.06-3.10 (1H, m), 3.13-3.18 (1H, m), 3.26-3.32 (1H, m), 3.39-3.44 (1H, m), 3.85 (1H, ddd, J = 11.0 Hz, 8.5 Hz, 4.5 Hz), 6.87-6.92 (2H, m). |
| 92 | — | NMR2: 1.74 (1H, dt, J = 14.0 Hz, 3.5 Hz), 1.97 (1H, d, J = 11.0 Hz), 2.21 (1H, ddd, J = 14.0 Hz, 10.5 Hz, 4.5 Hz), 2.72 (1H, d, J = 4.5 Hz), 2.80 (1H, dd, J = 11.0 Hz, 9.0 Hz), 2.99-3.04 (1H, m), 3.10 (1H, d, J = 4.5 Hz), 3.24-3.29 (1H, m), 3.47-3.52 (1H, m), 3.96 (1H, ddd, J = 11.0 Hz, 9.0 Hz, 4.5 Hz), 6.91 (1H, t, J = 9.0 Hz), 7.04-7.08 (2H, m). |
| 93 | 92 | NMR2: 1.74 (1H, dt, J = 14.0 Hz, 3.5 Hz), 1.96 (1H, d, J = 11.0 Hz), 2.21 (1H, ddd, J = 14.0 Hz, 11.0 Hz, 4.5 Hz), 2.72 (1H, d, J = 4.5 Hz), 2.80 (1H, dd, J = 11.0 Hz, 9.0 Hz), 2.98-3.04 (1H, m), 3.10 (1H, d, J = 4.5 Hz), 3.24-3.29 (1H, m), 3.48-3.52 (1H, m), 3.96 (1H, ddd, J = 11.0 Hz, 9.0 Hz, 4.5 Hz), 6.85 (1H, t, J = 9.0 Hz), 7.18-7.20 (2H, m). |
| 94 | — | NMR2: 1.61-1.65 (2H, m), 2.03-2.09 (2H, m), 2.73 (2H, s), 3.14-3.18 (2H, m), 3.21-3.25 (2H, m), 6.89-6.23 (1H, m), 7.03-7.07 (2H, m). |
| 95 | 94 | NMR2: 1.60-1.65 (2H, m), 1.92-1.97 (2H, m), 2.71 (2H, s), 3.19-3.23 (2H, m), 3.34-3.39 (2H, m), 6.85-6.91 (2H, m). |
| 96 | 70 | NMR2: 1.12 (9H, s), 3.91 (2H, s), 6.35 (1H, dd, J = 8.1 Hz, 1.4 Hz), 6.54 (1H, dd, J = 8.1 Hz, 1.4 Hz), 6.68 (1H, t, J = 8.1 Hz), 7.33-7.38 (4H, m), 7.39-7.43 (2H, m), 7.66-7.70 (4H, m), 8.62 (1H, brs). |
| 97 | — | NMR2: 1.11 (9H, s), 3.93 (2H, s), 6.49 (1H, d, J = 8.9 Hz), 6.76 (1H, d, J = 8.9 Hz), 7.34-7.40 (4H, m), 7.40-7.45 (2H, m), 7.64-7.69 (5H, m). |

TABLE 3-1

| EX | STR |
|---|---|
| 1 | (structure) |
| 2 | (structure) |

TABLE 3-1-continued

| EX | STR |
|---|---|
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 3-2
| EX | STR |
|---|---|
| 15 | 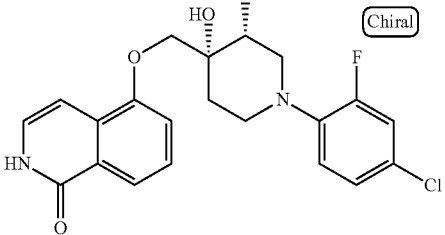 |
| 16 | 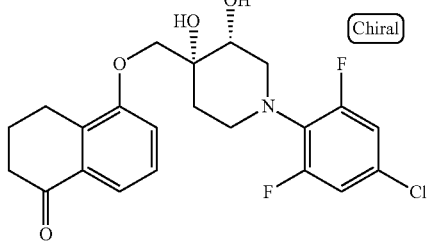 |
| 17 | 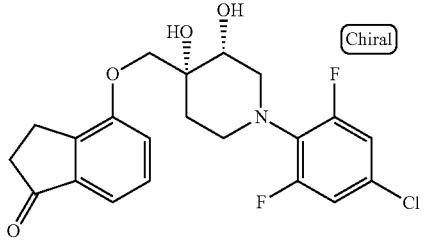 |
| 18 | 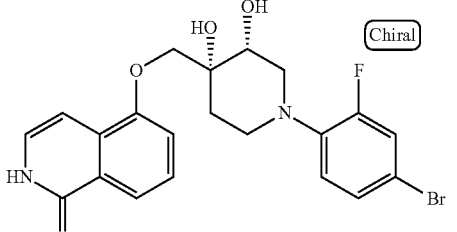 |
| 19 | 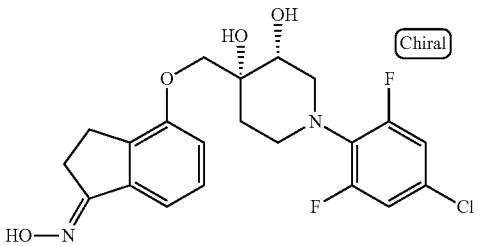 |
| 20 | 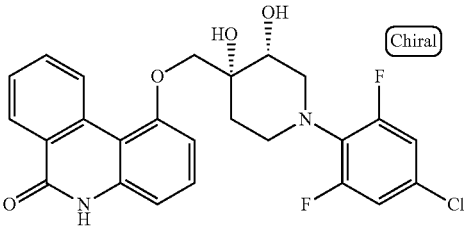 |
| 21 | 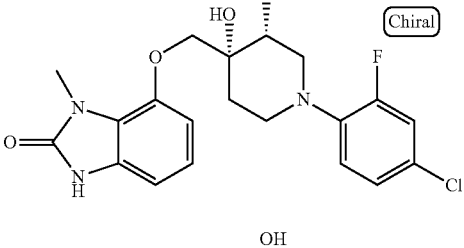 |
| 22 | 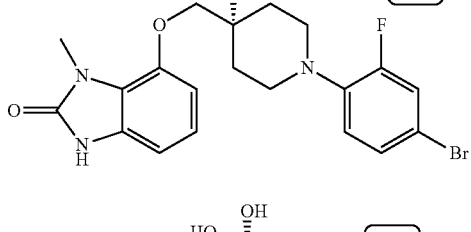 |
| 23 | 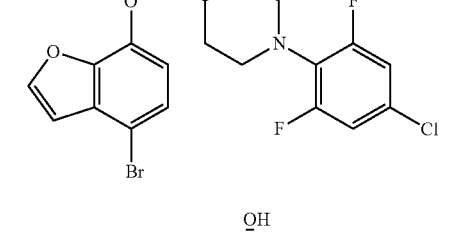 |
| 24 | 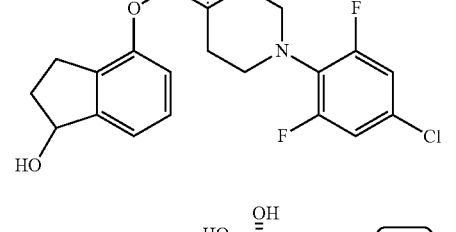 |
| 25 | 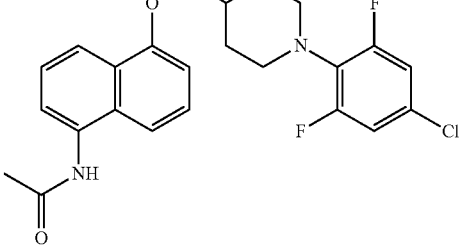 |
| 26 | 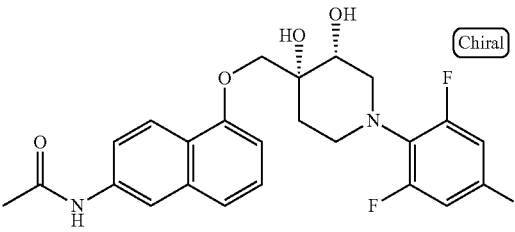 |

TABLE 3-2-continued

| EX | STR |
|---|---|
| 27 | (chiral structure: 3,4-dihydroisoquinolin-1(2H)-one-5-yloxy-methyl piperidine with 4-chloro-2,6-difluorophenyl) |
| 28 | (chiral structure: 1H-indazol-4-yloxy-methyl piperidine with 4-chloro-2,6-difluorophenyl) |

TABLE 3-3

| EX | STR |
|---|---|
| 29 | (chiral structure: 3-methoxyquinoxalin-5-yloxy-methyl piperidine with 4-chloro-2,6-difluorophenyl) |
| 30 | (chiral structure: 3-methoxyquinoxalin-5-yloxy-methyl piperidine with 4-chloro-2-fluorophenyl) |
| 31 | (chiral structure: 3-methoxyquinoxalin-5-yloxy-methyl piperidine with 4-bromo-2-fluorophenyl) |
| 32 | (chiral structure: 3-methylbenzo[d]isoxazol-4-yloxy-methyl piperidine with 4-chloro-2,6-difluorophenyl) |

TABLE 3-3-continued

| EX | STR |
|---|---|
| 33 | (chiral structure: 2-(4-fluorophenyl)-1H-benzimidazol-4-yloxy-methyl piperidine with 4-chloro-2,6-difluorophenyl) |
| 34 | (chiral structure: 1H-benzimidazol-4-yloxy-methyl piperidine with 4-chloro-2,6-difluorophenyl) |
| 35 | (chiral structure: 3-methoxyquinoxalin-5-yloxy-methyl piperidine with 4-chloro-2,6-difluorophenyl) |
| 36 | (chiral structure: 3-methoxyquinoxalin-5-yloxy-methyl piperidine with 4-chloro-2-fluorophenyl) |
| 37 | (chiral structure: 3-methoxyquinoxalin-5-yloxy-methyl piperidine with 4-bromo-2-fluorophenyl) |
| 38 | (chiral structure: 2-methylbenzo[d]oxazol-4-yloxy-methyl piperidine with 4-chloro-2,6-difluorophenyl) |

TABLE 3-3-continued
| EX | STR |
|---|---|
| 39 | 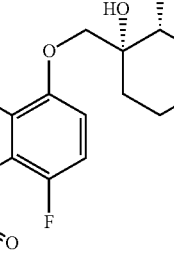 |
| 40 | 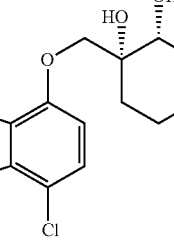 |
| 41 | 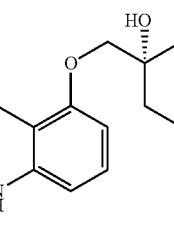 |
| 42 | 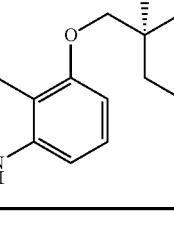 |
TABLE 3-4
| EX | STR |
|---|---|
| 43 | 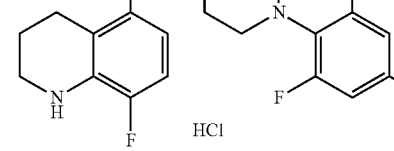 |
TABLE 3-4-continued
| EX | STR |
|---|---|
| 44 | 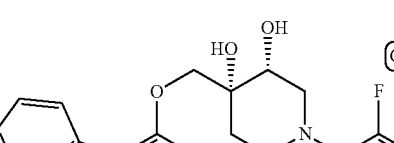 HCl |
| 45 | 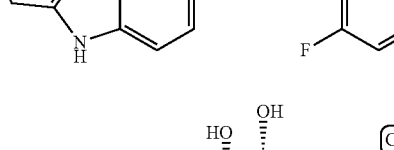 |
| 46 | 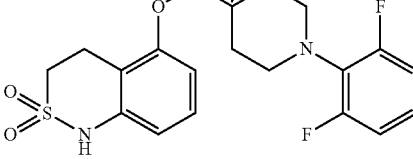 |
| 47 | 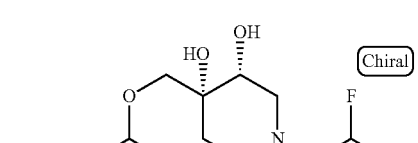 |
| 48 | 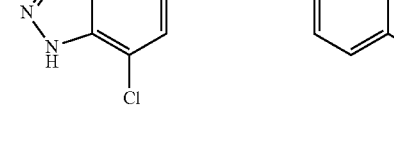 |
| 49 | |

TABLE 3-4-continued

| EX | STR |
|---|---|
| 50 | (structure) |
| 51 | (structure) |
| 52 | (structure) |
| 53 | (structure) |
| 54 | (structure) |
| 55 | (structure) |
| 56 | (structure) |

TABLE 3-5

| EX | STR |
|---|---|
| 57 | (structure) |
| 58 | (structure) |
| 59 | (structure) |
| 60 | (structure) |

TABLE 3-5-continued
| EX | STR |
|---|---|
| 61 | 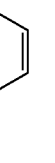 |
| 62 | 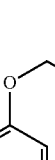 |
| 63 | 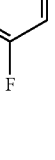 |
| 64 | 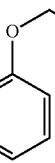 |
| 65 |  |
| 66 | 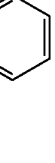 |
| 67 | 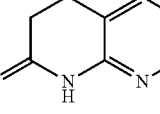 |
| 68 |  |
| 69 | 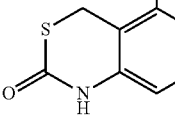 |
| 70 |  |
TABLE 3-6
| EX | STR |
|---|---|
| 71 | 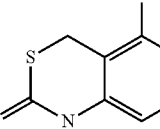 |
| 72 | 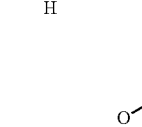 |

TABLE 3-6-continued
| EX | STR |
|---|---|
| 73 | 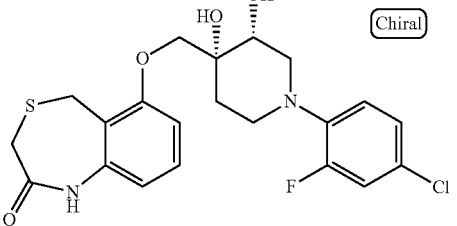 |
| 74 | 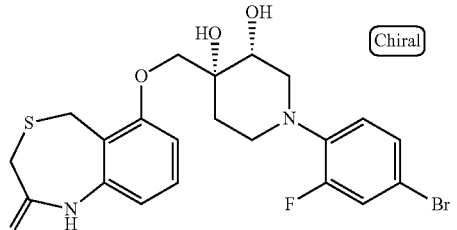 |
| 75 | 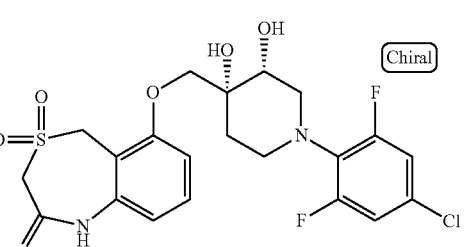 |
| 76 | 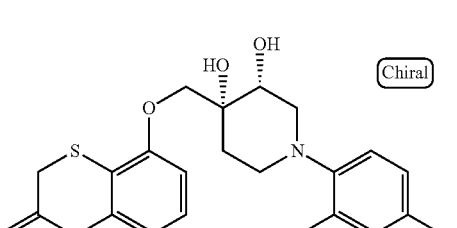 |
| 77 | 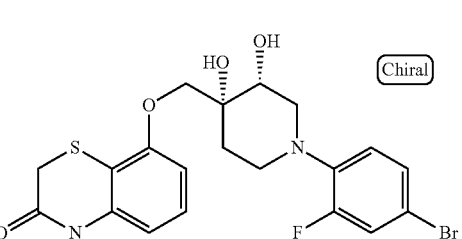 |
| 78 | 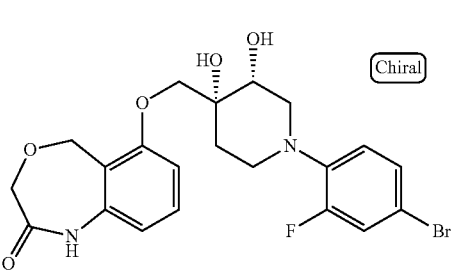 |
| 79 | 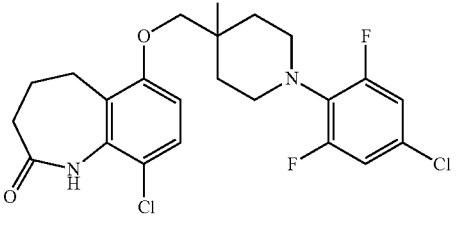 |
| 80 | 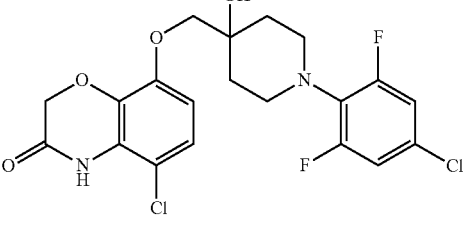 |
| 81 | 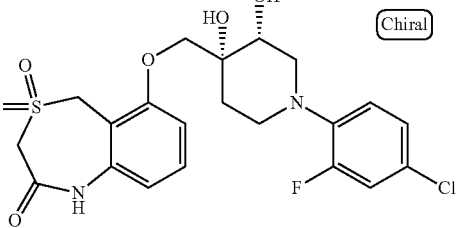 |
| 82 | 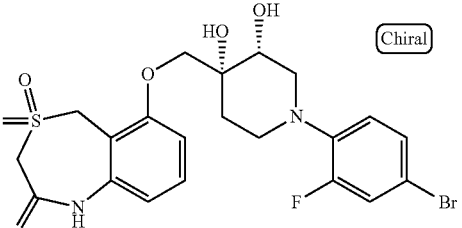 |
| 83 | 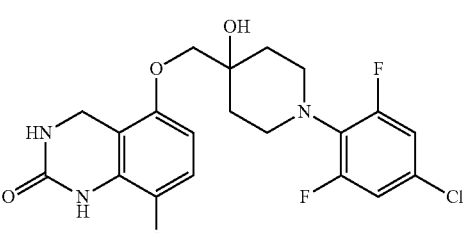 |
| 84 | 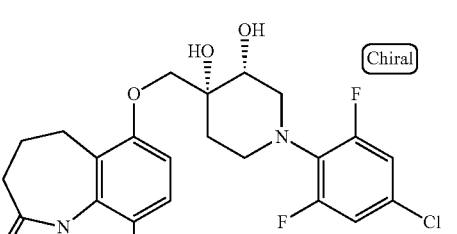 |

TABLE 3-7
| EX | STR |
|---|---|
| 85 | 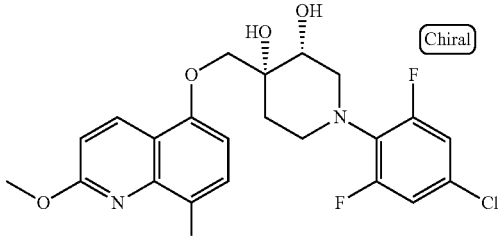 |
| 86 | 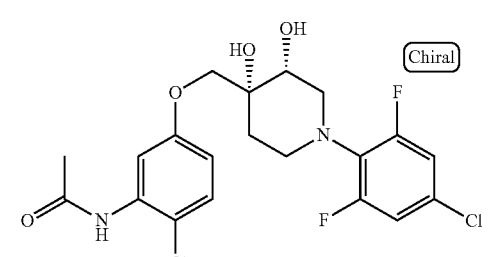 |
| 87 | 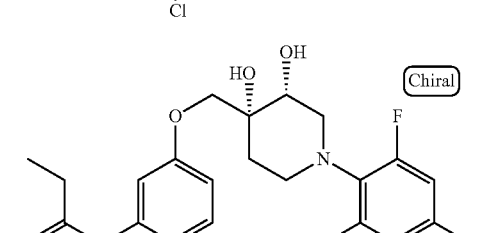 |
| 88 | 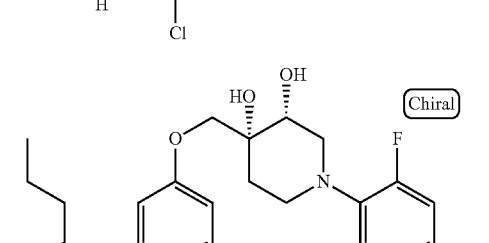 |
| 89 | 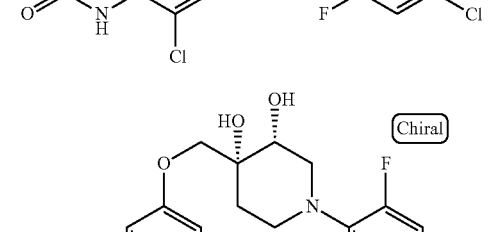 |
| 90 | 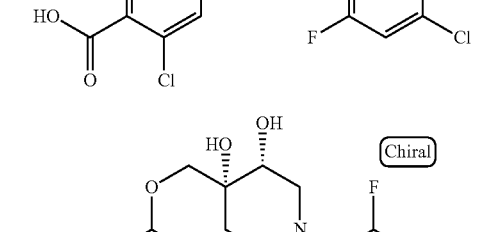 |
| 91 | 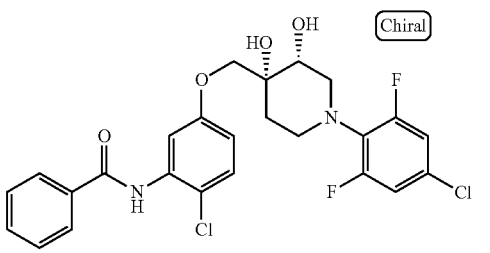 |
| 92 | 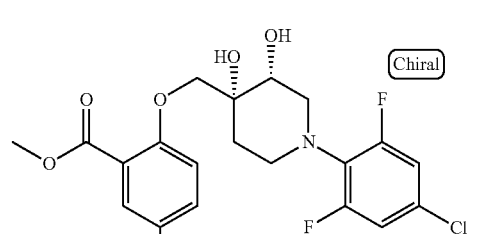 |
| 93 | 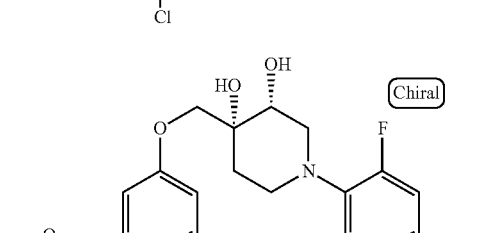 |
| 94 | 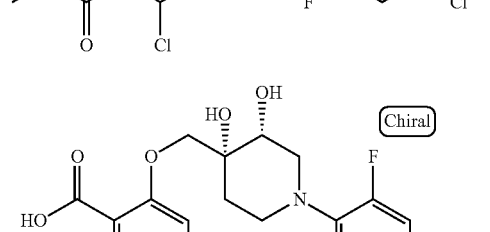 |
| 95 | 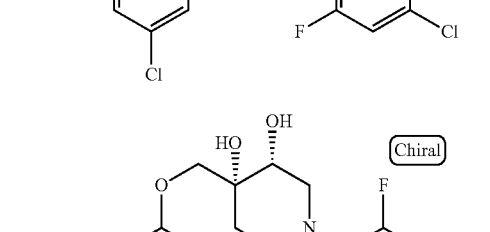 |
| 96 | 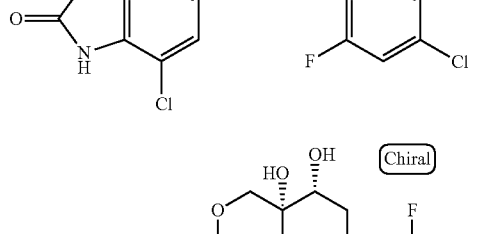 |

TABLE 3-7-continued
| EX | STR |
|---|---|
| 97 | 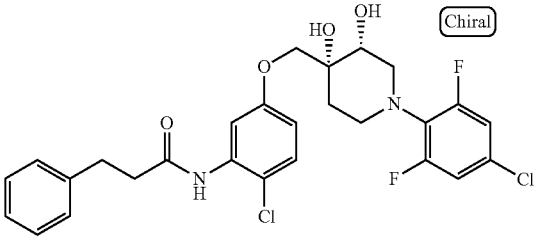 |
| 98 | 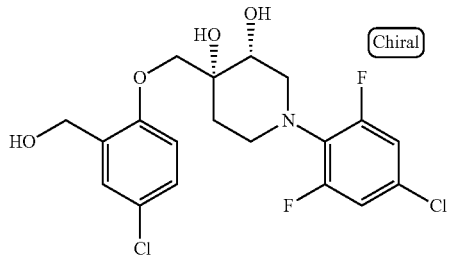 |
TABLE 3-8
| EX | STR |
|---|---|
| 99 | 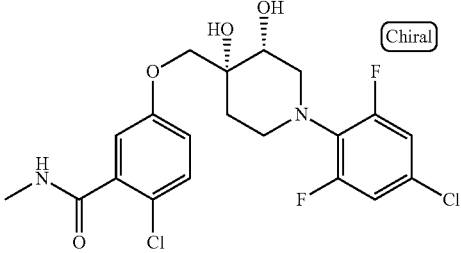 |
| 100 | 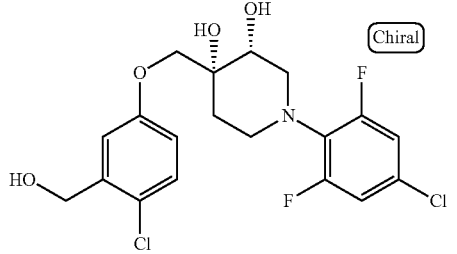 |
| 101 | 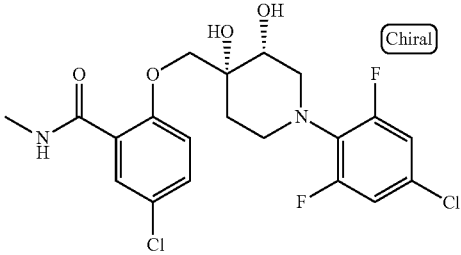 |
TABLE 3-8-continued
| EX | STR |
|---|---|
| 102 | 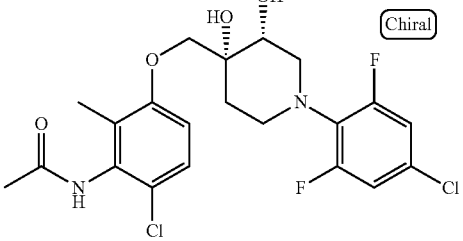 |
| 103 | 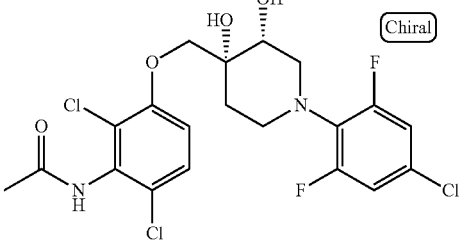 |
| 104 | 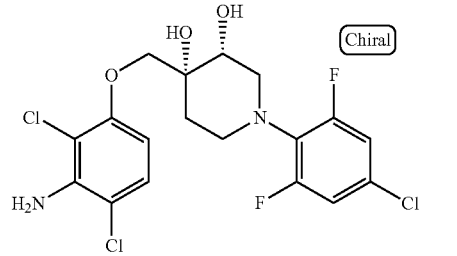 |
| 105 | 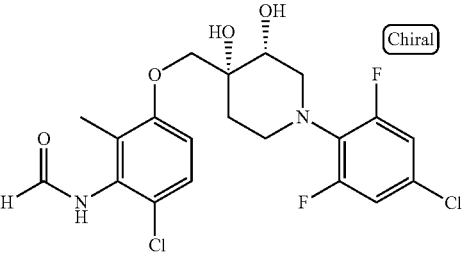 |
| 106 | 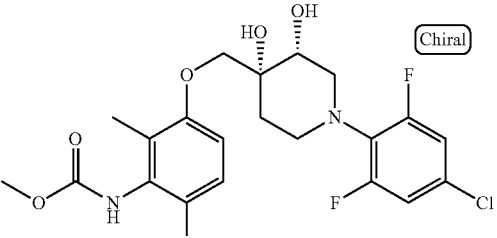 |
| 107 | 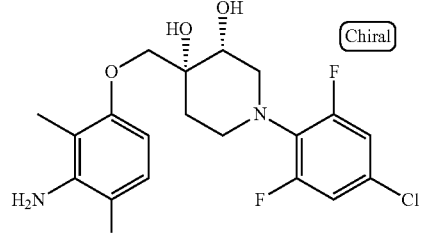 |

TABLE 3-8-continued

| EX | STR |
|---|---|
| 108 | (chemical structure) |
| 109 | (chemical structure) |
| 110 | (chemical structure) |
| 111 | (chemical structure) |
| 112 | (chemical structure) |

TABLE 3-9

| EX | STR |
|---|---|
| 113 | (chemical structure) |
| 114 | (chemical structure) |
| 115 | (chemical structure) |
| 116 | (chemical structure) |
| 117 | (chemical structure) |
| 118 | (chemical structure) |

TABLE 3-9-continued
| EX | STR |
|---|---|
| 119 | 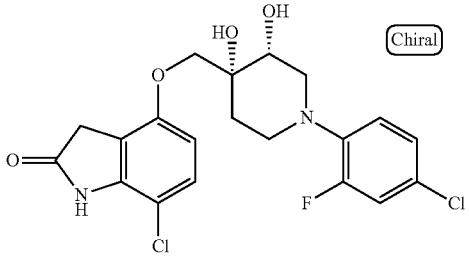 |
| 120 | 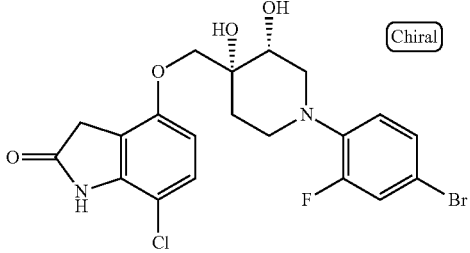 |
| 121 | 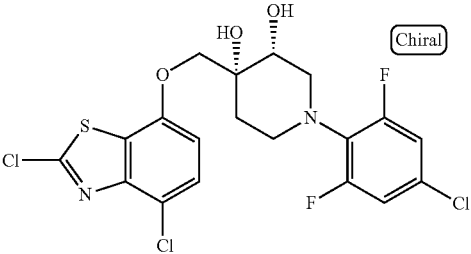 |
| 122 | 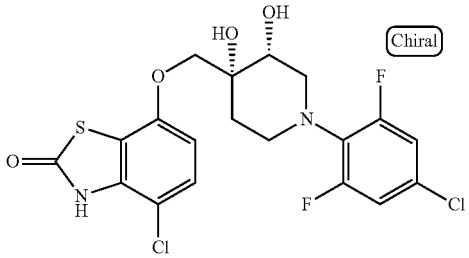 |
| 123 | 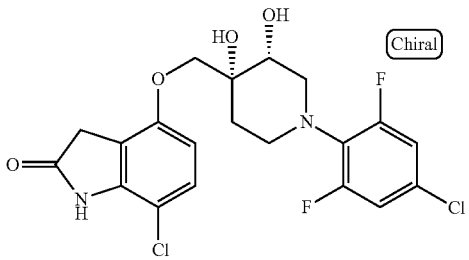 |
| 124 | 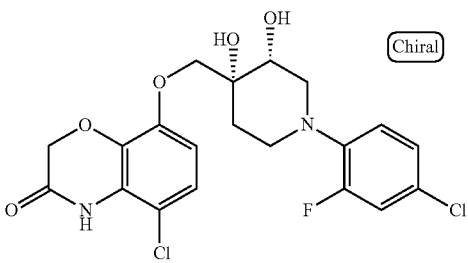 |
| 125 | 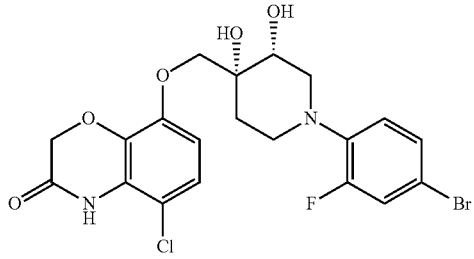 |
| 126 | 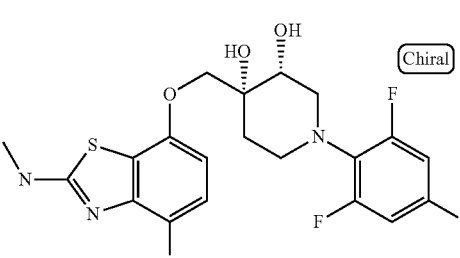 |
TABLE 3-10
| EX | STR |
|---|---|
| 127 |  |
| 128 |  |
| 129 |  |

TABLE 3-10-continued
| EX | STR |
|---|---|
| 130 | 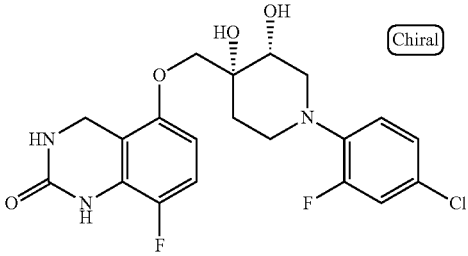 |
| 131 | 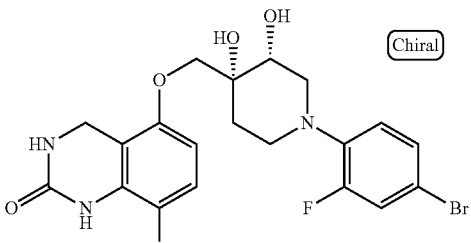 |
| 132 | 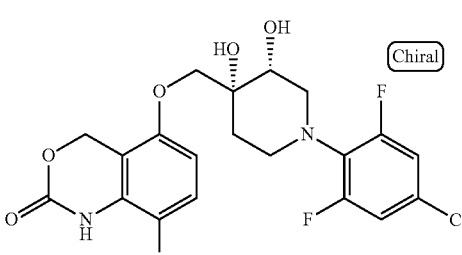 |
| 133 | 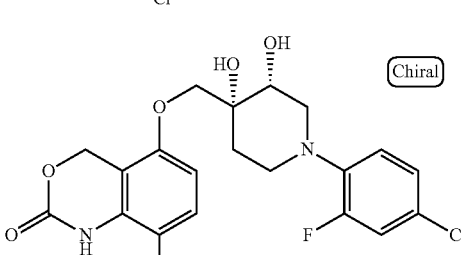 |
| 134 | 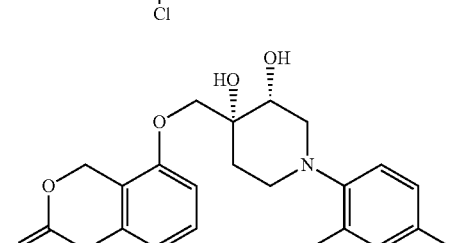 |
| 135 | 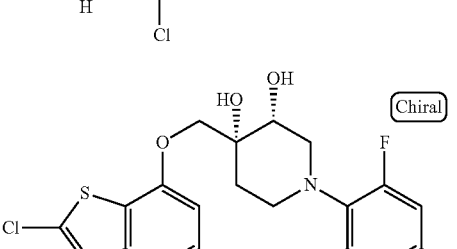 |
| 136 | 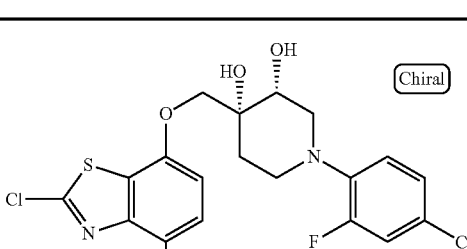 |
| 137 | 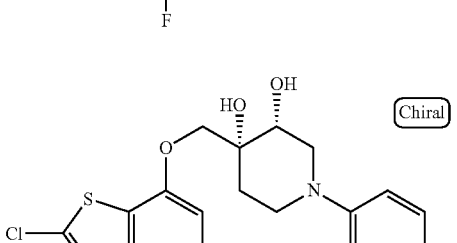 |
| 138 | 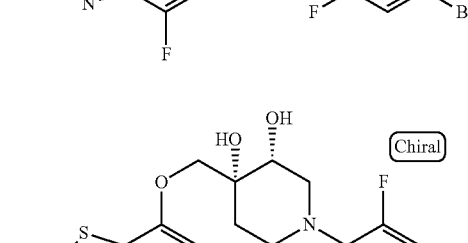 |
| 139 | 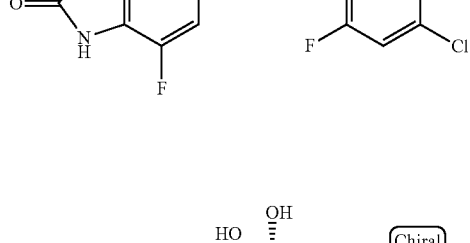 |
| 140 | 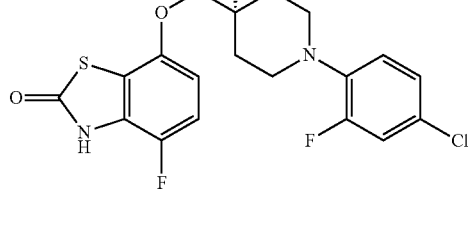 |

TABLE 3-11

| EX | STR |
|---|---|
| 141 | (structure) |
| 142 | (structure) |
| 143 | (structure, Chiral) |
| 144 | (structure, Chiral) |
| 145 | (structure) |
| 146 | (structure, Chiral) |
| 147 | (structure) |

TABLE 4-1

| EX | Prop | Data |
|---|---|---|
| 1 | — | NMR2; 1.96-2.11 (4H, m), 2.18 (1H, brs), 3.13-3.23 (2H, m), 3.25-3.33 (2H, m), 4.08 (2H, s), 6.97 (1H, t, J = 8.5 Hz), 7.03-7.10 (3H, m), 7.53 (1H, t, J = 8.1 Hz), 7.60 (1H, d, J = 8.3 Hz), 7.98-8.02 (1H, m), 8.56 (1H, d, J = 5.9 Hz), 9.23-9.26 (1H, m). |
| 2 | 1 | NMR2; 1.86-1.93 (2H, m), 1.93-2.02 (2H, m), 2.10 (1H, s), 3.07-3.15 (2H, m), 3.47-3.56 (2H, m), 4.00 (2H, s), 4.12 (3H, s), 6.65 (1H, dd, J = 8.7 Hz, 3.4 Hz), 6.85-6.93 (2H, m), 6.95 (1H, d, J = 9.1 Hz), 7.24 (1H, dd, J = 10.6 Hz, 8.7 Hz), 8.37 (1H, dd, J = 9.1 Hz, 1.6 Hz). |
| 3 | 1 | NMR2; 1.94-2.13 (4H, m), 2.20 (1H, brs), 3.13-3.22 (2H, m), 3.26-3.34 (2H, m), 4.08 (2H, s), 6.91 (1H, d, J = 7.6 Hz), 6.96 (1H, t, J = 8.9 Hz), 7.04-7.11 (2H, m), 7.41 (1H, dd, J = 8.5 Hz, 4.3 Hz), 7.62 (1H, t, J = 8.4 Hz), 7.75 (1H, d, J = 8.6 Hz), 8.55-8.60 (1H, m), 8.93 (1H, dd, J = 4.2 Hz, 1.7 Hz). |
| 4 | 1 | NMR2; 1.92-1.98 (2H, m), 1.98-2.06 (2H, m), 2.08 (1H, s), 3.11-3.19 (2H, m), 3.23-3.31 (2H, m), 4.00 (2H, s), 4.12 (3H, s), 6.65 (1H, dd, J = 8.6 Hz, 3.4 Hz), 6.92-6.98 (2H, m), 7.03-7.09 (2H, m), 7.24 (1H, dd, J = 10.5 Hz, 8.6 Hz), 8.37 (1H, dd, J = 9.1 Hz, 1.6 Hz). |

TABLE 4-1-continued

| EX | Prop | Data |
|---|---|---|
| 5 | — | NMR2; 1.69-1.78 (2H, m), 1.91-2.01 (2H, m), 3.03-3.12 (2H, m), 3.15-3.23 (2H, m), 4.49 (2H, s), 4.96 (1H, brs), 6.79 (1H, d, J = 9.4 Hz), 6.89-6.95 (1H, m), 6.99-7.06 (2H, m), 7.27-7.32 (1H, m), 7.52 (1H, d, J = 8.6 Hz), 7.58-7.65 (2H, m), 7.79 (1H, d, J = 9.4 Hz). |
| 6 | — | NMR1; 1.72-1.80 (1H, m), 2.05-2.15 (1H, m), 2.89-3.05 (2H, m), 3.20-3.29 (1H, m), 3.36-3.42 (1H, m), 3.90 (1H, d, J = 9.0 Hz), 3.90-3.98 (1H, m), 4.30 (1H, d, J = 9.0 Hz), 4.66 (1H, brs), 4.96 (1H, d, J = 6.1 Hz), 7.24 (1H, d, J = 8.5 Hz), 7.25-7.34 (2H, m), 7.70 (1H, d, J = 8.5 Hz), 7.74 (1H, dd, J = 8.5 Hz, 4.2 Hz), 8.52 (1H, dd, J = 8.5 Hz, 1.6 Hz), 9.03 (1H, dd, J = 4.2 Hz, 1.6 Hz). |
| 7 | 6 | NMR1; 1.67-1.76 (1H, m), 1.85-1.96 (1H, m), 2.86-3.05 (2H, m), 3.18-3.26 (1H, m), 3.30-3.40 (1H, m), 3.70-3.78 (1H, m), 3.87 (1H, d, J = 9.0 Hz), 4.16 (1H, d, J = 9.0 Hz), 4.25-4.38 (2H, m), 4.52 (1H, brs), 4.89 (1H, d, J = 6.2 Hz), 7.20 (1H, d, J = 8.1 Hz), 7.23-7.32 (3H, m), 7.45 (1H, t, J = 7.8 Hz), 8.54 (1H, brs). |
| 8 | 6 | NMR1; 1.67-1.76 (1H, m), 1.83-1.93 (1H, m), 2.86-3.01 (2H, m), 3.17-3.26 (1H, m), 3.29-3.39 (1H, m), 3.67-3.76 (1H, m), 3.88 (1H, d, J = 9.1 Hz), 4.14 (1H, d, J = 9.1 Hz), 4.21-4.33 (2H, m), 4.59 (1H, brs), 4.89 (1H, d, J = 6.2 Hz), 7.20 (1H, d, J = 8.7 Hz), 7.23-7.32 (2H, m), 7.40 (1H, d, J = 8.7 Hz), 8.66 (1H, brs). |

TABLE 4-2

| EX | Prop | Data |
|---|---|---|
| 9 | 6 | NMR1; 1.49 (9H, s), 1.70-1.79 (1H, m), 1.84-1.96 (1H, m), 2.86-3.02 (2H, m), 3.18-3.27 (1H, m), 3.28-3.39 (1H, m), 3.70-3.79 (1H, m), 3.88 (1H, d, J = 9.1 Hz), 4.15 (1H, d, J = 9.1 Hz), 4.45-4.47 (2H, m), 4.58 (1H, brs), 4.88 (1H, brs), 7.17 (1H, d, J = 8.2 Hz), 7.19 (1H, d, J = 7.6 Hz), 7.23-7.33 (2H, m), 7.42 (1H, dd, J = 8.2 Hz, 7.6 Hz). |
| 10 | 6 | NMR1; 1.28-1.38 (1H, m), 1.57-1.69 (1H, m), 2.75-2.84 (1H, m), 2.94-3.02 (1H, m), 3.06-3.14 (1H, m), 3.58-3.67 (1H, m), 4.08 (1H, d, J = 13.8 Hz), 4.11 (1H, brs), 4.31 (1H, d, J = 13.8 Hz), 4.73 (1H, brs), 5.24 (1H, brs), 7.19 (1H, dd, J = 7.9 Hz, 1.2 Hz), 7.22-7.30 (2H, m), 7.35 (1H, dd, J = 8.0 Hz, 7.9 Hz), 7.58 (1H, dd, J = 8.0 Hz, 1.2 Hz), 8.33 (1H, s), 9.80 (1H, brs). |
| 11 | 6 | NMR1; 1.69-1.78 (1H, m), 1.89-1.99 (1H, m), 2.88-3.03 (2H, m), 3.17-3.27 (1H, m), 3.30-3.38 (1H, m), 3.51 (3H, s), 3.72-3.81 (1H, m), 3.80 (1H, d, J = 8.9 Hz), 4.13 (1H, d, J = 8.9 Hz), 4.57 (1H, brs), 4.95 (1H, d, J = 5.5 Hz), 6.62 (1H, d, J = 7.8 Hz), 6.67 (1H, d, J = 8.2 Hz), 6.92 (1H, dd, J = 8.2 Hz, 7.8 Hz), 7.23-7.33 (2H, m), 10.83 (1H, brs). |
| 12 | 6 | NMR1; 1.71-1.81 (1H, m), 1.87-1.98 (1H, m), 2.81-2.90 (1H, m), 2.93-3.03 (1H, m), 3.05-3.13 (1H, m), 3.14-3.21 (1H, m), 3.74-3.84 (1H, m), 3.88 (1H, d, J = 9.1 Hz), 4.14 (1H, d, J = 9.1 Hz), 4.21-4.33 (2H, m), 4.61 (1H, brs), 4.94 (1H, d, J = 6.4 Hz), 6.98-7.06 (1H, m), 7.14-7.19 (1H, m), 7.21 (1H, d, J = 8.7 Hz), 7.28-7.37 (1H, m), 7.40 (1H, d, J = 8.7 Hz), 8.67 (1H, brs). |
| 13 | 6 | NMR1; 1.72-1.80 (1H, m), 1.86-1.98 (1H, m), 2.80-2.91 (1H, m), 2.93-3.03 (1H, m), 3.06-3.13 (1H, m), 3.14-3.21 (1H, m), 3.74-3.83 (1H, m), 3.89 (1H, d, J = 9.1 Hz), 4.14 (1H, d, J = 9.1 Hz), 4.21-4.33 (2H, m), 4.61 (1H, brs), 4.94 (1H, d, J = 6.4 Hz), 7.04-7.16 (1H, m), 7.20 (1H, d, J = 8.7 Hz), 7.26-7.32 (1H, m), 7.40 (1H, d, J = 8.7 Hz), 7.39-7.46 (1H, m), 8.67 (1H, brs). |
| 14 | 6 | NMR1; 1.73-1.84 (1H, m), 1.92-2.03 (1H, m), 2.89-3.05 (2H, m), 3.20-3.29 (1H, m), 3.33-3.43 (1H, m), 3.76-3.84 (1H, m), 3.86 (1H, d, J = 8.9 Hz), 4.17 (1H, d, J = 8.9 Hz), 4.64 (1H, brs), 4.93 (1H, d, J = 6.5 Hz), 6.74 (1H, d, J = 7.3 Hz), 7.17-7.25 (2H, m), 7.25-7.33 (2H, m), 7.41 (1H, t, J = 8.0 Hz), 7.75 (1H, d, J = 8.0 Hz), 11.3-11.4 (1H, m). |
| 15 | 6 | NMR1; 1.78-1.88 (1H, m), 1.96-2.08 (1H, m), 2.84-2.94 (1H, m), 2.97-3.07 (1H, m), 3.10-3.17 (1H, m), 3.18-3.25 (1H, m), 3.87 (1H, d, J = 9.1 Hz), 3.84-3.92 (1H, m), 4.18 (1H, d, J = 9.1 Hz), 4.66 (1H, brs), 4.99 (1H, d, J = 6.4 Hz), 6.73 (1H, d, J = 7.3 Hz), 7.10 (1H, t, J = 9.0 Hz), 7.15-7.27 (3H, m), 7.33 (1H, dd, J = 12.5 Hz, 2.4 Hz), 7.41 (1H, t, J = 8.1 Hz), 7.75 (1H, d, J = 8.1 Hz), 11.3-11.4 (1H, m). |

TABLE 4-3

| EX | Prop | Data |
|---|---|---|
| 16 | 6 | NMR2; 1.94-2.00 (2H, m), 2.10-2.18 (2H, m), 2.58 (1H, d, J = 7.1 Hz), 2.61-2.67 (2H, m), 2.71 (1H, brs), 2.85-3.00 (2H, m), 3.01-3.09 (1H, m), 3.23-3.33 (2H, m), 3.36-3.45 (1H, m), 3.98-4.04 (1H, m), 4.04 (1H, d, J = 9.1 Hz), 4.12 (1H, d, J = 9.1 Hz), 6.86-6.94 (2H, m), 7.06 (1H, dd, J = 8.1 Hz, 0.7 Hz), 7.26-7.31 (1H, m), 7.70 (1H, d, J = 8.0 Hz). |
| 17 | 6 | NMR1; 1.67-1.78 (1H, m), 1.91-2.03 (1H, m), 2.60-2.68 (2H, m), 2.87-2.95 (1H, m), 2.96-3.04 (3H, m), 3.17-3.27 (1H, m), 3.34-3.40 (1H, m), 3.75-3.88 (1H, m), 3.83 (1H, d, J = 9.0 Hz), 4.16 (1H, d, J = 9.0 Hz), 4.58 (1H, brs), 4.90 (1H, d, J = 6.5 Hz), 7.22 (1H, d, J = 7.6 Hz), 7.24 (1H, d, J = 7.9 Hz), 7.24-7.32 (2H, m), 7.40 (1H, dd, J = 7.9 Hz, 7.6 Hz). |
| 18 | 6 | NMR1; 1.78-1.88 (1H, m), 1.96-2.08 (1H, m), 2.84-2.94 (1H, m), 2.96-3.07 (1H, m), 3.10-3.17 (1H, m), 3.18-3.26 (1H, m), 3.86 (1H, d, J = 8.9 Hz), 3.84-3.02 (1H, m), 4.17 (1H, d, J = 8.9 Hz), 4.66 (1H, brs), 4.99 (1H, d, J = 6.4 Hz), 6.72 (1H, d, J = 7.3 Hz), 7.05 (1H, t, J = 9.0 Hz), 7.15-7.25 (2H, m), 7.28-7.33 (1H, m), 7.42 (1H, t, J = 8.0 Hz), 7.43 (1H, dd, J = 12.2 Hz, 2.3 Hz), 7.75 (1H, d, J = 8.0 Hz), 11.3-11.4 (1H, m). |
| 19 | — | NMR1: 1.64-1.74 (1H, m), 1.89-2.02 (1H, m), 2.75-2.82 (2H, m), 2.86-3.02 (4H, m), 3.17-3.26 (1H, m), 3.31-3.39 (1H, m), 3.73 (1H, d, J = 9.1 Hz), 3.73-3.81 (1H, m), 4.10 (1H, d, J = 9.1 Hz), 4.52 (1H, brs), 4.86 (1H, d, J = 6.5 Hz), 6.92 (1H, d, J = 7.9 Hz), 7.13 (1H, d, J = 7.6 Hz), 7.24 (1H, dd, J = 7.9 Hz, 7.6 Hz), 7.24-7.32 (2H, m), 10.84 (1H, brs). |
| 20 | 6 | NMR1; 1.81-1.91 (1H, m), 2.10-2.21 (1H, m), 2.94-3.09 (2H, m), 3.23-3.32 (1H, m), 3.38-3.46 (1H, m), 3.97 (1H, d, J = 8.8 Hz), 3.96-4.03 (1H, m), 4.32 (1H, d, J = 8.8 Hz), 4.69 (1H, brs), 5.06 (1H, d, J = 5.5 Hz), 6.94 (1H, d, J = 8.1 Hz), 7.04 (1H, d, J = 8.1 Hz), 7.29-7.37 (2H, m), 7.44 (1H, d, J = 8.1 Hz), 7.60-7.66 (1H, m) 7.69-7.75 (1H, m), 8.38 (1H, dd, J = 8.0 Hz, 1.5 Hz), 9.39 (1H, d, J = 8.4 Hz), 11.70 (1H, brs). |
| 21 | 6 | NMR1; 1.72-1.83 (1H, m), 1.90-2.02 (1H, m), 2.85-2.95 (1H, m), 2.98-3.09 (1H, m), 3.11-3.18 (1H, m), 3.18-3.26 (1H, m), 3.45 (3H, s), 3.76-3.83 (1H, m), 3.83 (1H, d, J = 8.8 Hz), 4.12 (1H, d, J = 8.8 Hz), 4.59 (1H, brs), 4.99 (1H, d, J = 6.3 Hz), 6.62 (1H, d, J = 7.4 Hz), 6.67 (1H, d, J = 8.2 Hz), 6.91 (1H, dd, J = 8.2 Hz, 7.4 Hz), 7.00-7.08 (1H, m), 7.17 (1H, dd, J = 8.7 Hz, 2.0 Hz), 7.31 (1H, dd, J = 12.5 Hz, 2.4 Hz), 10.82 (1H, brs). |
| 22 | 6 | NMR1; 1.73-1.83 (1H, m), 1.90-2.02 (1H, m), 2.86-2.94 (1H, m), 2.98-3.09 (1H, m), 3.11-3.18 (1H, m), 3.18-3.26 (1H, m), 3.45 (3H, s), 3.76-3.83 (1H, m), 3.82 (1H, d, J = 8.8 Hz), 4.12 (1H, d, J = 8.8 Hz), 4.60 (1H, brs), 4.99 (1H, d, J = 6.3 Hz), 6.62 (1H, d, J = 7.8 Hz), 6.67 (1H, d, J = 8.0 Hz), 6.91 (1H, dd, J = 8.0 Hz, 7.8 Hz), 7.00-7.08 (1H, m), 7.29 (1H, dd, J = 8.6 Hz, 1.6 Hz), 7.41 (1H, dd, J = 12.3 Hz, 2.3 Hz), 10.82 (1H, brs). |

TABLE 4-4

| EX | Prop | Data |
|---|---|---|
| 23 | 6 | NMR1; 1.68-1.77 (1H, m), 1.93-2.03 (1H, m), 2.87-3.03 (2H, m), 3.18-3.27 (1H, m), 3.33-3.39 (1H, m), 3.76-3.84 (1H, m), 3.89 (1H, d, J = 9.0 Hz), 4.24 (1H, d, J = 9.0 Hz), 4.61 (1H, brs), 4.93 (1H, d, J = 6.4 Hz), 6.90 (1H, d, J = 2.2 Hz), 6.94 (1H, d, J = 8.6 Hz), 7.24-7.33 (2H, m), 7.38 (1H, d, J = 8.6 Hz), 8.11 (1H, d, J = 2.2 Hz). |
| 24 | — | NMR1; 1.61-1.69 (1H, m), 1.71-1.81 (1H, m), 1.88-1.99 (1H, m), 2.27-2.38 (1H, m), 2.56-2.66 (1H, m), 2.82-3.02 (3H, m), 3.16-3.25 (1H, m), 3.31-3.39 (1H, m), 3.65-3.71 (1H, m), 3.72-3.80 (1H, m), 4.03-4.11 (1H, m), 4.48 (1H, brs), 4.80-4.86 (1H, m), 5.00-5.07 (1H, m), 5.15-5.20 (1H, m), 6.79 (1H, d, J = 8.1 Hz), 6.93 (1H, d, J = 7.5 Hz), 7.16 (1H, dd, J = 8.1 Hz, 7.5 Hz), 7.23-7.31 (2H, m). |
| 25 | 6 | NMR1; 1.79-1.89 (1H, m), 1.99-2.10 (1H, m), 2.18 (3H, s), 2.92-3.07 (2H, m), 3.22-3.32 (1H, m), 3.35-3.46 (1H, m), 3.83-3.92 (1H, m), 3.93 (1H, d, J = 8.9 Hz), 4.23 (1H, d, J = 8.9 Hz), 4.67 (1H, brs), 4.93 (1H, d, J = 6.5 Hz), 6.99 (1H, d, J = 7.6 Hz), 7.25-7.34 (2H, m), 7.42-7.45 (2H, m), 7.65 (1H, d, J = 7.6 Hz), 7.72 (1H, d, J = 7.4 Hz), 8.06 (1H, d, J = 8.4 Hz), 9.87 (1H, brs). |
| 26 | 6 | NMR1; 1.79-1.89 (1H, m), 1.97-2.09 (1H, m), 2.10 (3H, s), 2.92-3.07 (2H, m), 3.22-3.31 (1H, m), 3.35-3.45 (1H, m), 3.81-3.90 (1H, m), 3.91 (1H, d, J = 8.9 Hz), 4.20 (1H, d, J = 8.9 Hz), 4.64 (1H, brs), 4.92 (1H, d, J = 6.5 Hz), 6.81-6.87 (1H, m), |

TABLE 4-4-continued

| EX | Prop | Data |
|---|---|---|
| | | 7.25-7.33 (2H, m), 7.34-7.41 (2H, m), 7.54 (1H, dd, J = 9.1 Hz, 2.0 Hz), 8.12 (1H, d, J = 9.1 Hz), 8.28 (1H, d, J = 2.0 Hz), 10.15 (1H, brs). |
| 27 | 6 | NMR1; 1.66-1.78 (1H, m), 1.87-2.01 (1H, m), 2.80-3.04 (4H, m), 3.18-3.28 (1H, m), 3.31-3.42 (3H, m), 3.71-3.82 (1H, m), 3.75 (1H, d, J = 9.1 Hz), 4.09 (1H, d, J = 9.1 Hz), 4.56 (1H, brs), 4.90 (1H, d, J = 6.5 Hz), 7.14 (1H, d, J = 8.1 Hz), 7.23-7.35 (3H, m), 7.47 (1H, t, J = 7.7 Hz), 7.91 (1H, brs). |
| 28 | 6 | NMR1; 1.71-1.83 (1H, m), 1.91-2.02 (1H, m), 2.89-3.05 (2H, m), 3.20-3.29 (1H, m), 3.32-3.42 (1H, m), 3.76-3.85 (1H, m), 3.91 (1H, d, J = 9.0 Hz), 4.20 (1H, d, J = 9.0 Hz), 4.59 (1H, brs), 4.89 (1H, d, J = 6.5 Hz), 6.54 (1H, d, J = 7.7 Hz), 7.08 (1H, d, J = 8.4 Hz), 7.24 (1H, dd, J = 8.4 Hz, 7.7 Hz), 7.25-7.35 (2H, m), 8.02 (1H, s), 13.03 (1H, brs). |
| 29 | 6 | NMR2; 1.75-1.83 (1H, m), 1.92-1.98 (1H, m), 2.97-3.03 (1H, m), 3.23-3.29 (2H, m), 3.43-3.52 (1H, m), 3.74 (1H, brs), 4.08-4.17 (1H, m), 4.10 (3H, s), 4.12 (1H, d, J = 9.3 Hz), 4.40 (1H, d, J = 9.3 Hz), 4.98 (1H, d, J = 3.6 Hz), 6.84-6.91 (2H, m), 7.01 (1H, dd, J = 7.8 Hz, 1.1 Hz), 7.50 (1H, dd, J = 8.5 Hz, 1.1 Hz), 7.60 (1H, t, J = 8.2 Hz), 8.39 (1H, s). |

TABLE 4-5

| EX | Prop | Data |
|---|---|---|
| 30 | 6 | NMR2; 1.80-1.89 (1H, m), 1.96-2.03 (1H, m), 2.85-2.93 (1H, m), 3.03-3.12 (1H, m), 3.19-3.25 (1H, m), 3.41-3.47 (1H, m), 3.77 (1H, brs), 4.10 (3H, s), 4.11 (1H, d, J = 9.3 Hz), 4.18-4.24 (1H, m), 4.41 (1H, d, J = 9.3 Hz), 5.09 (1H, d, J = 3.4 Hz), 6.92-6.97 (1H, m), 7.01 (1H, dd, J = 7.8 Hz, 1.1 Hz), 7.03-7.08 (2H, m), 7.51 (1H, dd, J = 8.5 Hz, 1.1 Hz), 7.60 (1H, t, J = 8.2 Hz), 8.39 (1H, s). |
| 31 | 6 | NMR2; 1.80-1.88 (1H, m), 1.97-2.02 (1H, m), 2.85-2.92 (1H, m), 3.03-3.11 (1H, m), 3.19-3.26 (1H, m), 3.41-3.47 (1H, m), 3.76 (1H, brs), 4.10 (3H, s), 4.11 (1H, d, J = 9.3 Hz), 4.18-4.24 (1H, m), 4.41 (1H, d, J = 9.3 Hz), 5.09 (1H, d, J = 3.4 Hz), 6.86-6.92 (1H, m), 7.01 (1H, dd, J = 7.8 Hz, 0.9 Hz), 7.16-7.22 (2H, m), 7.51 (1H, dd, J = 8.5 Hz, 0.9 Hz), 7.60 (1H, t, J = 8.2 Hz), 8.39 (1H, s). |
| 32 | 6 | NMR1; 1.70-1.80 (1H, m), 1.95-2.06 (1H, m), 2.62 (3H, s), 2.90-3.05 (2H, m), 3.19-3.29 (1H, m), 3.33-3.42 (1H, m), 3.78-3.86 (1H, m), 3.88 (1H, d, J = 8.9 Hz), 4.22 (1H, d, J = 8.9 Hz), 4.64 (1H, brs), 4.98 (1H, d, J = 6.3 Hz), 6.82 (1H, d, J = 8.0 Hz), 7.22 (1H, d, J = 8.4 Hz), 7.24-7.33 (2H, m), 8.02 (1H, s), 7.55 (1H, dd, J = 8.4 Hz, 8.0 Hz). |
| 33 | 6 | NMR1; 1.62-1.99 (1H, m), 2.01-2.12 (1H, m), 2.89-3.08 (2H, m), 3.20-3.32 (1H, m), 3.34-3.45 (1H, m), 3.84-4.03 (2H, m), 4.17-4.45 (1H, m), 4.50-4.70 (1H, m), 4.80-5.30 (1H, m), 6.70-6.84 (1H, m), 7.02-7.20 (2H, m), 7.25-7.34 (2H, m), 7.37-7.45 (2H, m), 8.14-8.35 (2H, m), 12.60-13.10 (1H, m). |
| 34 | 6 | NMR1; 1.62-1.86 (1H, m), 2.00-2.11 (1H, m), 2.88-3.04 (2H, m), 3.19-3.29 (1H, m), 3.32-3.43 (1H, m), 3.83-3.95 (2H, m), 4.15-4.42 (1H, m), 4.48-4.62 (1H, m), 4.70-5.33 (1H, m), 6.67-6.80 (1H, m), 7.04-7.23 (2H, m), 7.24-7.33 (2H, m), 8.12 (1H, s), 12.20-13.00 (1H, m). |
| 35 | 6 | NMR2; 1.74-11.82 (1H, m), 1.90-1.96 (1H, m), 2.97-3.03 (1H, m), 3.20-3.29 (2H, m), 3.42-3.51 (1H, m), 3.65 (1H, brs), 4.10 (3H, s), 4.12 (1H, d, J = 9.2 Hz), 4.14-4.20 (1H, m), 4.41 (1H, d, J = 9.2 Hz), 4.81 (1H, d, J = 2.5 Hz), 6.84-6.92 (2H, m), 7.11 (1H, d, J = 7.8 Hz), 7.47-7.52 (1H, m), 7.69 (1H, d, J = 8.4 Hz), 8.51 (1H, s). |
| 36 | 6 | NMR2; 1.78-1.87 (1H, m), 1.95-2.01 (1H, m), 2.83-2.89 (1H, m), 3.02-3.10 (1H, m), 3.20-3.26 (1H, m), 3.39-3.45 (1H, m), 3.65 (1H, d, J = 2.2 Hz), 4.11 (3H, s), 4.12 (1H, d, J = 9.2 Hz), 4.21-4.27 (1H, m), 4.43 (1H, d, J = 9.2 Hz), 4.91 (1H, d, J = 2.5 Hz), 6.94 (1H, t, J = 8.7 Hz), 7.03-7.08 (2H, m), 7.11 (1H, dd, J = 7.9 Hz, 1.0 Hz), 7.48-7.52 (1H, m), 7.70 (1H, dd, J = 8.4 Hz, 1.0 Hz), 8.52 (1H, s). |

TABLE 4-6

| EX | Prop | Data |
|---|---|---|
| 37 | 6 | NMR2; 1.78-1.86 (1H, m), 1.95-2.01 (1H, m), 2.82-2.89 (1H, m), 3.02-3.10 (1H, m), 3.20-3.27 (1H, m), 3.40-3.46 (1H, m), 3.63-3.68 (1H, m), 4.10 (3H, s), 4.11 (1H, d, J = 9.1 Hz), 4.21-4.27 (1H, m), 4.43 (1H, d, J = 9.1 Hz), 4.91 (1H, d, J = 2.5 Hz), 6.89 (1H, t, J = 8.8 Hz), 7.11 (1H, d, J = 7.9 Hz), 7.16-7.22 (2H, m), 7.50 (1H, dt, J = 1.3 Hz, 8.2 Hz), 7.69 (1H, d, J = 8.4 Hz), 8.52 (1H, d, J = 2.0 Hz). |
| 38 | 6 | NMR1; 1.64-1.74 (1H, m), 1.95-2.06 (1H, m), 2.60 (3H, s), 2.87-3.04 (2H, m), 3.18-3.28 (1H, m), 3.32-3.39 (1H, m), 3.78-3.87 (1H, m), 3.92 (1H, d, J = 9.0 Hz), 4.31 (1H, d, J = 9.0 Hz), 4.57 (1H, brs), 4.89 (1H, d, J = 6.5 Hz), 6.90 (1H, dd, J = 7.8 Hz, 1.2 Hz), 7.20-7.34 (4H, m). |
| 39 | 6 | NMR1; 1.64-1.74 (1H, m), 1.75-1.99 (3H, m), 2.04 (3H, brs), 2.52-2.87 (4H, m), 2.87-3.02 (2H, m), 3.17-3.26 (1H, m), 3.32-3.39 (1H, m), 3.70 (1H, d, J = 8.7 Hz), 3.72-3.80 (1H, m), 4.04 (1H, d, J = 8.7 Hz), 4.53 (1H, brs), 4.87 (1H, d, J = 6.5 Hz), 6.74-6.88 (1H, m), 6.98-7.17 (1H, m), 7.22-7.33 (2H, m). |
| 40 | 6 | NMR1; 1.75-1.85 (1H, m), 1.88-1.99 (1H, m), 2.88-3.04 (2H, m), 3.18-3.28 (1H, m), 3.30-3.40 (1H, m), 3.74-3.83 (1H, m), 3.93 (1H, d, J = 9.1 Hz), 4.20 (1H, d, J = 9.1 Hz), 4.61 (1H, brs), 4.91 (1H, d, J = 6.5 Hz), 6.57 (1H, d, J = 8.2 Hz), 7.24-7.33 (1H, m), 7.32 (1H, d, J = 8.2 Hz), 8.14 (1H, s), 13.55 (1H, brs). |
| 41 | 6 | NMR1; 1.67-1.74 (1H, m), 1.81-1.91 (1H, m), 2.85-2.94 (1H, m), 2.88 (3H, s), 2.94-3.00 (1H, m), 3.18-3.25 (1H, m), 3.29-3.38 (1H, m), 3.67-3.74 (1H, m), 3.74 (1H, d, J = 9.0 Hz), 4.01 (1H, d, J = 9.0 Hz), 4.33 (1H, d, J = 15.1 Hz), 4.38 (1H, d, J = 15.1 Hz), 4.53 (1H, s), 4.86 (1H, d, J = 6.5 Hz), 6.37 (1H, d, J = 8.1 Hz), 6.50 (1H, d, J = 8.1 Hz), 7.07 (1H, t, J = 8.1 Hz), 7.24-7.32 (2H, m), 9.13 (1H, s). |
| 42 | 6 | NMR1; 1.70-1.76 (1H, m), 1.87-1.96 (1H, m), 2.83-2.90 (1H, m), 2.86 (3H, s), 2.96-3.05 (1H, m), 3.09-3.15 (1H, m), 3.15-3.21 (1H, m), 3.73 (1H, d, J = 9.0 Hz), 3.75-3.81 (1H, m), 4.02 (1H, d, J = 9.0 Hz), 4.30 (1H, d, J = 15.0 Hz), 4.35 (1H, d, J = 15.0 Hz), 4.56 (1H, s), 4.91 (1H, d, J = 6.4 Hz), 6.36 (1H, d, J = 7.9 Hz), 6.49 (1H, d, J = 8.2 Hz), 7.04-7.12 (2H, m), 7.18 (1H, dd, J = 8.6 Hz, 2.0 Hz), 7.32 (1H, dd, J = 12.5 Hz, 2.4 Hz), 9.13 (1H, s). |
| 43 | 6 | NMR1; 1.69-1.76 (1H, m), 1.87-1.97 (1H, m), 2.83-2.90 (1H, m), 2.86 (3H, s), 2.96-3.04 (1H, m), 3.09-3.16 (1H, m), 3.16-3.22 (1H, m), 3.73 (1H, d, J = 9.0 Hz), 3.74-3.80 (1H, m), 4.02 (1H, d, J = 9.0 Hz), 4.30 (1H, d, J = 15.1 Hz), 4.35 (1H, d, J = 15.1 Hz), 4.56 (1H, s), 4.92 (1H, d, J = 6.4 Hz), 6.37 (1H, d, J = 8.0 Hz), 6.49 (1H, d, J = 8.3 Hz), 7.00-7.10 (2H, m), 7.29 (1H, dd, J = 8.6 Hz, 1.7 Hz), 7.42 (1H, dd, J = 12.3 Hz, 2.2 Hz), 9.13 (1H, s). |

TABLE 4-7

| EX | Prop | Data |
|---|---|---|
| 44 | — | NMR1; 1.63-1.73(1H, m), 1.85-1.99(3H, m), 2.60-2.72(2H, m), 2.85-2.93(1H, m), 2.94-3.01(1H, m), 3.16-3.28(3H, m), 3.29-3.39(1H, m), 3.66(1H, d, J = 8.8 Hz), 3.75(1H, dd, J = 10.5 Hz, 5.1 Hz), 4.01(1H, d, J = 8.8 Hz), 6.00-7.20(4H, br), 6.48-6.60(1H, m), 7.02(1H, t, J = 9.6 Hz), 7.23-7.32(2H, m). |
| 45 | 6 | NMR1; 1.76-1.86(1H, m), 2.19-2.30(1H, m), 2.96-3.11(2H, m), 3.23-3.32(1H, m), 3.38-3.47(1H, m), 3.89(1H, d, J = 8.7 Hz), 4.01-4.09(1H, m) 4.33(1H, d, J = 8.7 Hz), 4.62(1H, brs), 4.97(1H, d, J = 6.4 Hz), 6.98(1H, d, J = 6.4 Hz), 7.08(1H, d, J = 8.0 Hz), 7.10(1H, dt, J = 0.7 Hz, 8.0 Hz), 7.27-7.38(4H, m), 7.46(1H, d, J = 8.0 Hz), 8.24(1H, d, J =7.8 Hz), 11.27(1H, brs). |
| 46 | 6 | NMR1; 1.55-1.67(2H, m), 2.73-2.83(1H, m), 2.88-3.06(2H, m), 3.09-3.28(3H, m), 3.44-3.56(3H, m), 3.88(1H, d, J = 15.8 Hz), 3.98(1H, d, J = 15.8 Hz), 4.23(1H, brs), 4.98(1H, d, J = 6.8 Hz), 6.57 (1H, d, J = 7.9 Hz), 7.03(1H, dd, J = 8.2 Hz, 7.9 Hz), 7.08(1H, d, J = 8.2 Hz), 7.21-7.30(2H, m), 9.72(1H, brs). |
| 47 | 6 | NMR1; 1.79-1.89(1H, m), 1.93-2.04(1H, m), 2.83-2.93(1H, m), 2.96-3.06(1H, m), 3.08-3.24(2H, m), 3.81-3.89(1H, m), 3.93(1H, d, J = 9.1 Hz), 4.20(1H, d, J = 9.1 Hz), 4.64(1H, brs), 4.97(1H, d, J = 6.4 Hz), 6.57(1H, d, J = 8.2 Hz), 7.06-7.14(1H, m), 7.18(1H, dd, J = 8.7 Hz, 2.0 Hz), 7.32(1H, d, J = 8.2 Hz), 7.33(1H, dd, J = 12.5 Hz, 2.4 Hz), 8.16(1H, s), 13.54(1H, brs). |

TABLE 4-7-continued

| EX | Prop | Data |
|----|------|------|
| 48 | 6 | NMR1; 1.79-1.88(1H, m), 1.93-2.04(1H, m), 2.83-2.92(1H, m), 2.96-3.05(1H, m), 3.08-3.24(2H, m), 3.81-3.89(1H, m), 3.93(1H, d, J = 9.1 Hz), 4.20(1H, d, J = 9.1 Hz), 4.64(1H, brs), 4.97(1H, d, J = 6.3 Hz), 6.56(1H, d, J = 8.2 Hz), 7.00-7.10(1H, m), 7.27-7.36(2H, m), 7.43(1H, dd, J = 12.3 Hz, 2.3 Hz), 8.16(1H, s), 13.54(1H, brs). |
| 49 | — | NMR1; 1.70-1.79(1H, m), 2.02-2.13(1H, m), 2.79-2.78(1H, m), 2.94-3.03(1H, m), 3.06-3.14(1H, m), 3.14-3.21(1H, m), 3.81(1H, d, J = 8.9 Hz), 3.89-3.98(1H, m), 4.22(1H, d, J = 8.9 Hz), 4.59(1H, s), 4.96(1H, d, J = 6.2 Hz), 6.84-6.90(2H, m), 7.09(1H, t, J = 9.2 Hz), 7.18(1H, dd, J = 8.7 Hz, 1.9 Hz), 7.34(1H, dd, J = 12.5 Hz, 2.4 Hz), 7.47(1H, t, J = 8.3 Hz,), 8.13(1H, d, J = 2.4 Hz), 12.38(1H, s). |
| 50 | 49 | NMR1; 1.70-1.79(1H, m), 2.02-2.12(1H, m), 2.80-2.88(1H, m), 2.94-3.03(1H, m), 3.06-3.13(1H, m), 3.13-3.22(1H, m), 3.81(1H, d, J = 8.9 Hz), 3.89-3.98(1H, m), 4.22(1H, d, J = 8.9 Hz), 4.60(1H, s), 4.96(1H, d, J = 6.2 Hz), 6.84-6.90(2H, m), 7.04(1H, t, J = 9.1 Hz), 7.30(1H, dd, J = 8.6 Hz, 1.7 Hz), 7.44(1H, dd, J = 12.3 Hz, 2.3 Hz), 7.47(1H, t, J = 8.3 Hz), 8.12(1H, s), 12.38(1H, s). |

TABLE 4-8

| EX | Prop | Data |
|----|------|------|
| 51 | 49 | NMR1; 1.82-1.92(1H, m), 2.00-2.08(1H, m), 2.89-2.96(1H, m), 2.96-3.05(1H, m), 3.10-3.22(2H, m), 3.75-3.83(1H, m), 4.12(2H, s), 4.74(1H, d, J = 7.2 Hz), 5.05(1H, s), 7.10(1H, t, J = 9.1 Hz), 7.16-7.21(2H, m), 7.25(1H, t, J = 8.1 Hz), 7.33(1H, dd, J = 12.5 Hz, 2.4 Hz), 7.39(1H, dd, J = 8.1 Hz, 0.7 Hz), 8.21(1H, s), 12.06(1H, s). |
| 52 | 49 | NMR1; 1.82-1.92(1H, m), 2.00-2.08(1H, m), 2.89-2.96(1H, m), 2.96-3.05(1H, m), 3.11-3.21(2H, m), 3.75-3.83(1H, m), 4.12(2H, s), 4.75(1H, d, J = 7.8 Hz), 5.05(1H, s), 7.05(1H, t, J = 9.1 Hz), 7.19(1H, dd, J = 8.1 Hz, 0.8 Hz), 7.25(1H, t, J = 8.1 Hz), 7.30(1H, dd, J = 8.6 Hz, 1.8 Hz), 7.39(1H, dd, J = 8.0 Hz, 0.7 Hz), 7.43(1H, dd, J = 12.3 Hz, 2.2 Hz), 8.21(1H, s), 12.06(1H, s). |
| 53 | — | NMR2; 1.73-1.82(1H, m), 1.90-1.96(1H, m), 2.96-3.03(1H, m), 3.19-3.30(2H, m), 3.42-3.50(1H, m), 3.62(1H, brs), 3.69(3H, s), 4.08-4.15(1H, m), 4.09(1H, d, J = 9.2 Hz), 4.36(1H, d, J = 9.2 Hz), 4.70(1H, d, J = 3.5 Hz), 6.85-6.92(3H, m), 6.99(1H, d, J = 8.6 Hz), 7.54(1H, t, J = 8.4 Hz), 8.22(1H, s). |
| 54 | — | NMR1; 1.67-1.73(1H, m), 1.98-2.09(1H, m), 2.88-2.95(1H, m), 2.95-3.02(1H, m), 3.19-3.27(1H, m), 3.29-3.40(1H, m), 3.80(1H, d, J = 9.0 Hz), 3.82-3.89(1H, m), 4.22(1H, d, J = 9.0 Hz), 4.58(1H, s), 4.89(1H, d, J = 6.3 Hz), 6.87(2H, dd, J = 8.3 Hz, 2.3 Hz), 7.26-7.33(2H, m), 7.47(1H, t, J = 8.3 Hz), 8.14(1H, s), 12.38(1H, s). |
| 55 | — | NMR2; 1.95-2.01(1H, m), 2.01-2.10(1H, m), 2.47-2.51(1H, m), 2.63(1H, brs), 3.04-3.10(1H, m), 3.24-3.35(2H, m), 3.35-3.42(1H, m), 3.98-4.05(1H, m), 4.02(3H, s), 4.12(1H, d, J = 9.3 Hz), 4.16(1H, d, J = 9.3 Hz), 6.87-6.94(2H, m), 7.18(1H, dd, J = 8.1 Hz, 1.2 Hz), 7.27(1H, t, J = 8.1 Hz), 7.52(1H, dd, J = 8.1 Hz, 1.2 Hz), 8.26(1H, s). |
| 56 | — | NMR1; 1.71-1.80(1H, m), 2.00-2.08(1H, m), 2.90-3.00(2H, m), 3.25-3.42(2H, m), 3.64-3.71(1H, m), 4.11(1H, d, J = 9.0 Hz), 4.15(1H, d, J = 9.0 Hz), 4.68(1H, d, J = 7.4 Hz), 5.08(1H, s), 7.19(1H, dd, J = 8.1 Hz, 0.8 Hz), 7.25(1H, t, J = 8.1 Hz), 7.25-7.32(2H, m), 7.39(1H, dd, J = 8.1 Hz, 0.8 Hz), 8.20(1H, s), 12.01(1H, brs). |
| 57 | 6 | NMR1; 1.67-1.77(1H, m), 1.88-1.99(1H, m), 2.88-3.04(2H, m), 3.17-3.26(1H, m), 3.31-3.39(1H, m), 3.72-3.81(1H, m), 3.86(1H, d, J = 9.1 Hz), 4.19(1H, d, J = 9.1 Hz), 4.61(1H, brs), 4.93(1H, d, J = 6.3 Hz), 7.22-7.31(3H, m), 7.32-7.39(2H, m), 7.52(1H, d, J = 10.3 Hz), 7.68(1H, d, J = 10.3 Hz). |

TABLE 4-9

| EX | Prop | Data |
|---|---|---|
| 58 | 6 | NMR1; 1.75-1.94(2H, m), 2.88-3.03(2H, m), 3.19-3.29(1H, m), 3.31-3.41(1H, m), 3.69-3.78(1H, m), 3.89(1H, d, J = 9.0 Hz), 4.10(1H, d, J = 9.0 Hz), 4.69(1H, brs), 4.93(1H, d, J = 6.5 Hz), 5.24(2H, s), 6.79(1H, d, J = 8.4 Hz), 6.91(1H, d, J = 8.4 Hz), 7.20-7.43(9H, m), 7.80(1H, d, J = 10.4 Hz). |
| 59 | 6 | NMR1; 1.61-1.71(2H, m), 2.72-2.89(2H, m), 2.94-3.06(2H, m), 3.08-3.16(1H, m), 3.18-3.28(1H, m), 3.47-3.61(3H, m), 3.89(1H, d, J = 15.8 Hz), 3.98(1H, d, J = 15.8 Hz), 4.26(1H, brs), 5.04(1H, d, J = 6.6 Hz), 6.57(1H, d, J = 7.7 Hz), 6.97-7.11 (3H, m), 7.15(1H, dd, J = 8.7 Hz, 1.8 Hz), 7.30(1H, dd, J = 12.5 Hz, 2.4 Hz), 9.73(1H, brs). |
| 60 | 6 | NMR1; 1.60-1.70(2H, m), 2.72-2.90(2H, m), 2.94-3.07(2H, m), 3.08-3.17(1H, m), 3.18-3.29(1H, m), 3.46-3.61(3H, m), 3.89(1H, d, J = 15.8 Hz), 3.97(1H, d, J = 15.8 Hz), 4.26(1H, brs), 5.04(1H, d, J = 6.4 Hz), 6.57(1H, d, J = 7.7 Hz), 6.90-7.12 (3H, m), 7.27(1H, d, J = 8.4 Hz), 7.39(1H, dd, J = 12.1 Hz, 1.5 Hz), 9.73(1H, brs). |
| 61 | 24 | NMR1; 1.60-1.72(3H, m), 1.77-2.02(3H, m), 2.51-2.68(2H, m), 2.86-3.02(2H, m), 3.16-3.25(1H, m), 3.32-3.40(1H, m), 3.60-3.67(1H, m), 3.74-3.83(1H, m), 3.99-4.07(1H, m), 4.48(1H, brs), 4.49-4.59(1H, m), 4.78-4.90(1H, m), 5.00-5.10 (1H, m), 6.76(1H, d, J = 8.0 Hz), 7.00(1H, d, J = 7.7 Hz), 7.11 (1H, dd, J = 8.0 Hz, 7.7 Hz), 7.23-7.32(2H, m). |
| 62 | 6 | NMR1; 1.78-1.86(2H, m), 2.12(3H, s), 2.88-3.02(2H, m), 3.20-3.29(1H, m), 3.30-3.38(1H, m), 3.66-3.74(1H, m), 3.88-3.95(1H, m), 4.00-4.06(1H, m), 4.79-4.87(2H, m), 6.83-6.91(1H, m), 7.02-7.09(1H, m), 7.23-7.22(2H, m), 7.83-7.92(1H, m), 9.13(1H, brs) |
| 63 | 6 | NMR1; 1.72-1.78(1H, m), 1.82-1.91(1H, m), 2.86-2.93(1H, m), 2.93-3.00(1H, m), 3.18-3.26(1H, m), 3.30-3.38(1H, m), 3.67-3.73(1H, m), 3.8(1H, d, J = 9.0 Hz), 4.04(1H, d, J = 9.0 Hz), 4.16(1H, d, J = 15.1 Hz), 4.23(1H, d, J = 15.1 Hz), 4.58(1H, s), 4.86(1H, d, J = 6.6 Hz), 6.62(1H, d, J = 8.1 Hz), 6.73(1H, d, J = 8.1 Hz), 7.19(1H, t, J = 8.1 Hz), 7.24-7.31(2H, m), 10.70(1H, s). |
| 64 | 6 | NMR1; 1.62-1.70(1H, m), 1.95-2.04(1H, m), 2.88-2.94(1H, m), 2.94-3.00(1H, m), 3.18-3.24(1H, m), 3.30-3.38(1H, m), 3.38-3.45(2H, m), 3.68(1H, d, J = 8.7 Hz), 3.78-3.83(1H, m), 4.11(1H, d, J = 8.7 Hz), 4.52(1H, s), 4.88(1H, d, J = 6.3 Hz), 6.60(1H, d, J = 8.1 Hz), 6.67(1H, d, J = 8.1 Hz), 7.11(1H, t, J = 8.1 Hz), 7.24-7.31(2H, m), 10.52(1H, s). |

TABLE 4-10

| EX | Prop | Data |
|---|---|---|
| 65 | 6 | NMR1; 1.66-1.72(1H, m), 1.83-1.92(1H, m), 2.88-2.93(1H, m), 2.93-3.00(1H, m), 3.18-3.24(1H, m), 3.30-3.38(1H, m), 3.68-3.75(1H, m), 3.70(1H, d, J = 8.7 Hz), 4.02(1H, d, J = 8.7 Hz), 4.36(2H, s), 4.55(1H, s), 4.80-4.89(2H, m), 4.88(1H, d, J = 6.5 Hz), 6.66(1H, d, J = 8.2 Hz), 6.74(1H, d, J = 8.2 Hz), 7.17(1H, t, J = 8.2 Hz), 7.24-7.31(2H, m), 10.07(1H, s). |
| 66 | 6 | NMR1; 1.70-1.76(1H, m), 1.85-1.94(1H, m), 2.86-2.94(1H, m), 2.90(2H, s), 2.94-3.01(1H, m), 3.18-3.25(1H, m), 3.29-3.39(1H, m), 3.69-3.76(1H, m), 3.78(1H, d, J = 8.9 Hz), 3.83(1H, d, J = 12.6 Hz), 3.89(1H, d, J = 12.6 Hz), 4.09(1H, d, J = 8.9 Hz), 4.58(1H, s), 4.86(1H, d, J = 6.6 Hz), 6.65(1H, d, J = 8.1 Hz), 6.91(1H, d, J = 8.1 Hz), 7.23-7.31(3H, m), 9.63(1H, s). |
| 67 | 6 | NMR1; 1.68-1.74(1H, m), 1.83-1.92(1H, m), 2.44-2.55(2H, m), 2.75-2.87(2H, m), 2.87-2.93(1H, m), 2.93-3.00(1H, m), 3.19-3.26(1H, m), 3.26-3.38(1H, m), 3.68-3.75(1H, m), 3.82 (1H, d, J = 9.1 Hz), 4.12(1H, d, J = 9.1 Hz), 4.61(1H, s), 4.92 (1H, d, J = 6.5 Hz), 6.71(1H, d, J = 5.8 Hz), 7.24-7.31(2H, m), 8.01(1H, d, J = 5.8 Hz), 10.29(1H, s). |
| 68 | 6 | NMR1; 1.74-1.83(1H, m), 1.88-1.98(1H, m), 2.82-2.90(1H, m), 2.94-3.02(1H, m), 3.07-3.14(1H, m), 3.14-3.20(1H, m), 3.74-3.82(1H, m), 3.80(1H, d, J = 8.9 Hz), 4.05(1H, d, J = 8.9 Hz), 4.15(1H, d, J = 15.0 Hz), 4.22(1H, d, J = 15.0 Hz), 4.60(1H, s), 4.92(1H, d, J = 6.5 Hz), 6.62(1H, d, J = 8.0 Hz), 6.72(1H, d, J = 8.0 Hz), 7.08(1H, t, J = 9.1 Hz), 7.15-7.22(2H, m), 7.32(1H, dd, J = 12.5 Hz, 2.4 Hz), 10.69(1H, s). |
| 69 | 6 | NMR1; 1.74-1.81(1H, m), 1.88-1.97(1H, m), 2.82-2.90(1H, m), 2.94-3.02(1H, m), 3.08-3.14(1H, m), 3.14-3.21(1H, m), 3.75-3.33(1H, m), 3.80(1H, d, J = 9.0 Hz), 4.05(1H, d, J = 9.0 Hz), 4.15(1H, d, J = 15.0 Hz), 4.21(1H, d, J = 15.0 Hz), 4.60(1H, |

TABLE 4-10-continued

| EX | Prop | Data |
|---|---|---|
| | | s), 4.92(1H, d, J = 6.5 Hz), 6.62(1H, d, J = 8.0 Hz), 6.72(1H, d, J = 8.0 Hz), 7.03(1H, t, J = 9.2 Hz), 7.19(1H, t, J = 8.0 Hz), 7.29(1H, dd, J = 8.6 Hz, 1.8 Hz), 7.42(1H, dd, J = 12.3 Hz, 2.2 Hz), 10.69(1H, s). |
| 70 | 6 | NMR1; 1.71-1.80(1H, m), 1.88-1.97(1H, m), 2.44-2.50(2H, m), 2.73-2.90(3H, m), 2.93-3.02(1H, m), 3.07-3.13(1H, m), 3.13-3.21(1H, m), 3.74-3.81(1H, m), 3.83(1H, d, J = 9.0 Hz), 4.12(1H, d, J = 9.0 Hz), 4.63(1H, s), 4.97(1H, d, J = 6.4 Hz), 6.71(1H, d, J = 5.9 Hz), 7.08(1H, t, J = 9.1 Hz), 7.17(1H, dd, J = 8.6 Hz, 2.0 Hz), 7.32(1H, dd, J = 12.5 Hz, 2.4 Hz), 8.01(1H, d, J = 5.9 Hz), 10.29(1H, s). |

TABLE 4-11

| EX | Prop | Data |
|---|---|---|
| 71 | 6 | NMR1; 1.71-1.79(1H, m), 1.88-1.98(1H, m), 2.43-2.50(2H, m), 2.73-2.90(3H, m), 2.93-3.03(1H, m), 3.07-3.13(1H, m), 3.13-3.21(1H, m), 3.74-3.80(1H, m), 3.83(1H, d, J = 9.1 Hz), 4.12(1H, d, J = 9.1 Hz), 4.63(1H, s), 4.98(1H, d, J = 6.4 Hz), 6.71(1H, d, J = 5.9 Hz), 7.02(1H, t, J = 9.1 Hz), 7.29(1H, dd, J = 8.6 Hz, 1.7 Hz), 7.42(1H, dd, J = 12.2 Hz, 2.2 Hz), 8.01(1H, d, J = 5.9 Hz), 10.29(1H, s). |
| 72 | 6 | NMR1; 1.70-1.77(1H, m), 1.87-1.96(1H, m), 2.81-2.88(1H, m), 2.94-3.02(1H, m), 3.06-3.13(1H, m), 3.13-3.21(1H, m), 3.73(1H, d, J = 8.9 Hz), 3.73-3.80(1H, m), 4.03(1H, d, J = 8.9 Hz), 4.35(2H, s), 4.57(1H, s), 4.78-4.87(2H, m), 4.94(1H, d, J = 6.4 Hz), 6.66(1H, d, J = 8.1 Hz), 6.75(1H, d, J = 8.1 Hz), 7.08(1H, t, J = 9.1 Hz), 7.14-7.20(2H, m), 7.32(1H, dd, J = 12.4 Hz, 2.4 Hz), 10.07(1H, s). |
| 73 | 6 | NMR1; 1.73-1.80(1H, m), 1.90-1.99(1H, m), 2.82-2.90(1H, m), 2.90(2H, s), 2.96-3.02(1H, m), 3.08-3.14(1H, m), 3.14-3.22(1H, m), 3.75-3.90(4H, m), 4.10(1H, d, J = 8.9 Hz), 4.60(1H, s), 4.92(1H, d, J = 6.5 Hz), 6.65(1H, d, J = 8.1 Hz), 6.91(1H, d, J = 8.1 Hz), 7.07(1H, t, J = 9.1 Hz), 7.17(1H, dd, J = 8.7 Hz, 2.1 Hz), 7.26(1H, t, J = 8.1 Hz), 7.32(1H, dd, J = 12.5 Hz, 2.4 Hz), 9.63(1H, s). |
| 74 | — | NMR1; 1.73-1.80(1H, m), 1.89-1.98(1H, m), 2.82-2.90(1H, m), 2.89(2H, s), 2.96-3.03(1H, m), 3.09-3.15(1H, m), 3.15-3.22(1H, m), 3.74-3.90(4H, m), 4.10(1H, d, J = 8.9 Hz), 4.61(1H, s), 4.92(1H, d, J = 6.4 Hz), 6.65(1H, d, J = 8.0 Hz,), 6.91(1H, d, J = 8.0 Hz), 7.02(1H, t, J = 9.1 Hz), 7.24-7.31(2H, m), 7.41(1H, dd, J = 12.3 Hz, 2.3 Hz), 9.63(1H, s). |
| 75 | 6 | NMR1; 1.76-1.83(1H, m), 1.84-1.94(1H, m), 2.88-2.95(1H, m), 2.95-3.01(1H, m), 3.19-3.27(1H, m), 3.27-3.39(1H, m), 3.70-3.77(1H, m), 3.83(1H, d, J = 8.9 Hz), 3.93-4.02(2H, m), 4.08(1H, d, J = 8.9 Hz), 4.44(1H, d, J = 14.1 Hz), 4.66(1H, s), 4.67(1H, d, J = 14.1 Hz), 4.81(1H, d, J = 6.7 Hz), 6.81(1H, d, J = 8.0 Hz), 6.99(1H, d, J = 8.0 Hz), 7.24-7.31(2H, m), 7.42(1H, t, J = 8.0 Hz), 10.56(1H, brs). |
| 76 | 6 | NMR1; 1.68-1.74(1H, m), 1.98-2.08(1H, m), 2.80-2.88(1H, m), 2.94-3.02(1H, m), 3.07-3.14(1H, m), 3.14-3.22(1H, m), 3.34-3.43(2H, m), 3.70(1H, d, J = 8.7 Hz), 3.82-3.90(1H, m), 4.12(1H, d, J = 8.7 Hz), 4.54(1H, s), 4.94(1H, d, J = 6.2 Hz), 6.60(1H, d, J = 8.0 Hz), 6.67(1H, d, J = 8.0 Hz), 7.08(1H, t, J = 9.1 Hz), 7.11(1H, t, J = 8.0 Hz), 7.18(1H, dd, J = 8.5 Hz, 2.1 Hz), 7.32(1H, d, J = 12.5 Hz, 2.4 Hz), 10.52(1H, s). |

TABLE 4-12

| EX | Prop | Data |
|---|---|---|
| 77 | 6 | NMR1; 1.68-1.74(1H, m), 1.98-2.08(1H, m), 2.80-2.88(1H, m), 2.94-3.02(1H, m), 3.08-3.14(1H, m), 3.14-3.21(1H, m), 3.34-3.42(2H, m), 3.70(1H, d, J = 8.8 Hz), 3.82-3.90(1H, m), 4.12(1H, d, J = 8.8 Hz), 4.55(1H, s), 4.93(1H, d, J = 6.3 Hz), 6.60(1H, d, J = 8.0 Hz), 6.67(1H, d, J = 8.0 Hz), 7.02(1H, t, J = 9.1 Hz), 7.11(1H, t, J = 8.0 Hz), 7.29(1H, dd, J = 8.6 Hz, 1.8 Hz), 7.42(1H, d, J = 12.2 Hz, 2.3 Hz), 10.52(1H, s). |

TABLE 4-12-continued

| EX | Prop | Data |
|---|---|---|
| 78 | 6 | NMR1; 1.70-1.78(1H, m), 1.87-1.95(1H, m), 2.81-2.88(1H, m), 2.94-3.02(1H, m), 3.07-3.13(1H, m), 3.13-3.20(1H, m), 3.73(1H, d, J = 8.9 Hz), 3.73-3.80(1H, m), 4.03(1H, d, J = 8.9 Hz), 4.35(2H, s), 4.58(1H, s), 4.78-4.87(2H, m), 4.94(1H, d, J = 6.4 Hz), 6.66(1H, d, J = 8.1 Hz), 6.75(1H, d, J = 8.1 Hz), 7.02(1H, t, J = 9.1 Hz), 7.17(1H, t, J = 8.1 Hz), 7.29(1H, dd, J = 8.6 Hz, 1.7 Hz), 7.42(1H, dd, J = 12.2 Hz, 2.3 Hz), 10.07(1H, s). |
| 79 | 6 | NMR1; 1.61-1.66(2H, m), 1.76-1.82(2H, m), 2.03-2.13(4H, m), 2.80-2.83(2H, m), 2.95-3.00(2H, m), 3.33-3.40(2H, m), 3.81(2H, s), 4.74(1H, brs), 6.88(1H, d, J = 9.0 Hz), 7.24-7.29(2H, m), 7.31(1H, d, J = 9.0 Hz), 9.26(1H, brs). |
| 80 | 6 | NMR1; 1.57-1.61(2H, m), 1.78-1.84(2H, m), 2.94-2.98(2H, m), 3.32-3.38(2H, m), 3.81(2H, s), 4.61(2H, s), 4.69(1H, brs), 6.77(1H, d, J = 9.0 Hz), 7.02(1H, d, J = 9.0 Hz), 7.24-7.30(2H, m), 10.40(1H, brs). |
| 81 | 74 | NMR1; 1.79-1.87(1H, m), 1.90-1.99(1H, m), 2.83-2.91(1H, m), 2.95-3.04(1H, m), 3.08-3.15(1H, m), 3.15-3.21(1H, m), 3.77-3.83(1H, m), 3.84(1H, d, J = 8.9 Hz), 3.92-4.01(2H, m), 4.09(1H, d, J = 8.9 Hz), 4.43(1H, d, J = 14.1 Hz), 4.65(1H, d, J = 14.1 Hz), 4.68(1H, s), 4.86(1H, d, J = 6.6 Hz), 6.81(1H, d, J = 8.0 Hz), 6.99(1H, d, J = 8.0 Hz), 7.08(1H, t, J = 9.1 Hz), 7.17(1H, dd, J = 8.7 Hz, 1.9 Hz), 7.32(1H, dd, J = 12.5 Hz, 2.4 Hz), 7.42(1H, t, J = 8.0 Hz), 10.56(1H, brs). |
| 82 | 74 | NMR1; 1.80-1.87(1H, m), 1.90-1.99(1H, m), 2.83-2.91(1H, m), 2.95-3.03(1H, m), 3.09-3.15(1H, m), 3.15-3.22(1H, m), 3.77-3.83(1H, m), 3.84(1H, d, J = 9.0 Hz), 3.92-4.01(2H, m), 4.09(1H, d, J = 9.0 Hz), 4.43(1H, d, J = 14.1 Hz), 4.65(1H, d, J = 14.1 Hz), 4.68(1H, s), 4.86(1H, d, J = 6.6 Hz), 6.81(1H, d, J = 8.1 Hz), 6.99(1H, d, J = 8.1 Hz), 7.03(1H, t, J = 9.1 Hz), 7.29(1H, dd, J = 8.6 Hz, 1.8 Hz), 7.39-7.44(2H, m), 10.56(1H, brs). |
| 83 | 6 | NMR1; 1.58-1.62(2H, m), 1.72-1.79(2H, m), 2.94-2.98(2H, m), 3.33-3.39(2H, m), 3.75(2H, s), 4.34(2H, s), 4.72(1H, brs), 6.47(1H, dd, J = 3.5 Hz, 9.1 Hz), 6.93(1H, brs), 6.99(1H, dd, J = 9.1 Hz, 10.0 Hz), 7.24-7.29(2H, m), 8.92(1H, brs). |

TABLE 4-13

| EX | Prop | Data |
|---|---|---|
| 84 | 6 | NMR2; 1.93-1.96(2H, m), 2.18-2.27(2H, m), 2.37(2H, t, J = 7.3 Hz), 2.52-2.54(1H, m), 2.64(1H, brs), 2.95-2.95(2H, m), 3.02-3.06(1H, m), 3.23-3.31(2H, m), 3.36-3.41(1H, m), 3.95-3.99(1H, m), 4.01(1H, d, J = 9.2 Hz), 4.07(1H, d, J = 9.2 Hz), 6.74(1H, d, J = 8.9 Hz), 6.87-6.92(2H, m), 7.20(1H, brs), 7.25(1H, d, J = 8.9 Hz). |
| 85 | 6 | NMR2; 2.01-2.05(2H, m), 2.45(1H, d, J = 7.5 Hz), 2.69(1H, brs), 3.05-3.09(1H, m), 3.26-3.34(2H, m), 3.39-3.44(1H, m), 4.12(3H, s), 4.13(1H, d, J = 9.2 Hz), 4.20(1H, 4.04-4.08(1H, m), d, J = 9.2 Hz), 6.68(1H, dd, J = 3.3 Hz, 8.6 Hz), 6.88-6.94(2H, m), 6.95(1H, d, J = 9.1 Hz), 7.24(1H, dd, J = 8.6 Hz, 10.5 Hz), 6.85(1H, dd, J = 1.3 Hz, 9.1 Hz). |
| 86 | 6 | NMR1; 1.66-1.68(1H, m), 1.84-1.90(1H, m), 2.10(3H, s), 2.86-2.91(1H, m), 2.93-2.97(1H, m), 3.17-3.22(1H, m), 3.29-3.35(1H, m), 3.67-3.72(1H, m), 3.67(1H, d, J = 8.8 Hz), 4.01(1H, d, J = 8.8 Hz), 4.56(1H, brs), 4.89(1H, d, J = 6.5 Hz), 6.78(1H, dd, J = 2.8 Hz, 8.9 Hz), 7.25-7.31(2H, m), 7.36(1H, d, J = 8.9 Hz), 7.45(1H, d, J = 2.8 Hz), 9.42(1H, brs). |
| 87 | 6 | NMR2; 1.28(3H, t, J = 7.6 Hz), 1.86-1.94(2H, m), 2.48(2H, q, J = 7.6 Hz), 2.70(1H, d, J = 6.9 Hz), 2.72(1H, brs), 2.98-3.03(1H, m), 3.20-3.28(2H, m), 3.34-3.40(1H, m), 3.92-3.95(1H, m), 4.03(1H, d, J = 9.4 Hz), 4.07(1H, d, J = 9.4 Hz), 6.64(1H, dd, J = 2.9 Hz, 8.9 Hz), 6.85-6.91(2H, m), 7.25(1H, d, J = 8.9 Hz), 7.65(1H, brs), 8.16(1H, d, J = 2.9 Hz). |
| 88 | 6 | NMR2; 1.04(3H, t, J = 7.4 Hz), 1.75-1.82(2H, m), 1.86-1.94(2H, m), 2.42(2H, t, J = 7.5 Hz), 2.70(1H, d, J = 7.0 Hz), 2.72(1H, brs), 2.98-3.03(1H, m), 3.20-3.28(2H, m), 3.34-3.40(1H, m), 3.92-3.96(1H, m), 4.02(1H, d, J = 9.4 Hz), 4.07(1H, d, J = 9.4 Hz), 6.64(1H, dd, J = 3.0 Hz, 8.9 Hz), 6.85-6.91(2H, m), 7.26(1H, d, J = 8.9 Hz), 7.63(1H, brs), 8.15(1H, d, J = 3.0 Hz). |

TABLE 4-13-continued

| EX | Prop | Data |
|---|---|---|
| 89 | — | NMR1; 1.67-1.71(1H, m), 1.83-1.90(1H, m), 2.87-2.90(1H, m), 2.94-2.97(1H, m), 3.18-3.22(1H, m), 3.29-3.36(1H, m), 3.68-3.73(1H, m), 3.77(1H, d, J = 9.0 Hz), 4.07(1H, d, J = 9.0 Hz), 4.57(1H, brs), 4.90(1H, d, J = 6.4 Hz), 7.15(1H, dd, J = 3.1 Hz, 8.9 Hz), 7.25-7.31(2H, m), 7.32(1H, d, J = 3.1 Hz), 7.44(1H, d, J = 8.9 Hz), 13.43(1H, brs). |
| 90 | — | NMR2; 1.94-1.98(2H, m), 2.53(1H, d, J = 7.2 Hz), 2.68(1H, brs), 2.72-2.74(2H, m), 3.01-3.08(3H, m), 3.25-3.31(2H, m), 3.36-3.41(1H, m), 3.98-4.02(1H, m), 4.09(1H, d, J = 9.2 Hz), 4.13(1H, d, J = 9.2 Hz), 6.87-6.93(2H, m), 7.00(1H, d, J = 8.6 Hz), 7.27(1H, d, J = 8.6 Hz). |

TABLE 4-14

| EX | Prop | Data |
|---|---|---|
| 91 | 6 | NMR2; 1.89-1.97(2H, m), 2.70(1H, d, J = 7.0 Hz), 2.74(1H, brs), 3.00-3.04(1H, m), 3.22-3.30(2H, m), 3.36-3.41(1H, m), 3.95-3.99(1H, m), 4.08(1H, d, J = 9.3 Hz), 4.12(1H, d, J = 9.3 Hz), 6.70(1H, dd, J = 3.0 Hz, 8.9 Hz), 6.86-6.91(2H, m), 7.32(1H, d, J = 8.9 Hz), 7.52-7.55(2H, m), 7.59-7.62(1H, m), 7.92-7.93(2H, m), 8.33(1H, d, J = 3.0 Hz), 8.48(1H, brs). |
| 92 | 90 | NMR2; 1.73-1.78(1H, m), 1.89-1.92(1H, m), 2.96-3.00(1H, m), 3.18-3.28(2H, m), 3.41-3.47(1H, m), 3.69(1H, brs), 3.91(3H, s), 4.03-4.06(1H, m), 4.04(1H, d, J = 9.0 Hz), 4.14(1H, d, J = 9.0 Hz), 4.53(1H, d, J = 3.7 Hz), 6.85-6.90(2H, m), 6.95(1H, d, J = 8.9 Hz), 7.47(1H, dd, J = 2.7 Hz, 8.9 Hz), 7.93(1H, d, J = 2.7 Hz). |
| 93 | 90 | NMR2; 1.89-1.97(2H, m), 2.51(1H, d, J = 7.3 Hz), 2.69(1H, brs), 3.00-3.04(1H, m), 3.22-3.29(2H, m), 3.34-3.40(1H, m), 3.93-3.98(1H, m), 3.94(3H, m), 4.01(1H, d, J = 9.1 Hz), 4.08(1H, d, J = 9.1 Hz), 6.86-6.92(2H, m), 7.02(1H, dd, J = 3.1 Hz, 8.9 Hz), 7.36(1H, d, J = 8.9 Hz), 7.40(1H, d, J = 3.1 Hz). |
| 94 | — | NMR1; 1.62-1.65(1H, m), 1.95-2.01(1H, m), 2.86-2.91(1H, m), 2.94-2.97(1H, m), 3.17-3.21(1H, m), 3.29-3.38(1H, m), 3.74(1H, d, J = 8.8 Hz), 3.76-3.81(1H, m), 4.14(1H, d, J = 8.8 Hz), 4.52(1H, brs), 4.86(1H, d, J = 5.1 Hz), 7.16(1H, d, J = 8.9 Hz), 7.24-7.30(2H, m), 7.55(1H, dd, J = 2.8 Hz, 8.9 Hz), 7.64(1H, d, J = 2.7 Hz), 12.98(1H, brs). |
| 95 | 6 | NMR1; 1.65-1.70(1H, m), 1.84-1.90(1H, m), 2.87-2.91(1H, m), 2.94-2.97(1H, m), 3.18-3.22(1H, m), 3.29-3.38(1H, m), 3.49(2H, d, J = 5.2 Hz), 3.68-3.72(1H, m), 3.77(1H, d, J = 9.0 Hz), 4.06(1H, d, J = 9.0 Hz), 4.52(1H, brs), 4.85(1H, d, J = 6.5 Hz), 6.66(1H, d, J = 9.0 Hz), 7.19(1H, d, J = 9.0 Hz), 7.25-7.31(2H, m), 10.74(1H, brs). |
| 96 | 6 | NMR2; 1.85-1.93(2H, m), 2.69(1H, d, J = 7.0 Hz), 2.72(1H, brs), 2.98-3.02(1H, m), 3.20-3.27(2H, m), 3.34-3.39(1H, m), 3.80(2H, s), 3.91-3.95(1H, m), 4.00(1H, d, J = 9.4 Hz), 4.05(1H, d, J = 9.4 Hz), 6.61(1H, dd, J = 3.0 Hz, 8.9 Hz), 6.85-6.91(2H, m), 7.17(1H, d, J = 8.9 Hz), 7.35-7.38(3H, m), 7.41-7.44(2H, m), 7.67(1H, brs), 8.11(1H, d, J = 3.0 Hz). |
| 97 | 6 | NMR2; 1.87-1.95(2H, m), 2.68(1H, d, J = 7.0 Hz), 2.71(1H, brs), 2.74-2.78(2H, m), 2.99-3.03(1H, m), 3.06-3.09(2H, m), 3.21-3.28(2H, m), 3.34-3.40(1H, m), 3.92-3.96(1H, m), 4.02(1H, d, J = 9.4 Hz), 4.07(1H, d, J = 9.4 Hz), 6.63(1H, dd, J = 3.0 Hz, 8.9 Hz), 6.86-6.91(2H, m), 7.21-7.27(4H m), 7.30-7.33(2H, m), 7.53(1H, brs), 8.13(1H, d, J = 3.0 Hz). |

TABLE 4-15

| EX | Prop | Data |
|---|---|---|
| 98 | — | NMR2; 1.82-1.88(1H, m), 1.93-1.97(1H, m), 2.59(1H, dd, J = 3.3 Hz, 5.1 Hz), 2.98-3.03(1H, m), 3.18-3.26(2H, m), 3.26(1H, d, J = 6.5 Hz), 3.32(1H, brs), 3.35-3.40(1H, m), 3.93-3.97(1H, m), 4.04(1H, d, J = 9.3 Hz), 4.08(1H, d, J = 9.3 Hz), 4.57(1H, dd, J = 3.3 Hz, 12.4 Hz), 4.76(1H, dd, J = 5.1 Hz, 12.4 Hz), 6.84(1H, d, J = 8.3 Hz), 6.86-6.91(2H, m), 7.23-7.26(2H, m). |

TABLE 4-15-continued

| EX | Prop | Data |
|---|---|---|
| 99 | — | NMR2; 1.87-1.95(2H, m), 2.64(1H, d, J = 7.2 Hz), 2.74(1H, brs), 2.99-3.03(1H, m), 3.03(3H, d, J = 4.9 Hz), 3.20-3.28(2H, m), 3.34-3.39(1H, m), 3.92-3.97(1H, m), 4.01(1H, d, J = 9.2 Hz), 4.07(1H, d, J = 9.2 Hz), 6.35(1H, q, J = 4.9 Hz), 6.86-6.91(2H, m), 6.95(1H, dd, J = 3.1 Hz, 8.8 Hz), 7.30(1H, d, J = 8.8 Hz), 7.31(1H, d, J = 3.1 Hz). |
| 100 | — | NMR2; 1.86-1.98(3H, m), 2.55(1H, d, J = 7.1 Hz), 2.71(1H, brs), 2.99-3.04(1H, m), 3.22-3.29(2H, m), 3.34-3.40(1H, m), 3.94-3.98(1H, m), 4.00(1H, d, J = 9.2 Hz), 4.09(1H, d, J = 9.2 Hz), 4.76(2H, d, J = 6.2 Hz), 6.82(1H, dd, J = 3.0 Hz, 8.7 Hz), 6.86-6.92(2H, m), 7.12(1H, d, J = 3.0 Hz), 7.27(1H, d, J = 8.7 Hz). |
| 101 | 99 | NMR2; 1.86-1.96(2H, m), 2.93(3H, d, J = 4.8 Hz), 3.00-3.05(1H, m), 3.23-3.33(2H, m), 3.39-3.45(1H, m), 3.41(1H, brs), 3.83(1H, d, J = 6.8 Hz), 3.94-3.98(1H, m), 4.02(1H, d, J = 9.0 Hz), 4.13(1H, d, J = 9.0 Hz), 6.85(1H, d, J = 8.8 Hz), 6.87-6.93(2H, m), 7.29(1H, dd, J = 2.7 Hz, 8.8 Hz), 7.83(1H, d, J = 2.7 Hz), 7.88(1H, q, J = 4.8 Hz). |
| 102 | 6 | NMR2; 1.90-1.98(2H, m), 2.16(3H, s), 2.25(3H, s), 2.64(1H, d, J = 7.1 Hz), 2.72(1H, brs), 3.00-3.04(1H, m), 3.21-3.28(2H, m), 3.36-3.41(1H, m), 3.96-3.99(1H, m), 3.96(1H, d, J = 9.2 Hz), 4.04(1H, d, J = 9.2 Hz), 6.77(1H, d, J = 8.9 Hz), 6.86-6.91(2H, m), 6.96(1H, brs), 7.23(1H, d, J = 8.9 Hz). |
| 103 | 6 | NMR2; 1.84-1.97(2H, m), 2.26(3H, s), 2.87-2.89(1H, m), 2.93(1H, brs), 3.00-3.04(1H, m), 3.20-3.28(2H, m), 3.37-3.42(1H, m), 3.99-4.03(1H, m), 4.06(1H, d, J = 9.0 Hz), 4.10(1H, d, J = 9.0 Hz), 6.84-6.91(3H, m), 6.96( 1H, brs), 7.34(1H, d, J = 8.6 Hz). |
| 104 | 6 | NMR2; 1.81-1.87(1H, m), 1.93-1.97(1H, m), 2.96-3.04(3H, m), 3.21-3.26(2H, m), 3.37-3.44(1H, m), 4.00-4.05(1H, m), 4.04(1H, d, J = 9.1 Hz), 4.08(1H, d, J = 9.1 Hz), 4.52(2H, brs), 6.32(1H, d, J = 8.9 Hz), 6.86-6.91(2H, m), 7.13(1H, d, J = 8.9 Hz). |
| 105 | 6 | NMR1; 1.67-1.73(1H, m), 1.90-1.98(1H, m), 2.06(3H, s), 2.88-2.93(1H, m), 2.95-2.99(1H, m), 3.18-3.24(1H, m), 3.31-3.37(1H, m), 3.71(1H, d, J = 11.1 Hz), 3.71-3.79(1H, m), 4.06(1H, d, J = 11.1 Hz), 4.55(1H, brs), 4.90(1H, d, J = 8.0 Hz), 6.93(1H, d, J = 11.2 Hz), 7.24-7.31(2H, m), 7.31(1H, d, J = 11.2 Hz), 8.27(1H, d, J = 1.8 Hz), 9.79(1H, d, J = 1.8 Hz). |

TABLE 4-16

| EX | Prop | Data |
|---|---|---|
| 106 | 90 | NMR2; 1.89-1.98(2H, m), 2.21(3H, s), 2.52(1H, d, J = 8.9 Hz), 2.67(1H, brs), 3.00-3.05(1H, m), 3.21-3.30(2H, m), 3.35-3.42(1H, m), 3.78(3H, s), 3.95-4.01(1H, m), 3.97(1H, d, J = 11.4 Hz), 4.07(1H, d, J = 11.4 Hz), 6.30(1H, brs), 6.77(1H, d, J = 11.1 Hz), 6.86-6.92(2H, m), 7.23(1H, d, J = 11.1 Hz). |
| 107 | 90 | NMR2; 1.87-1.98(2H, m), 2.11(3H, s), 2.54(1H, d, J = 8.7 Hz), 2.68(1H, brs), 3.00-3.05(1H, m), 3.21-3.30(2H, m), 3.35-3.42(1H, m), 3.94(1H, d, J = 11.5 Hz), 3.95-4.01(1HH, m), 4.05(2H, brs), 4.06(1H, d, J = 11.5 Hz), 6.32(1H, d, J = 11.0 Hz), 6.85-6.92(2H, m), 7.08(1H, d, J = 11.1 Hz). |
| 108 | 1 | NMR1; 1.66-1.79(2H, m), 2.77-2.82(1H, m), 2.95-3.00(1H, m), 3.13-3.25(2H, m), 3.63-3.69(1H, m), 3.68(1H, d, J = 17.1 Hz), 3.79(1H, d, J = 17.1 Hz), 4.59(1H, brs), 4.96(1H, d, J = 7.6 Hz), 6.82(1H, d, J = 10.5 Hz), 7.20-7.27(2H, m), 7.43(1H, d, J = 11.0 Hz), 7.65(1H, d, J = 10.5 Hz), 8.29(1H, d, J = 11.0 Hz), 10.70(1H, brs). |
| 109 | 90 | NMR2; 1.20(3H, t, J = 7.2 Hz), 1.88-1.94(1H, m), 1.98-2.02(1H, m), 2.56-2.66(2H, m), 2.79-2.83(1H, m), 2.87-2.93(1H, m), 2.98-3.04(2H, m), 3.13(1H, brs), 3.21-3.25(1H, m), 3.27-3.32(1H, m), 3.39-3.45(1H, m), 3.92(1H, d, J = 9.0 Hz), 3.93-3.98(1H, m), 4.10(1H, d, J = 9.0 Hz), 4.10(2H, q, J = 7.2 Hz), 6.81(1H, dd, J = 4.5 Hz, 8.6 Hz), 6.86-6.91(4H, m). |
| 110 | 90 | NMR2; 1.86-1.92(1H, m), 1.99-2.03(1H, m), 2.56-2.72(2H, m), 2.73-2.81(1H, m), 2.84-2.93(2H, m), 2.97-3.10(2H, m), 3.17-3.25(1H, m), 3.26-3.34(1H, m), 3.35-3.45(1H, m), 3.89(1H, d, J = 9.1 Hz), 3.92-3.95(1H, m), 4.08(1H, d, J = 9.1 Hz), 6.77(1H, dd, J = 4.5 Hz, 8.9 Hz) , 6.85-6.91(4H, m). |
| 111 | 6 | NMR1; 1.63-1.67(1H, m), 1.87-1.94(1H, m), 2.86-2.91(1H, m), 2.93-2.97(1H, m), 3.17-3.40(2H, m), 3.70(1H, d, J = 9.1 Hz), 3.71-3.75(1H, m), 4.07(1H, d, J = 9.1 Hz), 4.52(1H, brs), |

TABLE 4-16-continued

| EX | Prop | Data |
|---|---|---|
| | | 4.61(2H, s), 4.87(1H, d, J = 6.4 Hz), 6.76(1H, d, J-9.0 Hz), 7.04(1H, d, J = 9.0 Hz), 7.25-7.31(2H, m), 10.40(1H, brs). |
| 112 | 90 | NMR2; 1.24(3H, t, J = 7.2 Hz), 1.82-1.88(1H, m), 1.97-2.01(1H, m), 2.86(1H, d, J = 8.0 Hz), 2.97-3.02(1H, m), 3.19-3.23(1H, m), 3.24-3.30(1H, m), 3.31(1H, brs), 3.40-3.46(1H, m), 3.53(1H, d, J = 14.7 Hz), 3.70(1H, d, J = 14.7 Hz), 3.86-3.90 (1H, m), 3.93(1H, d, J = 9.0 Hz), 4.11-4.17(3H, m), 6.83-6.91 (3H, m), 6.94-6.98(2H, m). |
| 113 | 90 | NMR2; 1.91-1.97(1H, m), 1.99-2.03(1H, m), 2.73(1H, d, J = 6.7 Hz), 2.84(1H, brs), 3.03-3.07(1H, m), 3.25-3.32(2H, m), 3.39-3.44(1H, m), 4.02-4.06(1H, m), 4.14(1H, d, J = 9.2 Hz), 4.24(1H, d, J = 9.2 Hz), 6.52(1H, d, J = 8.3 Hz), 6.67(1H, dd, J = 2.3 Hz, 3.2 Hz), 6.87-6.92(2H, m), 7.10(1H, d, J = 8.3 Hz), 7.20-7.21(1H, m), 8.40(1H, brs). |

TABLE 4-17

| EX | Prop | Data |
|---|---|---|
| 114 | — | NMR2; 1.85-1.91(1H, m), 2.03-2.07(1H, m), 2.41-2.47(1H, m), 2.52-2.58(1H, m), 2.84-2.89(1H, m), 2.97-3.02(1H, m), 3.10-3.16(1H, m), 3.19-3.33(3H, m), 3.40-3.46(1H, m), 3.89(1H, d, J = 8.9 Hz), 3.88-3.94(1H, m), 3.93(1H, brs), 4.09(1H, d, J = 8.9 Hz), 5.47(1H, brs), 5.52(1H, brs), 6.78-6.81(1H, m), 6.85-6.90(4H, m). |
| 115 | — | NMR2; 1.80-1.97(2H, m), 2.90-4.20(1H, m), 6.74-6.95(5H, m), |
| 116 | — | NMR2; 1.75-2.03(5H, m), 2.66-2.71(1H, m), 2.84-3.03(3H, m), 3.19-3.22(1H, m), 3.25-3.30(1H, m), 3.35-3.41(1H, m), 3.59-3.75(3H, m), 3.90-3.96(1H, m), 3.91(1H, d, J = 9.0 Hz), 4.11(1H, d, J = 9.0 Hz), 6.78-6.91(5H, m). |
| 117 | — | NMR2; 1.86-1.92(1H, m), 1.97-2.01(1H, m), 2.96-3.01(1H, m), 3.17-3.28(3H, m), 3.36-3.42(1H, m), 3.44(1H, brs), 3.49(1H, d, J = 14.7 Hz), 3.59(1H, d, J = 14.7 Hz), 3.89-3.93(1H, m), 3.95(1H, d, J = 9.0 Hz), 4.08(1H, d, J = 9.0 Hz), 5.61(1H, brs), 5.85(1H, brs), 6.84(1H, dd J = 4.6 Hz, 9.7 Hz), 6.85-6.90(2H, m), 6.93-6.98(2H, m). |
| 118 | — | NMR2; 1.82-1.99(3H, m), 2.79-2.84(1H, m), 2.96-3.04(2H, m), 3.06(1H, brs), 3.19-3.28(3H, m), 3.36-3.42(1H, m), 3.82-3.98(3H, m), 3.94(1H, d, J = 9.1 Hz), 4.07(1H, d, J = 9.1 Hz), 6.81-6.92(5H, m). |
| 119 | 6 | NMR1; 1.70-1.74(1H, m), 1.88-1.94(1H, m), 2.81-2.86(1H, m), 2.94-2.99(1H, m), 3.07-3.11(1H, m), 3.14-3.18(1H, m), 3.45-3.49(2H, m), 3.74-3.79(2H, m), 4.07(1H, d, J = 9.0 Hz), 4.54(1H, brs), 4.90(1H, d, J = 6.4 Hz), 6.65(1H, d, J = 9.0 Hz), 7.08(1H, t, J = 9.1 Hz), 7.16-7.19(1H, m), 7.20(1H, d, J = 9.0 Hz), 7.32(1H, dd, J = 2.4 Hz, 12.5 Hz), 10.73(1H, brs). |
| 120 | 6 | NMR1; 1.70-1.74(1H, m), 1.88-1.94(1H, m), 2.81-2.86(1H, m), 2.94-2.99(1H, m), 3.07-3.12(1H, m), 3.14-3.19(1H, m), 3.40-3.49(2H, m), 3.74-3.79(2H, m), 4.07(1H, d, J = 9.0 Hz), 4.54(1H, brs), 4.90(1H, d, J = 6.5 Hz), 6.65(1H, d, J = 9.0 Hz), 7.02(1H, t, J = 9.1 Hz), 7.19(1H, d, J = 9.0 Hz), 7.28-7.30(1H, m), 7.42(1H, dd, J = 2.3 Hz, 12.2 Hz), 10.73(1H, brs). |
| 121 | 6 | NMR2; 1.93-2.02(2H, m), 2.52(1H, d, J = 7.6 Hz), 2.64(1H, brs), 3.03-3.08(1H, m), 3.24-3.32(2H, m), 3.36-3.42(1H, m), 3.97-4.01(1H, m), 3.92(1H, d, J = 9.2 Hz), 4.21(1H, d, J = 9.2 Hz), 6.87(1H, d, J = 8.7 Hz), 6.88-6.93(2H, m), 7.43(1H, d, J = 8.7 Hz). |
| 122 | 19 | NMR2; 1.90-1.98(2H, m), 2.38(1H, d, J = 7.8 Hz), 2.61(1H, brs), 3.02-3.07(1H, m), 3.23-3.30(2H, s), 3.34-3.40(1H, m), 3.91-3.96(1H, m), 4.10(1H, d, J = 9.3 Hz), 4.18(1H, d, J = 9.3 Hz), 6.69(1H, d, J = 8.9 Hz), 6.87-6.92(2H, m), 7.22(1H, d, J = 8.7 Hz), 8.28(1H, brs). |

TABLE 4-18

| EX | Prop | Data |
|---|---|---|
| 123 | — | NMR1; 1.65-1.69(1H, m), 1.85-1.91(1H, m), 2.87-2.92(1H, m), 2.94-2.98(1H, m), 3.10-3.22(2H, m), 3.40-3.44(2H, m), 3.68-3.74(1H, m), 3.73(1H, d, J = 8.9 Hz), 4.04(1H, d, J = 8.9 Hz), 4.48(1H, brs), 4.82(1H, d, J = 6.6 Hz), 6.57(1H, dd, J = 3.3 Hz, 9.2 Hz), 7.05(1H, dd, J = 9.2 Hz, 9.8 Hz), 7.24-7.30(2H, m), 10.83(1H, brs). |
| 124 | 6 | NMR1; 1.67-1.72(1H, m), 1.91-1.98(1H, m), 2.79-2.84(1H, m), 2.93-2.98(1H, m), 3.05-3.10(1H, m), 3.13-3.17(1H, m), 3.71(1H, d, J = 9.0 Hz), 3.78-3.82(1H, m), 4.08(1H, d, J = 9.0 Hz), 4.54(1H, brs), 4.60(2H, s), 4.93(1H, d, J = 6.3 Hz), 6.75(1H, d, J = 9.0 Hz), 7.04(1H, d, J = 9.0 Hz), 7.05-7.09(1H, m), 7.16-7.19(1H, m), 7.33(1H, dd, J = 2.4 Hz, 12.5 Hz), 10.40 (1H, brs). |
| 125 | 6 | NMR1; 1.67-1.72(1H, m), 1.91-1.98(1H, m), 2.79-2.83(1H, m), 2.93-2.98(1H, m), 3.05-3.10(1H, m), 3.13-3.17(1H, m), 3.71(1H, d, J = 9.0 Hz), 3.78-3.82(1H, m), 4.08(1H, d, J = 9.0 Hz), 4.53(1H, brs), 4.60(2H, s), 4.92(1H, d, J = 6.3 Hz), 6.75(1H, d, J = 9.0 Hz), 7.02(1H, t, J = 9.1 Hz), 7.03(1H, d, J = 9.0 Hz), 7.28-7.31(1H, m), 7.43(1H, dd, J = 2.3 Hz, 12.2 Hz), 10.40(1H, brs). |
| 126 | — | NMR1; 1.66-1.70(1H, m), 1.86-1.92(1H, m), 2.88-2.93(1H, m), 2.94-2.98(1H, m), 2.95(3H, d, J = 4.7 Hz), 3.17-3.53(2H, m), 3.70-3.74(1H, m), 3.82(1H, d, J = 8.9 Hz), 4.17(1H, d, J = 8.9 Hz), 4.58(1H, brs), 4.92(1H, d, J = 6.4 Hz), 6.69(1H, d, J = 8.7 Hz), 7.25(1H, d, J = 8.7 Hz), 7.25-7.31(2H, m), 8.25(1H, d, J = 4.7 Hz). |
| 127 | — | NMR1; 1.64-1.68(1H, m), 1.87-1.93(1H, m), 2.88-2.93(1H, m), 2.95-2.98(1H, m), 3.18-3.45(2H, m), 3.71-3.74(1H, m), 3.80(1H, d, J = 8.9 Hz), 4.17(1H, d, J = 8.9 Hz), 4.57(1H, brs), 4.91(1H, brs), 6.68(1H, d, J = 8.7 Hz), 7.23(1H, d, J = 8.7 Hz), 7.25-7.31(2H, m), 7.83(2H, brs). |
| 128 | 6 | NMR2; 1.92-2.04(2H, m), 2.63(1H, d, J = 7.0 Hz), 2.78(1H, brs), 3.03-3.08(1H, m), 3.25-3.33(2H, m), 3.39-3.45(1H, m), 3.96(3H, s), 4.01-4.06(1H, m), 4.12(1H, d, J = 9.2 Hz), 4.22(1H d, J = 9.2 Hz), 6.42(1H, dd, J = 2.9 Hz, 8.5 Hz), 6.87-6.92(2H, m), 6.93(1H, dd, J = 8.5 Hz, 10.4 Hz), 7.32-7.33(1H, m), 9.05(1H, brs). |
| 129 | 6 | NMR1; 1.63-1.68(1H, m), 1.82-1.88(1H, m), 2.86-2.91(1H, m), 2.93-2.97(1H, m), 3.18-3.22(1H, m), 3.24-3.27(1H, m), 3.65-3.71(1H, m), 3.67(1H, d, J = 8.8 Hz), 3.99(1H, d, J = 8.8 Hz), 4.27-4.36(2H, m), 4.55(1H, brs), 4.89(1H, d, J = 6.5 Hz), 6.46(1H, dd, J = 3.5 Hz, 9.1 Hz), 6.90-6.92(1H, m), 7.00(1H, dd, J = 9.1 Hz, 10.0 Hz), 7.24-7.30(2H, m), 8.94(1H, brs). |

TABLE 4-19

| EX | Prop | Data |
|---|---|---|
| 130 | 6 | NMR1; 1.68-1.72(1H, m), 1.86-1.92(1H, m), 2.81-2.85(1H, m), 2.93-2.99(1H, m), 3.06-3.10(1H, m), 3.13-3.16(1H, m), 3.69(1H, d, J = 8.8 Hz), 3.73-3.77(1H, m), 4.00(1H, d, J = 8.8 Hz), 4.27-4.35(2H, m), 4.57(1H, brs), 4.95(1H, d, J = 6.4 Hz), 6.46(1H, dd, J = 3.5 Hz, 9.1 Hz), 6.88-6.90(1H, m), 7.01(1H, dd, J = 9.1 Hz, 9.9 Hz), 7.06-7.09(1H, m), 7.16-7.19(1H, m), 7.32(1H, dd, J = 2.4 Hz, 12.5 Hz), 8.94(1H, brs). |
| 131 | 6 | NMR1; 1.68-1.72(1H, m), 1.86-1.92(1H, m), 2.81-2.85(1H, m), 2.93-2.98(1H, m), 3.06-3.10(1H, m), 3.13-3.17(1H, m), 3.69(1H, d, J = 8.8 Hz), 3.73-3.77(1H, m), 3.99(1H, d, J = 8.8 Hz), 4.27-4.35(2H, m), 4.57(1H, brs), 4.95(1H, d, J = 6.4 Hz), 6.46(1H, dd, J = 3.5 Hz, 9.1 Hz), 6.88-6.90(1H, m), 6.98-7.04(2H, m), 7.28-7.31(1H, m), 7.42(1H, dd, J = 2.3 Hz, 12.2 Hz), 8.94(1H, brs). |
| 132 | 6 | NMR1; 1.69-1.74(1H, m), 1.78-1.84(1H, m), 2.87-2.92(1H, m), 2.94-2.97(1H, m), 3.19-3.23(1H, m), 3.25-3.33(1H, m), 3.64-3.69(1H, m), 3.82(1H, d, J = 9.1 Hz), 4.04(1H, d, J = 9.1 Hz), 4.62(1H, brs), 4.89(1H, d, J = 6.6 Hz), 5.29(1H, d, J = 14.0 Hz), 5.36(1H, d, J = 14.0 Hz), 6.74(1H, d, J = 9.0 Hz), 7.25-7.30(2H, m), 7.34(1H, d, J = 9.0 Hz), 9.86(1H, brs). |
| 133 | 6 | NMR1; 1.74-1.78(1H, m), 1.83-1.89(1H, m), 2.83-2.87(1H, m), 2.94-3.00(1H, m), 3.07-3.12(1H, m), 3.14-3.18(1H, m), 3.71-3.76(1H, m), 3.83(1H, d, J = 9.1 Hz), 4.04(1H, d, J = 9.1 Hz), 4.64(1H, brs), 4.95(1H, d, J = 6.5 Hz), 5.29(1H, d, J = 14.1 Hz), 5.35(1H, d, J = 14.1 Hz), 6.74(1H, d, J = 9.0 Hz), 7.06-7.10(1H, m), 7.16-7.19(1H, m), 7.32(1H, dd, J = 2.5 Hz, 12.4 Hz), 7.34(1H, d, J = 9.0 Hz), 9.85(1H, brs). |

TABLE 4-19-continued

| EX | Prop | Data |
| --- | --- | --- |
| 134 | 6 | NMR1; 1.74-1.78(1H, m), 1.83-1.89(1H, m), 2.83-2.87(1H, m), 2.94-3.00(1H, m), 3.08-3.12(1H, m), 3.15-3.19(1H, m), 3.71-3.75(1H, m), 3.83(1H, d, J = 9.1 Hz), 4.04(1H, d, J = 9.1 Hz), 4.65(1H, brs), 4.96(1H, d, J = 6.5 Hz), 5.29(1H, d, J = 14.1 Hz), 5.35(1H, d, J = 14.1 Hz), 6.74(1H, d, J = 9.0 Hz), 7.03 (1H, t, J = 9.2 Hz), 7.28-7.31(1H, m), 7.34(1H, d, J = 9.0 Hz), 7.42(1H, dd, J = 2.3 Hz, 12.3 Hz), 9.85(1H, brs). |
| 135 | 6 | NMR1; 1.71-1.75(1H, m), 1.84-1.90(1H, m), 2.89-2.94(1H, m), 2.96-2.99(1H, m), 3.20-3.24(1H, m), 3.31-3.36(1H, m), 3.69-3.73(1H, m), 3.96(1H, d, J = 9.1 Hz), 4.24(1H, d, J = 9.1 Hz), 4.65(1H, brs), 4.94(1H, d, J = 6.4 Hz), 7.13(1H, dd, J = 3.2 Hz, 8.9 Hz), 7.26-7.31(2H, m), 7.40(1H, dd, J = 8.9 Hz, 10.4 Hz). |

TABLE 4-20

| EX | Prop | Data |
| --- | --- | --- |
| 136 | 6 | NMR1; 1.75-1.79(1H, m), 1.87-1.94(1H, m), 2.84-2.88(1H, m), 2.96-3.01(1H, m), 3.09-3.13(1H, m), 3.16-3.20(1H, m), 3.75-3.79(1H, m), 3.98(1H, d, J = 9.1 Hz), 4.24(1H, d, J = 9.1 Hz), 4.67(1H, brs), 5.00(1H, d, J = 6.3 Hz), 7.09(1H, t, J = 9.1 Hz), 7.13(1H, dd, J = 3.2 Hz, 9.0 Hz), 7.17-7.19(1H, m), 7.33(1H, dd, J = 2.4 Hz, 12.5 Hz), 7.40(1H, dd, J = 9.0 Hz, 10.4 Hz). |
| 137 | 6 | NMR1; 1.75-1.79(1H, m), 1.87-1.94(1H, m), 2.84-2.88(1H, m), 2.96-3.01(1H, m), 3.10-3.14(1H, m), 3.17-3.20(1H, m), 3.75-3.79(1H, m), 3.98(1H, d, J = 9.1 Hz), 4.24(1H, d, J = 9.1 Hz), 4.68(1H, brs), 5.00(1H, d, J = 6.3 Hz), 7.03(1H, t, J = 9.1 Hz), 7.13(1H, dd, J = 3.2 Hz, 9.0 Hz), 7.29-7.31(1H, m), 7.40(1H, dd, J = 9.0 Hz, 10.4 Hz), 7.43(1H, dd, J = 2.3 Hz, 12.2 Hz). |
| 138 | — | NMR1; 1.65-1.70(1H, m), 1.82-1.88(1H, m), 2.88-2.93(1H, m), 2.95-2.99(1H, m), 3.17-3.23(1H, m), 3.29-3.36(1H, m), 3.65-3.72(1H, m), 3.82(1H, d, J = 9.0 Hz), 4.14(1H, d, J = 9.0 Hz), 4.62(1H, brs), 4.96(1H, d, J = 6.3 Hz), 6.78(1H, dd, J = 3.3 Hz, 9.2 Hz), 7.17(1H, dd, J = 9.2 Hz, 10.2 Hz), 7.24-7.30(2H, m), 12.47(1H, brs). |
| 139 | 138 | NMR1: 1.70-1.74(1H, m), 1.84-1.91(1H, m), 2.82-2.86(1H, m), 2.94-3.00(1H, m), 3.08-3.12(1H, m), 3.15-3.19(1H, m), 3.72-3.76(1H, m), 3.84(1H, d, J = 9.0 Hz), 4.14(1H, d, J = 9.0 Hz), 4.60(1H, brs), 4.97(1H, d, J = 6.2 Hz), 6.77(1H, dd, J = 3.3 Hz, 9.2 Hz), 7.06-7.10(1H, m), 7.14-7.19(2H, m), 7.32(1 H, dd, J = 2.4 Hz, 12.5 Hz), 12.43(1H, brs). |
| 140 | 138 | NMR1; 1.70-1.74(1H, m), 1.84-1.91(1H, m), 2.81-2.86(1H, m), 2.94-3.00(1H, m), 3.08-3.12(1H, m), 3.15-3.19(1H, m), 3.72-3.76(1H, m), 3.84(1H, d, J = 9.0 Hz), 4.14(1H, d, J = 9.0 Hz), 4.60(1H, brs), 4.97(1H, d, J = 6.3 Hz), 6.77(1H, dd, J = 3.3 Hz, 9.1 Hz), 7.02(1H, t, J = 9.1 Hz), 7.16(1H, dd, J = 9.3 Hz, 10.1 Hz), 7.28-7.31(1H, m), 7.42(1H, dd, J = 2.3 Hz, 12.3 Hz), 12.43(1H, brs). |
| 141 | 6 | NMR1; 1.62-1.66(2H, m), 1.71-1.77(2H, m), 2.95-2.99(2H, m), 3.33-3.39(2H, m), 3.82(2H, s), 4.73(1H, brs), 5.33(2H, s), 6.48(1H, d, J = 8.0 Hz), 6.66(1H, d, J = 8.3 Hz), 7.18(1H, dd, J = 8.0 Hz, 8.3 Hz), 7.24-7.30(2H, m), 10.10(1H, brs). |
| 142 | 6 | NMR2; 1.81-1.86(2H, m), 1.87-1.93(2H, m), 2.01(1H, brs), 3.07-3.12(2H, m), 3.45-3.51(2H, m), 4.02(2H, s), 6.82(1H, dd, J = 3.1 Hz, 8.9 Hz), 6.86-6.91(2H, m), 7.14(1H, d, J = 8.9 Hz, 9.6 Hz). |

TABLE 4-21

| EX | Prop | Data |
| --- | --- | --- |
| 143 | 6 | NMR1; 1.58-1.68(1H, m), 1.81-1.93(1H, m), 2.75-2.85(1H, m), 2.89-3.01(1H, m), 3.11-3.21(1H, m), 3.24-3.34(1H, m), 3.40-3.51(2H, m), 3.63-3.82(4H, m), 4.02-4.08(1H, m), 4.50(1H, brs), 4.65(1H, brs), 4.82-4.88(1H, m), 7.05-7.12(2H, m), 7.13-7.22(3H, m). |

TABLE 4-21-continued

| EX | Prop | Data |
|---|---|---|
| 144 | 1 | NMR1; 1.67-1.81(1H, m), 1.85-1.96(1H, m), 2.88-3.04(2H, m), 3.17-3.28(1H, m), 3.30-3.40(1H, m), 3.50(3H, s), 3.70-3.79(1H, m), 3.72(3H, s), 3.84-3.91(1H, m), 4.13-4.19(1H, m), 4.61(1H, brs), 4.96-5.03(1H, m), 7.02(1H, d, J = 8.4 Hz), 7.05(1H, d, J = 7.9 Hz), 7.25(1H, dd, J = 8.4 Hz, 7.9 Hz), 7.24-7.34(2H. m). |
| 145 | — | NMR2; 1.78-1.89(4H, m), 2.03(1H, brs), 3.05-3.10(2H, m), 3.43-3.50(2H, m), 3.52(2H, s), 3.88(2H, s), 6.50(1H, dd, J = 3.3 Hz, 9.2 Hz), 6.85-6.91(2H, m), 6.96(1H, t, J = 9.2 Hz), 7.49(1H, brs). |
| 146 | 1 | NMR1; 1.64-1.77(1H, m), 2.01-2.10(1H, m), 2.89-3.02(2H, m), 3.24-3.42(2H, m), 3.52(3H, s), 3.58-3.70(1H, m), 4.03-4.09(1H, m), 4.10-4.17(1H, m), 4.67(1H, brs), 5.15(1H, brs), 6.90(1H, d, J = 8.0 Hz), 6.99(1H, d, J = 8.1 Hz), 7.16(1H, dd, J = 8.1 Hz, 8.0 Hz), 7.24-7.33(2H. m), 11.43(1H, brs). |
| 147 | — | NMR1; 1.59-1.64(2H, m), 1.74-1.80(2H, m), 2.95-3.00(2H, m), 3.33-3.39(2H, m), 3.90(2H, s), 4.75(1H, brs), 6.79(1H, dd, J = 3.3 Hz, 9.2 Hz), 7.13-7.17(1H, m), 7.24-7.29(2H, m), 12.41(1H, brs). |

INDUSTRIAL APPLICABILITY

The present invention may provide compounds with potent antibacterial activity against tuberculosis bacteria, multidrug-resistant tuberculosis bacteria, and/or non-tuberculous mycobacteria.

The invention claimed is:

1. A compound of Formula [I] or a salt thereof:

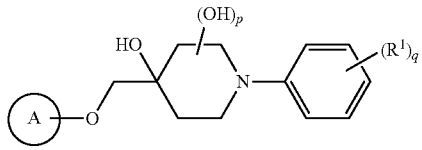

wherein Ring A is an optionally substituted hydrocarbon ring or optionally substituted heterocycle, provided that Ring A is not carbostyril or dihydrocarbostyril;

$R^1$ is halogen, —CN, —NO$_2$, —OH, —CHO, —COOH, —SH, —SO$_2$H, —SO$_3$H, optionally substituted C$_{1-6}$ alkyl, optionally substituted C$_{2-6}$ alkenyl, optionally substituted C$_{2-6}$ alkynyl, optionally substituted C$_{1-6}$ alkoxy, optionally substituted C$_{2-6}$ alkenyl-O—, optionally substituted C$_{2-6}$ alkynyl-O—, optionally substituted C$_{1-6}$ alkyl-CO—, optionally substituted C$_{2-6}$ alkenyl-CO—, optionally substituted C$_{2-6}$ alkynyl-CO—, optionally substituted C$_{1-6}$ alkyl-COO—, optionally substituted C$_{1-6}$ alkoxy-CO—, optionally substituted C$_{1-6}$ alkyl-S—, optionally substituted C$_{1-6}$ alkyl-SO—, optionally substituted C$_{1-6}$ alkyl-SO$_2$—, optionally substituted C$_{3-6}$ cycloalkyl, optionally substituted C$_{3-6}$ cycloalkenyl, optionally substituted C$_{3-6}$ cycloalkoxy, optionally substituted C$_{3-6}$ cycloalkenyl-O—, optionally substituted C$_{3-6}$ cycloalkyl-CO—, optionally substituted C$_{3-6}$ cycloalkoxy-CO—, optionally substituted C$_{6-14}$ aryl, optionally substituted C$_{6-14}$ aryl-O—, optionally substituted C$_{6-14}$ aryl-CO—, optionally substituted C$_{6-14}$ aryl-O—CO—, optionally substituted C$_{7-17}$ aralkyl, optionally substituted C$_{7-17}$ aralkyl-O—, optionally substituted C$_{7-17}$ aralkyl-CO—, optionally substituted C$_{7-17}$ aralkyl-O—CO—, amino, wherein the amino group may be optionally substituted with the same or different at least one group of —CHO, optionally substituted C$_{1-6}$ alkyl, optionally substituted C$_{1-6}$ alkyl-CO—, optionally substituted C$_{1-6}$ alkoxy-CO—, or optionally substituted C$_{6-14}$ aryl-CO—, or —CONH$_2$, wherein the amino group may be optionally substituted with the same or different at least one group of —CHO, optionally substituted C$_{1-6}$ alkyl, optionally substituted C$_{1-6}$ alkyl-CO—, optionally substituted C$_{1-6}$ alkoxy-CO—, or optionally substituted C$_{6-14}$ aryl-CO—;

p is an integer of 0 to 4; and q is an integer of 1 to 5;

provided that when q is 2 or more, then each of $R^1$ may be different from each other.

2. The compound according to claim 1 or a salt thereof, wherein Ring A is an optionally substituted 6-membered monocyclic hydrocarbon ring, optionally substituted 6-membered monocyclic heterocycle, optionally substituted 7- to 12-membered bicyclic hydrocarbon ring, or optionally substituted 7- to 12-membered bicyclic or tricyclic heterocycle, the heterocycle group comprising as a ring member atom 1 to 5 heteroatoms independently selected from the group consisting of nitrogen, oxygen, and sulfur;

a substituent of Ring A is at least one group independently selected from the group consisting of:

(1) halogen,
(2) —CN,
(3) —NO$_2$,
(4) =N—OH,
(5) —OH,
(6) =O,
(7) =S,
(8) C$_{1-6}$ alkyl optionally substituted with at least one group independently selected from the group consisting of:
 (i) halogen,
 (ii) —OH,
 (iii) —COOR$^a$ wherein R$^a$ is hydrogen or C$_{1-6}$ alkyl,
 (iv) —C$_{6-10}$ aryl, and
 (v) —CONR$^b$R$^c$ wherein R$^b$ and R$^c$ are each independently hydrogen or C$_{1-6}$ alkyl,
(9) C$_{1-6}$ alkoxy optionally substituted with the same or different at least one halogen,
(10) —COR$^d$ wherein R$^d$ is —OH, C$_{1-6}$ alkyl, or C$_{1-6}$ alkoxy,
(11) C$_{1-6}$ alkyl-S—,

(12) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(13) —CONR$^b$R$^c$ wherein R$^b$ and R$^c$ are the same as defined above,
(14) —NR$^b$R$^c$ wherein R$^b$ and R$^c$ are the same as defined above,
(15) C$_{6-10}$ aryl optionally substituted with the same or different at least one halogen,
(16) C$_{6-10}$ aryl-O—,
(17) C$_{7-12}$ aralkyl-O—, and
(18) saturated 3- to 6-membered nitrogen-containing heteromonocycle optionally substituted with at least one =O;
provided that when Ring A is a monocyclic aromatic ring, a substituent thereof is not optionally substituted C$_{6-10}$ aryl.

3. The compound according to claim 1 or a salt thereof, wherein Ring A has any one of the structures of Formulae (A-I) to (A-III):

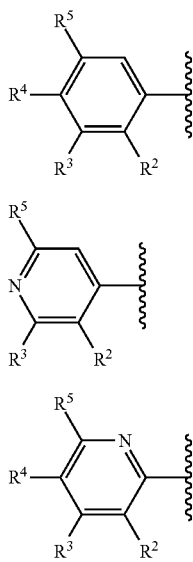

wherein R$^2$, R$^3$, R$^4$, and R$^5$ are each independently
(a1) hydrogen,
(a2) halogen,
(a3) —CN,
(a4) —NO$_2$,
(a5) —OH,
(a6) C$_{1-6}$ alkyl optionally substituted with at least one group independently selected from the group consisting of:
 (i) halogen,
 (ii) —OH,
 (iii) —COOR$^a$ wherein R$^a$ is hydrogen or C$_{1-6}$ alkyl,
 (iv) —C$_{6-10}$ aryl, and
 (v) —CONR$^b$R$^c$ wherein R$^b$ and R$^c$ are each independently hydrogen or C$_{1-6}$ alkyl,
(a7) C$_{1-6}$ alkoxy optionally substituted with the same or different at least one halogen,
(a8) —COR$^d$ wherein R$^d$ is —OH, C$_{1-6}$ alkyl, or C$_{1-6}$ alkoxy,
(a9) C$_{1-6}$ alkyl-S—,
(a10) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(a11) —CONR$^b$R$^c$ wherein R$^b$ and R$^c$ are the same as defined above,
(a12) —NR$^b$R$^c$ wherein R$^b$ and R$^c$ are the same as defined above,
(a13) C$_{6-10}$ aryl-O—,
(a14) C$_{7-12}$ aralkyl-O—, or
(a15) saturated 3- to 6-membered nitrogen-containing heteromonocycle optionally substituted with at least one =O;
R$^2$ and R$^3$ may alternatively combine together with the carbon atoms to which they attach to form a monocyclic or fused ring, Ring B, wherein Ring B may be optionally substituted with R$^6$ and Ring A comprising Ring B forms a 7- to 12-membered bicyclic hydrocarbon ring or 7- to 12-membered bicyclic or tricyclic heterocycle, and/or
R$^4$ and R$^5$ may alternatively combine together with the carbon atoms to which they attach to form a monocyclic or fused ring, Ring C, wherein Ring C may be optionally substituted with R$^6$ and Ring A comprising Ring C forms a 7- to 12-membered bicyclic hydrocarbon ring or 7- to 12-membered bicyclic or tricyclic heterocycle;
R$^6$ is 1 to 6 groups independently selected from the group consisting of:
(b1) halogen,
(b2) —CN,
(b3) —NO$_2$,
(b4) =N—OH,
(b5) —OH,
(b6) =O,
(b7) =S,
(b8) C$_{1-6}$ alkyl optionally substituted with at least one group independently selected from the group consisting of:
 (i) halogen,
 (ii) —OH,
 (iii) —COOR$^a$ wherein R$^a$ is hydrogen or C$_{1-6}$ alkyl,
 (iv) —C$_{6-10}$ aryl, and
 (v) —CONR$^b$R$^c$ wherein R$^b$ and R$^c$ are each independently hydrogen or C$_{1-6}$ alkyl,
(b9) C$_{1-6}$ alkoxy optionally substituted with the same or different at least one halogen,
(b10) —COR$^d$ wherein R$^d$ is —OH, C$_{1-6}$ alkyl, or C$_{1-6}$ alkoxy,
(b11) C$_{1-6}$ alkyl-S—,
(b12) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(b13) —CONR$^b$R$^c$ wherein R$^b$ and R$^c$ are the same as defined above,
(b14) —NR$^b$R$^c$ wherein R$^b$ and R$^c$ are the same as defined above, and
(b15) C$_{6-10}$ aryl optionally substituted with the same or different at least one halogen; and
a wavy line is a binding point.

4. The compound according to claim 3 or a salt thereof, wherein R$^2$, R$^3$, R$^4$, and R$^5$ are each independently
(a1) hydrogen,
(a2) halogen,
(a3) C$_{1-6}$ alkyl optionally substituted with at least one group independently selected from the group consisting of:
 (i) halogen,
 (ii) —OH,
 (iii) —COOR$^a$ wherein R$^a$ is hydrogen or C$_{1-6}$ alkyl, and (iv) —CONR$^b$R$^c$ wherein R$^b$ and R$^c$ are each independently hydrogen or C$_{1-6}$ alkyl,
(a4) —COOR$^f$ wherein R$^f$ is hydrogen or C$_{1-6}$ alkyl,
(a5) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(a6) —CONR$^b$R$^c$ wherein R$^b$ and R$^c$ are the same as defined above,
(a7) —NR$^b$R$^c$ wherein R$^b$ and R$^c$ are the same as defined above, or
(a8) saturated 3- to 6-membered nitrogen-containing heteromonocycle optionally substituted with at least one =O;
R$^2$ and R$^3$ may alternatively combine together with the carbon atoms to which they attach to form a monocyclic or fused ring, Ring B, wherein Ring B may be optionally substituted with R$^6$ and Ring A comprising Ring B forms a 7- to 12-membered bicyclic hydrocarbon ring or 7- to 12-membered bicyclic or tricyclic heterocycle, and/or
R$^4$ and R$^5$ may alternatively combine together with the carbon atoms to which they attach to form a monocyclic or fused ring, Ring C, wherein Ring C may be optionally substituted with R$^6$ and Ring A comprising Ring C forms a 7- to 12-membered bicyclic hydrocarbon ring or 7- to 12-membered bicyclic or tricyclic heterocycle; and
R$^6$ is 1 to 4 groups independently selected from the group consisting of:
(b1) halogen,
(b2) =N—OH,
(b3) —OH,
(b4) =O,
(b5) =S,
(b6) C$_{1-6}$ alkyl optionally substituted with the same or different at least one halogen or C$_{6-10}$ aryl,
(b7) C$_{1-6}$ alkoxy,
(b8) —COR$^d$ wherein R$^d$ is —OH, C$_{1-6}$ alkyl, or C$_{1-6}$ alkoxy,
(b9) —NHCOR$^e$ wherein R$^e$ is the same as defined above,
(b10) —NR$^b$R$^c$ wherein R$^b$ and R$^c$ are the same as defined above, and
(b11) C$_{6-10}$ aryl optionally substituted with the same or different at least one halogen.

5. The compound according to claim 1 or a salt thereof, wherein Ring A is
(1) a benzene ring optionally substituted with 1 to 3 groups independently selected from the group consisting of:
(i) halogen,
(ii) C$_{1-6}$ alkyl optionally substituted with at least one group independently selected from the group consisting of halogen, —OH, —COOH, —CONH$_2$, and C$_{1-6}$ alkoxy-CO—,
(iii) —COOR$^f$ wherein R$^f$ is hydrogen or C$_{1-6}$ alkyl,
(iv) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(v) —CONR$^b$R$^c$ wherein R$^b$ and R$^c$ are each independently hydrogen or C$_{1-6}$ alkyl,
(vi) —NR$^b$R$^c$ wherein R$^b$ and R$^c$ are the same as defined above, and
(vii) saturated 3- to 6-membered nitrogen-containing heteromonocycle optionally substituted with at least one =O, or
(2) a dihydroindene, naphthalene, tetrahydronaphthalene, indole, dihydroindole, dihydroisoindole, benzofuran, indazole, benzimidazole, dihydrobenzimidazole, benzoxazole, benzisoxazole, benzothiazole, dihydrobenzothiazole, quinoline, dihydroquinoline, tetrahydroquinoline, isoquinoline, dihydroisoquinoline, tetrahydroisoquinoline, tetrahydronaphthyridine, quinoxaline, dihydroquinoxaline, tetrahydroquinoxaline, benzoxathiin, dihydroquinazoline, tetrahydroquinazoline, dihydrobenzoxazine, benzothiazine, dihydrobenzothiazine, tetrahydrobenzazepine, tetrahydrobenzoxazepine, tetrahydrobenzothiazepine, carbazole, or dihydrophenanthridine ring, the ring being optionally substituted with 1 to 4 groups independently selected from the group consisting of:
(i) halogen,
(ii) =N—OH,
(iii) —OH,
(iv) =O,
(v) =S,
(vi) C$_{1-6}$ alkyl optionally substituted with the same or different at least one C$_{6-10}$ aryl,
(vii) C$_{1-6}$ alkoxy,
(viii) —COR$^d$ wherein R$^d$ is —OH, C$_{1-6}$ alkyl, or C$_{1-6}$ alkoxy,
(ix) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(x) —NR$^b$R$^c$ wherein R$^b$ and R$^c$ are each independently hydrogen or C$_{1-6}$ alkyl, and
(xi) C$_{6-10}$ aryl optionally substituted with the same or different at least one halogen.

6. The compound according to claim 1 or a salt thereof, wherein Ring A is
(1) a benzene ring optionally substituted with 1 to 3 groups independently selected from the group consisting of:
(i) halogen,
(ii) C$_{1-6}$ alkyl optionally substituted with at least one group independently selected from the group consisting of halogen, —OH, —COOH, —CONH$_2$, and C$_{1-6}$ alkoxy-CO—,
(iii) —COOR$^f$ wherein R$^f$ is hydrogen or C$_{1-6}$ alkyl,
(iv) —NHCOR$^e$ wherein R$^e$ is hydrogen, C$_{1-6}$ alkyl, C$_{1-6}$ alkoxy, C$_{6-10}$ aryl, or C$_{7-12}$ aralkyl,
(v) —CONR$^b$R$^c$ wherein R$^b$ and R$^c$ are each independently hydrogen or C$_{1-6}$ alkyl,
(vi) —NR$^b$R$^c$ wherein R$^b$ and R are the same as defined above, and
(vii) saturated 3- to 6-membered nitrogen-containing heteromonocycle optionally substituted with at least one =O,
(2) indole optionally substituted with 1 to 3 groups independently selected from the group consisting of halogen and C$_{1-6}$ alkoxy-CO—,
(3) dihydroindole optionally substituted with 1 to 3 groups independently selected from the group consisting of halogen and =O,
(4) dihydroisoindole optionally substituted with 1 to 3 groups independently selected from the group consisting of halogen, C$_{1-6}$ alkyl, and =O,
(5) dihydroindene optionally substituted with 1 to 3 groups independently selected from the group consisting of halogen, —OH, =N—OH, and =O,
(6) benzofuran optionally substituted with the same or different at least one halogen,
(7) indazole optionally substituted with the same or different at least one halogen,
(8) benzimidazole optionally substituted with phenyl optionally substituted with the same or different at least one halogen, (9) dihydrobenzimidazole optionally substituted with 1 to 3 groups independently selected from the group consisting of $C_{1-6}$ alkyl and =O,
(10) benzoxazole optionally substituted with the same or different at least one $C_{1-6}$ alkyl,
(11) benzisoxazole optionally substituted with the same or different at least one $C_{1-6}$ alkyl,
(12) benzothiazole optionally substituted with 1 to 3 groups independently selected from the group consisting of halogen, —NH$_2$, and mono-($C_{1-6}$ alkyl)-amino,
(13) dihydrobenzothiazole optionally substituted with 1 to 3 groups independently selected from the group consisting of halogen and =O,
(14) naphthalene optionally substituted with the same or different at least one —NHCO—$C_{1-6}$ alkyl,
(15) tetrahydronaphthalene optionally substituted with 1 to 3 groups independently selected from the group consisting of —OH and =O,
(16) quinoline optionally substituted with 1 to 3 groups independently selected from the group consisting of halogen and $C_{1-6}$ alkoxy,
(17) dihydroquinoline optionally substituted with 1 to 3 groups independently selected from the group consisting of halogen and =S,
(18) tetrahydroquinoline optionally substituted with 1 to 3 groups independently selected from the group consisting of halogen and $C_{1-6}$ alkyl-CO—,
(19) isoquinoline,
(20) dihydroisoquinoline optionally substituted with at least one =O,
(21) tetrahydroisoquinoline optionally substituted with at least one =O,
(22) tetrahydronaphthyridine optionally substituted with at least one =O,
(23) quinoxaline optionally substituted with the same or different at least one $C_{1-6}$ alkoxy,
(24) dihydroquinoxaline optionally substituted with 1 to 4 groups independently selected from the group consisting of $C_{1-6}$ alkyl and =O,
(25) tetrahydroquinoxaline optionally substituted with 1 to 4 groups independently selected from the group consisting of halogen, $C_{1-6}$ alkyl, and =O,
(26) benzoxathiin optionally substituted with at least one =O,
(27) dihydroquinazoline optionally substituted with at least one =O,
(28) tetrahydroquinazoline optionally substituted with 1 to 3 groups independently selected from the group consisting of halogen, $C_{1-6}$ alkyl, and =O,
(29) dihydrobenzoxazine optionally substituted with 1 to 3 groups independently selected from the group consisting of halogen and =O,
(30) benzothiazine optionally substituted with 1 to 3 groups independently selected from the group consisting of =O and benzyl,
(31) dihydrobenzothiazine optionally substituted with at least one =O,
(32) tetrahydrobenzazepine optionally substituted with 1 to 3 groups independently selected from the group consisting of halogen and =O,
(33) tetrahydrobenzoxazepine optionally substituted with at least one =O,
(34) tetrahydrobenzothiazepine optionally substituted with at least one =O,
(35) carbazole, or
(36) dihydrophenanthridine optionally substituted with at least one =O.

7. The compound according to claim 1 or a salt thereof, wherein R$^1$ is the same or different
(1) halogen,
(2) —CN,
(3) —NO$_2$,
(4) —OH,
(5) $C_{1-6}$ alkyl optionally substituted with at least one group independently selected from the group consisting of:
  (i) halogen,
  (ii) —OH,
  (iii) $C_{1-6}$ alkoxy, and
  (iv) $C_{6-10}$ aryl-O— optionally substituted with the same or different at least one halogen,
(6) $C_{1-6}$ alkoxy optionally substituted with at least one group independently selected from the group consisting of:
  (i) halogen,
  (ii) $C_{1-6}$ alkoxy optionally substituted with the same or different at least one $C_{1-6}$ alkoxy,
  (iii) $C_{6-10}$ aryl-O— optionally substituted with the same or different at least one halogen,
  (iv) heterocycle optionally substituted with the same or different at least one $C_{1-6}$ alkyl optionally substituted with the same or different at least one halogen, and
  (v) amino optionally substituted with the same or different 1 or 2 $C_{1-6}$ alkyl,
(7) $C_{1-6}$ alkoxy-CO—,
(8) $C_{1-6}$ alkyl-S—,
(9) $C_{6-10}$ aryl optionally substituted with the same or different at least one halogen,
(10) $C_{6-10}$ aryl-O—, or
(11) $C_{7-15}$ aralkyl-O— optionally substituted with at least one group independently selected from the group consisting of:
  (i) halogen,
  (ii) $C_{1-6}$ alkyl optionally substituted with the same or different at least one halogen, and
  (iii) $C_{1-6}$ alkoxy optionally substituted with the same or different at least one halogen.

8. The compound according to claim 1 or a salt thereof, wherein R$^1$ is the same or different
(1) halogen,
(2) $C_{1-6}$ alkyl optionally substituted with the same or different at least one halogen, or
(3) $C_{1-6}$ alkoxy optionally substituted with the same or different at least one halogen.

9. The compound according to claim 1 or a salt thereof, wherein Ring A is
(1) a benzene ring optionally substituted with 1 to 3 groups independently selected from the group consisting of fluoro, chloro, methyl, —CH$_2$OH, —CH$_2$CH$_2$OH, —CH$_2$CH$_2$CH$_2$OH, —CH$_2$COOH, —CH$_2$CH$_2$COOH, —CH$_2$COOCH$_2$CH$_3$, —CH$_2$CH$_2$COOCH$_2$CH$_3$, —CH$_2$CONH$_2$, —CH$_2$CH$_2$CONH$_2$, —COOH, —NH$_2$, —COOCH$_3$, —CONHCH$_3$, —NHCHO, —NHCOCH$_3$, —NHCOCH$_2$CH$_3$, —NHCO(CH$_2$)$_2$CH$_3$, —NHCOOCH$_3$, —NHCOPh, —NHCOCH$_2$Ph, —NHCO(CH$_2$)$_2$Ph, and oxoimidazolidinyl,
(2) indole optionally substituted with 1 or 2 groups independently selected from the group consisting of fluoro, chloro, and —COOCH$_3$,
(3) dihydroindole optionally substituted with 1 or 2 groups independently selected from the group consisting of fluoro, chloro, and =O, (4) dihydroisoindole optionally substituted with 1 or 2 groups independently selected from the group consisting of chloro, tert-butyl, and =O,
(5) dihydroindene optionally substituted with 1 or 2 groups independently selected from the group consisting of chloro, —OH, =N—OH, and =O,
(6) benzofuran optionally substituted with one bromo,
(7) indazole optionally substituted with one chloro,
(8) benzimidazole optionally substituted with one fluorophenyl,
(9) dihydrobenzimidazole optionally substituted with 1 or 2 groups independently selected from the group consisting of methyl and =O,
(10) benzoxazole optionally substituted with one methyl,
(11) benzisoxazole optionally substituted with one methyl,
(12) benzothiazole optionally substituted with 1 or 2 groups independently selected from the group consisting of fluoro, chloro, —NH$_2$, and methylamino,
(13) dihydrobenzothiazole optionally substituted with 1 or 2 groups independently selected from the group consisting of fluoro, chloro, and =O,
(14) naphthalene optionally substituted with one —NHCOCH$_3$,
(15) tetrahydronaphthalene optionally substituted with one —OH or one =O,
(16) quinoline optionally substituted with 1 or 2 groups independently selected from the group consisting of fluoro, chloro, and methoxy,
(17) dihydroquinoline optionally substituted with 1 or 2 groups independently selected from the group consisting of chloro and =S,
(18) tetrahydroquinoline optionally substituted with one fluoro or one —COCH$_3$,
(19) isoquinoline,
(20) dihydroisoquinoline optionally substituted with one =O,
(21) tetrahydroisoquinoline optionally substituted with one =O,
(22) tetrahydronaphthyridine optionally substituted with one =O,
(23) quinoxaline optionally substituted with one methoxy,
(24) dihydroquinoxaline optionally substituted with 1 or 2 groups independently selected from the group consisting of methyl and =O,
(25) tetrahydroquinoxaline optionally substituted with 1 to 4 groups independently selected from the group consisting of fluoro, methyl, and =O,
(26) benzoxathiin optionally substituted with 1 or 2 =O,
(27) dihydroquinazoline optionally substituted with one =O,
(28) tetrahydroquinazoline optionally substituted with 1 or 2 groups independently selected from the group consisting of methyl, fluoro, and =O,
(29) dihydrobenzoxazine optionally substituted with 1 or 2 groups independently selected from the group consisting of chloro and =O,
(30) benzothiazine optionally substituted with 1 to 3 groups independently selected from the group consisting of benzyl and =O,
(31) dihydrobenzothiazine optionally substituted with 1 or 2 =O,
(32) tetrahydrobenzazepine optionally substituted with 1 or 2 groups independently selected from the group consisting of chloro and =O,
(33) tetrahydrobenzoxazepine optionally substituted with one =O,
(34) tetrahydrobenzothiazepine optionally substituted with 1 to 3 =O,
(35) carbazole, or
(36) dihydrophenanthridine optionally substituted with one =O;
R$^1$ is the same or different fluoro, chloro, or bromo;
p is an integer of 0 or 1; and
q is an integer of 2 or 3.

10. The compound according to claim 1 or a salt thereof, which is selected from the group consisting of the following compounds:
1-(4-chloro-2-fluorophenyl)-4-(isoquinolin-5-yloxymethyl)piperidin-4-ol;
(3R,4R)-1-(4-chloro-2,6-difluorophenyl)-4-[(5-chloroquinolin-8-yl)oxymethyl]piperidine-3,4-diol;
2-tert-butyl-4-[[(3R,4R)-1-(4-chloro-2,6-difluorophenyl)-3,4-dihydroxypiperidin-4-yl]methoxy]-3H-isoindol-1-one;
3-methyl-4-[[(3R,4R)-1-(4-chloro-2,6-difluorophenyl)-3,4-dihydroxypiperidin-4-yl]methoxy]-1H-benzimidazol-2-one;
4-[[(3R,4R)-1-(4-chloro-2,6-difluorophenyl)-3,4-dihydroxypiperidin-4-yl]methoxy]-2,3-dihydroinden-1-one;
(3R,4R)-4-[(4-bromo-1-benzofuran-7-yl)oxymethyl]-1-(4-chloro-2,6-difluorophenyl)piperidine-3,4-diol;
(3R,4R)-1-(4-chloro-2,6-difluorophenyl)-4-[(1-hydroxy-2,3-dihydro-1H-inden-4-yl)oxymethyl]piperidine-3,4-diol;
(3R,4R)-1-(4-chloro-2,6-difluorophenyl)-4-(1H-indazol-4-yloxymethyl)piperidine-3,4-diol;
(3R,4R)-1-(4-chloro-2,6-difluorophenyl)-4-[(3-methyl-1,2-benzoxazol-4-yl)oxymethyl]piperidine-3,4-diol;
(3R,4R)-4-(1H-benzimidazol-4-yloxymethyl)-1-(4-chloro-2,6-difluorophenyl)piperidine-3,4-diol;
3-methyl-5-[[(3R,4R)-1-(4-chloro-2,6-difluorophenyl)-3,4-dihydroxypiperidin-4-yl]methoxy]-1,4-dihydroquinazolin-2-one;
(3R,4R)-1-(4-chloro-2,6-difluorophenyl)-4-[(8-fluoro-1,2,3,4-tetrahydroquinolin-5-yl)oxymethyl]piperidine-3,4-diol;
(3R,4R)-1-(4-chloro-2-fluorophenyl)-4-[(7-chloro-1H-indazol-4-yl)oxymethyl]piperidine-3,4-diol;
5-[[(3R,4R)-1-(4-bromo-2-fluorophenyl)-3,4-dihydroxypiperidin-4-yl]methoxy]-1H-quinoxalin-2-one;
8-[[(3R,4R)-1-(4-chloro-2-fluorophenyl)-3,4-dihydroxypiperidin-4-yl]methoxy]-1H-quinoxalin-2-one;
1-methyl-5-[[(3R,4R)-1-(4-chloro-2,6-difluorophenyl)-3,4-dihydroxypiperidin-4-yl]methoxy]quinoxalin-2-one;
N-[5-fluoro-2-[[(3R,4R)-1-(4-chloro-2,6-difluorophenyl)-3,4-dihydroxypiperidin-4-yl]methoxy]phenyl]acetamide;
6-[[(3R,4R)-1-(4-chloro-2,6-difluorophenyl)-3,4-dihydroxypiperidin-4-yl]methoxy]-1,5-dihydro-4,1-benzoxazepin-2-one;
5-[[(3R,4R)-1-(4-chloro-2-fluorophenyl)-3,4-dihydroxypiperidin-4-yl]methoxy]-1,4-dihydro-3,1-benzothiazin-2-one;
5-[[(3R,4R)-1-(4-bromo-2-fluorophenyl)-3,4-dihydroxypiperidin-4-yl]methoxy]-3,4-dihydro-1H-1,8-naphthyridin-2-one;
6-[[(3R,4R)-1-(4-chloro-2,6-difluorophenyl)-3,4-dihydroxypiperidin-4-yl]methoxy]-1,5-dihydro-4,1-benzothiazepin-2-one;
8-[[(3R,4R)-1-(4-chloro-2-fluorophenyl)-3,4-dihydroxypiperidin-4-yl]methoxy]-4H-1,4-benzothiazin-3-one;

9-chloro-6-[[1-(4-chloro-2,6-difluorophenyl)-4-hydroxypiperidin-4-yl]methoxy]-1,3,4,5-tetrahydro-1-benzazepin-2-one;
5-chloro-8-[[1-(4-chloro-2,6-difluorophenyl)-4-hydroxypiperidin-4-yl]methoxy]-4H-1,4-benzoxazin-3-one;
9-chloro-6-[[(3R,4R)-1-(4-chloro-2,6-difluorophenyl)-3,4-dihydroxypiperidin-4-yl]methoxy]-1,3,4,5-tetrahydro-1-benzazepin-2-one;
7-chloro-4-[[(3R,4R)-1-(4-chloro-2,6-difluorophenyl)-3,4-dihydroxypiperidin-4-yl]methoxy]-2,3-dihydroinden-1-one;
methyl 5-chloro-2-[[(3R,4R)-1-(4-chloro-2,6-difluorophenyl)-3,4-dihydroxypiperidin-4-yl]methoxy]benzoate;
7-chloro-4-[[(3R,4R)-1-(4-chloro-2,6-difluorophenyl)-3,4-dihydroxypiperidin-4-yl]methoxy]-1,3-dihydroindol-2-one;
(3R,4R)-1-(4-chloro-2,6-difluorophenyl)-4-[[4-chloro-2-(hydroxymethyl)phenoxy]methyl]piperidine-3,4-diol;
5-chloro-2-[[(3R,4R)-1-(4-chloro-2,6-difluorophenyl)-3,4-dihydroxypiperidin-4-yl]methoxy]-N-methylbenzamide;
N-[6-chloro-3-[[(3R,4R)-1-(4-chloro-2,6-difluorophenyl)-3,4-dihydroxypiperidin-4-yl]methoxy]-2-methylphenyl]formamide;
8-chloro-5-[[(3R,4R)-1-(4-chloro-2,6-difluorophenyl)-3,4-dihydroxypiperidin-4-yl]methoxy]-1H-quinoline-2-thione;
5-chloro-8-[[(3R,4R)-1-(4-chloro-2,6-difluorophenyl)-3,4-dihydroxypiperidin-4-yl]methoxy]-4H-1,4-benzoxazin-3-one;
(3R,4R)-1-(4-chloro-2,6-difluorophenyl)-4-[(7-chloro-1H-indole-4-yl)oxymethyl]piperidine-3,4-diol;
2-[5-fluoro-2-[[(3R,4R)-1-(4-chloro-2,6-difluorophenyl)-3,4-dihydroxypiperidin-4-yl]methoxy]phenyl]acetamide;
7-chloro-4-[[(3R,4R)-1-(4-bromo-2-fluorophenyl)-3,4-dihydroxypiperidin-4-yl]methoxy]-1,3-dihydroindol-2-one;
4-chloro-7-[[(3R,4R)-1-(4-chloro-2,6-difluorophenyl)-3,4-dihydroxypiperidin-4-yl]methoxy]-3H-1,3-benzothiazol-2-one;
(3R,4R)-4-[(2-amino-4-chloro-1,3-benzothiazol-7-yl)oxymethyl]-1-(4-chloro-2,6-difluorophenyl)piperidine-3,4-diol;
8-fluoro-5-[[(3R,4R)-1-(4-bromo-2-fluorophenyl)-3,4-dihydroxypiperidin-4-yl]methoxy]-3,4-dihydro-1H-quinazolin-2-one;
8-chloro-5-[[(3R,4R)-1-(4-chloro-2-fluorophenyl)-3,4-dihydroxypiperidin-4-yl]methoxy]-1,4-dihydro-3,1-benzoxazin-2-one;
(3R,4R)-1-(4-chloro-2,6-difluorophenyl)-4-[(2-chloro-4-fluoro-1,3-benzothiazol-7-yl)oxymethyl]piperidine-3,4-diol;
4-fluoro-7-[[(3R,4R)-1-(4-bromo-2-fluorophenyl)-3,4-dihydroxypiperidin-4-yl]methoxy]-3H-1,3-benzothiazol-2-one;
5-[[1-(4-chloro-2,6-difluorophenyl)-4-hydroxypiperidin-4-yl]methoxy]-1,4-dihydro-3,1-benzoxazin-2-one;
4-[[1-(4-chloro-2,6-difluorophenyl)-4-hydroxypiperidin-4-yl]methoxy]-7-fluoro-1,3-dihydroindol-2-one;
8-[[(3R,4R)-1-(4-chloro-2,6-difluorophenyl)-3,4-dihydroxypiperidin-4-yl]methoxy]-4-methyl-1H-quinoxaline-2,3-dione; and
7-[[1-(4-chloro-2,6-difluorophenyl)-4-hydroxypiperidin-4-yl]methoxy]-4-fluoro-3H-1,3-benzothiazol-2-one.

11. A pharmaceutical composition comprising a compound or a salt thereof according to claim 1 and a pharmaceutically acceptable carrier.

12. A medicinal agent for diagnosing, preventing, and/or treating tuberculosis, comprising a compound or a salt thereof according to claim 1 and a pharmaceutically acceptable carrier.

13. A compound or a salt thereof according to claim 1 for use in diagnosing, preventing, and/or treating tuberculosis.

14. A method of diagnosing, preventing, and/or treating tuberculosis, comprising administering an effective amount of a compound or a salt thereof according to claim 1 to a subject.

* * * * *